United States Patent
Goshgarian et al.

(10) Patent No.: US 10,342,612 B2
(45) Date of Patent: Jul. 9, 2019

(54) CATHETER APPARATUSES, SYSTEMS, AND METHODS FOR RENAL NEUROMODULATION

(71) Applicant: Medtronic Ardian Luxembourg S.a.r.l., Luxembourg (LU)

(72) Inventors: Justin Goshgarian, Santa Rosa, CA (US); Benjamin J. Clark, Redwood City, CA (US); Rajeshkumar Dhamodharasamy, Santa Rosa, CA (US); Mark S. Leung, Duncan (CA); Maria G. Aboytes, Mountain View, VA (US)

(73) Assignee: Medtronic Ardian Luxembourg S.a.r.l., Luxembourg (LU)

(*) Notice: Subject to any disclaimer, the term of this patent is extended or adjusted under 35 U.S.C. 154(b) by 0 days.

(21) Appl. No.: 15/812,947

(22) Filed: Nov. 14, 2017

(65) Prior Publication Data

US 2018/0147005 A1 May 31, 2018

Related U.S. Application Data

(63) Continuation of application No. 15/466,734, filed on Mar. 22, 2017, now Pat. No. 9,855,097, which is a (Continued)

(51) Int. Cl.
*A61N 1/36* (2006.01)
*A61B 18/14* (2006.01)
(Continued)

(52) U.S. Cl.
CPC .......... *A61B 18/1492* (2013.01); *A61B 18/02* (2013.01); *A61B 2017/00323* (2013.01);
(Continued)

(58) Field of Classification Search
CPC .. A61B 2018/00404; A61B 2018/0051; A61B 2018/00577; A61B 2018/00583
See application file for complete search history.

(56) References Cited

U.S. PATENT DOCUMENTS

| 4,602,624 A | 7/1986 | Naples et al. |
|---|---|---|
| 4,649,936 A | 3/1987 | Ungar et al. |

(Continued)

FOREIGN PATENT DOCUMENTS

| CN | 2782017 | 5/2006 |
|---|---|---|
| CN | 201356648 | 12/2009 |

(Continued)

OTHER PUBLICATIONS

Allen, E.V., Sympathectomy for essential hypertension, Circulation, 1952, 6:131-140.

(Continued)

*Primary Examiner* — Paula J Stice

(57) ABSTRACT

Catheter apparatuses, systems, and methods for achieving renal neuromodulation by intravascular access are disclosed herein. One aspect of the present application, for example, is directed to apparatuses, systems, and methods that incorporate a catheter treatment device comprising an elongated shaft. The elongated shaft is sized and configured to deliver an energy delivery element to a renal artery via an intravascular path. Thermal or electrical renal neuromodulation may be achieved via direct and/or via indirect application of thermal and/or electrical energy to heat or cool, or otherwise electrically modulate, neural fibers that contribute to renal function, or of vascular structures that feed or perfuse the neural fibers.

22 Claims, 73 Drawing Sheets

Related U.S. Application Data continuation of application No. 14/741,320, filed on Jun. 16, 2015, now Pat. No. 9,636,173, which is a continuation of application No. 13/279,205, filed on Oct. 21, 2011, now Pat. No. 9,084,610.

(60) Provisional application No. 61/405,472, filed on Oct. 21, 2010.

(51) Int. Cl.
    *A61B 18/02*     (2006.01)
    *A61B 17/00*     (2006.01)
    *A61B 18/00*     (2006.01)
    *A61B 18/18*     (2006.01)

(52) U.S. Cl.
    CPC ............ *A61B 2017/00331* (2013.01); *A61B 2018/00047* (2013.01); *A61B 2018/00404* (2013.01); *A61B 2018/00434* (2013.01); *A61B 2018/00511* (2013.01); *A61B 2018/00577* (2013.01); *A61B 2018/1807* (2013.01); *A61N 1/3606* (2013.01); *A61N 1/36057* (2013.01)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 4,998,923 A | 3/1991 | Samson et al. |
| 5,037,391 A | 8/1991 | Hammerslag et al. |
| 5,139,496 A | 8/1992 | Hed |
| 5,158,564 A | 10/1992 | Schnepp-Pesch et al. |
| 5,170,803 A | 12/1992 | Hewson et al. |
| 5,203,772 A | 4/1993 | Hammerslag et al. |
| 5,267,954 A | 12/1993 | Nita |
| 5,300,068 A | 4/1994 | Rosar et al. |
| 5,312,328 A | 5/1994 | Nita et al. |
| 5,322,064 A | 6/1994 | Lundquist |
| 5,330,518 A | 6/1994 | Neilson et al. |
| 5,358,514 A | 10/1994 | Schulman et al. |
| 5,368,557 A | 11/1994 | Nita et al. |
| 5,368,558 A | 11/1994 | Nita |
| 5,368,591 A | 11/1994 | Lennox et al. |
| 5,368,592 A | 11/1994 | Stern et al. |
| 5,382,228 A | 1/1995 | Nita et al. |
| 5,399,164 A | 3/1995 | Snoke et al. |
| 5,405,318 A | 4/1995 | Nita |
| 5,415,633 A | 5/1995 | Lazarus et al. |
| 5,423,744 A | 6/1995 | Gencheff et al. |
| 5,425,364 A | 6/1995 | Imran |
| 5,437,288 A | 8/1995 | Schwartz et al. |
| 5,441,483 A | 8/1995 | Avitall |
| 5,445,148 A | 8/1995 | Jaraczewski et al. |
| 5,454,788 A | 10/1995 | Walker et al. |
| 5,474,530 A | 12/1995 | Passafaro et al. |
| 5,477,856 A | 12/1995 | Lundquist |
| 5,484,400 A | 1/1996 | Edwards et al. |
| 5,487,757 A | 1/1996 | Truckai et al. |
| 5,545,161 A | 8/1996 | Imran |
| 5,545,200 A | 8/1996 | Nguyen et al. |
| 5,554,114 A | 9/1996 | Wallace et al. |
| 5,558,643 A | 9/1996 | Samson et al. |
| 5,571,147 A | 11/1996 | Sluijter et al. |
| 5,582,609 A | 12/1996 | Swanson et al. |
| 5,588,964 A | 12/1996 | Imran et al. |
| 5,599,345 A | 2/1997 | Edwards et al. |
| 5,601,526 A | 2/1997 | Chapelon et al. |
| 5,626,576 A | 5/1997 | Janssen |
| 5,628,775 A | 5/1997 | Jackson et al. |
| 5,630,837 A | 5/1997 | Crowley |
| 5,658,278 A | 8/1997 | Imran et al. |
| 5,667,490 A | 9/1997 | Keith et al. |
| 5,672,174 A | 9/1997 | Gough et al. |
| 5,688,266 A | 11/1997 | Edwards et al. |
| 5,695,506 A | 12/1997 | Pike et al. |
| 5,697,928 A | 12/1997 | Walcott et al. |
| 5,700,282 A | 12/1997 | Zabara |
| 5,707,400 A | 1/1998 | Terry, Jr. et al. |
| 5,709,874 A | 1/1998 | Hanson et al. |
| 5,741,429 A | 4/1998 | Donadio, III et al. |
| 5,743,903 A | 4/1998 | Stern et al. |
| 5,755,753 A | 5/1998 | Knowlton |
| 5,766,167 A | 6/1998 | Eggers et al. |
| 5,772,590 A | 6/1998 | Webster, Jr. |
| 5,800,432 A | 9/1998 | Swanson |
| 5,807,249 A | 9/1998 | Qin et al. |
| 5,823,955 A | 10/1998 | Kuck et al. |
| 5,827,272 A | 10/1998 | Breining et al. |
| 5,843,152 A | 12/1998 | Tu et al. |
| 5,860,974 A | 1/1999 | Abele |
| 5,865,787 A | 2/1999 | Shapland et al. |
| 5,869,127 A | 2/1999 | Zhong |
| 5,871,444 A | 2/1999 | Ouchi |
| 5,871,483 A | 2/1999 | Jackson et al. |
| 5,891,114 A | 4/1999 | Chien et al. |
| 5,893,885 A | 4/1999 | Webster et al. |
| 5,895,378 A | 4/1999 | Berenstein et al. |
| 5,899,898 A | 5/1999 | Arless et al. |
| 5,904,667 A | 5/1999 | Falwell |
| 5,916,192 A | 6/1999 | Nita et al. |
| 5,916,214 A | 6/1999 | Cosio et al. |
| 5,931,830 A | 8/1999 | Jacobsen et al. |
| 5,935,102 A | 8/1999 | Bowden et al. |
| 5,935,124 A | 8/1999 | Klumb et al. |
| 5,944,710 A | 8/1999 | Dev et al. |
| 5,951,539 A | 9/1999 | Nita et al. |
| 5,954,719 A | 9/1999 | Chen et al. |
| 5,957,882 A | 9/1999 | Nita et al. |
| 5,961,511 A | 10/1999 | Mortier et al. |
| 5,967,978 A | 10/1999 | Littmann et al. |
| 5,971,975 A | 10/1999 | Mills et al. |
| 5,980,563 A | 11/1999 | Tu et al. |
| 5,983,141 A | 11/1999 | Sluijter et al. |
| 5,987,344 A | 11/1999 | West |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,048,338 A | 4/2000 | Larson et al. |
| 6,066,134 A | 5/2000 | Eggers et al. |
| 6,066,139 A | 5/2000 | Ryan et al. |
| 6,071,277 A | 6/2000 | Farley et al. |
| 6,079,414 A | 6/2000 | Roth |
| 6,080,171 A | 6/2000 | Keith et al. |
| 6,081,749 A | 6/2000 | Ingle et al. |
| 6,090,104 A | 7/2000 | Webster |
| 6,091,995 A | 7/2000 | Ingle et al. |
| 6,099,524 A | 8/2000 | Lipson et al. |
| 6,102,890 A | 8/2000 | Stivland et al. |
| 6,106,518 A | 8/2000 | Wittenberger et al. |
| 6,110,187 A | 8/2000 | Donlon |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,159,187 A | 12/2000 | Park et al. |
| 6,161,048 A | 12/2000 | Sluijter et al. |
| 6,165,163 A | 12/2000 | Chien et al. |
| 6,179,835 B1 | 1/2001 | Panescu et al. |
| 6,210,362 B1 | 4/2001 | Ponzi |
| 6,210,406 B1 | 4/2001 | Webster |
| 6,216,704 B1 | 4/2001 | Ingle et al. |
| 6,217,576 B1 | 4/2001 | Tu et al. |
| 6,219,577 B1 | 4/2001 | Brown, III et al. |
| 6,224,592 B1 | 5/2001 | Eggers et al. |
| 6,245,020 B1 | 6/2001 | Moore et al. |
| 6,245,045 B1 | 6/2001 | Stratienko |
| 6,246,912 B1 | 6/2001 | Sluijter et al. |
| 6,246,914 B1 | 6/2001 | De La Rama et al. |
| 6,254,588 B1 | 7/2001 | Jones et al. |
| 6,263,224 B1 | 7/2001 | West |

(56) References Cited

U.S. PATENT DOCUMENTS

| | | |
|---|---|---|
| 6,273,876 B1 | 8/2001 | Klima et al. |
| 6,273,886 B1 | 8/2001 | Edwards et al. |
| 6,283,951 B1 | 9/2001 | Flaherty et al. |
| 6,283,960 B1 | 9/2001 | Ashley |
| 6,287,301 B1 | 9/2001 | Thompson et al. |
| 6,292,695 B1 | 9/2001 | Webster, Jr. et al. |
| 6,293,943 B1 | 9/2001 | Panescu et al. |
| 6,298,256 B1 | 10/2001 | Meyer |
| 6,299,623 B1 | 10/2001 | Wulfman |
| 6,314,325 B1 | 11/2001 | Fitz |
| 6,322,558 B1 | 11/2001 | Taylor et al. |
| 6,322,559 B1 | 11/2001 | Daulton et al. |
| 6,346,074 B1 | 2/2002 | Roth |
| 6,350,276 B1 | 2/2002 | Knowlton |
| 6,371,965 B2 | 4/2002 | Gifford, III et al. |
| 6,387,105 B1 | 5/2002 | Gifford, III et al. |
| 6,401,720 B1 | 6/2002 | Stevens et al. |
| 6,405,732 B1 | 6/2002 | Edwards et al. |
| 6,413,255 B1 | 7/2002 | Stern |
| 6,427,089 B1 | 7/2002 | Knowlton |
| 6,428,536 B2 | 8/2002 | Panescu et al. |
| 6,443,965 B1 | 9/2002 | Gifford, III et al. |
| 6,447,505 B2 | 9/2002 | McGovern et al. |
| 6,451,034 B1 | 9/2002 | Gifford, III et al. |
| 6,454,757 B1 | 9/2002 | Nita et al. |
| 6,454,775 B1 | 9/2002 | Demarais et al. |
| 6,470,219 B1 | 10/2002 | Edwards et al. |
| 6,475,215 B1 | 11/2002 | Tanrisever |
| 6,482,202 B1 | 11/2002 | Goble et al. |
| 6,488,679 B1 | 12/2002 | Swanson et al. |
| 6,491,705 B2 | 12/2002 | Gifford, III et al. |
| 6,497,711 B1 | 12/2002 | Plaia et al. |
| 6,500,172 B1 | 12/2002 | Panescu et al. |
| 6,506,189 B1 | 1/2003 | Rittman, III et al. |
| 6,508,804 B2 | 1/2003 | Sarge et al. |
| 6,514,226 B1 | 2/2003 | Levin et al. |
| 6,514,236 B1 | 2/2003 | Stratienko |
| 6,517,572 B2 | 2/2003 | Kugler et al. |
| 6,522,926 B1 | 2/2003 | Kieval et al. |
| 6,527,765 B2 | 3/2003 | Kelman et al. |
| 6,542,781 B1 | 4/2003 | Koblish et al. |
| 6,549,800 B1 | 4/2003 | Atalar et al. |
| 6,558,381 B2 | 5/2003 | Ingle et al. |
| 6,562,034 B2 | 5/2003 | Edwards et al. |
| 6,565,582 B2 | 5/2003 | Gifford, III et al. |
| 6,569,177 B1 | 5/2003 | Dillard et al. |
| 6,585,718 B2 | 7/2003 | Hayzelden et al. |
| 6,589,238 B2 | 7/2003 | Edwards et al. |
| 6,610,046 B1 | 8/2003 | Usami et al. |
| 6,611,720 B2 | 8/2003 | Hata et al. |
| 6,613,046 B1 | 9/2003 | Jenkins et al. |
| 6,616,624 B1 | 9/2003 | Kieval |
| 6,622,731 B2 | 9/2003 | Daniel et al. |
| 6,628,976 B1 | 9/2003 | Fuimaono et al. |
| 6,632,193 B1 | 10/2003 | Davison et al. |
| 6,635,054 B2 | 10/2003 | Fjield et al. |
| 6,640,120 B1 | 10/2003 | Swanson et al. |
| 6,648,854 B1 | 11/2003 | Patterson et al. |
| 6,651,672 B2 | 11/2003 | Roth |
| 6,656,195 B2 | 12/2003 | Peters et al. |
| 6,659,981 B2 | 12/2003 | Stewart et al. |
| 6,669,670 B1 | 12/2003 | Muni et al. |
| 6,669,692 B1 | 12/2003 | Nelson et al. |
| 6,676,678 B2 | 1/2004 | Gifford, III et al. |
| 6,679,268 B2 | 1/2004 | Stevens et al. |
| 6,682,541 B1 | 1/2004 | Gifford, III et al. |
| 6,685,648 B2 | 2/2004 | Flaherty et al. |
| 6,695,857 B2 | 2/2004 | Gifford, III et al. |
| 6,699,257 B2 | 3/2004 | Gifford, III et al. |
| 6,702,811 B2 | 3/2004 | Stewart et al. |
| 6,706,010 B1 | 3/2004 | Miki et al. |
| 6,711,444 B2 | 3/2004 | Koblish |
| 6,716,207 B2 | 4/2004 | Farnholtz |
| 6,723,043 B2 | 4/2004 | Kleeman et al. |
| 6,736,835 B2 | 5/2004 | Pellegrino et al. |
| 6,745,080 B2 | 6/2004 | Koblish |
| 6,746,474 B2 | 6/2004 | Saadat |
| 6,749,560 B1 | 6/2004 | Konstorum et al. |
| 6,752,805 B2 | 6/2004 | Maguire et al. |
| 6,770,070 B1 | 8/2004 | Balbierz |
| 6,790,206 B2 | 9/2004 | Panescu |
| 6,817,999 B2 | 11/2004 | Berube et al. |
| 6,829,497 B2 | 12/2004 | Mogul |
| 6,830,568 B1 | 12/2004 | Kesten et al. |
| 6,845,267 B2 | 1/2005 | Harrison et al. |
| 6,849,075 B2 | 2/2005 | Bertolero et al. |
| 6,850,801 B2 | 2/2005 | Kieval et al. |
| 6,869,431 B2 | 3/2005 | Maguire et al. |
| 6,884,260 B2 | 4/2005 | Kugler et al. |
| 6,885,888 B2 | 4/2005 | Rezai |
| 6,887,235 B2 | 5/2005 | O'Connor et al. |
| 6,889,694 B2 | 5/2005 | Hooven |
| 6,890,329 B2 | 5/2005 | Carroll et al. |
| 6,893,436 B2 | 5/2005 | Woodard et al. |
| 6,909,009 B2 | 6/2005 | Koridze |
| 6,915,806 B2 | 7/2005 | Pacek et al. |
| 6,917,834 B2 | 7/2005 | Koblish et al. |
| 6,923,808 B2 | 8/2005 | Taimisto |
| 6,926,669 B1 | 8/2005 | Stewart et al. |
| 6,926,713 B2 | 8/2005 | Rioux et al. |
| 6,939,346 B2 | 9/2005 | Kannenberg et al. |
| 6,945,956 B2 | 9/2005 | Waldhauser et al. |
| 6,949,097 B2 | 9/2005 | Stewart et al. |
| 6,955,175 B2 | 10/2005 | Stevens et al. |
| 6,966,908 B2 | 11/2005 | Maguire et al. |
| 6,972,015 B2 | 12/2005 | Joye et al. |
| 6,984,238 B2 | 1/2006 | Gifford, III et al. |
| 7,058,456 B2 | 6/2006 | Pierce |
| 7,066,900 B2 | 6/2006 | Botto et al. |
| 7,087,051 B2 | 8/2006 | Bourne et al. |
| 7,100,614 B2 | 9/2006 | Stevens et al. |
| 7,102,151 B2 | 9/2006 | Reinberg et al. |
| 7,110,828 B2 | 9/2006 | Kolberg et al. |
| 7,112,211 B2 | 9/2006 | Gifford, III et al. |
| 7,115,183 B2 | 10/2006 | Larson et al. |
| 7,137,990 B2 | 11/2006 | Hebert et al. |
| 7,149,574 B2 | 12/2006 | Yun et al. |
| 7,153,315 B2 | 12/2006 | Miller |
| 7,162,303 B2 | 1/2007 | Levin et al. |
| 7,172,610 B2 | 2/2007 | Heitzmann et al. |
| 7,184,811 B2 | 2/2007 | Phan et al. |
| 7,192,427 B2 | 3/2007 | Chapelon et al. |
| 7,221,979 B2 | 5/2007 | Zhou et al. |
| 7,232,458 B2 | 6/2007 | Saadat |
| 7,238,184 B2 | 7/2007 | Megerman et al. |
| 7,241,273 B2 | 7/2007 | Maguire et al. |
| 7,276,062 B2 | 10/2007 | McDaniel et al. |
| 7,294,127 B2 | 11/2007 | Leung et al. |
| 7,311,705 B2 | 12/2007 | Sra |
| 7,338,467 B2 | 3/2008 | Lutter |
| 7,367,972 B2 | 5/2008 | Francischelli et al. |
| 7,381,200 B2 | 6/2008 | Katoh et al. |
| 7,390,894 B2 | 6/2008 | Weinshilboum et al. |
| 7,393,338 B2 | 7/2008 | Nita |
| 7,402,151 B2 | 7/2008 | Rosenman et al. |
| 7,407,671 B2 | 8/2008 | McBride et al. |
| 7,486,805 B2 | 2/2009 | Krattiger |
| 7,488,338 B2 | 2/2009 | Eidenschink |
| 7,494,486 B2 | 2/2009 | Mische et al. |
| 7,494,488 B2 | 2/2009 | Weber et al. |
| 7,497,858 B2 | 3/2009 | Chapelon et al. |
| 7,500,985 B2 | 3/2009 | Saadat |
| 7,505,816 B2 | 3/2009 | Schmeling et al. |
| 7,517,349 B2 | 4/2009 | Truckai et al. |
| 7,520,863 B2 | 4/2009 | Grewe et al. |
| 7,540,865 B2 | 6/2009 | Griffin et al. |
| 7,563,247 B2 | 7/2009 | Maguire et al. |
| 7,598,228 B2 | 10/2009 | Hattori et al. |
| 7,617,005 B2 | 11/2009 | Demarais et al. |
| 7,620,451 B2 | 11/2009 | Demarais et al. |
| 7,637,903 B2 | 12/2009 | Lentz et al. |
| 7,647,115 B2 | 1/2010 | Levin et al. |
| 7,653,438 B2 | 1/2010 | Deem et al. |
| 7,682,319 B2 | 3/2010 | Martin et al. |

(56) References Cited

U.S. PATENT DOCUMENTS

| | | |
|---|---|---|
| 7,699,809 B2 | 4/2010 | Urmey |
| 7,706,894 B2 | 4/2010 | Stewart et al. |
| 7,708,704 B2 | 5/2010 | Mitelberg et al. |
| 7,717,853 B2 | 5/2010 | Nita |
| 7,717,948 B2 | 5/2010 | Demarais et al. |
| 7,727,187 B2 | 6/2010 | Lentz |
| 7,758,520 B2 | 7/2010 | Griffin et al. |
| 7,763,012 B2 | 7/2010 | Petrick et al. |
| 7,771,410 B2 | 8/2010 | Venturelli |
| 7,771,421 B2 | 8/2010 | Stewart et al. |
| 7,778,703 B2 | 8/2010 | Gross et al. |
| 7,780,660 B2 | 8/2010 | Bourne et al. |
| 7,785,289 B2 | 8/2010 | Rios et al. |
| 7,799,021 B2 | 9/2010 | Leung et al. |
| 7,806,871 B2 | 10/2010 | Li et al. |
| 7,811,265 B2 | 10/2010 | Hering et al. |
| 7,811,281 B1 | 10/2010 | Rentrop |
| 7,815,637 B2 | 10/2010 | Ormsby et al. |
| 7,816,511 B2 | 10/2010 | Kawashima et al. |
| 7,819,866 B2 | 10/2010 | Bednarek |
| 7,846,157 B2 | 12/2010 | Kozel |
| 7,850,685 B2 | 12/2010 | Kunis et al. |
| 7,862,565 B2 | 1/2011 | Eder et al. |
| 7,863,897 B2 | 1/2011 | Slocum, Jr. et al. |
| 7,896,873 B2 | 3/2011 | Hiller et al. |
| 7,905,862 B2 | 3/2011 | Sampson |
| 7,938,830 B2 | 5/2011 | Saadat et al. |
| 7,967,816 B2 | 6/2011 | Ocel et al. |
| 7,989,042 B2 | 8/2011 | Obara et al. |
| 8,007,440 B2 | 8/2011 | Magnin et al. |
| 8,007,462 B2 | 8/2011 | Gibson et al. |
| 8,027,718 B2 | 9/2011 | Spinner et al. |
| 8,043,288 B2 | 10/2011 | Dando et al. |
| 8,075,580 B2 | 12/2011 | Makower |
| 8,088,127 B2 | 1/2012 | Mayse et al. |
| 8,092,444 B2 | 1/2012 | Lentz et al. |
| 8,124,876 B2 | 2/2012 | Dayton et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,172,829 B2 | 5/2012 | Farnholtz |
| 8,175,711 B2 | 5/2012 | Demarais et al. |
| 8,190,238 B2 | 5/2012 | Moll et al. |
| 8,241,217 B2 | 8/2012 | Chiang et al. |
| 8,251,977 B2 | 8/2012 | Partlett |
| 8,292,881 B2 | 10/2012 | Brannan et al. |
| 8,343,145 B2 | 1/2013 | Brannan |
| 8,364,237 B2 | 1/2013 | Stone et al. |
| 8,376,865 B2 | 2/2013 | Forster et al. |
| 8,388,680 B2 | 3/2013 | Starksen et al. |
| 8,398,629 B2 | 3/2013 | Thistle |
| 8,401,650 B2 | 3/2013 | Simon et al. |
| 8,409,193 B2 | 4/2013 | Young et al. |
| 8,409,195 B2 | 4/2013 | Young |
| 8,418,362 B2 | 4/2013 | Zerfas et al. |
| 8,473,023 B2 | 6/2013 | Worley et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,728,075 B2 | 5/2014 | Wu et al. |
| 8,740,849 B1 | 6/2014 | Fischell et al. |
| 8,740,895 B2 | 6/2014 | Mayse et al. |
| 8,974,451 B2 | 3/2015 | Smith |
| 8,986,300 B2 | 3/2015 | Govari et al. |
| 9,162,046 B2 | 10/2015 | Hill et al. |
| 9,192,435 B2 | 11/2015 | Jenson |
| 2001/0007071 A1* | 7/2001 | Koblish .......... A61B 18/1492 606/41 |
| 2002/0022864 A1 | 2/2002 | Mahvi et al. |
| 2002/0062123 A1 | 5/2002 | McClurken et al. |
| 2002/0065515 A1 | 5/2002 | Falwell et al. |
| 2002/0065542 A1 | 5/2002 | Lax et al. |
| 2002/0107511 A1 | 8/2002 | Collins et al. |
| 2002/0128662 A1 | 9/2002 | Brock et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2002/0198520 A1 | 12/2002 | Coen et al. |
| 2003/0004510 A1 | 1/2003 | Wham et al. |
| 2003/0050635 A1 | 3/2003 | Truckai et al. |
| 2003/0050681 A1 | 3/2003 | Pianca et al. |
| 2003/0055422 A1 | 3/2003 | Lesh |
| 2003/0060858 A1 | 3/2003 | Kieval et al. |
| 2003/0065317 A1 | 4/2003 | Rudie et al. |
| 2003/0074039 A1 | 4/2003 | Puskas |
| 2003/0078644 A1 | 4/2003 | Phan |
| 2003/0092995 A1 | 5/2003 | Thompson |
| 2003/0109778 A1 | 6/2003 | Rashidi |
| 2003/0125720 A1 | 7/2003 | Woodward et al. |
| 2003/0125790 A1 | 7/2003 | Fastovsky et al. |
| 2003/0139689 A1 | 7/2003 | Shturman et al. |
| 2003/0181897 A1 | 9/2003 | Thomas et al. |
| 2003/0199863 A1 | 10/2003 | Swanson et al. |
| 2003/0212394 A1 | 11/2003 | Pearson et al. |
| 2003/0216792 A1 | 11/2003 | Levin et al. |
| 2003/0220639 A1 | 11/2003 | Chapelon et al. |
| 2003/0229340 A1 | 12/2003 | Sherry et al. |
| 2003/0233099 A1 | 12/2003 | Danaek et al. |
| 2004/0006359 A1 | 1/2004 | Laguna |
| 2004/0010289 A1 | 1/2004 | Biggs et al. |
| 2004/0073141 A1 | 4/2004 | Hartley et al. |
| 2004/0073206 A1 | 4/2004 | Foley et al. |
| 2004/0088002 A1 | 5/2004 | Boyle et al. |
| 2004/0187875 A1 | 9/2004 | He et al. |
| 2004/0215186 A1 | 10/2004 | Cornelius et al. |
| 2005/0004515 A1 | 1/2005 | Hart et al. |
| 2005/0004644 A1 | 1/2005 | Kelsch et al. |
| 2005/0010095 A1 | 1/2005 | Stewart et al. |
| 2005/0080374 A1 | 4/2005 | Esch et al. |
| 2005/0080409 A1 | 4/2005 | Young et al. |
| 2005/0096647 A1 | 5/2005 | Steinke et al. |
| 2005/0187455 A1 | 8/2005 | Rashidi |
| 2005/0187579 A1 | 8/2005 | Danek et al. |
| 2005/0228286 A1 | 10/2005 | Messerly et al. |
| 2005/0228460 A1 | 10/2005 | Levin et al. |
| 2005/0240229 A1 | 10/2005 | Whitehurst et al. |
| 2005/0267010 A1* | 12/2005 | Goodson .......... A61K 38/2242 514/12.4 |
| 2005/0273006 A1 | 12/2005 | Stewart et al. |
| 2005/0288730 A1 | 12/2005 | Deem et al. |
| 2006/0004323 A1 | 1/2006 | Chang et al. |
| 2006/0004346 A1 | 1/2006 | Begg |
| 2006/0025765 A1 | 2/2006 | Landman et al. |
| 2006/0074403 A1 | 4/2006 | Rafiee |
| 2006/0085054 A1 | 4/2006 | Zikorus et al. |
| 2006/0089637 A1 | 4/2006 | Werneth et al. |
| 2006/0095029 A1 | 5/2006 | Young et al. |
| 2006/0100618 A1 | 5/2006 | Chan et al. |
| 2006/0122587 A1 | 6/2006 | Sharareh |
| 2006/0142753 A1 | 6/2006 | Francischelli et al. |
| 2006/0167498 A1 | 7/2006 | DiLorenzo |
| 2006/0184221 A1 | 8/2006 | Stewart et al. |
| 2006/0206150 A1 | 9/2006 | Demarais et al. |
| 2006/0224153 A1 | 10/2006 | Fischell et al. |
| 2006/0247266 A1 | 11/2006 | Yamada et al. |
| 2006/0263393 A1 | 11/2006 | Demopulos et al. |
| 2006/0271111 A1 | 11/2006 | Demarais et al. |
| 2006/0276846 A1 | 12/2006 | Malecki et al. |
| 2006/0287644 A1 | 12/2006 | Inganas et al. |
| 2007/0027390 A1 | 2/2007 | Maschke et al. |
| 2007/0049924 A1 | 3/2007 | Rahn |
| 2007/0066878 A1 | 3/2007 | Worley et al. |
| 2007/0067008 A1 | 3/2007 | Scheiner et al. |
| 2007/0073151 A1 | 3/2007 | Lee |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0129720 A1* | 6/2007 | Demarais .......... A61N 1/0551 606/41 |
| 2007/0135875 A1 | 6/2007 | Demarais et al. |

(56) References Cited

U.S. PATENT DOCUMENTS

| | | |
|---|---|---|
| 2007/0149963 A1 | 6/2007 | Matsukuma et al. |
| 2007/0156114 A1 | 7/2007 | Worley et al. |
| 2007/0156131 A1 | 7/2007 | Datta |
| 2007/0179496 A1 | 8/2007 | Swoyer et al. |
| 2007/0197891 A1 | 8/2007 | Shachar et al. |
| 2007/0225781 A1 | 9/2007 | Saadat et al. |
| 2007/0265687 A1 | 11/2007 | Deem et al. |
| 2007/0270779 A1 | 11/2007 | Jacobs et al. |
| 2007/0270791 A1 | 11/2007 | Wang et al. |
| 2008/0004658 A1 | 1/2008 | Malecki et al. |
| 2008/0015562 A1 | 1/2008 | Hong et al. |
| 2008/0071269 A1 | 3/2008 | Hilario et al. |
| 2008/0077119 A1 | 3/2008 | Snyder et al. |
| 2008/0086047 A1 | 4/2008 | McDaniel et al. |
| 2008/0091193 A1 | 4/2008 | Kauphusman et al. |
| 2008/0108867 A1 | 5/2008 | Zhou |
| 2008/0140072 A1 | 6/2008 | Stangenes et al. |
| 2008/0177205 A1 | 7/2008 | De La Rama et al. |
| 2008/0188928 A1* | 8/2008 | Salahieh ............ A61M 25/0054 623/2.11 |
| 2008/0255642 A1 | 10/2008 | Zarins et al. |
| 2008/0287918 A1 | 11/2008 | Rosenman et al. |
| 2008/0319513 A1 | 12/2008 | Pu et al. |
| 2009/0012465 A1 | 1/2009 | Latini |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0118620 A1 | 5/2009 | Tgavalekos et al. |
| 2009/0149848 A1 | 6/2009 | Werneth et al. |
| 2009/0157048 A1 | 6/2009 | Sutermeister et al. |
| 2009/0163850 A1 | 6/2009 | Betts et al. |
| 2009/0171333 A1 | 7/2009 | Hon |
| 2009/0221955 A1 | 9/2009 | Babaev |
| 2009/0306650 A1 | 12/2009 | Govari et al. |
| 2009/0312606 A1 | 12/2009 | Dayton et al. |
| 2010/0030061 A1 | 2/2010 | Canfield et al. |
| 2010/0049186 A1 | 2/2010 | Ingle et al. |
| 2010/0069882 A1 | 3/2010 | Jennings et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0168740 A1 | 7/2010 | Stewart et al. |
| 2010/0179512 A1 | 7/2010 | Chong et al. |
| 2010/0191112 A1 | 7/2010 | Demarais et al. |
| 2010/0217184 A1 | 8/2010 | Koblish et al. |
| 2010/0222851 A1 | 9/2010 | Deem et al. |
| 2010/0222854 A1 | 9/2010 | Demarais et al. |
| 2010/0249604 A1 | 9/2010 | Hastings et al. |
| 2010/0286684 A1* | 11/2010 | Hata ................ A61B 18/1492 606/33 |
| 2010/0312141 A1 | 12/2010 | Keast et al. |
| 2010/0324482 A1 | 12/2010 | Farnholtz |
| 2011/0021976 A1 | 1/2011 | Li et al. |
| 2011/0028962 A1 | 2/2011 | Werneth et al. |
| 2011/0034989 A1 | 2/2011 | Al-Marashi et al. |
| 2011/0054464 A1 | 3/2011 | Werneth et al. |
| 2011/0054465 A1 | 3/2011 | Werneth et al. |
| 2011/0071400 A1 | 3/2011 | Hastings et al. |
| 2011/0071401 A1 | 3/2011 | Hastings et al. |
| 2011/0112476 A1 | 5/2011 | Kauphusman et al. |
| 2011/0264011 A1 | 10/2011 | Wu et al. |
| 2011/0264075 A1 | 10/2011 | Leung et al. |
| 2011/0270173 A1 | 11/2011 | Gibson et al. |
| 2011/0319809 A1 | 12/2011 | Smith |
| 2012/0029512 A1 | 2/2012 | Willard et al. |
| 2012/0059241 A1 | 3/2012 | Hastings et al. |
| 2012/0130289 A1 | 5/2012 | Demarais et al. |
| 2012/0130345 A1 | 5/2012 | Levin et al. |
| 2012/0136350 A1 | 5/2012 | Goshgarian et al. |
| 2012/0172837 A1 | 7/2012 | Demarais et al. |
| 2012/0245577 A1 | 9/2012 | Mihalik et al. |
| 2012/0265066 A1 | 10/2012 | Crow et al. |
| 2013/0035681 A1 | 2/2013 | Subramaniam et al. |
| 2013/0066316 A1 | 3/2013 | Steinke et al. |
| 2013/0090647 A1 | 4/2013 | Smith |
| 2013/0090649 A1 | 4/2013 | Smith et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0123770 A1 | 5/2013 | Smith |
| 2013/0131667 A1 | 5/2013 | Jenson et al. |
| 2013/0172879 A1 | 7/2013 | Sutermeister et al. |
| 2013/0172881 A1 | 7/2013 | Hill et al. |
| 2013/0184642 A1 | 7/2013 | O'Donnell et al. |
| 2013/0184703 A1 | 7/2013 | Shireman et al. |
| 2013/0274730 A1 | 10/2013 | Anderson et al. |
| 2013/0274731 A1 | 10/2013 | Anderson et al. |
| 2013/0274737 A1 | 10/2013 | Wang et al. |
| 2013/0304047 A1 | 11/2013 | Grunewald et al. |
| 2014/0046229 A1 | 2/2014 | Hawkins et al. |
| 2014/0046313 A1 | 2/2014 | Pederson et al. |
| 2014/0058376 A1 | 2/2014 | Horn et al. |
| 2014/0094787 A1 | 4/2014 | Reynolds |
| 2014/0121641 A1 | 5/2014 | Fischell et al. |
| 2014/0121644 A1 | 5/2014 | Fischell et al. |
| 2014/0135715 A1 | 5/2014 | Lambert et al. |
| 2014/0135755 A1 | 5/2014 | Sutermeister et al. |
| 2014/0163360 A1 | 6/2014 | Stevens-Wright et al. |
| 2014/0214026 A1 | 7/2014 | Degen |
| 2014/0249524 A1 | 9/2014 | Kocur |
| 2014/0276613 A1 | 9/2014 | Goodman et al. |
| 2014/0276752 A1 | 9/2014 | Wang et al. |
| 2014/0276787 A1 | 9/2014 | Wang et al. |
| 2014/0358079 A1 | 12/2014 | Fischell et al. |
| 2014/0378967 A1 | 12/2014 | Willard et al. |
| 2015/0066013 A1 | 3/2015 | Salahieh et al. |
| 2015/0265339 A1 | 9/2015 | Lindquist et al. |
| 2016/0128765 A1 | 5/2016 | Schultz et al. |
| 2016/0143690 A1 | 5/2016 | Schultz et al. |

FOREIGN PATENT DOCUMENTS

| | | |
|---|---|---|
| CN | 102125460 | 7/2011 |
| CN | 102125725 | 7/2011 |
| CN | 2266245 | 12/2011 |
| CN | 102631240 | 8/2012 |
| CN | 102688093 | 9/2012 |
| CN | 102743225 | 10/2012 |
| CN | 102885648 | 1/2013 |
| CN | 102885649 | 1/2013 |
| CN | 102908188 | 2/2013 |
| CN | 102908189 | 2/2013 |
| CN | 103096826 | 5/2013 |
| DE | 102005041601 | 4/2007 |
| DE | 102012104705 | 12/2013 |
| EP | 348136 | 12/1989 |
| EP | 352955 | 1/1990 |
| EP | 647435 | 4/1995 |
| EP | 652026 | 5/1995 |
| EP | 664990 | 8/1995 |
| EP | 680351 | 11/1995 |
| EP | 0737487 | 10/1996 |
| EP | 512359 | 12/1996 |
| EP | 787019 | 8/1997 |
| EP | 542246 | 9/1997 |
| EP | 834289 | 4/1998 |
| EP | 862478 | 9/1998 |
| EP | 937481 | 8/1999 |
| EP | 944353 | 9/1999 |
| EP | 951244 | 10/1999 |
| EP | 984806 | 3/2000 |
| EP | 1005838 | 6/2000 |
| EP | 626818 | 5/2002 |
| EP | 727184 | 12/2002 |
| EP | 1286625 | 3/2003 |
| EP | 1374943 | 1/2004 |
| EP | 1634542 | 3/2006 |

(56) References Cited

FOREIGN PATENT DOCUMENTS

| | | |
|---|---|---|
| EP | 1656963 | 5/2006 |
| EP | 1709922 | 10/2006 |
| EP | 1768732 | 4/2007 |
| EP | 1787674 | 5/2007 |
| EP | 1824548 | 8/2007 |
| EP | 1827558 | 9/2007 |
| EP | 1857134 | 11/2007 |
| EP | 1906853 | 4/2008 |
| EP | 1968679 | 9/2008 |
| EP | 2027882 | 2/2009 |
| EP | 1326550 | 9/2009 |
| EP | 2239859 | 10/2010 |
| EP | 2320821 | 5/2011 |
| EP | 2340765 | 7/2011 |
| EP | 2389974 | 11/2011 |
| EP | 2398540 | 12/2011 |
| EP | 2445568 | 5/2012 |
| EP | 2563255 | 3/2013 |
| EP | 2747688 | 7/2014 |
| EP | 2759275 | 7/2014 |
| EP | 2759314 | 7/2014 |
| EP | 2760532 | 8/2014 |
| EP | 2804554 | 11/2014 |
| EP | 2900160 | 8/2015 |
| EP | 2900161 | 8/2015 |
| EP | 2928401 | 10/2015 |
| EP | 2990070 | 3/2016 |
| EP | 3010436 | 4/2016 |
| EP | 3020355 | 5/2016 |
| EP | 3023070 | 5/2016 |
| EP | 2429436 | 11/2016 |
| EP | 2768563 | 11/2016 |
| EP | 2598070 | 12/2016 |
| GB | 2313062 | 11/1997 |
| WO | 1991001772 | 2/1991 |
| WO | 1992015356 | 9/1992 |
| WO | WO-1994007446 A1 | 4/1994 |
| WO | 1994018896 | 9/1994 |
| WO | 1994019039 | 9/1994 |
| WO | 1994028809 | 12/1994 |
| WO | WO-1995025472 A1 | 9/1995 |
| WO | WO-1995031142 A1 | 11/1995 |
| WO | 1997029800 | 8/1997 |
| WO | WO-1997036548 A1 | 10/1997 |
| WO | 1997048435 | 12/1997 |
| WO | 1998043530 | 10/1998 |
| WO | WO-1998042403 A1 | 10/1998 |
| WO | 1998048885 | 11/1998 |
| WO | 1998050098 | 11/1998 |
| WO | 1998052637 | 11/1998 |
| WO | 1999000060 | 1/1999 |
| WO | WO-1999000060 A1 | 1/1999 |
| WO | 1999011313 | 3/1999 |
| WO | WO-2001022897 A1 | 4/2001 |
| WO | 2001037723 | 5/2001 |
| WO | 2001037746 | 5/2001 |
| WO | WO-2001070114 A1 | 9/2001 |
| WO | 2002028475 | 4/2002 |
| WO | 2002030310 | 4/2002 |
| WO | 2002080766 | 10/2002 |
| WO | 2002089908 | 11/2002 |
| WO | WO-2003022167 | 3/2003 |
| WO | WO-2003/082080 | 10/2003 |
| WO | WO-2005030072 A1 | 4/2005 |
| WO | WO--2005041748 A2 | 5/2005 |
| WO | WO-2005/110528 A1 | 11/2005 |
| WO | 2006009588 | 1/2006 |
| WO | 2006041881 | 4/2006 |
| WO | WO-2006041881 A2 | 4/2006 |
| WO | 2006065949 | 6/2006 |
| WO | 2006086152 | 8/2006 |
| WO | WO-2006105121 A2 | 10/2006 |
| WO | 2007001981 | 1/2007 |
| WO | WO-2007008954 A2 | 1/2007 |
| WO | 2007059277 | 5/2007 |
| WO | WO-2007078997 A2 | 7/2007 |
| WO | 2007117359 | 10/2007 |
| WO | 2007136979 | 11/2007 |
| WO | 2008010150 | 1/2008 |
| WO | 2008036281 | 3/2008 |
| WO | WO-2008049084 A2 | 4/2008 |
| WO | 2008064399 | 6/2008 |
| WO | 2008101244 | 8/2008 |
| WO | 2008139347 | 11/2008 |
| WO | 2009082635 | 7/2009 |
| WO | 2009086007 | 7/2009 |
| WO | 2009088678 | 7/2009 |
| WO | 2009137819 | 11/2009 |
| WO | 2010091701 | 8/2010 |
| WO | 2010134503 | 11/2010 |
| WO | 2011056311 | 5/2011 |
| WO | 2011139589 | 11/2011 |
| WO | 2012054906 | 4/2012 |
| WO | 2012100095 | 7/2012 |
| WO | 2013016203 | 1/2013 |
| WO | 2013055537 | 4/2013 |
| WO | 2013055685 | 4/2013 |
| WO | 2013055815 | 4/2013 |
| WO | 2013055826 | 4/2013 |
| WO | 2013056672 | 4/2013 |
| WO | 2013058962 | 4/2013 |
| WO | 2013106054 | 7/2013 |
| WO | 2013109318 | 7/2013 |
| WO | 2013158676 | 10/2013 |
| WO | 2013158678 | 10/2013 |
| WO | 2014012282 | 1/2014 |
| WO | 2014036163 | 3/2014 |
| WO | 2014089380 | 6/2014 |
| WO | 2014174662 | 10/2014 |
| WO | 2016090175 | 6/2016 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in

(56) References Cited

OTHER PUBLICATIONS

Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.

(56) References Cited

OTHER PUBLICATIONS

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S. J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D. L., et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.

(56) References Cited

OTHER PUBLICATIONS

Messerli, Franz H. et al. "Renal Denervation for Resistant Hypertension: Dead or Alive?" Healio: Cardiology today's Intervention, May/Jun. 2014, 2 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. 2465470, Granted Oct. 28, 2015, Date of Opposition Jul. 27, 2016, 34 pp.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper, et al., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 : 484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Search Report and Written Opinion dated Apr. 23, 2012 for PCT Application No. PCT/US2011/057402.
Search Report and Written Opinion dated Nov. 22, 2011 for PCT Application No. PCT/US2011/033491.
Search Report dated Oct. 17, 2013 for European Application No. 13159256.

* cited by examiner

*Arterial Vasculature*

*Venous Vasculature*

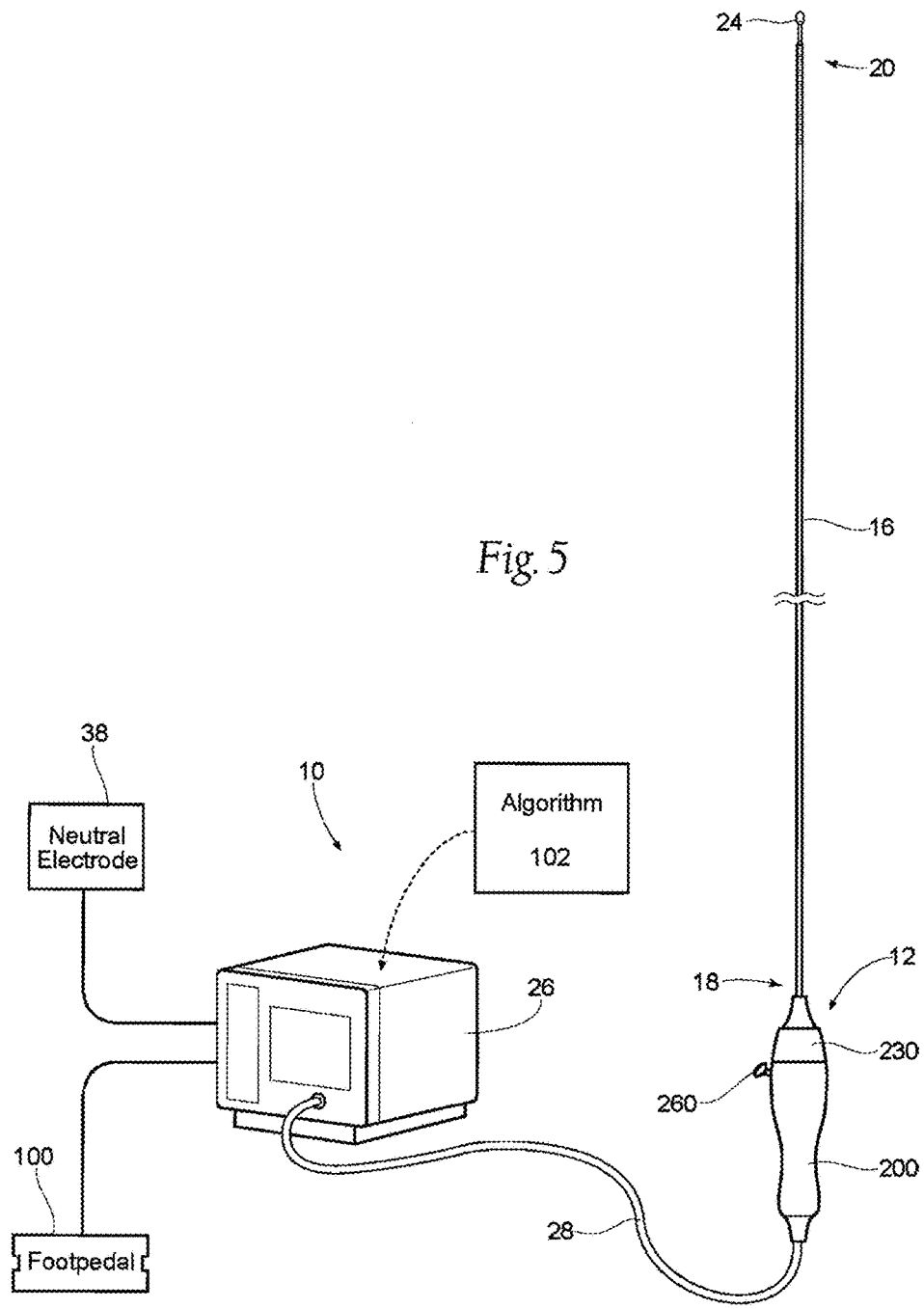

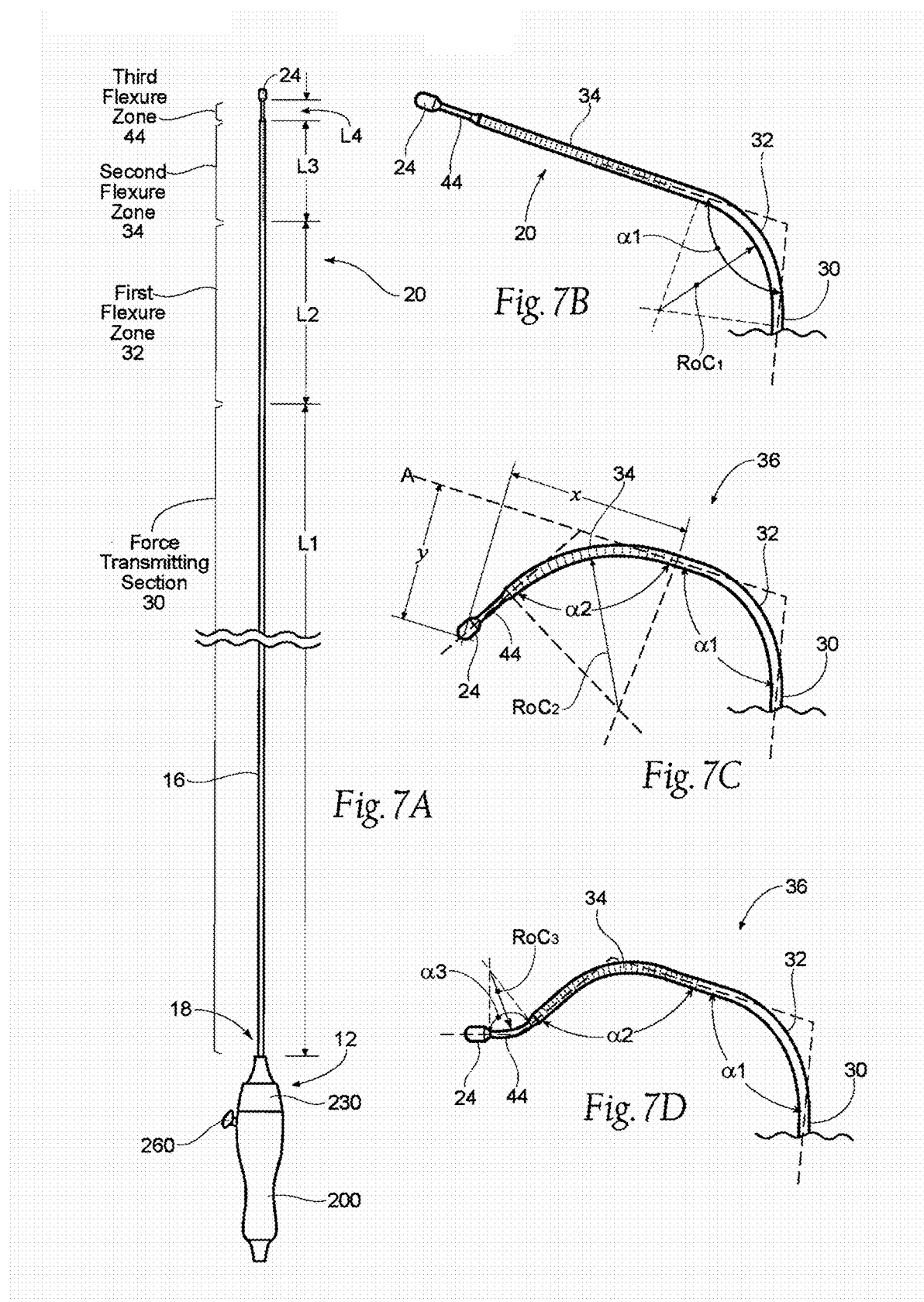

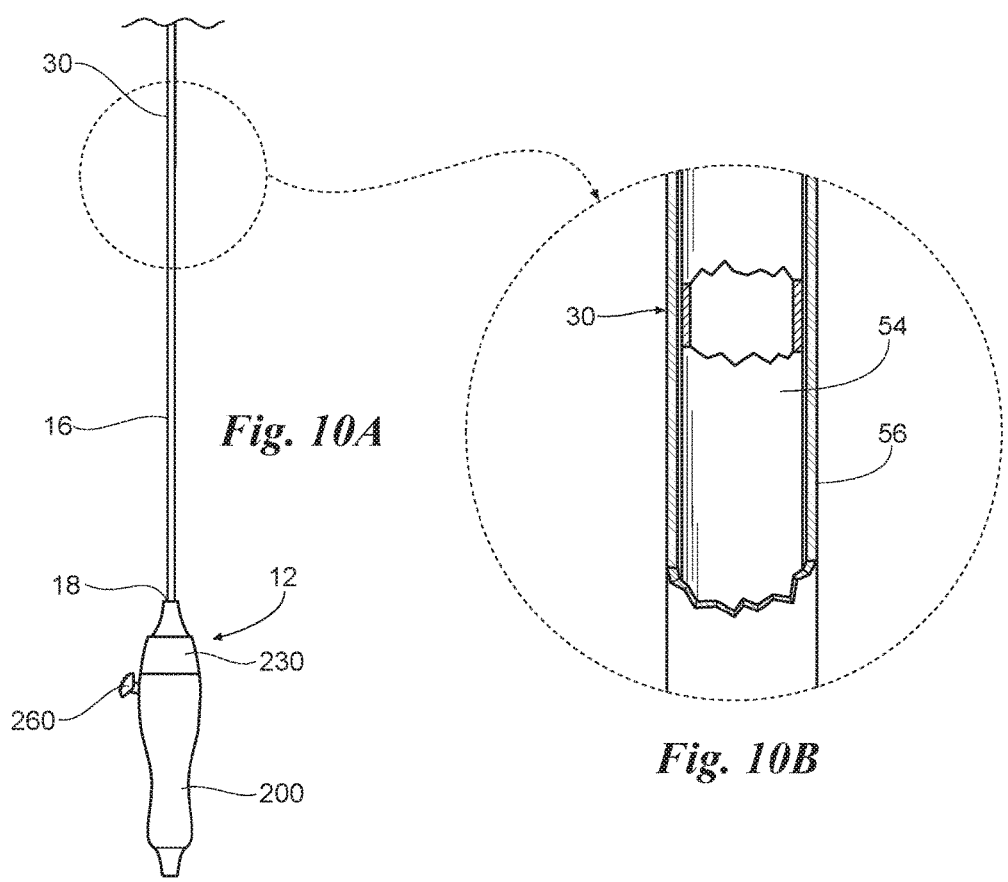

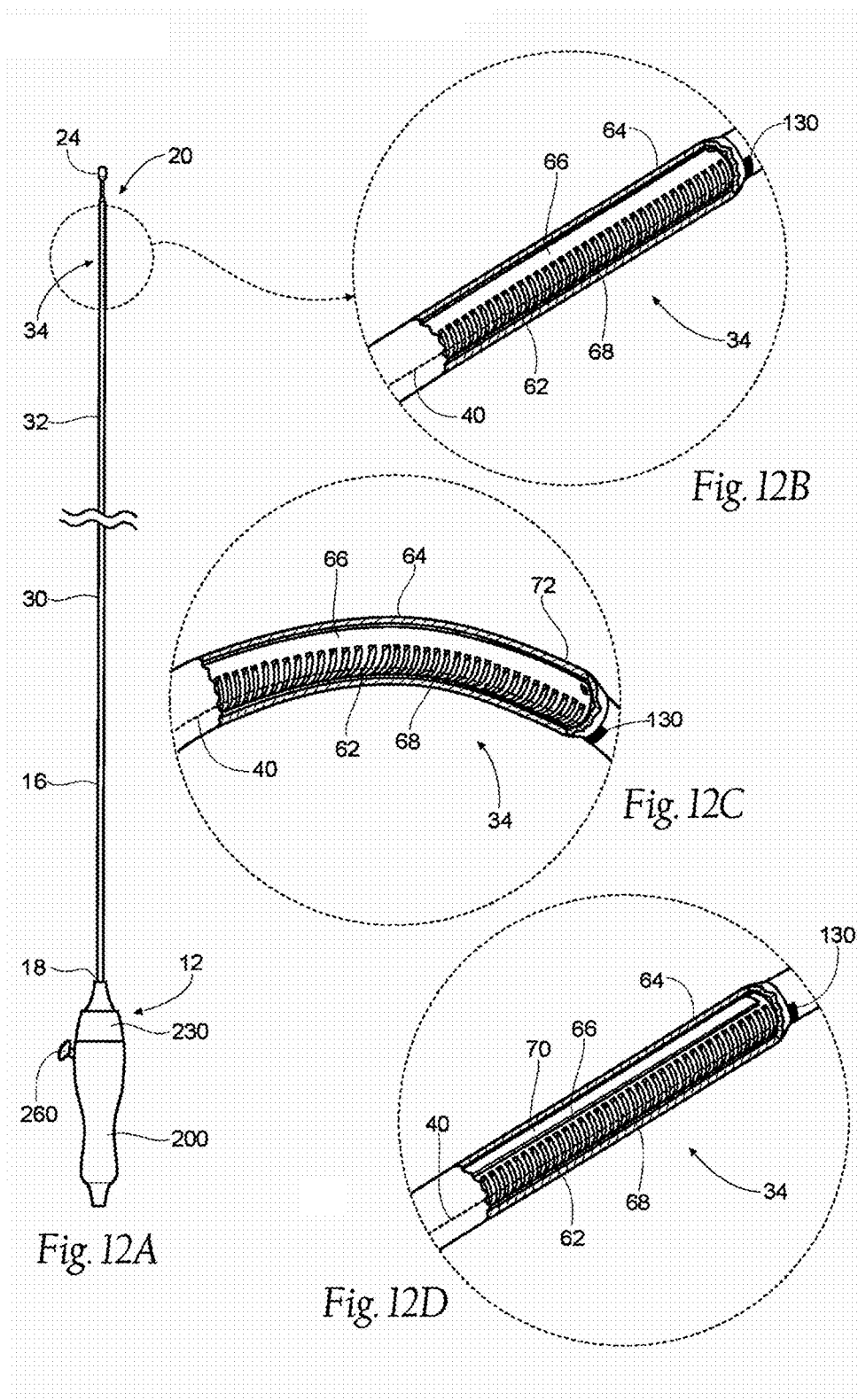

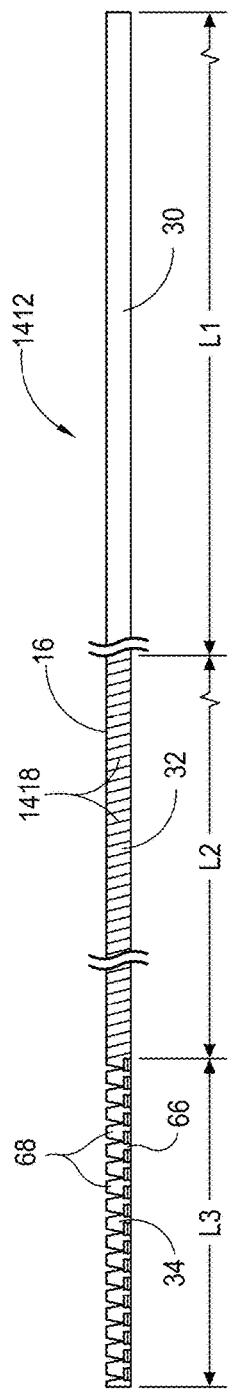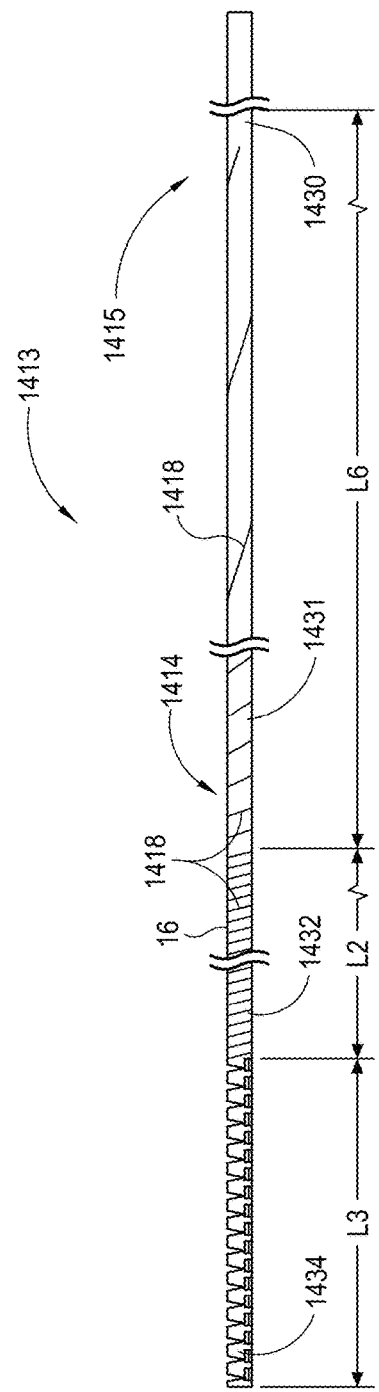
Fig. 14A
Fig. 14B

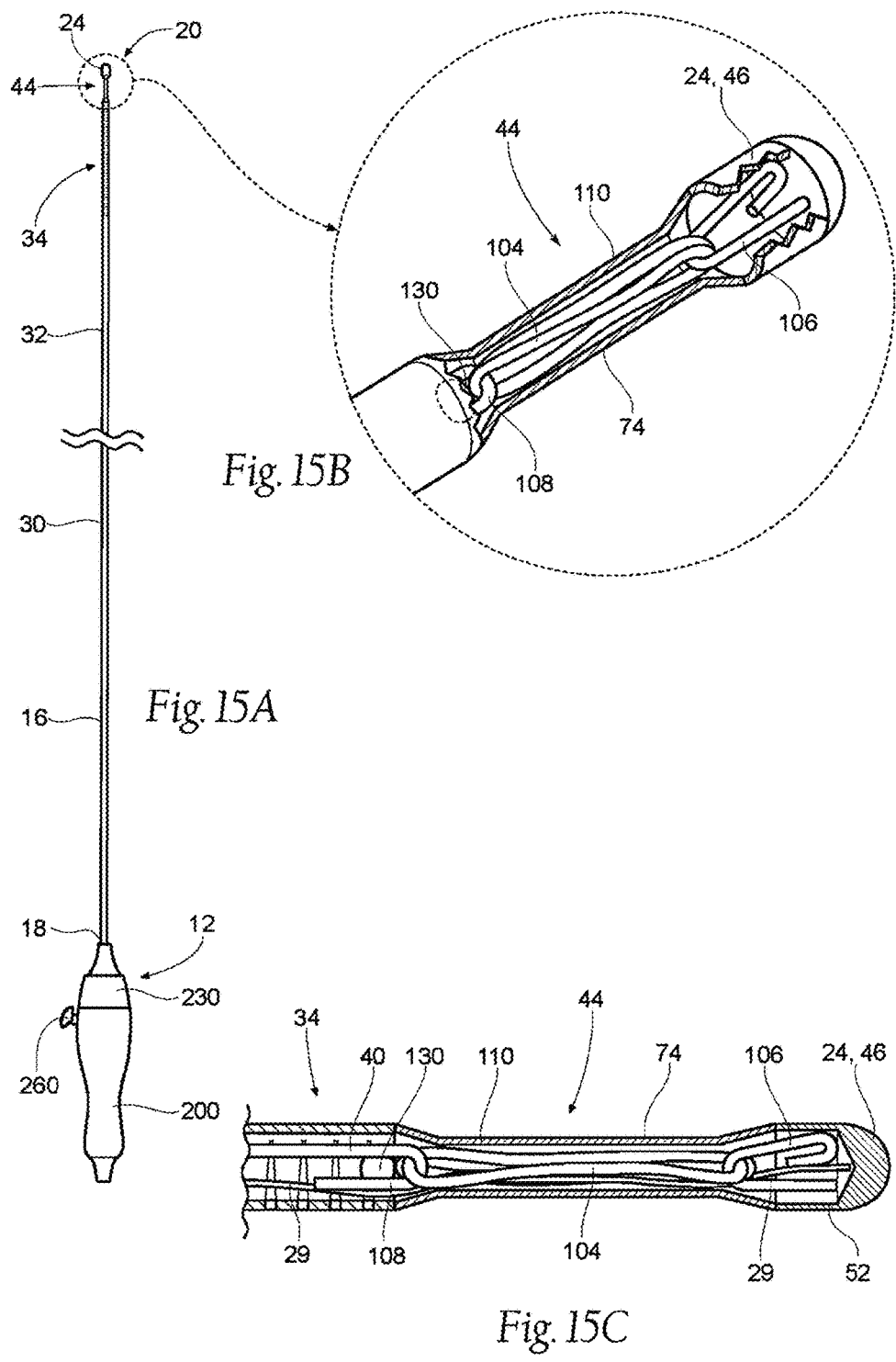

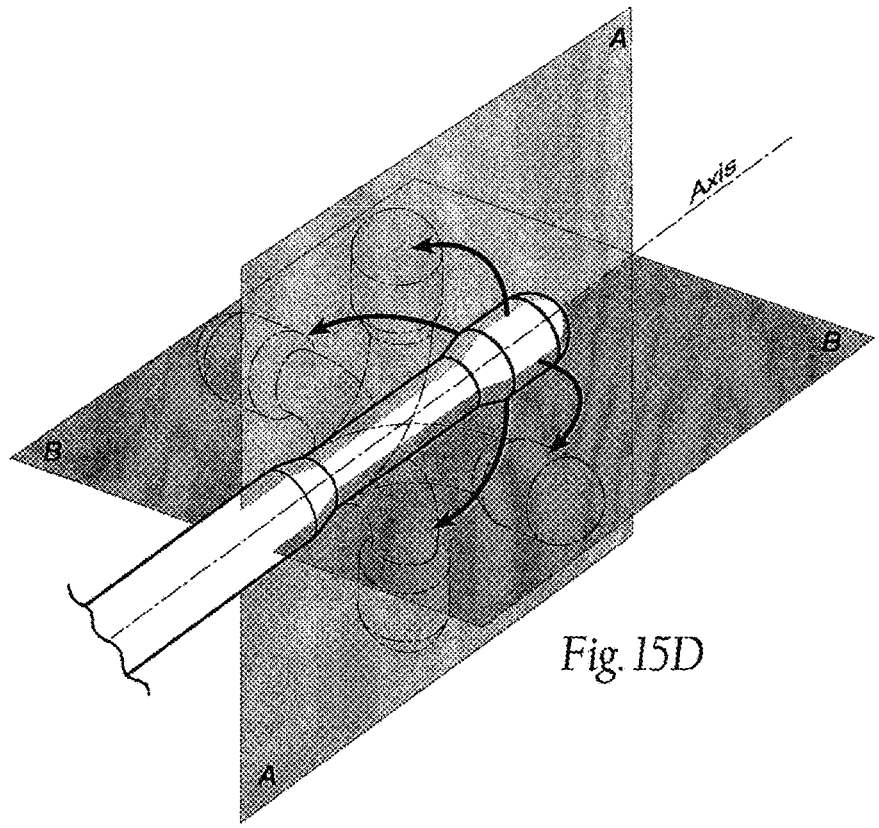
Fig. 15D
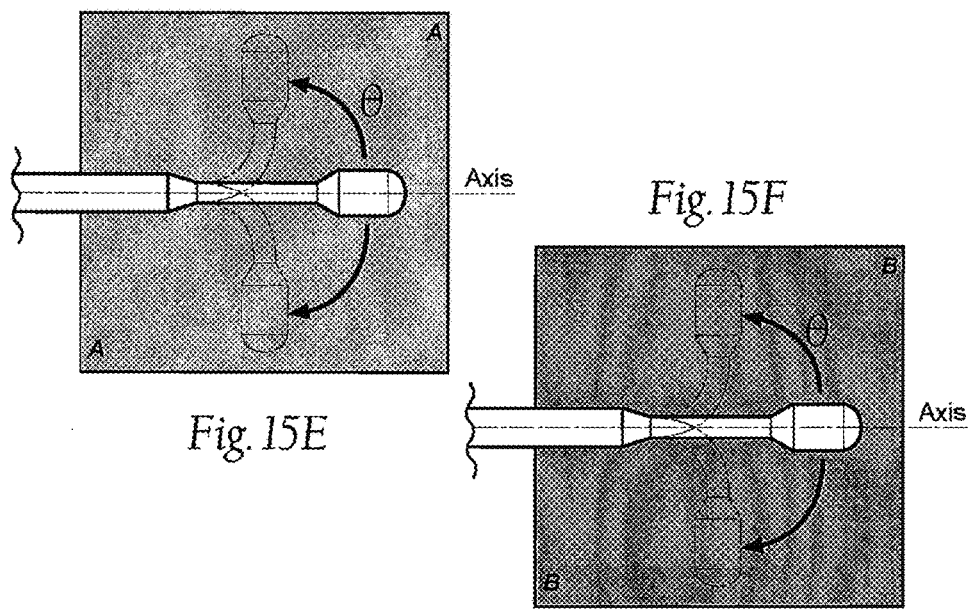
Fig. 15E
Fig. 15F

Renal Artery

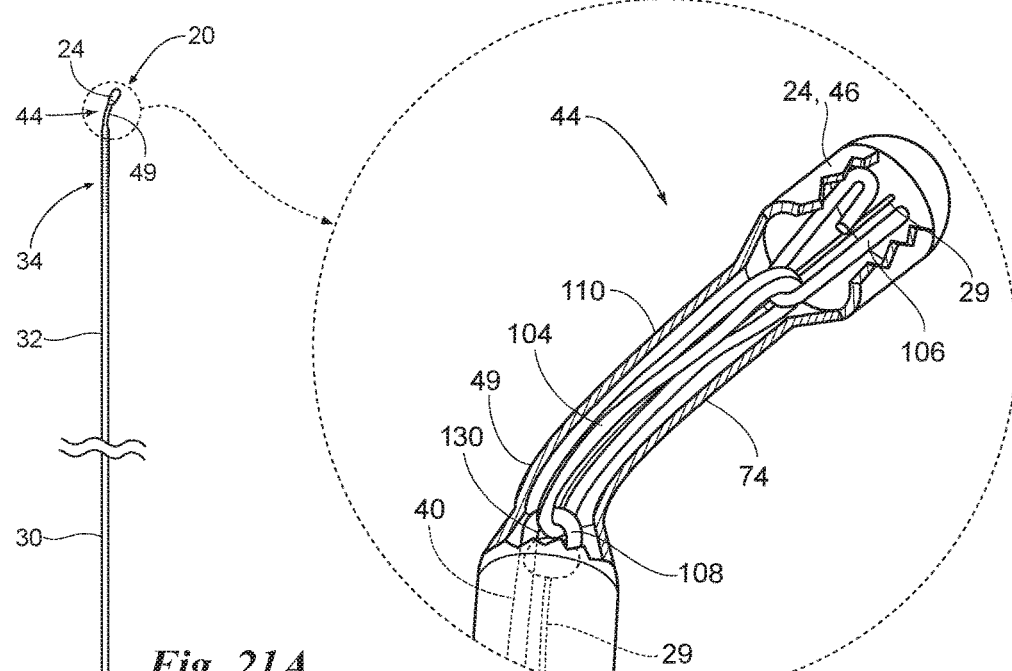
*Fig. 21A*
*Fig. 21B*
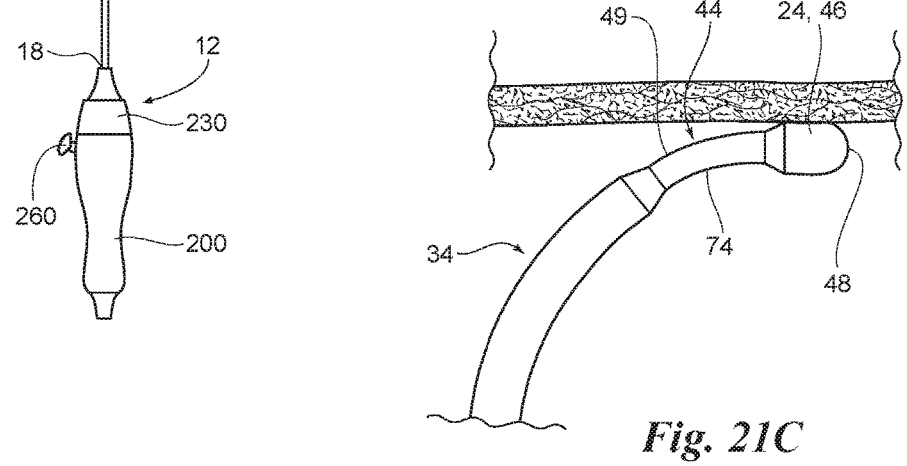
*Fig. 21C*

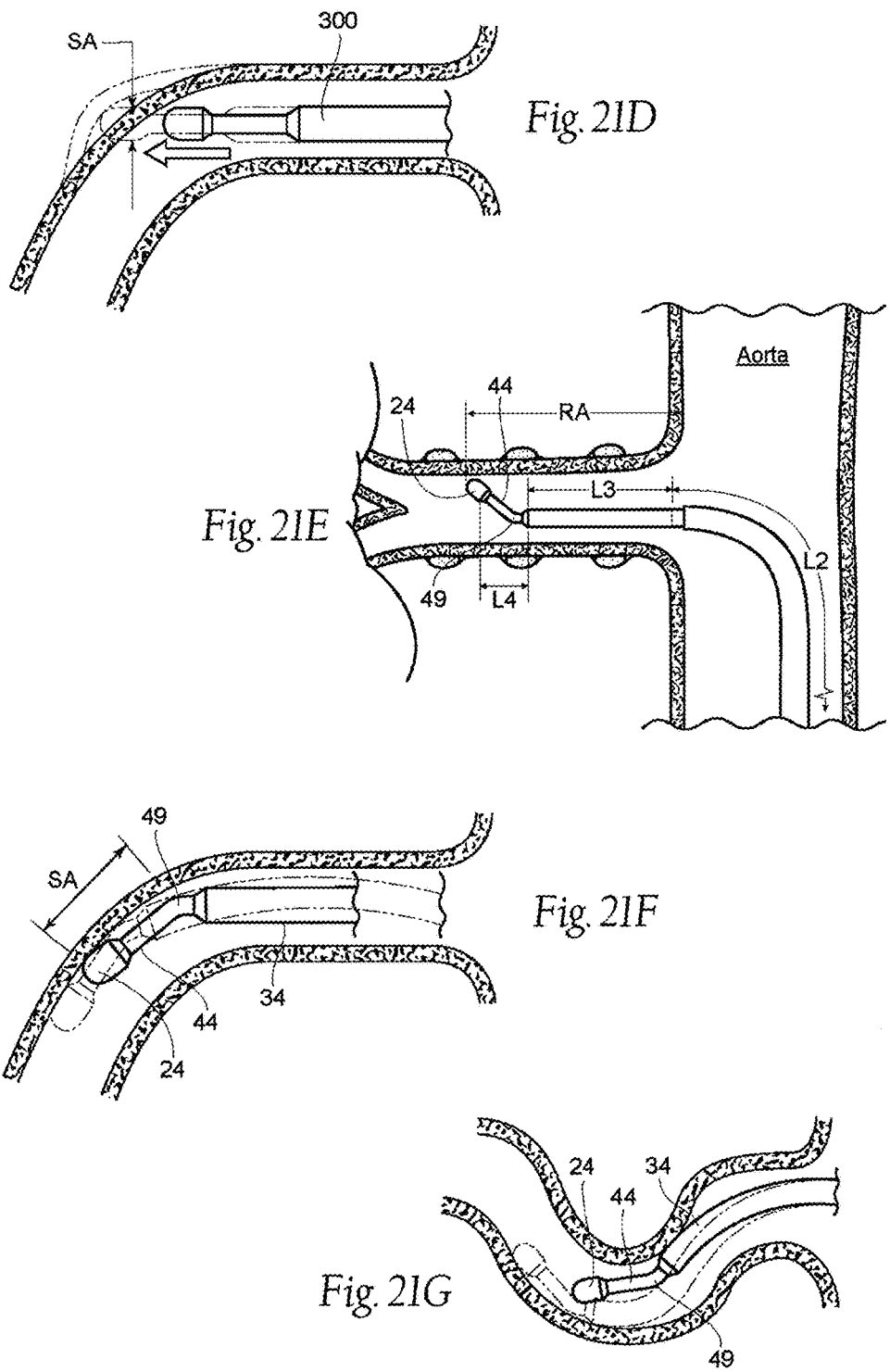

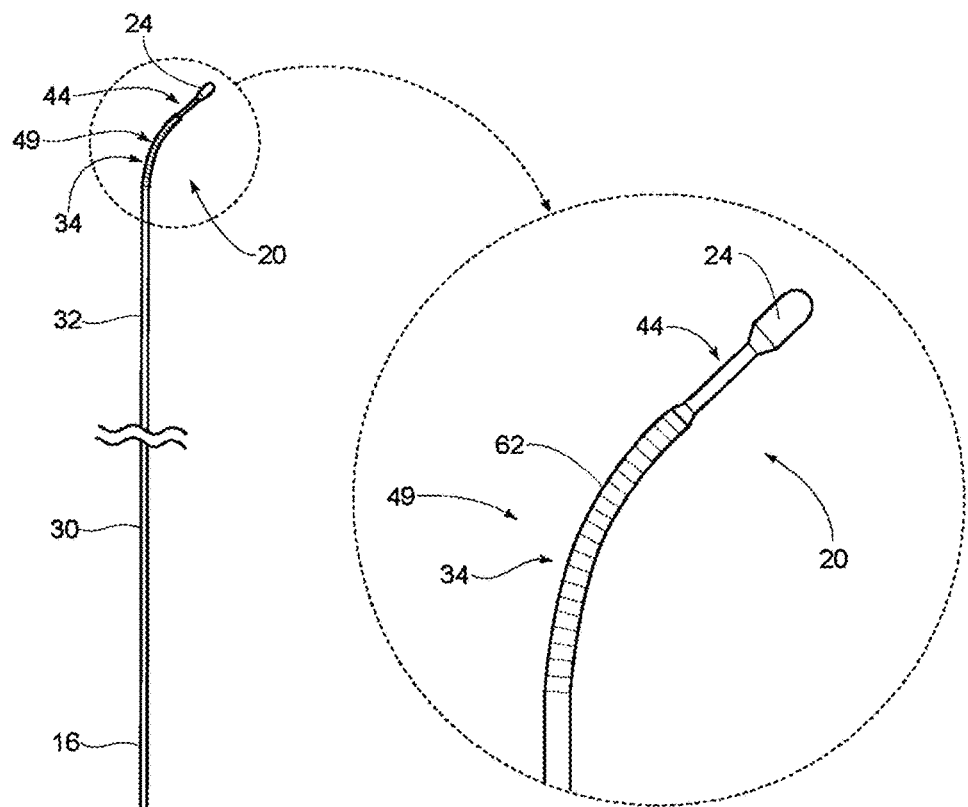
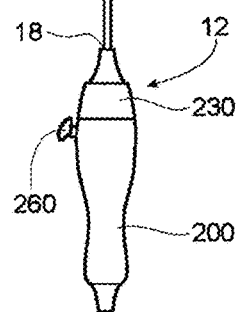
Fig. 22B
Fig. 22A

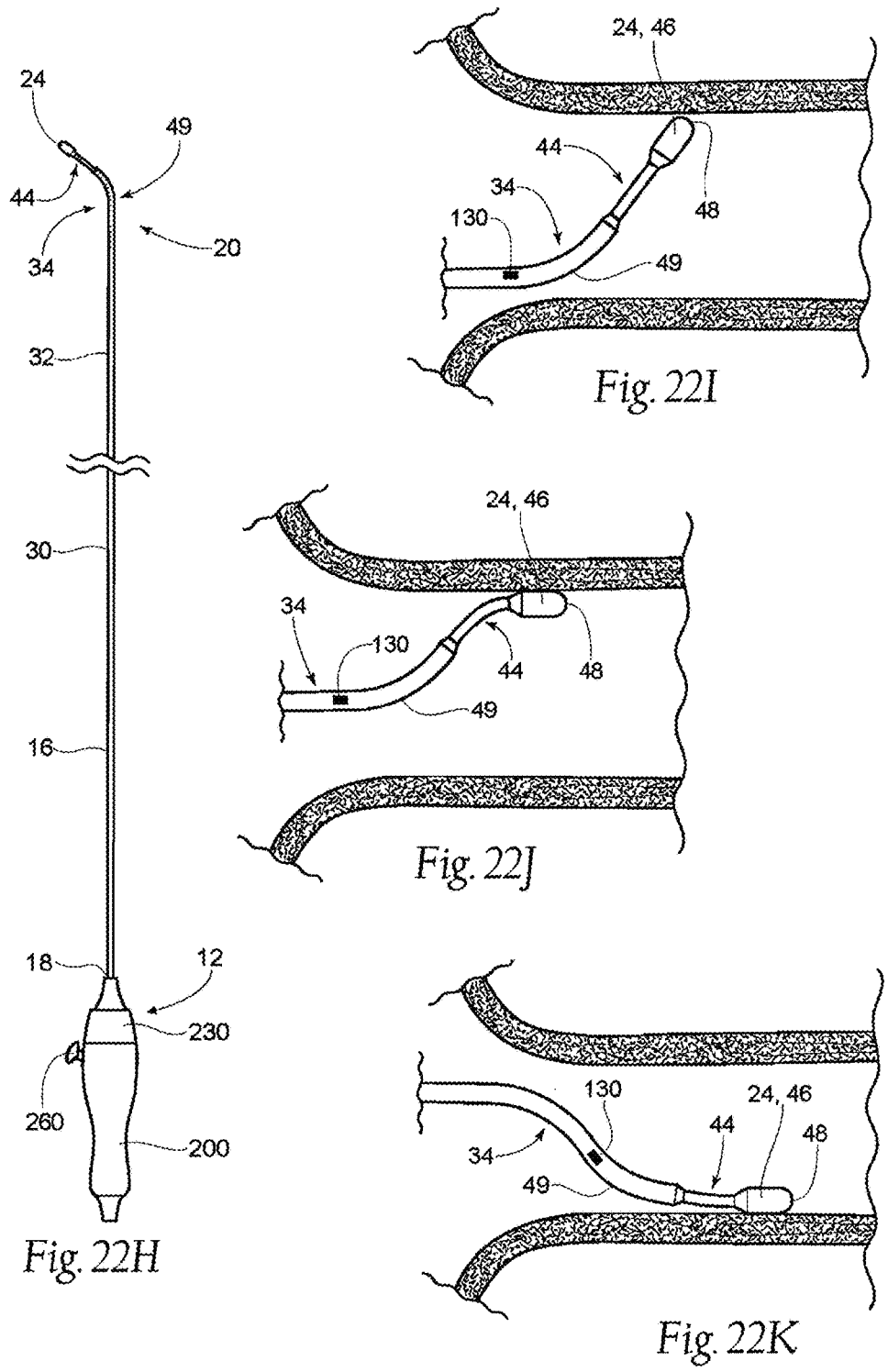

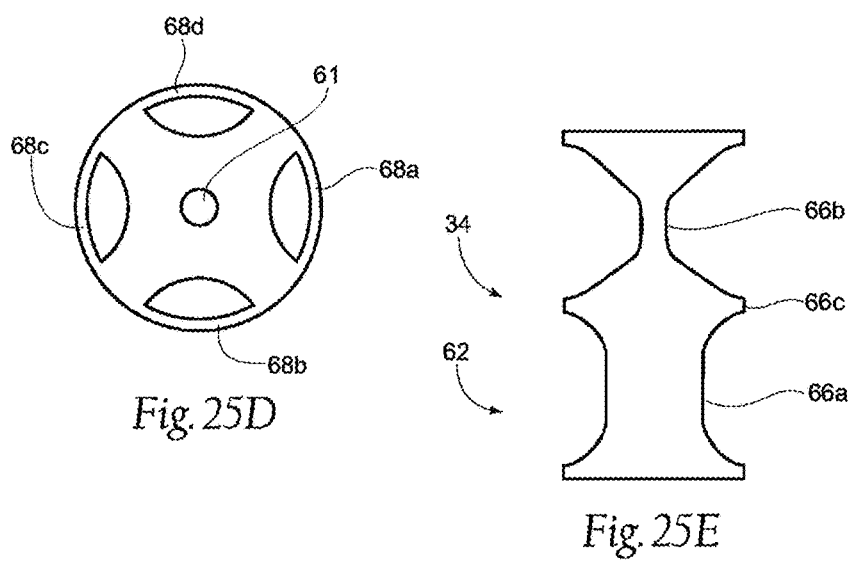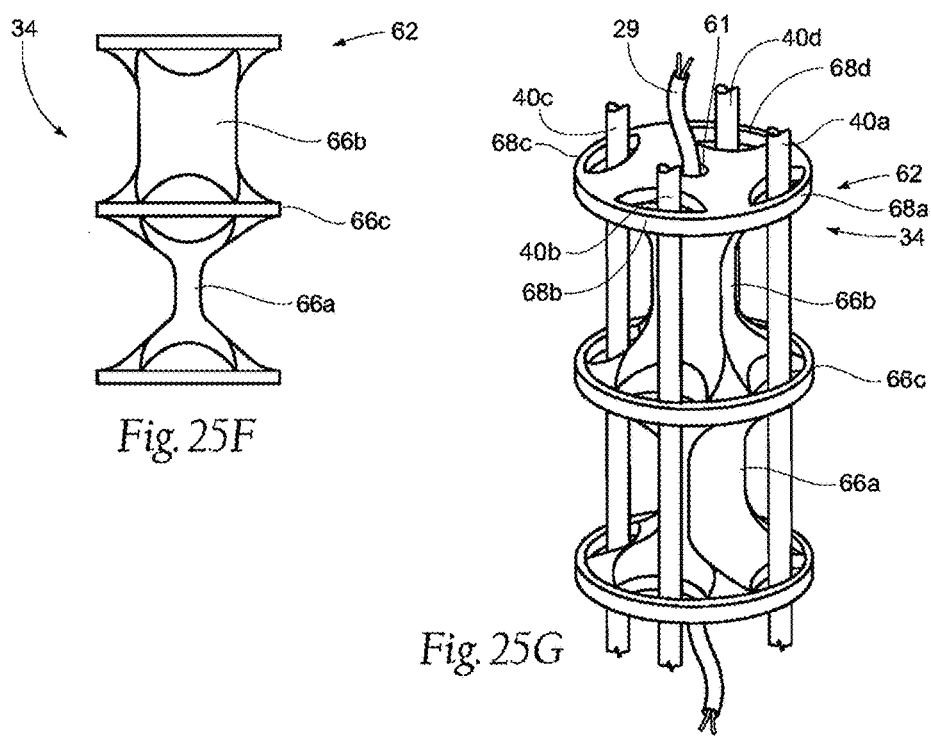

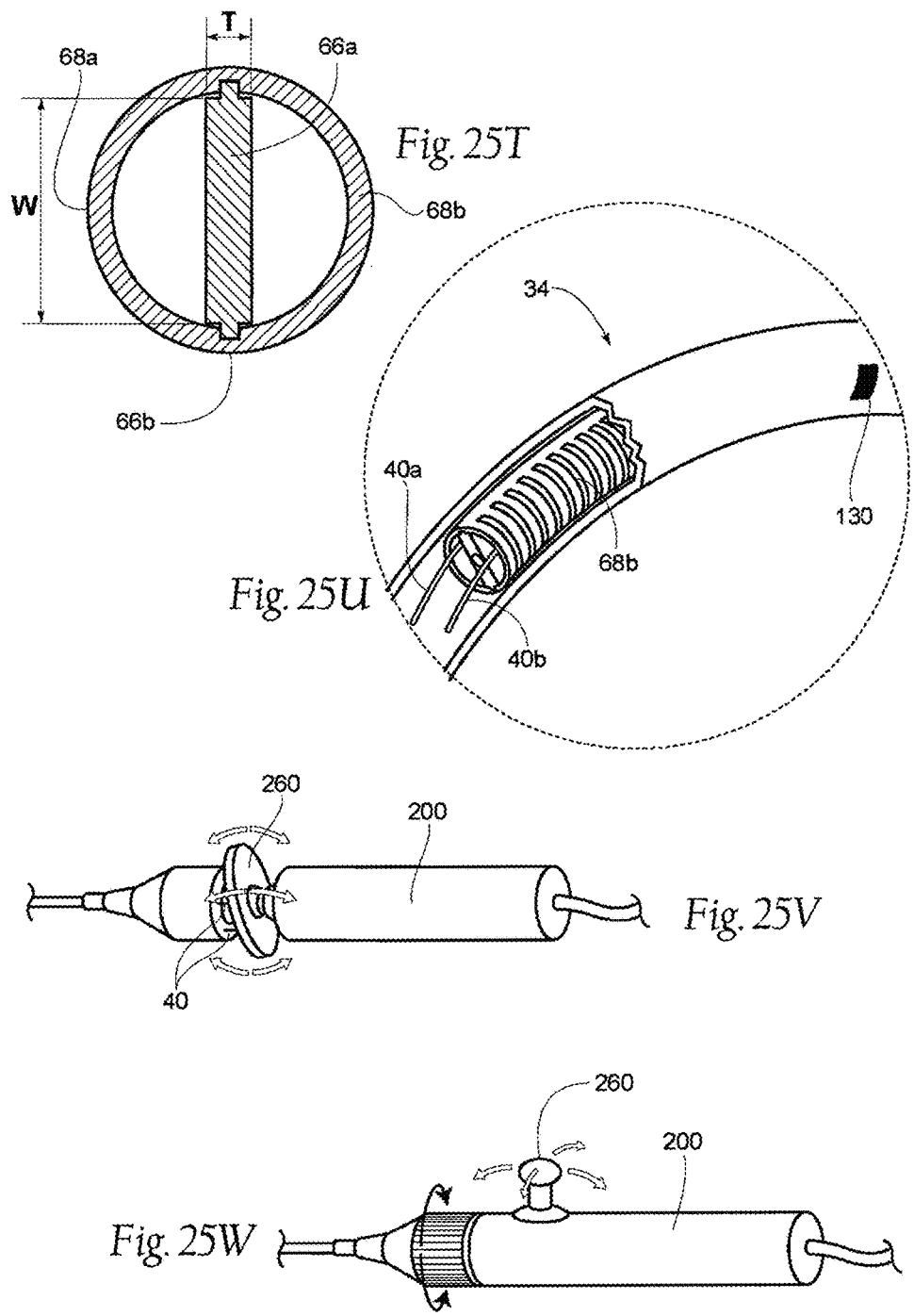

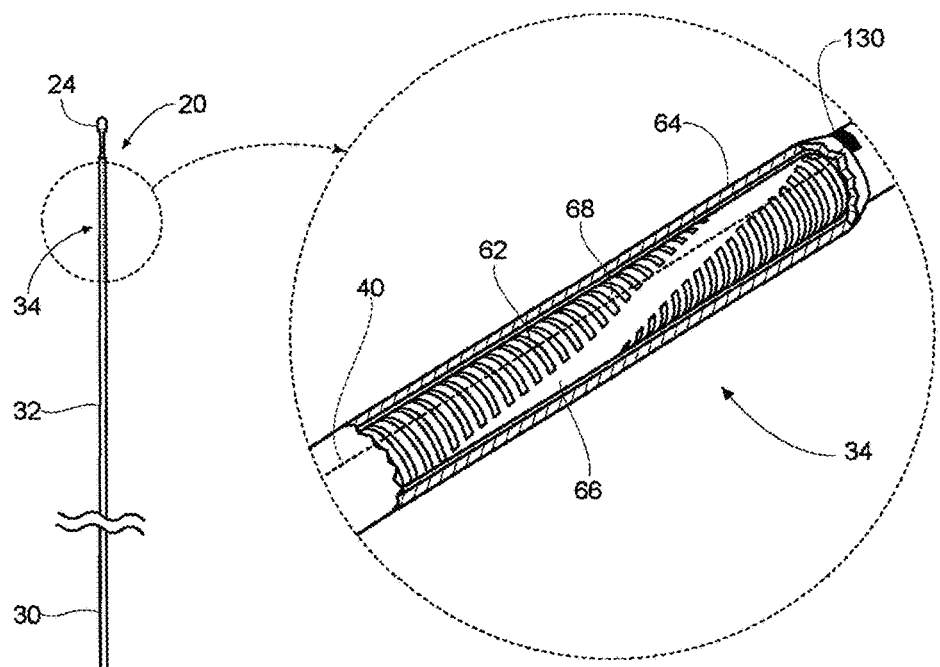
Fig. 26B
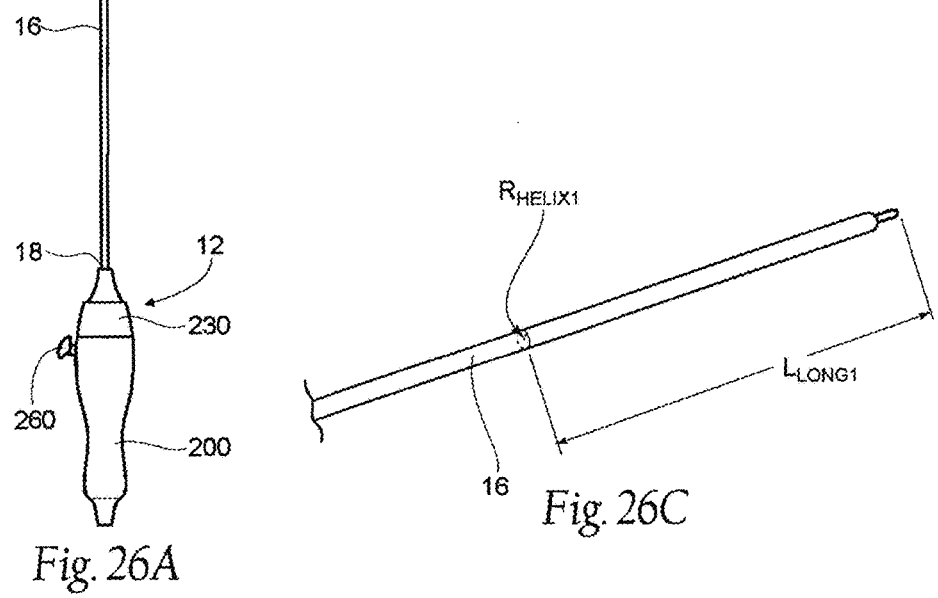
Fig. 26A
Fig. 26C

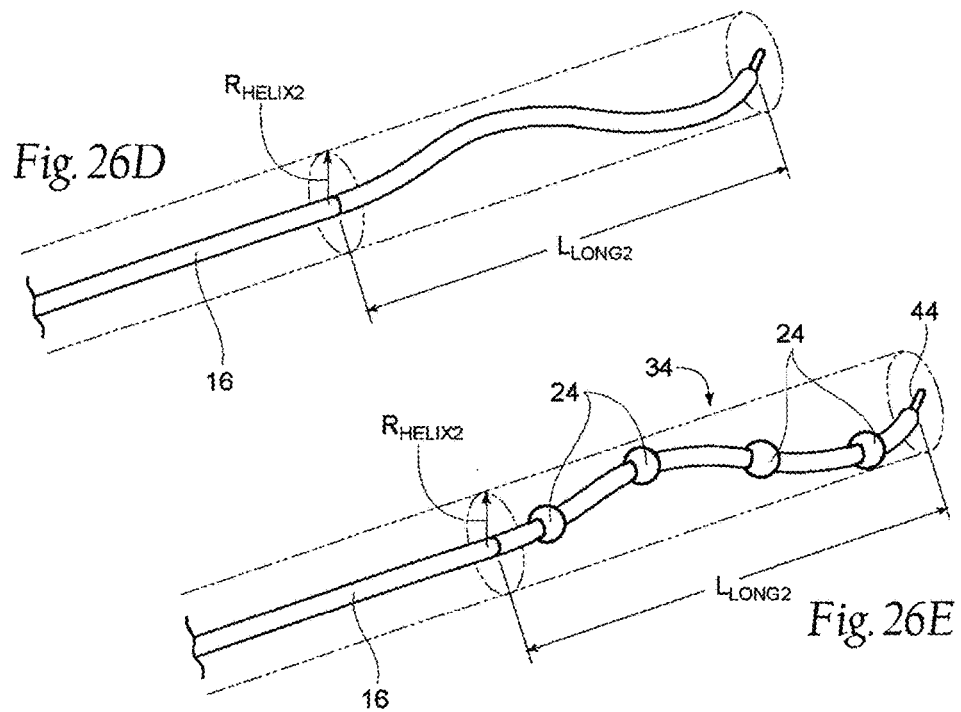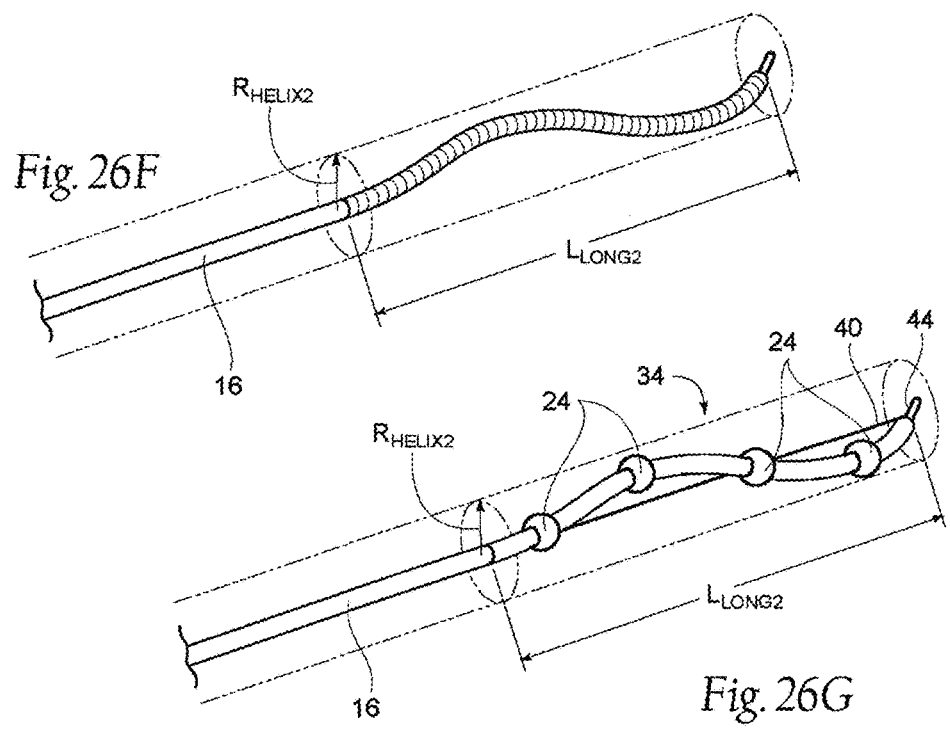

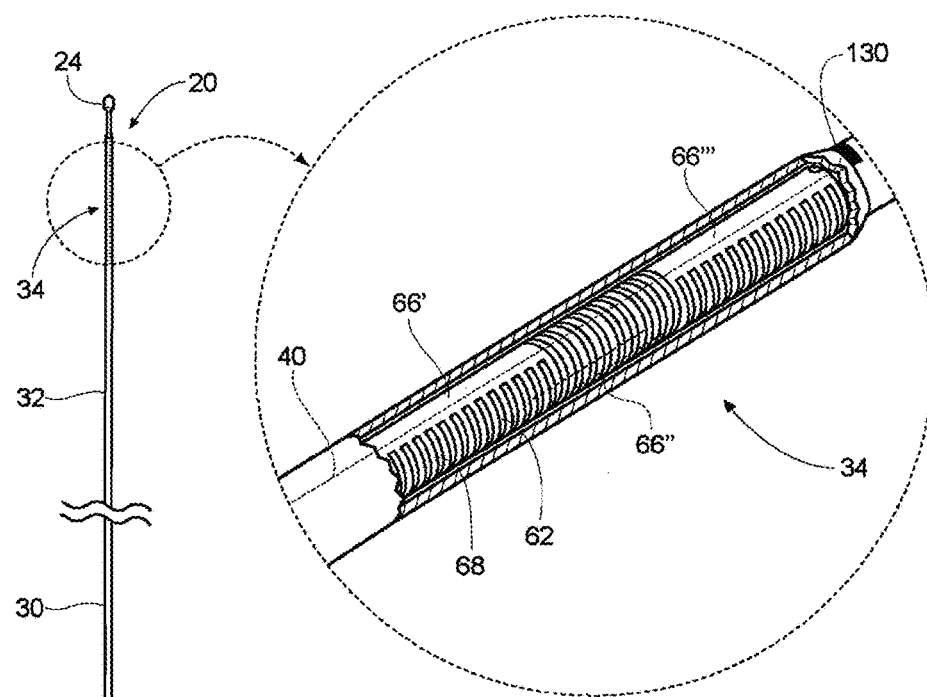
Fig. 27B
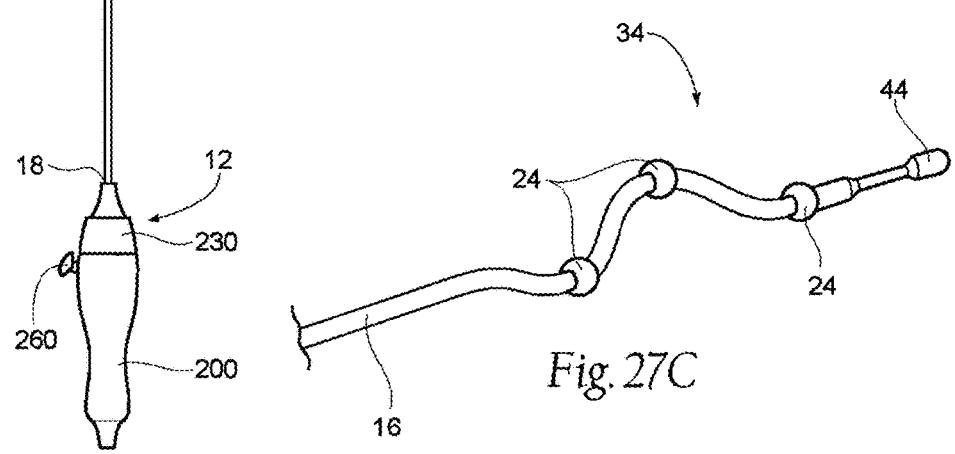
Fig. 27A
Fig. 27C

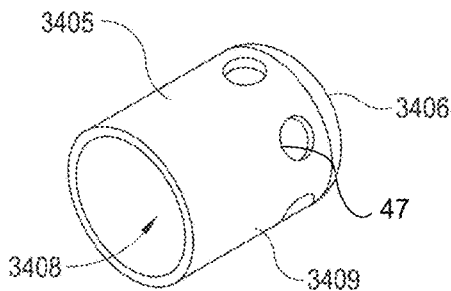
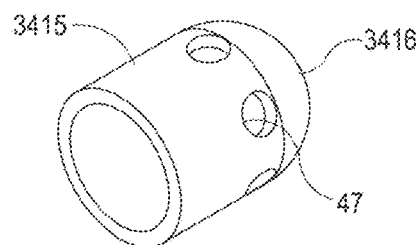
Fig. 34M    Fig. 34N
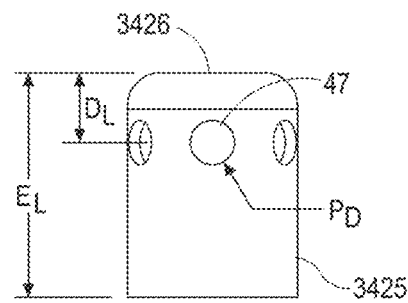
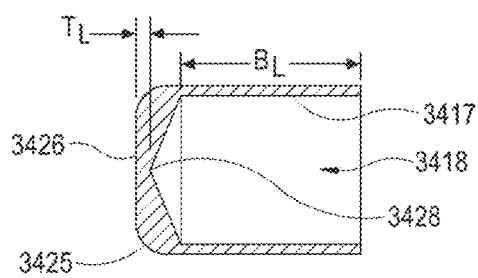
Fig. 34O    Fig. 34P
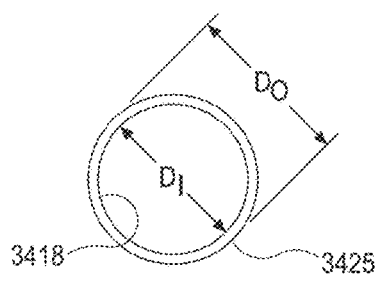
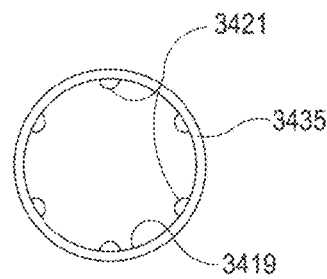
Fig. 34Q    Fig. 34R

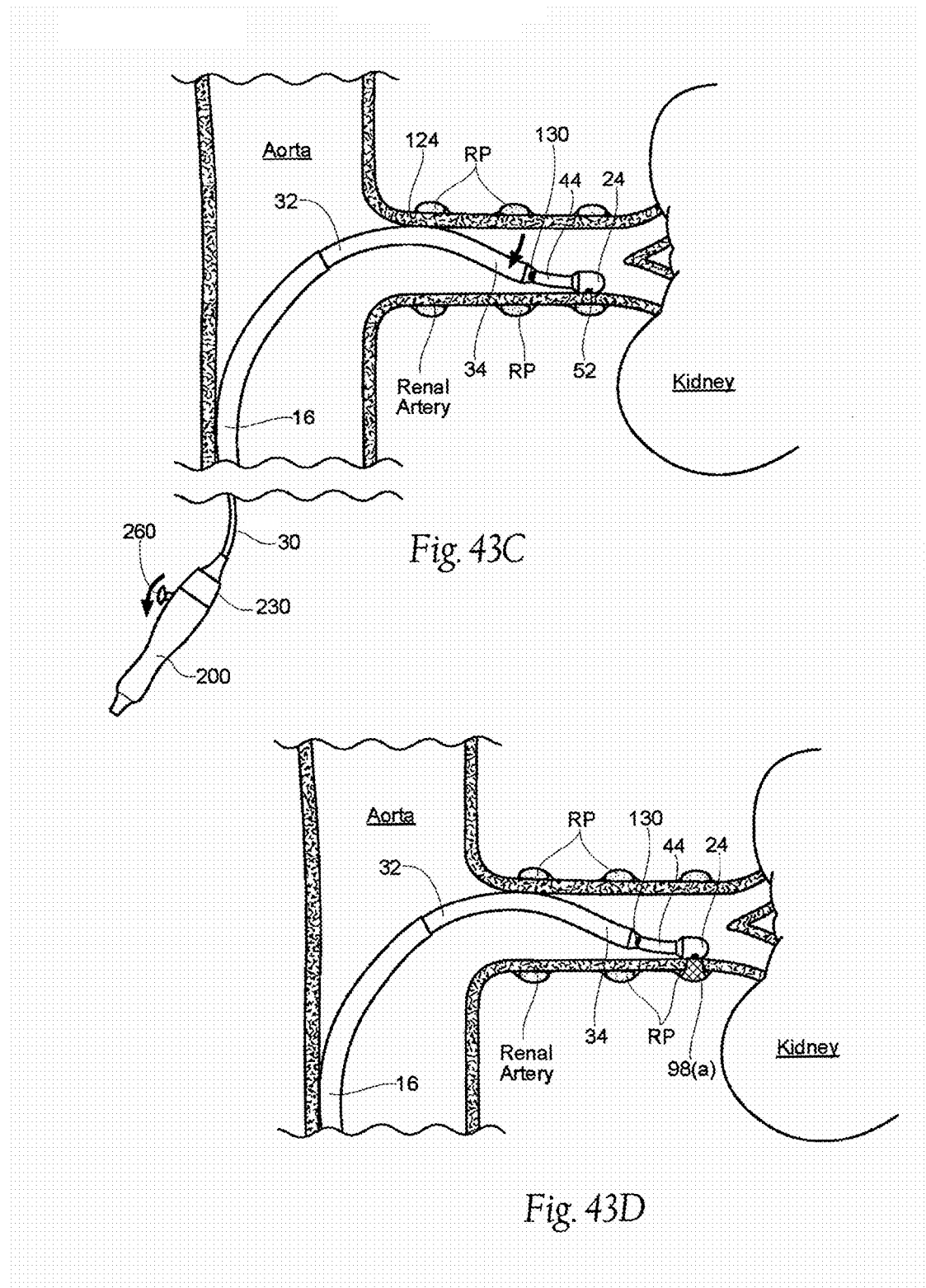

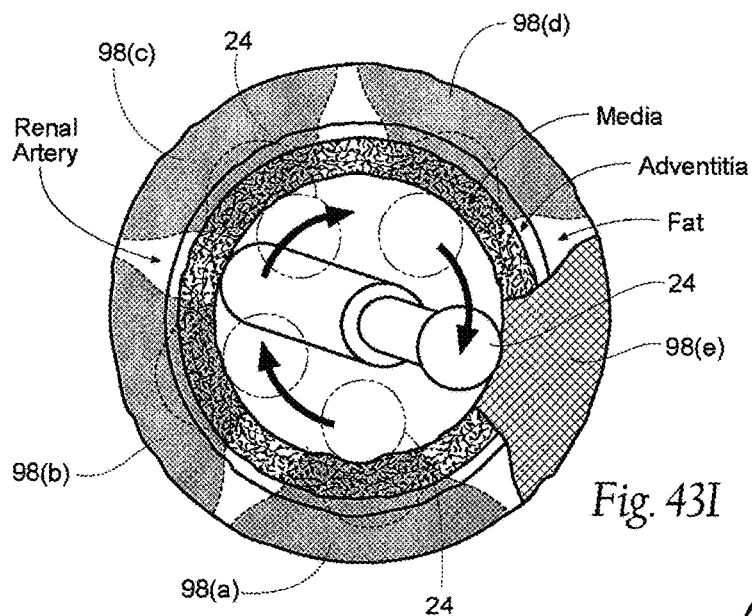
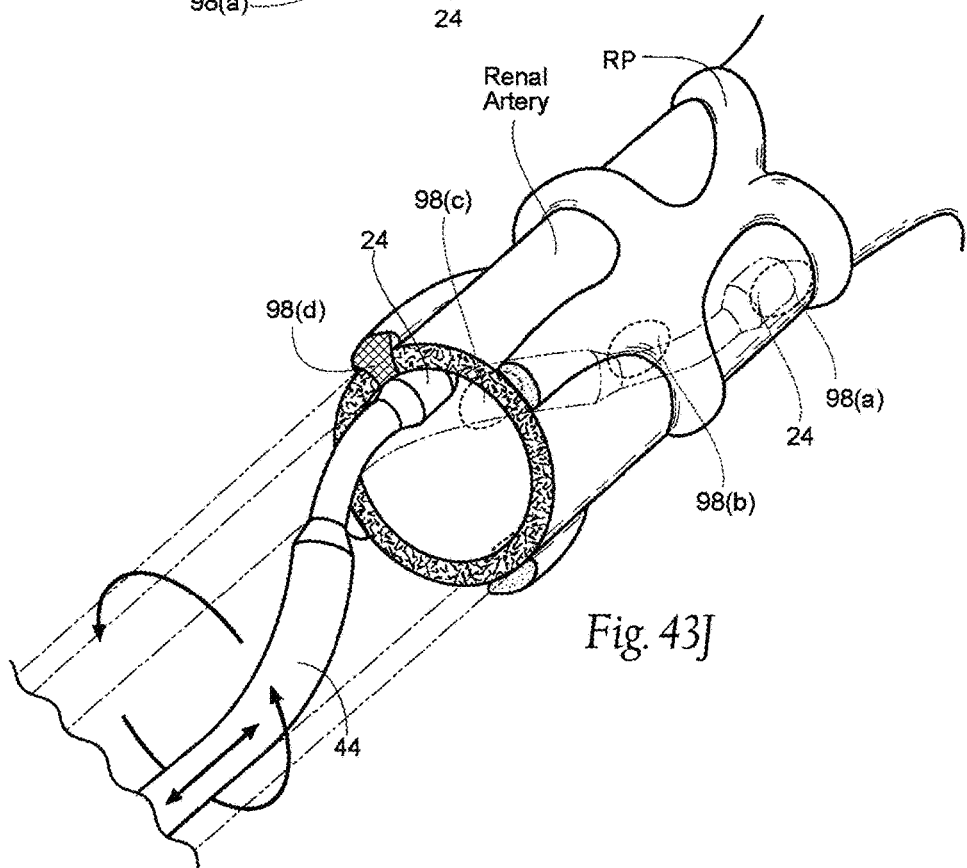

CATHETER APPARATUSES, SYSTEMS, AND METHODS FOR RENAL NEUROMODULATION

CROSS-REFERENCE TO RELATED APPLICATION(S)

This application is a Continuation of U.S. patent application Ser. No. 15/466,734, filed Mar. 22, 2017, now U.S. Pat. No. 9,855,097, which is a Continuation of U.S. patent application Ser. No. 14/741,320, filed Jun. 16, 2015, now U.S. Pat. No. 9,636,173, which is a Continuation of U.S. patent application Ser. No. 13/279,205, filed Oct. 21, 2011, now U.S. Pat. No. 9,084,610, which claims the benefit of U.S. Provisional Application No. 61/405,472, filed Oct. 21, 2010.

RELATED APPLICATIONS INCORPORATED BY REFERENCE

U.S. Provisional Application No. 61/328,105, filed Apr. 26, 2010, U.S. patent application Ser. No. 12/790,639, filed May 28, 2010, U.S. patent application Ser. No. 12/871,457, filed Aug. 30, 2010, and International Application No. PCT/US2011/033491, filed Apr. 21, 2011 are related to the present application, and the foregoing applications are incorporated herein by reference in their entireties. As such, components and features of embodiments disclosed in the applications incorporated by reference may be combined with various components and features disclosed and claimed in the present application.

TECHNICAL FIELD

The technologies disclosed in the present application generally relate to catheter apparatuses, systems and methods for intravascular neuromodulation. More particularly, the technologies disclosed herein relate to catheter apparatuses, systems, and methods for achieving intravascular renal neuromodulation via application of thermal and/or electrical energy.

BACKGROUND

Hypertension, heart failure, chronic kidney disease, insulin resistance, diabetes and metabolic syndrome represent a significant and growing global health issue. Current therapies for these conditions include non-pharmacological, pharmacological and device-based approaches. Despite this variety of treatment options, the rates of control of blood pressure and the therapeutic efforts to prevent progression of these disease states and their sequelae remain unsatisfactory. Although the reasons for this situation are manifold and include issues of non-compliance with prescribed therapy, heterogeneity in responses both in terms of efficacy and adverse event profile, and others, it is evident that alternative options are required to supplement the current therapeutic treatment regimes for these conditions.

Reduction of sympathetic renal nerve activity (e.g., via denervation), can reverse these processes. Medtronic Ardian LLC of Mountain View, Calif., discovered that an energy field, including and comprising an electric field, can initiate renal neuromodulation via denervation caused by irreversible electroporation, electrofusion, apoptosis, necrosis, ablation, thermal alteration, alteration of gene expression or another suitable modality.

Catheter-based intervention is widely used for medical treatments where access to a location in the body is obtained, for example, through a vessel of the cardiovascular system. Medtronic Ardian LLC has shown that an energy field can be applied to the sympathetic renal nerves from within a renal artery. The renal artery has features unique from other vessels or parts of the body and thus applying an energy field to the sympathetic renal nerves from within the renal artery is not trivial. Accordingly, a need exists for a catheter capable of effectively delivering energy to the renal sympathetic nerves from within a renal artery, where the catheter is better configured to i) navigate through a renal artery with reduced risk of applying traumatic force to the artery wall; ii) precisely place an energy delivery element at a desired location on the vessel wall; and iii) maintain stable contact between the energy delivery element and the location on the vessel wall during blood flow pulsatility and respiratory motion of the renal artery.

BRIEF DESCRIPTION OF THE DRAWINGS

FIG. 5 is a perspective view of a system for achieving intravascular, thermally-induced renal neuromodulation, comprising a treatment device and a generator.

FIGS. 7A to 7D are a series of views of the elongated shaft of the treatment device shown in FIG. 5, showing the different mechanical and functional regions that the elongated shaft incorporates.

FIGS. 10A and 10B show a representative embodiment of the force transmitting section of the elongated shaft of the treatment device shown in FIG. 5.

FIGS. 12A to 12D show a representative embodiment of the intermediate flexure zone of the elongated shaft of the treatment device shown in FIG. 5.

FIGS. 14A and 14B show portions of treatment devices having flexure zones configured in accordance with embodiments of the technology.

FIGS. 15A to 15C show a representative embodiment of the distal flexure zone of the elongated shaft of the treatment device shown in FIG. 5.

FIGS. 15D to 15F show multiple planar views of the bending capability of the distal flexure zone corresponding to the elongated shaft of the treatment device shown in FIG. 5.

FIGS. 21A to 21C show a representative embodiment of the third flexure zone of the elongated shaft of the treatment device shown in FIG. 5.

FIG. 21D shows an anatomic view of the placement of the treatment device shown in FIG. 5 within the dimensions of the renal artery.

FIGS. 21E to 21G show an anatomic view of the placement of the treatment device shown in FIG. 21A to 21C within the dimensions of the renal artery.

FIGS. 22A to 22G show additional alternative representative embodiments of an elongated shaft for a treatment device, showing second flexure zones comprising a preshaped bend.

FIGS. 22H to 22K show additional alternative representative embodiments of an elongated shaft for a treatment device, showing second flexure zones longitudinally offset from a pre-shaped bend.

FIGS. 25D to 25M show additional alternative representative embodiments of an elongated shaft for a treatment device like that shown in FIG. 25A, showing examples of the different structural, mechanical and functional regions that the elongated shaft can incorporate, wherein the second flexure zone comprises a centrally positioned spine.

FIGS. 25N to 25W show additional alternative representative embodiments of an elongated shaft for a treatment device like that shown in FIG. 25A, showing examples of the different structural, mechanical and functional regions that the elongated shaft can incorporate.

FIGS. 26A to 26L show additional alternative representative embodiments of an elongated shaft for a treatment device showing examples of shafts deforming in to helical shapes.

FIGS. 27A to 27F show additional alternative representative embodiments of an elongated shaft for a treatment device showing examples of shafts deforming in to a complex bend.

FIGS. 34M-34W illustrate electrodes configured to provide active cooling in accordance with embodiments of the technology.

FIGS. 43A to 43H show the intravascular delivery, placement, deflection, rotation, retraction, repositioning and use of a treatment device, like that shown in FIG. 5, to achieve thermally-induced renal neuromodulation from within a renal artery.

FIGS. 43I to 43K show the circumferential treatment effect resulting from intravascular use of a treatment device, like that shown in FIG. 5.

DETAILED DESCRIPTION

Figure 1:
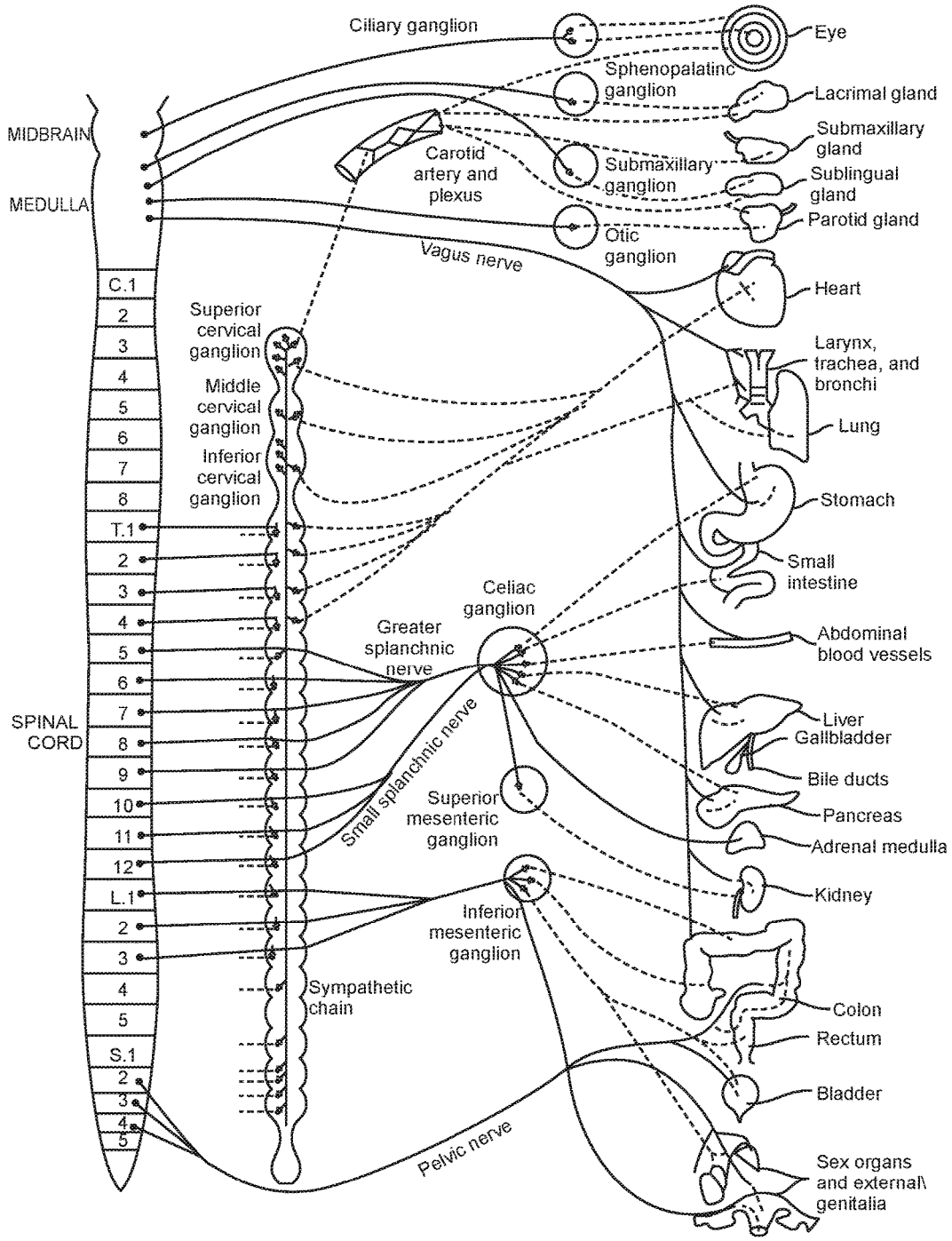
FIG. 1 is a conceptual illustration of the sympathetic nervous system (SNS) and how the brain communicates with the body via the SNS.

Although the disclosure hereof is detailed and exact to enable those skilled in the art to practice the disclosed technologies, the physical embodiments herein disclosed merely exemplify the various aspects of the invention, which may be embodied in other specific structures. While the preferred embodiment has been described, the details may be changed without departing from the invention, which is defined by the claims.

I. PERTINENT ANATOMY AND PHYSIOLOGY

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation can elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

As shown in FIG. 1, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons must travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 2:
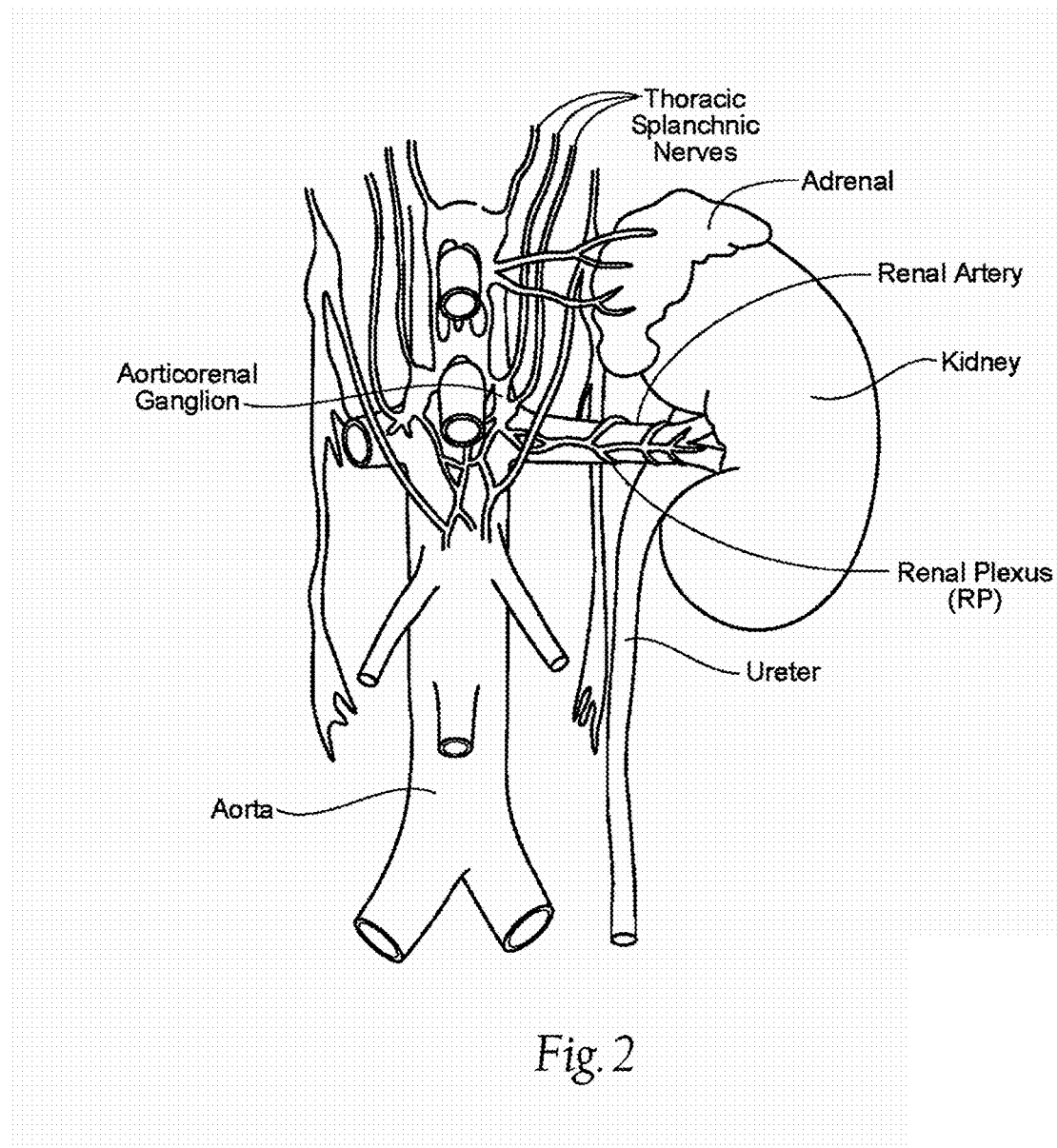
FIG. 2 is an enlarged anatomic view of nerves innervating a left kidney to form the renal plexus surrounding the left renal artery.

As FIG. 2 shows, the kidney is innervated by the renal plexus (RP), which is intimately associated with the renal artery. The renal plexus is an autonomic plexus that surrounds the renal artery and is embedded within the adventitia of the renal artery. The renal plexus extends along the renal artery until it arrives at the substance of the kidney. Fibers contributing to the renal plexus arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages can trigger changes in different parts of the body simultaneously. For example, the sympathetic nervous system can accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all cause death and death from cardiovascular disease. This is also true for patients suffering from diabetic or contrast nephropathy. There is compelling evidence that suggests that sensory afferent signals originating from the diseased kidneys are major contributors to the initiation and sustainment of elevated central sympathetic outflow in this patient group, which facilitates the occurrence of the well-known adverse consequences of chronic sympathetic overactivity such as hypertension, left ventricular hypertrophy, ventricular arrhythmias, sudden cardiac death, insulin resistance, diabetes and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 3A:
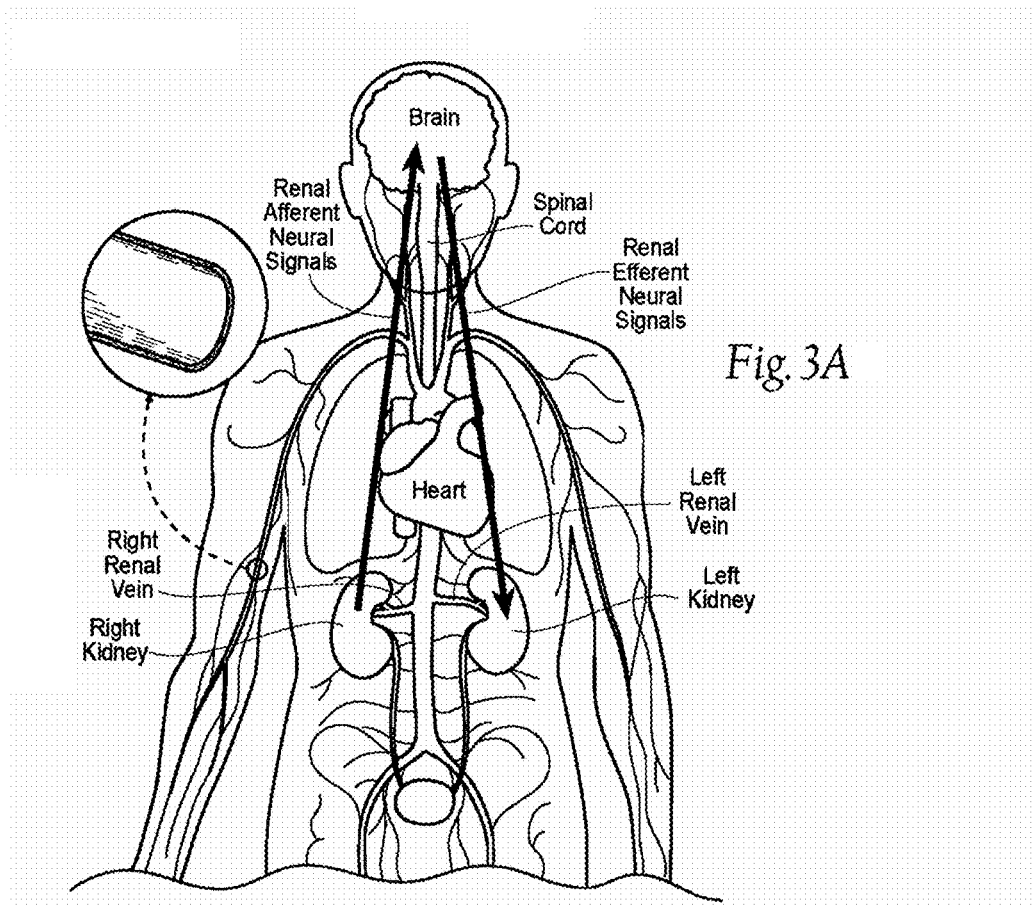
FIGS. 3A and 3B provide anatomic and conceptual views of a human body, respectively, depicting neural efferent and afferent communication between the brain and kidneys
Figure 3B:
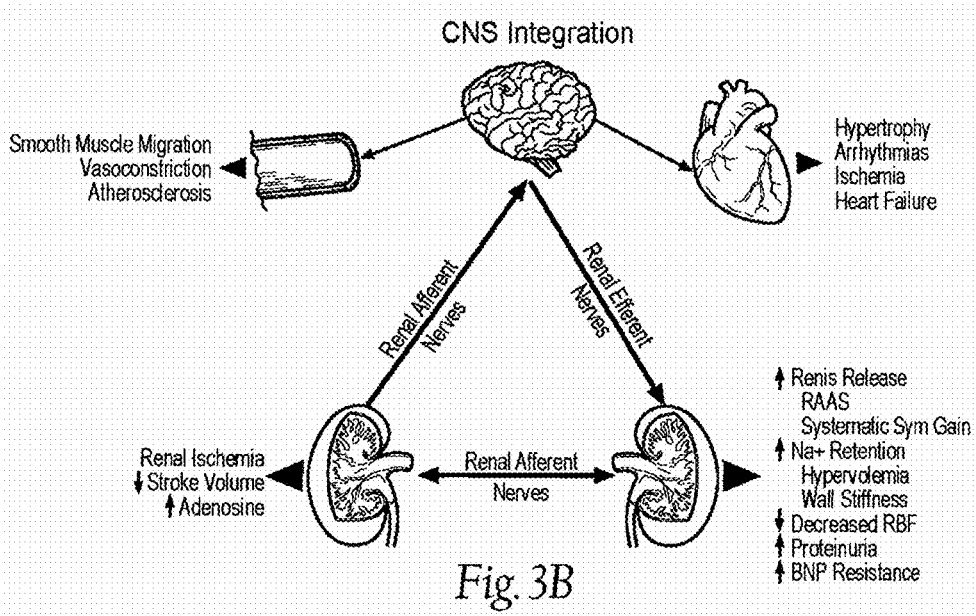

The kidneys communicate with integral structures in the central nervous system via renal sensory afferent nerves. Several forms of "renal injury" can induce activation of sensory afferent signals. For example, renal ischemia, reduction in stroke volume or renal blood flow, or an abundance of adenosine enzyme may trigger activation of afferent neural communication. As shown in FIGS. 3A and 3B, this afferent communication might be from the kidney to the brain or might be from one kidney to the other kidney (via the central nervous system). These afferent signals are centrally integrated and can result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) denervation of tissue with efferent sympathetic nerves will reduce inappropriate renin release, salt retention, and reduction of renal blood flow, and that (ii) denervation of tissue with afferent sensory nerves will reduce the systemic contribution to hypertension, and other disease states associated with increased central sympathetic tone, through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic and end stage renal disease, inappropriate fluid retention in heart failure, cardio-renal syndrome and sudden death. Since the reduction of afferent neural signals contributes to the systemic reduction of sympathetic tone/drive, renal denervation might also be useful in treating other conditions associated with systemic sympathetic hyperactivity. Accordingly, renal denervation can also benefit other organs and bodily structures innervated by sympathetic nerves, including those identified in FIG. 1. For example, a reduction in central sympathetic drive may reduce the insulin resistance that afflicts people with metabolic syndrome and Type II diabetics. Additionally, patients with osteoporosis are also sympathetically activated and might also benefit from the downregulation of sympathetic drive that accompanies renal denervation.

C. Achieving Intravascular Access to the Renal Artery

Figures 4A, 4B:
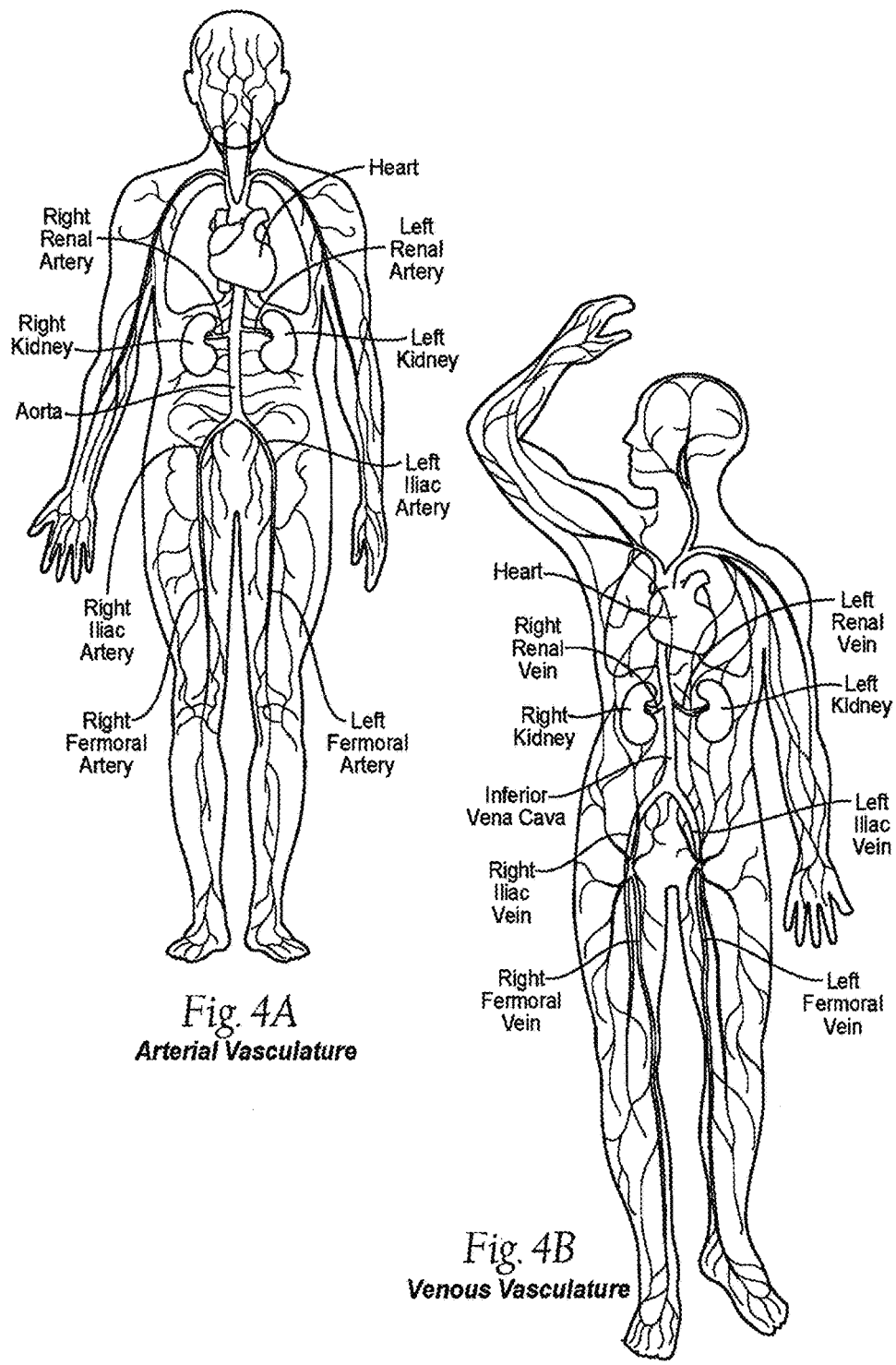
FIGS. 4A and 4B are, respectively, anatomic views of the arterial and venous vasculatures of a human.

In accordance with the present invention, neuromodulation of a left and/or right renal plexus (RP), which is intimately associated with a left and/or right renal artery, may be achieved through intravascular access. As FIG. 4A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 4B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery can be exposed and cannulated at the base of the femoral triangle, just inferior to the midpoint of the inguinal ligament. A catheter can be inserted through this access site, percutaneously into the femoral artery and passed into the iliac artery and aorta, into either the left or right renal artery. This comprises an intravascular path that offers minimally invasive access to a respective renal artery and/or other renal blood vessels.

The wrist, upper arm, and shoulder region provide other locations for introduction of catheters into the arterial system. Catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present invention through intravascular access, properties and characteristics of the renal vasculature may impose constraints upon and/or inform the design of apparatus, systems and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained below, may have bearing on the clinical safety and efficacy of the procedure and the specific design of the intravascular device. Properties of interest may include, for example, material/mechanical, spatial, fluid dynamic/hemodynamic and/or thermodynamic properties.

As discussed previously, a catheter can be advanced percutaneously into either the left or right renal artery via a minimally invasive intravascular path. However, minimally invasive renal arterial access can be challenging, for example, because, as compared to some other arteries that are routinely accessed using catheters, the renal arteries are often extremely tortuous, may be of relatively small diameter and/or may be of relatively short length. Furthermore, renal arterial atherosclerosis is common in many patients, particularly those with cardiovascular disease. Renal arterial anatomy also may vary significantly from patient to patient, further complicating minimally invasive access. Significant inter-patient variation may be seen, for example, in relative tortuosity, diameter, length and/or atherosclerotic plaque burden, as well as in the take-off angle at which a renal artery branches from the aorta. Apparatus, systems and methods for achieving renal neuromodulation via intravascular access must account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus comprises an energy delivery element, such as an electrode, consistent positioning and contact force application between the energy delivery element and the vessel wall is important for predictability and safety. However, navigation is impeded by the tight space within a renal artery, as well as tortuosity of the artery. Furthermore, respiration and/or the cardiac cycle may cause significant movement of the renal artery relative to the aorta, and the cardiac cycle and/or the neuromodulatory apparatus may transiently distend the renal artery, further complicating establishment of stable contact.

Even after accessing a renal artery and facilitating stable contact between neuromodulatory apparatus and a luminal surface of the artery, nerves in and around the adventia of the artery must be safely modulated via the neuromodulatory apparatus. Safely applying thermal treatment from within a renal artery is non-trivial given the potential clinical complications associated with such treatment. For example, the intima and media of the renal artery are highly vulnerable to thermal injury. As discussed in greater detail below, the Intima-Media Thickness separating the vessel lumen from its adventitia means that target renal nerves may be multiple millimeters distant from the luminal surface of the artery. Sufficient thermal energy must be delivered to the target renal nerves to modulate the target renal nerves without excessively heating and desiccating the vessel wall. Another potential clinical complication associated with excessive heating is thrombus formation from coagulating blood flowing through the artery. Given that this thrombus can cause a kidney infarct, thereby causing irreversible damage to the kidney, thermal treatment from within the renal artery must be applied carefully. Accordingly, the complex fluid mechanic and thermodynamic conditions present in the renal artery during treatment, particularly those that may impact heat transfer dynamics at the treatment site, can be important is applying thermal treatment from within the renal artery.

It is also desirable for the neuromodulatory apparatus to be configured to allow for adjustable positioning and repositioning of the energy delivery element within the renal artery since location of treatment may also impact clinical safety and efficacy. For example, it may be tempting to apply a full circumferential treatment from within the renal artery given that the renal nerves may be spaced circumferentially around a renal artery. However, the full-circle lesion likely resulting from a continuous circumferential treatment may create a heighten risk of renal artery stenosis, thereby negating any potential therapeutic benefit of the renal neuromodulation. Therefore, the formation of more complex lesions along a longitudinal dimension of the renal artery and/or repositioning of the neuromodulatory apparatus to multiple treatment locations may be desirable. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Based on the above described challenges of (1) renal artery intervention, (2) consistent and stable placement of the energy delivery element against the vessel wall, (3) safe application of thermal treatment across the vessel wall, and (4) positioning and repositioning the treatment apparatus to allow for multiple treatment locations, various independent and dependent properties of the renal vasculature that may be of interest include, for example, vessel diameter, length, intima-media thickness, coefficient of friction and tortuosity; distensibility, stiffness and modulus of elasticity of the vessel wall; peak systolic and end-diastolic blood flow velocity, as well as the mean systolic-diastolic peak blood flow velocity, mean/max volumetric blood flow rate; specific heat capacity of blood and/or of the vessel wall, thermal conductivity of blood and/or of the vessel wall, thermal convectivity of blood flow past a vessel wall treatment site and/or radiative heat transfer; and renal motion relative to the aorta, induced by respiration and/or blood flow pulsatility, as well as the take-off angle of a renal artery relative to the aorta. These properties will be discussed in greater detail with respect to the renal arteries. However, dependent on the apparatus, systems and methods utilized to achieve renal neuromodulation, such properties of the renal veins also may guide and/or constrain design characteristics.

Apparatus positioned within a renal artery must conform to the geometry of the artery. Renal artery vessel diameter, DRA, typically is in a range of about 2-10 mm, with an average of about 6 mm. Renal artery vessel length, LRA, between its ostium at the aorta/renal artery juncture and its distal branchings, generally is in a range of about 5-70 mm, more generally in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

Apparatus navigated within a renal artery also must contend with friction and tortuosity. The coefficient of friction, μ, (e.g., static or kinetic friction) at the wall of a renal artery generally is quite low, for example, generally is less than about 0.05, or less than about 0.03. Tortuosity, τ, a measure of the relative twistiness of a curved segment, has been quantified in various ways. The arc-chord ratio defines tortuosity as the length of a curve, Lcurve, divided by the chord, Ccurve, connecting the ends of the curve (i.e., the linear distance separating the ends of the curve):

$$\tau = L_{curve}/C_{curve} \qquad (1)$$

Renal artery tortuosity, as defined by the arc-chord ratio, is generally in the range of about 1-2.

The pressure change between diastole and systole changes the luminal diameter of the renal artery, providing information on the bulk material properties of the vessel. The Distensibility Coefficient, DC, a property dependent on actual blood pressure, captures the relationship between pulse pressure and diameter change:

$$DC = 2*((D_{sys} - D_{dia})/D_{dia})/\Delta P = 2*(\Delta D/D_{dia})/\Delta P, \quad (2)$$

where $D_{sys}$ is the systolic diameter of the renal artery, $D_{dia}$ is the diastolic diameter of the renal artery, and $\Delta D$ (which generally is less than about 1 mm, e.g., in the range of about 0.1 mm to 1 mm) is the difference between the two diameters:

$$\Delta D = D_{sys} - D_{dia} \quad (3)$$

The renal arterial Distensibility Coefficient is generally in the range of about 20-50 kPa-1*10−3.

The luminal diameter change during the cardiac cycle also may be used to determine renal arterial Stiffness, β. Unlike the Distensibility Coefficient, Stiffness is a dimensionless property and is independent of actual blood pressure in normotensive patients:

$$\beta = (\ln[BP_{sys}/BP_{dia}])/(\Delta D/D_{dia}) \quad (4)$$

Renal arterial Stiffness generally is in the range of about 3.5-4.5.

In combination with other geometric properties of the renal artery, the Distensibility Coefficient may be utilized to determine the renal artery's Incremental Modulus of Elasticity, Einc:

$$E_{inc} = 3(1 + (LCSA/IMCSA))/DC, \quad (5)$$

where LCSA is the luminal cross-sectional area and IMCSA is the intima-media cross-sectional area:

$$LCSA = \pi(D_{dia}/2)^2 \quad (6)$$

$$IMCSA = \pi(D_{dia}/2 + IMT)^2 - LCSA \quad (7)$$

For the renal artery, LCSA is in the range of about 7-50 mm2, IMCSA is in the range of about 5-80 mm2, and Einc is in the range of about 0.1-0.4 kPa*103.

For patients without significant Renal Arterial Stenosis (RAS), peak renal artery systolic blood flow velocity, vmax-sys, generally is less than about 200 cm/s; while peak renal artery end-diastolic blood flow velocity, vmax-dia, generally is less than about 150 cm/s, e.g., about 120 cm/s.

In addition to the blood flow velocity profile of a renal artery, volumetric flow rate also is of interest. Assuming Poiseulle flow, the volumetric flow rate through a tube, Φ, (often measured at the outlet of the tube) is defined as the average velocity of fluid flow through the tube, vavg, times the cross-sectional area of the tube:

$$\Phi = v_{avg} * \pi R^2 \quad (8)$$

By integrating the velocity profile (defined in Eq. 8 above) over all radii from 0 to R, it can be shown that:

$$\Phi = v_{avg} * \pi R^2 = (\pi R^4 * \Delta Pr)/8\eta \Delta x \quad (9)$$

As discussed previously, for the purposes of the renal artery, □η may be defined as ηblood, Δx may be defined as LRA, and R may be defined as DRA/2. The change in pressure, ΔPr, across the renal artery may be measured at a common point in the cardiac cycle (e.g., via a pressure-sensing guidewire) to determine the volumetric flow rate through the renal artery at the chosen common point in the cardiac cycle (e.g. during systole and/or during enddiastole).

Volumetric flow rate additionally or alternatively may be measured directly or may be determined from blood flow velocity measurements. The volumetric blood flow rate through a renal artery generally is in the range of about 500-1000 mL/min.

Thermodynamic properties of the renal artery also are of interest. Such properties include, for example, the specific heat capacity of blood and/or of the vessel wall, thermal conductivity of blood and/or of the vessel wall, thermal convectivity of blood flow past a vessel wall treatment site. Thermal radiation also may be of interest, but it is expected that the magnitude of conductive and/or convective heat transfer is significantly higher than the magnitude of radiative heat transfer.

The heat transfer coefficient may be empirically measured, or may be calculated as a function of the thermal conductivity, the vessel diameter and the Nusselt Number. The Nusselt Number is a function of the Reynolds Number and the Prandtl Number. Calculation of the Reynolds Number takes into account flow velocity and rate, as well as fluid viscosity and density, while calculation of the Prandtl Number takes into account specific heat, as well as fluid viscosity and thermal conductivity. The heat transfer coefficient of blood flowing through the renal artery is generally in the range of about 500-6000 W/m2K.

An additional property of the renal artery that may be of interest is the degree of renal motion relative to the aorta, induced by respiration and/or blood flow pulsatility. A patient's kidney, located at the distal end of the renal artery, can move as much as 5 cm cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

These and other properties of the renal vasculature may impose constraints upon and/or inform the design of apparatus, systems and methods for achieving renal neuromodulation via intravascular access. Specific design requirements may include accessing the renal artery, facilitating stable contact between neuromodulatory apparatus and a luminal surface or wall of the renal artery, and/or safely modulating the renal nerves with the neuromodulatory apparatus.

II. CATHETER APPARATUSES, SYSTEMS AND METHODS FOR RENAL NEUROMODULATION

A. Overview

FIG. 5 shows a system 10 for thermally inducing neuromodulation of a left and/or right renal plexus (RP) through intravascular access.

As just described, the left and/or right renal plexus (RP) surrounds the respective left and/or right renal artery. The renal plexus (RP) extends in intimate association with the respective renal artery into the substance of the kidney. The system thermally induces neuromodulation of a renal plexus (RP) by intravascular access into the respective left or right renal artery.

Figure 6A:
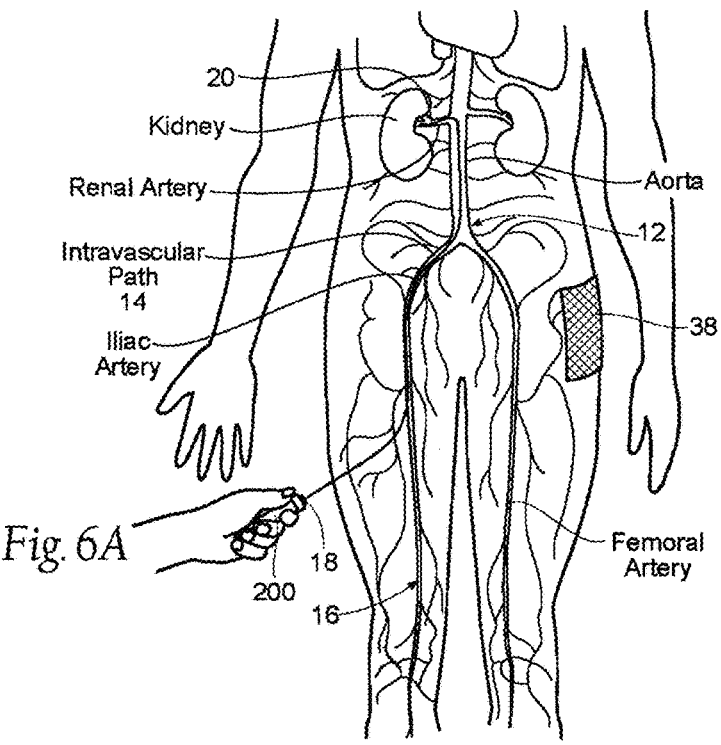
FIGS. 6A to 6D are anatomic views of the intravascular delivery, deflection and placement of various embodiments of the treatment device shown in FIG. 5 through the femoral artery and into a renal artery.

The system 10 includes an intravascular treatment device 12. The treatment device 12 provides access to the renal plexus (RP) through an intravascular path 14 that leads to a respective renal artery, as FIG. 6A shows.

As FIG. 5 shows, the treatment device 12 includes an elongated shaft 16 having a proximal end region or portion 18 and a distal end region or portion 20.

The proximal end region 18 of the elongated shaft 16 is optionally connected to a handle assembly 200. The handle assembly 200 is sized and configured to be securely or ergonomically held and manipulated by a caregiver outside an intravascular path 14 (see, e.g. FIGS. 16A and 6A). By manipulating the handle assembly 200 from outside the intravascular path 14, the caregiver can advance the elongated shaft 16 through the tortuous intravascular path 14 and remotely manipulate or actuate the distal end region 20. Image guidance, e.g., CT, radiographic, IVUS, OCT or another suitable guidance modality, or combinations thereof, can be used to aid the caregiver's manipulation.

Figure 6B:
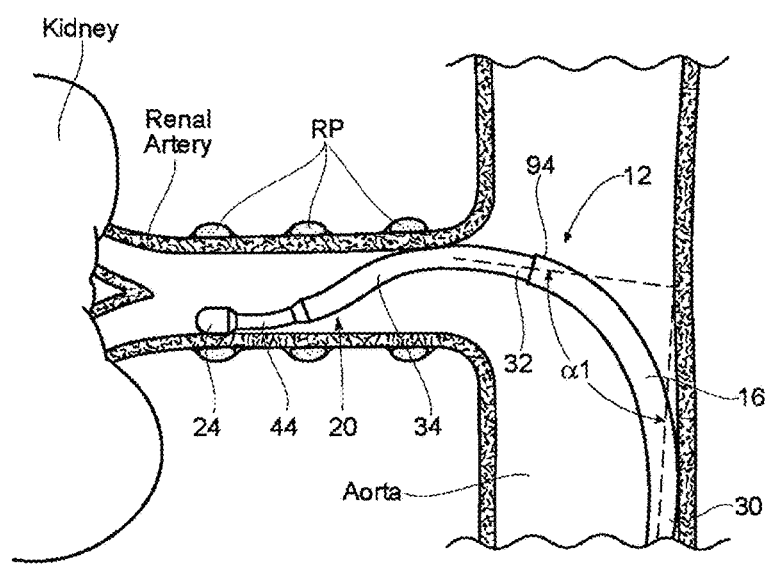
Figures 28A, 28B:
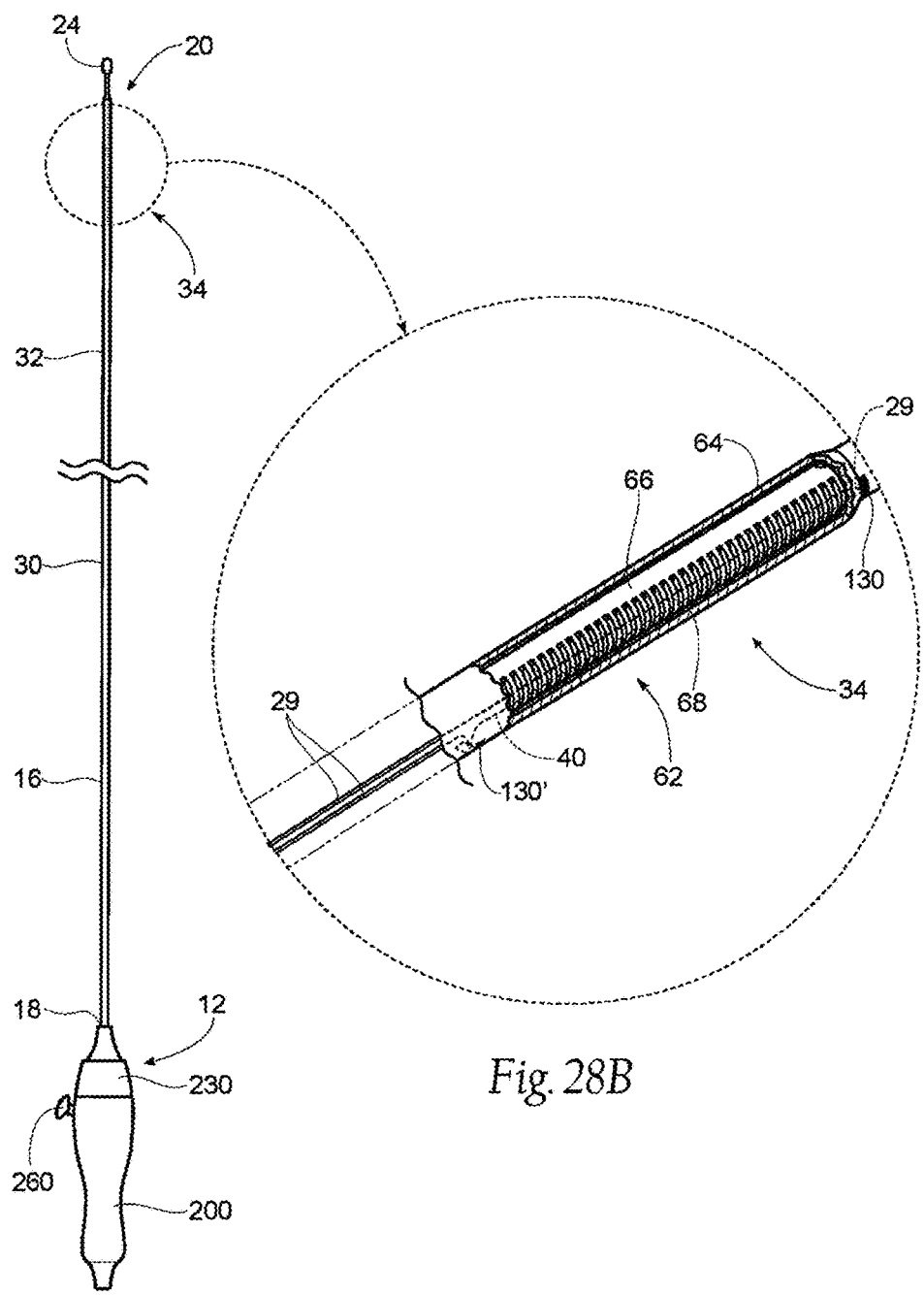
FIGS. 28A and 28B show additional alternative representative embodiments of an elongated shaft for a treatment device having an electrically activated deflectable section.

As shown in FIG. 6B, the distal end region 20 of the elongated shaft 16 can flex in a substantial fashion to gain entrance into a respective left/right renal artery by manipulation of the elongated shaft 16. As shown in FIGS. 28A and 28B, the distal end region 20 of the elongated shaft 16 can gain entrance to the renal artery via passage within a guide catheter 94. The distal end region 20 of the elongated shaft 16 carries at least one energy delivery element 24 (e.g., radiofrequency electrode, electrode, cooled radiofrequency electrode, thermal element, thermal heating element, electrically resistive heating element, cryoablation applicator, microwave antenna, ultrasound transducer, high intensity focused ultrasound transducer, laser emitter). The energy delivery element 24 is also specially sized and configured for manipulation and use within a renal artery.

As FIG. 6B shows, once entrance to a renal artery is gained, further manipulation of the distal end region 20 and the energy delivery element(s) 24 within the respective renal artery establishes proximity to and alignment between the energy delivery element(s) 24 and tissue along an interior wall of the respective renal artery. In some embodiments, manipulation of the distal end region 20 will also facilitate contact between the energy delivery element 24 and a wall of the renal artery. In the context of the present application, the phrasing "contact between an energy delivery element and a wall of the renal artery" generally means contiguous physical contact with or without atraumatic distension of the renal artery wall and without puncturing or perforating the renal artery wall.

In the representative embodiment of FIG. 6B, the thermal heating element 24 of distal end region 20 is positioned along a distal tip or end of the distal end region, e.g., at a distal end of an optional third or distal flexure zone 44. However, it should be understood that the distal end region 20 optionally may comprise one or more additional thermal heating elements that are positioned relatively more proximal. When multiple thermal heating elements are provided, the thermal heating elements may deliver power independently (i.e., may be used in a monopolar fashion), either simultaneously or progressively, and/or may deliver power between any desired combination of the elements (i.e., may be used in a bipolar fashion). Furthermore, the caregiver optionally may be capable of dynamically choosing which thermal heating element(s) are used for power delivery in order to form highly customizable lesion(s) within the renal artery, as desired.

Figure 6C:
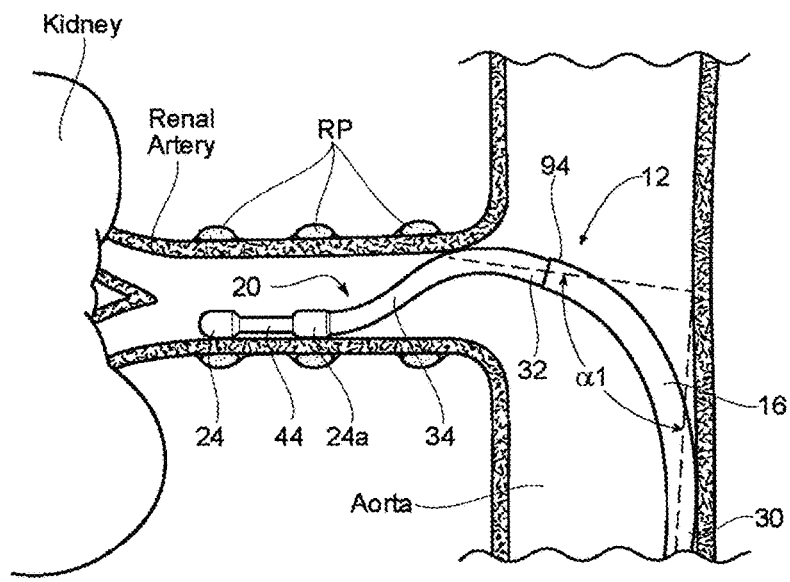

In one representative embodiment shown in FIG. 6C, one or more additional thermal heating elements 24a optionally may be positioned proximally of thermal heating element 24, e.g., along a third flexure zone 44, at a proximal region of the optional third flexure zone 44 and/or at a distal region of an optional second or intermediate flexure zone 34 for contacting an internal wall of the renal artery at position(s) longitudinally spaced, but generally in angular alignment, with the distally located thermal heating element 24. The spacing of the thermal heating elements 24 and 24a may be specified to provide a desired spacing between lesions formed when using the elements within a renal artery. In one representative embodiment, thermal heating elements 24 and 24a are spaced apart as far as about 1 cm. In other embodiments, the spacing between thermal heating elements 24 and 24a is in the range of about 2 mm to about 5 mm. In one representative embodiment, the thermal heating elements 24 and 24a are spaced apart about 5 mm. In another representative embodiment, the thermal heating elements 24 and 24a are spaced apart about 2 mm.

Figure 6D:
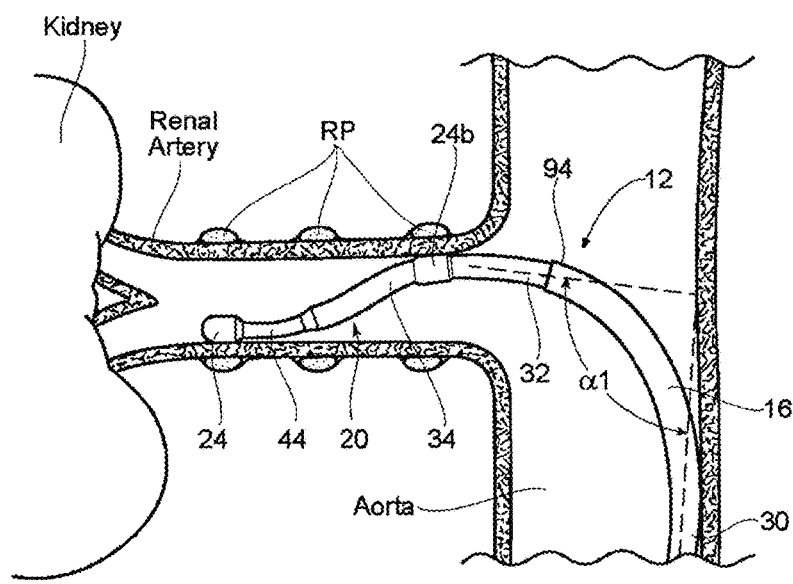

Additionally or alternatively, as shown in FIG. 6D, one or more thermal heating elements 24b may be positioned relatively more proximal for contacting an internal wall of the renal artery at position(s) that are longitudinally and angularly spaced (e.g., in angular opposition) from the distally located thermal heating element 24. Such thermal heating element(s) 24b may, for example, be positioned at an apex of a bend formed during deflection of the optional second flexure zone 34, at a proximal region of the optional second flexure zone 34, and/or at a distal region of a first or proximal flexure zone 32. The spacing separating thermal heating element 24b from thermal heating element 24 and/or from optional thermal heating element 24a may be specified as desired to provide desired longitudinal and angular spacing between lesions formed within renal vasculature. In one representative embodiment, thermal heating elements 24 and 24b are spaced apart about 5 mm to about 25 mm. In another representative embodiment, the thermal heating elements 24 and 24b can be spaced as far as about 30 mm. In another representative embodiment, the thermal heating elements 24 and 24b are spaced apart about 11 mm. In still another representative embodiment, the thermal heating elements 24 and 24b are spaced apart about 17.5 mm.

As also will be described in greater detail later, different sections of the elongated shaft 16 serve different mechanical functions when in use. The sections are thereby desirably differentiated in terms of their size, configuration and mechanical properties for (i) percutaneous introduction into a femoral artery through a small-diameter access site; (ii) atraumatic passage through the tortuous intravascular path 14 through an iliac artery, into the aorta, and into a respective left/right renal artery, including (iii) significant flexure near the junction of the left/right renal arteries and aorta to gain entry into the respective left or right renal artery; (iv) controlled translation, deflection, rotation and/or actuation within the respective renal artery to attain proximity to and a desired alignment with an interior wall of the respective renal artery; (v) the placement of at least one energy delivery element 24 into contact with tissue on the interior wall; (vi) allowing substantially stable contact force between the at least one energy delivery element and the interior wall during motion of the renal artery with respect to the aorta due to respiration and/or blood flow pulsatility; and (vii) repositioning via retraction and/or deflection in a multiple directions and/or rotation within the renal artery for subsequent treatment(s).

Referring back to FIG. 5, the system 10 also includes an energy generator 26 (e.g., a radiofrequency generator). Under the control of the caregiver or automated control algorithm 102 (as will be described in greater detail later), the generator 26 generates a selected form and magnitude of energy. A cable 28 operatively attached to the handle assembly 200 electrically connects the energy delivery element 24 to the generator 26. At least one supply wire (not shown) passing along the elongated shaft 16 or through a lumen in the elongated shaft 16 from the handle assembly 200 to the energy delivery element 24 conveys the treatment energy to the energy delivery element 24. A control mechanism, such as foot pedal 100, can be connected (e.g., pneumatically connected or electrically connected) to the generator 26 to allow the operator to initiate, terminate and, optionally, adjust various operational characteristics of the generator, including, but not limited to, power delivery.

For systems that provide for the delivery of a monopolar electric field via the energy delivery element 24, a neutral or dispersive electrode 38 can be electrically connected to the generator 26 and attached to the exterior of the patient. Additionally, one or more sensors 52 (see, e.g., FIGS. 9A and 9B), such as one or more temperature (e.g., thermocouple, thermistor, etc.), impedance, pressure, optical, flow, chemical or other sensors, can be located proximate to or within the energy delivery element and connected to one or more of the supply wires. For example, a total of two supply wires can be included, in which both wires could transmit the signal from the sensor and one wire could serve dual purpose and also convey the energy to the energy delivery element. Alternatively, both wires could transmit energy to the energy delivery element.

Once proximity between, alignment with, and contact between the energy delivery element 24 and tissue are established within the respective renal artery (as FIG. 6B shows), the purposeful application of energy from the generator 26 to tissue by the energy delivery element 24 induces one or more desired neuromodulating effects on localized regions of the renal artery and adjacent regions of the renal plexus (RP), which lay intimately within or adjacent to the adventitia of the renal artery. The purposeful application of the neuromodulating effects can achieve neuromodulation along all or a portion of the RP.

The neuromodulating effects can include both thermal ablation, non-ablative thermal alteration or damage (e.g., via sustained heating and/or resistive heating), and electromagnetic neuromodulation. Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration. Desired electromagnetic neuromodulation effects may include altering the electrical signals transmitted in a nerve.

Further details of special size, configuration, and mechanical properties of the elongated shaft 16, the distal end region 20 and the energy delivery element 24, as well as other aspects of the system 10, will now be described. In still other embodiments, the system 10 may have a different configuration and/or include different features. For example, alternative multi-energy delivery element devices, such as multi-electrode baskets, spirals or lassos, or balloon expandable devices, may be implemented to intravascularly deliver neuromodulatory treatment with or without contacting the vessel wall.

B. Size and Configuration of the Elongated Shaft for Achieving Intravascular Access to a Renal Artery As explained above, intravascular access to an interior of a renal artery can be achieved, for example, through the femoral artery. As FIG. 6A shows, the elongated shaft 16 is specially sized and configured to accommodate passage through this intravascular path 14, which leads from a percutaneous access site in the femoral artery to a targeted treatment site within a renal artery. In this way, the caregiver is able to orient the energy delivery element 24 within the renal artery for its intended purpose.

For practical purposes, the maximum outer dimension (e.g., diameter) of any section of the elongated shaft 16, including the energy delivery element 24 it carries, is dictated by the inner diameter of the guide catheter or delivery catheter through which the elongated shaft 16 is passed. Assuming, for example, that an 8 French guide catheter (which has an inner diameter of approximately 0.091 inches) would likely be, from a clinical perspective, the largest guide catheter used to access the renal artery, and allowing for a reasonable clearance tolerance between the energy delivery element 24 and the guide catheter, the maximum outer dimension can be realistically expressed as being less than or equal to approximately 0.085 inches. However, use of a smaller 5 French guide catheter 94 may require the use of smaller outer diameters along the elongated shaft 16. For example, an energy delivery element 24 that is to be routed within a 5 French guide catheter would have an outer dimension of no greater than 0.053 inches. In another example, an energy delivery element 24 that is to be routed within a 6 French guide catheter would have an outer dimension of no greater than 0.070 inches.

1. Force Transmitting Section

Figure 7E:
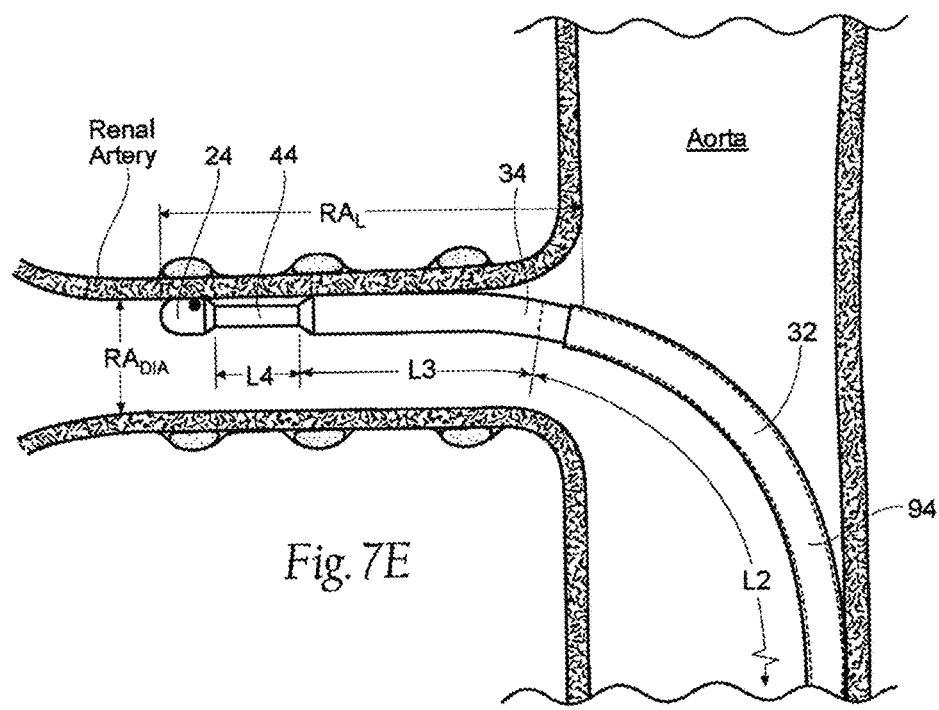
FIG. 7E shows an anatomic view of the placement of the treatment device shown in FIG. 5 within the dimensions of the renal artery.

As FIG. 7A shows, the proximal end region 18 of the elongated shaft 16 includes, coupled to the handle assembly 200, a force transmitting section 30. The force transmitting section 30 is sized and configured to possess selected mechanical properties that accommodate physical passage through and the transmission of forces within the intravascular path 14, as it leads from the accessed femoral artery (left or right), through the respective iliac branch artery and into the aorta, and in proximity to the targeted renal artery (left or right). The mechanical properties of the force transmitting section 30 include at least a preferred effective length (expressed in inches or centimeters). It should be understood that the term force transmitting section can be used interchangeably with elongated tubular shaft or proximal force transmitting section.

As FIG. 7A shows, the force transmitting section 30 includes a preferred effective length L1. The preferred effective length L1 is a function of the anatomic distance within the intravascular path 14 between the access site and a location proximate to the junction of the aorta and renal arteries. The preferred effective length L1 can be derived from textbooks of human anatomy, augmented by a caregiver's knowledge of the targeted site generally or as derived from prior analysis of the particular morphology of the targeted site. The preferred effective length L1 is also dependent on the length of the guide catheter that is used, if any. In a representative embodiment, for a normal human, the preferred effective length L1 comprises about 30 cm to about 110 cm. If no guide catheter is used, then the preferred effective length L1 comprises about 30 cm to about 35 cm. If a 55 cm length guide catheter is used, then the preferred effective length L1 comprises about 65 cm to about 70 cm. If a 90 cm length guide catheter is used, then the preferred effective length L1 comprises about 95 cm to about 105 cm.

The force transmitting section 30 also includes a preferred axial stiffness and a preferred torsional stiffness. The preferred axial stiffness expresses the capability of the force transmitting section 30 to be advanced or withdrawn along the length of the intravascular path 14 without buckling or substantial deformation. Since some axial deformation is necessary for the force transmitting section 30 to navigate the tortuous intravascular path 14 without providing too much resistance, the preferred axial stiffness of the force transmitting section should also provide this capability. The preferred torsional stiffness expresses the capability of the force transmitting section 30 to rotate the elongated shaft 16 about its longitudinal axis along its length without kinking or permanent deformation. As will be described in greater detail later, the ability to advance and retract, as well as rotate, the distal end region 20 of the elongated shaft 16 within the respective renal artery is desirable.

The desired magnitude of axial stiffness and rotational stiffness for the force transmitting section 30 can be obtained by selection of constituent material or materials to provide a desired elastic modulus (expressed in terms, e.g., of a Young's Modulus (E)) indicative of axial and torsional stiffnesses, as well as selecting the construct and configuration of the force transmitted section in terms of, e.g., its interior diameter, outer diameter, wall thickness, and structural features, including cross-sectional dimensions and geometry. Representative examples are described in greater detail below.

2. First Flexure Zone

As FIGS. 7A and 7B show, the distal end region 20 of the elongated shaft 16 is coupled to the force transmitting section 30. The length L1 of the force transmitting section 30 generally serves to bring the distal end region 20 into the vicinity of the junction of the respective renal artery and aorta (as FIG. 6B shows). The axial stiffness and torsional stiffness of the force transmitting region transfer axial and rotation forces from the handle assembly 200 to the distal end region 20, as will be described in greater detail later. It should be understood that the term first flexure zone can be used interchangeably with flexible tubular structure.

As shown in FIG. 7B, the distal end region 20 includes a first flexure zone 32 proximate to the force transmitting section 30. The first flexure zone 32 is sized and configured to have mechanical properties that accommodate significant flexure or bending at a prescribed preferred access angle α1 and provide for the transmission of torque during rotation, without fracture, collapse, substantial distortion, or significant twisting of the elongated shaft 16. The first flexure zone 32 should accommodate flexure sufficient for the distal end region 20 to advance via a guide catheter into the renal artery without substantially straightening out the guide catheter.

Angle α1 is defined by the angular deviation that the treatment device 12 must navigate to transition between the aorta (along which the force transmitting section 30 is aligned) and the targeted renal artery (along which the distal end region 20 is aligned) (this is also shown in FIG. 6B). This is the angle that the first flexure zone 32 must approximate to align the distal end region 20 of the elongated shaft 16 with the targeted renal artery, while the force transmitting section 30 of the elongated shaft 16 remains aligned with the native axis of the aorta (as FIG. 6B shows). The more tortuous a vessel, or the more severe the take-off angle between the renal artery and the aorta, the greater bend the first flexure zone 32 will need to make for the distal end region of the treatment device to access the renal artery and the smaller the angle α1.

When the catheter is outside the patient and the first flexure zone 32 is in a substantially straight, non-deflected configuration, angle α1 (as shown in FIG. 7B) is approximately 180°. Upon full deflection of the first flexure zone 32, the angle α1 is reduced to anywhere between about 30° and 180°. In a representative embodiment, upon full deflection angle α1 is about 30° to about 135°. In another representative embodiment, upon full deflection angle α1 is about 90°.

The first flexure zone 32 is sized and configured to possess mechanical properties that accommodate significant, abrupt flexure or bending at the access angle α1 near the junction of the aorta and the renal artery. Due to its size, configuration, and mechanical properties, the first flexure zone 32 must resolve these flexure or bending forces without fracture, collapse, distortion, or significant twisting. Such flexure or bending of the first flexure zone may occur at least in part within the distal region of a guide catheter without substantially straightening out the guide catheter. The resolution of these flexure or bending forces by the first flexure zone 32 makes it possible for the distal end region 20 of the elongated shaft 16 to gain entry along the intravascular path 14 into a targeted left or right renal artery.

The first flexure zone 32 is sized and configured in length L2 to be less than length L1 (see FIG. 7A). That is because the distance between the femoral access site and the junction of the aorta and renal artery (typically approximating about 40 cm to about 55 cm) is generally greater than the length of a renal artery between the aorta and the most distal treatment site along the length of the renal artery, which is typically less than about 7 cm. The preferred effective length L2 can be derived from textbooks of human anatomy, augmented with a caregiver's knowledge of the site generally or as derived from prior analysis of the particular morphology of the targeted site. For example, the length L2 generally may be less than about 15 cm, e.g., may be less than about 10 cm. In one representative embodiment, the length L2 may be about 9 cm.

Desirably, the length L2 is selected to make it possible to rest a portion of the first flexure zone 32 partially in the aorta at or near the length L1, as well as rest the remaining portion of the first flexure zone 32 partially within the renal artery (as FIG. 6B shows). In this way, the first flexure zone 32 defines a transitional bend that is supported and stable within the vasculature.

In the deflected configuration of FIG. 7B, the first flexure zone 32 comprises a radius of curvature RoC1. In embodiments where the curvature of first flexure zone 32 does not vary or is consistent along the length L2, the length L2 and the deflection angle α1 may define the radius of curvature RoC1. It should be understood that the curvature of first flexure zone 32, and thereby the radius of curvature RoC1 of the first flexure zone, alternatively may vary along the length L2.

In such embodiments where the curvature does not vary, the length L2 may define a fraction (180°−α1)/360° of the circumference C1 of a circle with an equivalent radius of curvature RoC1. Thus, the circumference of such an equivalent circle is:

$$C_1 = \frac{360°}{(180° - \alpha 1)} \times L2 = 2\pi \times RoC_1 \qquad (10)$$

Solving for the radius of curvature $RoC_1$:

$$RoC_1 = \frac{360° \times L2}{2\pi \times (180° - \alpha 1)} \qquad (11)$$

Thus, in a representative embodiment of the first flexure zone 32 where the curvature of the first flexure zone does not vary along the length L2, where the length L2 is less than or equal to about 9 cm, and where the angle α1 is about 30° to about 135°, the radius of curvature RoC1 is about 3.5 cm to about 11.5 cm. In a representative embodiment of first flexure zone 32 where the curvature of the first flexure zone does not vary along the length L2, where the length L2 is less than or equal to about 9 cm, and where the angle α1 is about 90°, the radius of curvature RoC1 is less than or equal to about 5.75 cm.

As will be apparent, Equation (11) may be rearranged such that the length L2 and the radius of curvature RoC1 define the angle α1. Furthermore, Equation (11) may be rearranged such that the radius of curvature RoC1 and the angle α1 define the length L2. Thus, in embodiments where the curvature of first flexure zone 34 does not vary along the length L2, any one of the length L2, angle α1 and radius of curvature RoC1 may be specified by specifying the other two variables.

As will be described in greater detail later, and as shown in FIG. 6B, the length L2 of the first flexure zone 32 optionally does not extend the full length of the targeted length of the renal artery. That is because the distal end region 20 of the elongated shaft 16 optionally includes one or more additional flexure zones, distal to the first flexure zone 32 (toward the substance of the kidney), to accommodate other different functions important to the therapeutic objectives of the treatment device 12. As will be described later, the ability to transmit torque through the first flexure zone 32 makes it possible to rotate the thermal heating device to properly position the energy delivery element within the renal artery for treatment.

In terms of axial and torsional stiffness, the mechanical properties of first flexure zone 32 can, and desirably do, differ from the mechanical properties of the force transmitting section 30. This is because the first flexure zone 32 and the force transmitting section serve different functions while in use. Alternatively, the mechanical properties of first flexure zone 32 and force transmitting section 30 can be similar.

The force transmitting section 30 serves in use to transmit axial load and torque over a relatively long length (L1) within the vascular pathway. In contrast, the first flexure zone 32 needs to transmit axial load and torque over a lesser length L2 proximate to or within a respective renal artery. Importantly, the first flexure zone 32 must abruptly conform to an access angle α1 near the junction of the aorta and the respective renal artery, without fracture, collapse, substantial distortion, or significant twisting, or straightening a guide catheter imparting the access angle α1. This is a function that the force transmitting zone need not perform. Accordingly, the first flexure zone 32 is sized and configured to be less stiff and to possess greater flexibility than the force transmitting section 30.

Additionally, the first flexure zone 32 may allow energy delivery element(s) 24 to maintain stable contact with the interior wall of the renal artery as the respective kidney moves due to patient respiration. As a patient breathes the kidney may move, causing the renal artery to pivot about the ostium, where the renal artery joins the aorta. Stable contact between the energy delivery element(s) 24 and the inner wall of the renal artery is desired during energy delivery. Therefore, the energy delivery element(s) 24 must move, along with the renal artery, relative to the aorta. The mechanical properties of the first flexure zone 32 that accommodate significant, abrupt flexure or bending at the access angle α1 near the junction of the aorta and the renal artery also allow the sections of the catheter distal to the first flexure zone 32 to pivot about the ostium without significant impediment, allowing the energy delivery element to maintain stable contact force with the inner wall of the renal artery. In some embodiments, deflectable section 34 distal to first flexure zone 32 may become stiffer than the first flexure zone 32 when it is controllably deflected. The additional stiffness of deflectable section 34 helps maintain a stable contact force between the energy delivery element 24 and an inner wall of the renal artery and allows the catheter to move with the renal artery relative to the aorta with sufficient freedom due to the flexible deformation of the first flexure zone 32. The renal artery pivots about the juncture with the aorta such that movement of the renal artery increases with distance from the juncture with the aorta. The length of the distal end region 20 distal to the first flexure zone 32 along with the length of the first flexure zone 32 is configured such that an increasing portion of the first flexure zone 32 is positioned in the renal artery the more distal the treatment site to provide sufficient increased flexibility in the region of the juncture with the aorta to allow stable contact force between the energy delivery element 24 and the more distal treatment site of the inner wall of the renal artery, especially during increased motion at the more distal treatment site.

The desired magnitude of axial stiffness, rotational stiffness, and flexibility for the first flexure zone 32 can be obtained by selection of constituent material or materials to provide a desired elastic modulus (expressed, e.g., in terms of a Young's Modulus (E)) indicative of flexibility, as well as selecting the construct and configuration of the force transmitting section, e.g., in terms of its interior diameter, outer diameter, wall thickness, and structural features, including cross-sectional dimensions and geometry. Representative examples will be described in greater detail later.

Although it is desirable that the force transmitting section 30 and the first flexure zone 32 have stiffness and flexibility properties that are unique to their respective functions, it is possible that the force transmitting section 30 and the first flexure zone 32 comprise the same materials, size and geometric configuration such that the force transmitting section 30 and the first flexure zone 32 constitute the same section.

3. Second Flexure Zone

As shown in FIGS. 7A, 7B, and 7C, the distal end region 20 of the elongated shaft 16 also optionally may include, distal to the first flexure zone 32, a second flexure zone 34. In some embodiments, the energy delivery element 24 may be supported by the second flexure zone 34. It should be understood that the term second flexure zone can be used interchangeably with deflectable section or intermediate flexure zone or deflectable tubular body or multi-directional deflectable assembly.

The second flexure zone 34 is sized, configured, and has the mechanical properties that accommodate additional flexure or bending, independent of the first flexure zone 32, at a preferred contact angle α2, without fracture, collapse, substantial distortion, or significant twisting. The second flexure zone 34 should also accommodate flexure sufficient for the distal end region 20 to advance via a guide catheter into the renal artery without straightening out the guide catheter. The second flexure zone 34 may be configured in some embodiments for controllable deflection in multiple directions.

The preferred contact angle α2 is defined by the angle through which the energy delivery element 24 can be radially deflected within the renal artery to establish contact between the energy delivery element 24 and an inner wall of the respective renal artery (as FIG. 6B shows). The magnitude of the contact angle α2 and the length of the second flexure zone L3 preferably are based on the native inside diameter of the respective renal artery where the energy delivery element 24 rests, which may vary between about 2 mm and about 10 mm, as well as the diameter of the energy delivery element 24. It is most common for the diameter of the renal artery to vary between about 2 mm and about 8 mm, with a mean diameter of about 6 mm.

The second flexure zone 34 extends distally from the first flexure zone 32 for a length L3 into the targeted renal artery (see FIG. 6B). Desirably, the length L3 is selected, taking into account the length L2 of the first flexure zone 32 that extends into the renal artery, as well as the anatomy of the respective renal artery, to actively place the energy delivery element 24 (carried at the end of the distal end region 20) at or near the targeted treatment site (as FIG. 6B shows). The length L3 can be derived, taking the length L2 into account, from textbooks of human anatomy, together with a caregiver's knowledge of the site generally or as derived from prior analysis of the particular morphology of the targeted site.

As FIG. 7A shows, the second flexure zone 34 is desirably sized and configured in length L3 to be less than length L2. This is because, in terms of length, the distance required for actively deflecting the energy delivery element 24 into contact with a wall of the renal artery is significantly less than the distance required for bending the elongated shaft 16 to gain access from the aorta into the renal artery. Thus, the length of the renal artery is occupied in large part by the second flexure zone 34 and not as much by the first flexure zone 32.

In a representative embodiment, L2 is less than or equal to about 9 cm and L3 is about 5 mm to about 15 mm. In certain embodiments, particularly for treatments in relatively long blood vessels, L3 can be less than or equal to about 20 mm. In another representative embodiment, and as described later in greater detail, L3 is less than or equal to about 12.5 mm. In another representative embodiment, particularly wherein second flexure zone comprises a hinge joint, L3 is no greater than 3 mm. about 12.5 mm.

When the catheter is outside the patient and the second flexure zone 34 is in a substantially straight, non-deflected configuration, contact angle α2 (as shown in FIG. 7C) is approximately 180°. Upon full deflection of the second flexure zone 34, the angle α2 is reduced to anywhere between about 45° and 180°. In a representative embodiment, upon full deflection, angle α2 is about 75° to about 135°. In another representative embodiment, upon full deflection, angle α2 is less than or equal to about 90°.

In the deflected configuration of FIG. 7C, the second flexure zone 34 comprises a radius of curvature RoC2. In embodiments where the curvature of second flexure zone 34 does not vary or is consistent along the length L3, the length L3 and the contact angle α2 may define the radius of curvature RoC2. It should be understood that the curvature of second flexure zone 34, and thereby the radius of curvature RoC2 of the second flexure zone, alternatively may vary along the length L3.

In such embodiments where the curvature does not vary, the length L3 may define a fraction (180°−α2)/360° of the circumference C2 of a circle with an equivalent radius of curvature RoC2. Thus, the circumference of such an equivalent circle is:

$$C_2 = \frac{360°}{(180° - \alpha 2)} \times L3 = 2\pi \times RoC_2 \quad (12)$$

Solving for the radius of curvature RoC2:

$$RoC_2 = \frac{360° \times L3}{2\pi \times (180° - \alpha 2)} \quad (13)$$

Thus, in a representative embodiment of the second flexure zone 34 where the curvature of the second flexure zone does not vary along the length L3, where the length L3 is about 5 mm to about 20 mm, and where the contact angle α2 is about 75° to about 135°, the radius of curvature RoC2 is about 3 mm to about 25 mm. In a representative embodiment of second flexure zone 34 where the curvature of the second flexure zone does not vary along the length L3, where the length L3 is about 12.5 mm, for example less than or equal to about 12.5 mm, and where the angle α2 is about 75° to about 135°, the radius of curvature RoC2 is about 7 mm to about 16 mm, for example less than or equal to about 15 mm. In a representative embodiment of second flexure zone 34 where the curvature of the second flexure zone does not vary along the length L3, where the length L3 is about 12.5 mm, and where the angle α2 is about 90°, the radius of curvature RoC2 is about 8 mm.

As will be apparent, Equation (13) may be rearranged such that the length L3 and the radius of curvature RoC2 define the contact angle α2. Furthermore, Equation (13) may be rearranged such that the radius of curvature RoC2 and the angle α2 define the length L3. Thus, in embodiments where the curvature of second flexure zone 34 does not vary along the length L3, any one of the length L3, angle α2 and radius of curvature RoC2 may be specified by specifying the other two variables.

In the deflected configuration of FIG. 7C, the second flexure zone 34 locates the energy delivery element 24 at a dimension Y from a longitudinal axis A of the second flexure zone 34 just distal of the first flexure zone 32. The dimension Y can vary from about 2 mm to about 20 mm. In some configurations, and given the dimension of most renal arteries, the dimension Y can be from about 5 mm to about 15 mm. Since the average diameter of most renal arteries is generally less than 10 mm as described below, it may be desirable for dimension Y to be less than or equal to 10 mm. For example the Y dimension can be 6 mm or 8 mm or anywhere between and including 6 mm to 10 mm.

By way of example, the average diameter of a human renal artery is from about 2 mm to about 8 mm, but may range from about 2 mm to about 10 mm. Accordingly, if the distal end of the first flexure zone 32 were positioned adjacent to a wall of an artery having an 8 mm diameter, the second flexure zone 34 would be capable of deflection sufficient for the energy delivery element 24 to contact the opposite wall of the artery. In other embodiments, however, the dimension Y may have a different value and may be oversized to facilitate contact in a straight or curved vessel. The second flexure zone 34 is also configured to locate the energy delivery element 24 at a dimension X from a distal end of the first flexure zone 32. The dimension X can vary, e.g., based on the dimension Y and the length L3.

As FIG. 7C shows, having first and second flexure zones 32 and 34, the distal end region 20 of the elongated shaft 16 can, in use, be placed into a complex, multi-bend structure 36. The complex, multi-bend structure 36 comprises one deflection region at the access angle α1 over a length L2 (the first flexure zone 32) and a second deflection region at the contact angle α2 over a length L3 (the second flexure zone 34). In the complex, multi-bend, both L2 and L3 and angle α1 and angle α2 can differ. This is because the angle α1 and length L2 are specially sized and configured to gain access from an aorta into a respective renal artery through a femoral artery access point, and the angle α2 and length L3 are specially sized and configured to align an energy delivery element 24 with an interior wall inside the renal artery.

In the illustrated embodiment (see, e.g., FIG. 7C), the second flexure zone 34 is sized and configured to allow a caregiver to remotely deflect the second flexure zone 34 within the renal artery, to radially position the energy delivery element 24 into contact with an inner wall of the renal artery.

In the illustrated embodiment, a control mechanism is coupled to the second flexure zone 34. The control mechanism includes a control wire 40 attached to the distal end of the second flexure zone 34 (a representative embodiment is shown in FIGS. 12B and 12C and will be described in greater detail later). It should be understood that the term control wire can be used interchangeably with flexure control element. The control wire 40 is passed proximally through the elongated shaft 16 and coupled to an actuator 260 (also called a flexure controller) on the handle assembly 200. Operation of the actuator 260 (e.g., by the caregiver pulling proximally on or pushing forward the actuator 260) pulls the control wire 40 back to apply a compressive and bending force to the second flexure zone 34 (as FIGS. 7C and 12C show) resulting in bending. The compressive force in combination with the optional directionally biased stiffness (described further below) of the second flexure zone 34 deflects the second flexure zone 34 and, thereby, radially moves the energy delivery element 24 toward an interior wall of the renal artery (as FIG. 6B shows).

Desirably, as will be described in greater detail later, the distal end region 20 of the elongated shaft 16 can be sized and configured to vary the stiffness of the second flexure zone 34 about its circumference. The variable circumferential stiffness imparts preferential and directional bending to the second flexure zone 34 (i.e., directionally biased stiffness). In response to operation of the actuator 260, the second flexure zone 34 may be configured to bend in a single preferential direction. Representative embodiments exemplifying this feature will be described in greater detail later. Additional representative embodiments depicting multidirectional bending will also be described later in greater detail.

The compressive and bending force and resulting directional bending from the deflection of the second flexure zone 34 has the consequence of altering the axial stiffness of the second flexure zone. The actuation of the control wire 40 serves to increase the axial stiffness of the second flexure zone. As will be described later, the axial stiffness of the deflected second flexure zone in combination with other flexible aspects of the distal end region of the catheter treatment device allows for favorable performance in a renal artery neuromodulation treatment.

In terms of axial and torsional stiffnesses, the mechanical properties of second flexure zone 34 can, and desirably do, differ from the mechanical properties of the first flexure zone 32. This is because the first flexure zone 32 and the second flexure zone 34 serve different functions while in use.

The first flexure zone 32 transmits axial load and torque over a longer length (L2) than the second flexure zone 34 (L3). Importantly, the second flexure zone 34 is also sized and configured to be deflected remotely within the renal artery by the caregiver. In this arrangement, less resistance to deflection is desirable. This is a function that the first flexure zone 32 need not perform. Accordingly, the second flexure zone 34 is desirably sized and configured to be less stiff (when the control wire 40 is not actuated) and, importantly, to possess greater flexibility than the first flexure zone 32 in at least one plane of motion.

Still, because the second flexure zone 34, being distal to the first flexure zone 32, precedes the first flexure zone 32 through the access angle access angle α1, the second flexure zone 34 also includes mechanical properties that accommodate its flexure or bending at the preferred access angle α1, without fracture, collapse, substantial distortion, or significant twisting of the elongated shaft 16.

The desired magnitude of axial stiffness, rotational stiffness, and flexibility for the second flexure zone 34 can be obtained by selection of constituent material or materials to provide a desired elastic modulus (expressed, e.g., in terms of a Young's Modulus (E)) indicative of flexibility, as well as by selecting the construct and configuration of the second flexure zone 34, e.g., in terms of its interior diameter, outer diameter, wall thickness, and structural features, including cross-sectional dimensions and geometry. Representative examples will be described in greater detail later. Axial stiffness, torsional stiffness, and flexibility are properties that can be measured and characterized in conventional ways.

As before described, both the first and second flexure zones 32 and 34 desirably include the mechanical properties of axial stiffness sufficient to transmit to the energy delivery element 24 an axial locating force. By pulling back on the handle assembly 200, axial forces are transmitted by the force transmitting section 30 and the first and second flexure zones 32 and 34 to retract the energy delivery element 24 in a proximal direction (away from the kidney) within the renal artery. Likewise, by pushing forward on the handle assembly 200, axial forces are transmitted by the force transmitting section 30 and the first and second flexure zones 32 and 34 to advance the energy delivery element 24 in a distal direction (toward the kidney) within the renal artery. Thus, proximal retraction of the distal end region 20 and energy delivery element 24 within the renal artery can be accomplished by the caregiver by manipulating the handle assembly 200 or shaft from outside the intravascular path 14.

As before described, both the first and second flexure zones 32 and 34 also desirably include torsional strength properties that will allow the transmission of sufficient rotational torque to rotate the distal end region 20 of the treatment device 12 such that the energy delivery element 24 is alongside the circumference of the blood vessel wall when the second flexure zone 34 is deflected. By pulling or pushing on the actuator to deflect the energy delivery element 24 such that it achieves vessel wall contact, and then rotating the force transmitting section 30 and, with it, the first and second flexure zones 32 and 34, the energy delivery element 24 can be rotated in a circumferential path within the renal artery. As described later, this rotating feature enables the clinical operator to maintain vessel wall contact as the energy delivery element 24 is being relocated to another treatment site. By maintaining wall contact in between treatments, the clinical operator is able to achieve wall contact in subsequent treatments with higher certainty in orientations with poor visualization.

4. Third Flexure Zone

As FIGS. 7A, 7B, 7C, and 7D show, the distal end region 20 of the elongated shaft 16 also optionally may include, distal to the optional second flexure zone 34, a third flexure zone 44. Third flexure zone may be used interchangeably with distal flexure zone and force dampening section. In this arrangement, the length L3 of the second flexure zone 34 may be shortened by a length L4, which comprises the length of the third flexure zone 44. In this arrangement, the energy delivery element 24 is carried at the end of the third flexure zone 44.

As FIG. 7D shows, the third flexure zone 44 is sized, configured, and has the mechanical properties that accommodate additional flexure or bending, independent of the first flexure zone 32 and the second flexure zone 34, at a preferred treatment angle α3. The third flexure zone 44 should also accommodate flexure sufficient for the distal end region 20 to advance via a guide catheter into the renal artery without straightening out the guide catheter or causing injury to the blood vessel. The treatment angle α3 provides for significant flexure about the axis of the distal end region 20 (a representative embodiment is shown in FIG. 15C). Not under the direct control of the physician, flexure at the third flexure zone occurs in response to contact between the energy delivery element 24 and wall tissue occasioned by the radial deflection of the energy delivery element 24 at the second flexure zone 34 (see FIG. 6B). Passive deflection of the third flexure zone provides the clinical operator with visual feedback via fluoroscopy or other angiographic guidance of vessel wall contact (as shown in FIGS. 46A to 46E). Additionally, the third flexure zone desirably orients the region of tissue contact along a side of the energy delivery element 24, thereby increasing the area of contact. The third flexure zone 44 also biases the energy delivery element 24 against tissue, thereby stabilizing the energy delivery element 24.

The function of the third flexure zone 44 provides additional benefits to the therapy. As actuation of the control wire 40 deflects the second flexure zone 34, pressing the energy delivery element 24 against an inner wall of an artery the third flexure zone effectively dampens the contact force between the energy delivery element 24 and the vessel wall. This effect is particularly valuable in a renal artery treatment due to movement of the renal artery caused by respiration and/or pulsatile flow. While the flexibility of the first flexure zone allows the distal end region of the treatment catheter to follow movement of the renal artery during respiration, the increased axial stiffness of the deflected second flexure zone provides helpful integrity to the distal end region to maintain contact between the energy delivery element and vessel wall. The third flexure zone helps soften or cushion the contact force so that atraumatic contact can be achieved and maintained, particularly during movement of the renal artery. By dampening this contact force, the third flexure zone minimizes the chance of mechanical injury to the vessel wall and avoids excessive contact between the energy delivery element and vessel wall (see discussion of active surface area).

As FIG. 7A shows, the third flexure zone 44 is desirably sized and configured in length L4 to be less than length L3. This is because, in terms of length, the distance required for orienting and stabilizing the energy delivery element 24 in contact with a wall of the renal artery is significantly less than the distance required for radially deflecting the energy delivery element 24 within the renal artery. In some embodiments, length L4 can be as long as about 1 cm. In other embodiments, the length L4 is from about 2 mm to about 5 mm. In one representative embodiment, the length L4 is less than or equal to about 5 mm. In another representative embodiment, the length L4 is less than or equal to about 2 mm. In another representative embodiment wherein the deflectable section 34 is comprised of a hinge joint, the length L4 is less than or equal to about 16 mm, which in this embodiment can be greater than the length L3 of the deflectable section 34.

When the catheter is outside the patient and the third flexure zone 44 is in a substantially straight, non-deflected configuration, treatment angle α3 (as shown in FIG. 7D) is approximately 180°. Upon full deflection of the third flexure zone 44, the angle α3 is reduced to anywhere between about 45° and 180°. In a representative embodiment, upon full deflection, angle α3 is about 75° to about 135°. In another representative embodiment, upon full deflection, angle α3 is about 90°.

In the passively deflected configuration of FIG. 7D, the third flexure zone 44 comprises a radius of curvature RoC3. In embodiments where the curvature of third flexure zone 44 does not vary or is consistent along the length L4, the length L4 and the contact angle α3 may define the radius of curvature RoC3. It should be understood that the curvature of third flexure zone 44, and thereby the radius of curvature RoC3 of the third flexure zone, alternatively may vary along the length L4.

In such embodiments where the curvature does not vary, the length L4 may define a fraction (180°−α3)/360° of the circumference C3 of a circle with an equivalent radius of curvature RoC3. Thus, the circumference of such an equivalent circle is:

$$C_3 = \frac{360°}{(180° - \alpha 3)} \times L4 = 2\pi \times RoC_3 \qquad (14)$$

Solving for the radius of curvature RoC2:

$$RoC_3 = \frac{360° \times L4}{2\pi \times (180° - \alpha 3)} \qquad (15)$$

Thus, in a representative embodiment of the third flexure zone 44 where the curvature of the third flexure zone does not vary along the length L4, where the length L4 is about 2 mm to about 5 mm, and where the contact angle α3 is about 75° to about 135°, the radius of curvature RoC3 is about 1 mm to about 6 mm.

As will be apparent, Equation (15) may be rearranged such that the length L4 and the radius of curvature RoC3 define the contact angle α3. Furthermore, Equation (15) may be rearranged such that the radius of curvature RoC3 and the angle α3 define the length L4. Thus, in embodiments where the curvature of third flexure zone 44 does not vary along the length L4, any one of the length L4, angle α3 and radius of curvature RoC3 may be specified by specifying the other two variables.

The mechanical properties of third flexure zone 44 and the second flexure zone 34 in terms of axial stiffness, torsional stiffness, and flexibility can be comparable. However, the third flexure zone 44 can be sized and configured to be less stiff and, importantly, to possess greater flexibility than the second flexure zone 34.

In the embodiment just described (and as shown in FIG. 7D), the distal end region 20 may comprise a first or proximal flexure zone 32, a second flexure zone 34, and a third flexure zone 44. The first, second and third flexure zones function independently from each other, so that the distal end region 20 of the elongated shaft 16 can, in use, be placed into a more compound, complex, multi-bend structure 36. The compound, complex, multi-bend structure 36 comprises a first deflection region at the access angle α1 over a length L2 (the first flexure zone 32); an second deflection region at the contact angle α2 over a length L3

(the second flexure zone 34); and a third deflection region at the treatment angle α3 over a length L4 (the third flexure zone 44). In the compound, complex, multi-bend structure 36, all lengths L2, L3, and L4 and all angles α1, α2, and α3 can differ. This is because the angle α1 and length L2 are specially sized and configured to gain access from an aorta into a respective renal artery through a femoral artery access point; the angle α2 and length L3 are specially sized and configured to align an energy delivery element 24 element with an interior wall inside the renal artery; and the angle α3 and length L4 are specially sized and configured to optimize surface contact between tissue and the energy delivery element.

The composite length of L2, L3 and L4 of the first, second and third flexure zones, respectively, of the distal end region 20, along with the length L1 of the force transmitting section 30 and the length L5 (see FIG. 8A) of the energy delivery element 24 (i.e., the composite length equal to L1+L2+L3+L4+L5), specifies a working length of the elongated shaft 16 of the treatment device 12. In some representative embodiments, this working length is about 40 cm to about 125 cm. In a representative embodiment where no guide catheter is used, then this working length may be about 40 cm to about 50 cm. If, alternatively, a 55 cm length guide catheter is used, then this working length may be about 70 cm to about 80 cm. If a 90 cm length guide catheter is used, then this working length may be about 105 cm to about 115 cm.

C. Size and Configuration of the Energy Delivery Element for Achieving Neuromodulation in a Renal Artery In some patients, it may be desirable to create multiple focal lesions that are circumferentially spaced along the longitudinal axis of the renal artery. However, it should be understood that a single focal lesion with desired longitudinal and/or circumferential dimensions, one or more full-circle lesions, multiple circumferentially spaced focal lesions at a common longitudinal position, and/or multiple longitudinally spaced focal lesions at a common circumferential position alternatively or additionally may be created.

Creating multiple focal lesions that are circumferentially spaced along the longitudinal axis of the renal artery avoids the creation of a full-circle lesion, thereby reducing a risk of vessel stenosis, while still providing the opportunity to circumferentially treat the renal plexus, which is distributed about the renal artery. It is desirable for each lesion to cover at least 10% of the vessel circumference to increase the probability of affecting the renal plexus. However, it is important that each lesion not be too large (e.g., >60% of vessel circumference) lest the risk of a stenotic effect increases (or other undesirable healing responses such as thrombus formation or collateral damage). In one embodiment the energy delivery element 24 is configured to create a lesion at least 30% (i.e., greater than or equal to 30%) of the vessel circumference. In another embodiment, the energy delivery element 24 is configured to create a lesion of greater than or equal to 30% but less than 60% of the vessel circumference. It is also important that each lesion be sufficiently deep to penetrate into and beyond the adventitia to thereby affect the renal plexus. However, lesions that are too deep (e.g., >5 mm) run the risk of interfering with non-target tissue and tissue structures (e.g., renal vein) so a controlled depth of thermal treatment is desirable.

As described in greater detail below, energy delivery element 24 may be delivered to a first treatment site within the renal artery such that the energy delivery element 24 is positioned in contact with an interior wall of the artery for treating the renal plexus (see FIG. 43C). Once positioned within the artery as desired, energy may be delivered via the energy delivery element to create a first focal lesion at this first treatment site (see FIG. 43D). The first focal lesion creates a first treatment zone 98a that is not continuous completely around the circumference of the renal artery in a radial plane or cross-section normal to the wall or to the longitudinal axis of the artery (i.e., the first focal lesion does not extend all the way around the circumference of the vessel wall). As a result, there is a discrete untreated zone about the circumference of the artery in the radial plane of the first treatment zone normal to the longitudinal axis of the artery.

Figure 43A:
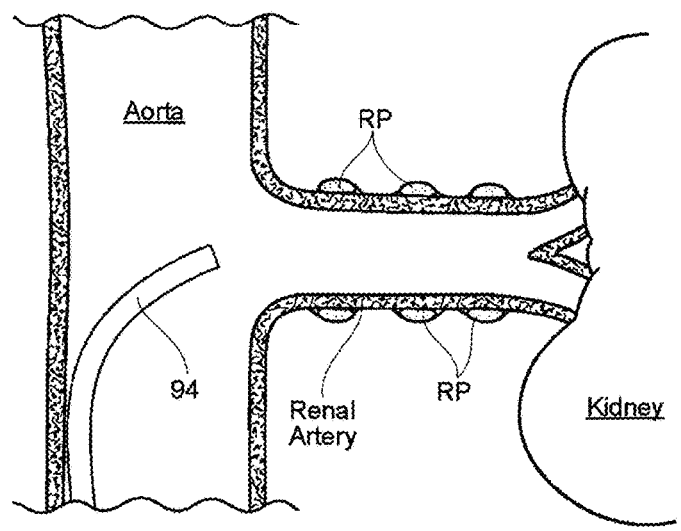
Figure 43B:
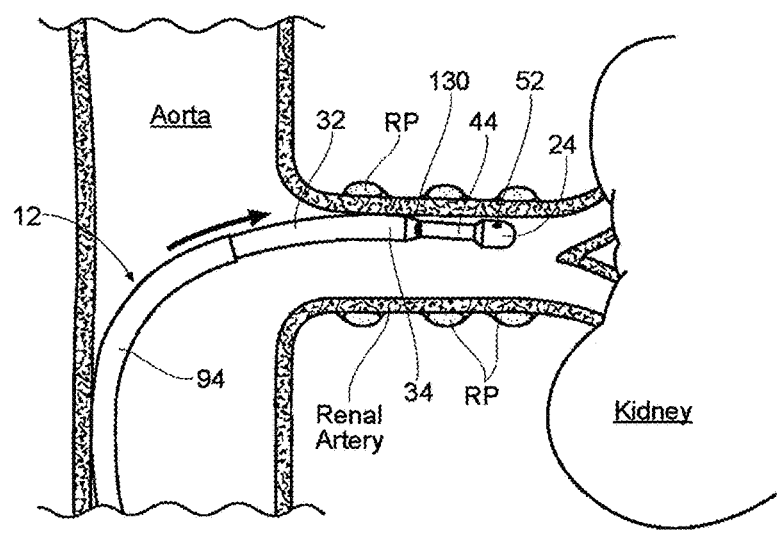
Figures 43E, 43F:
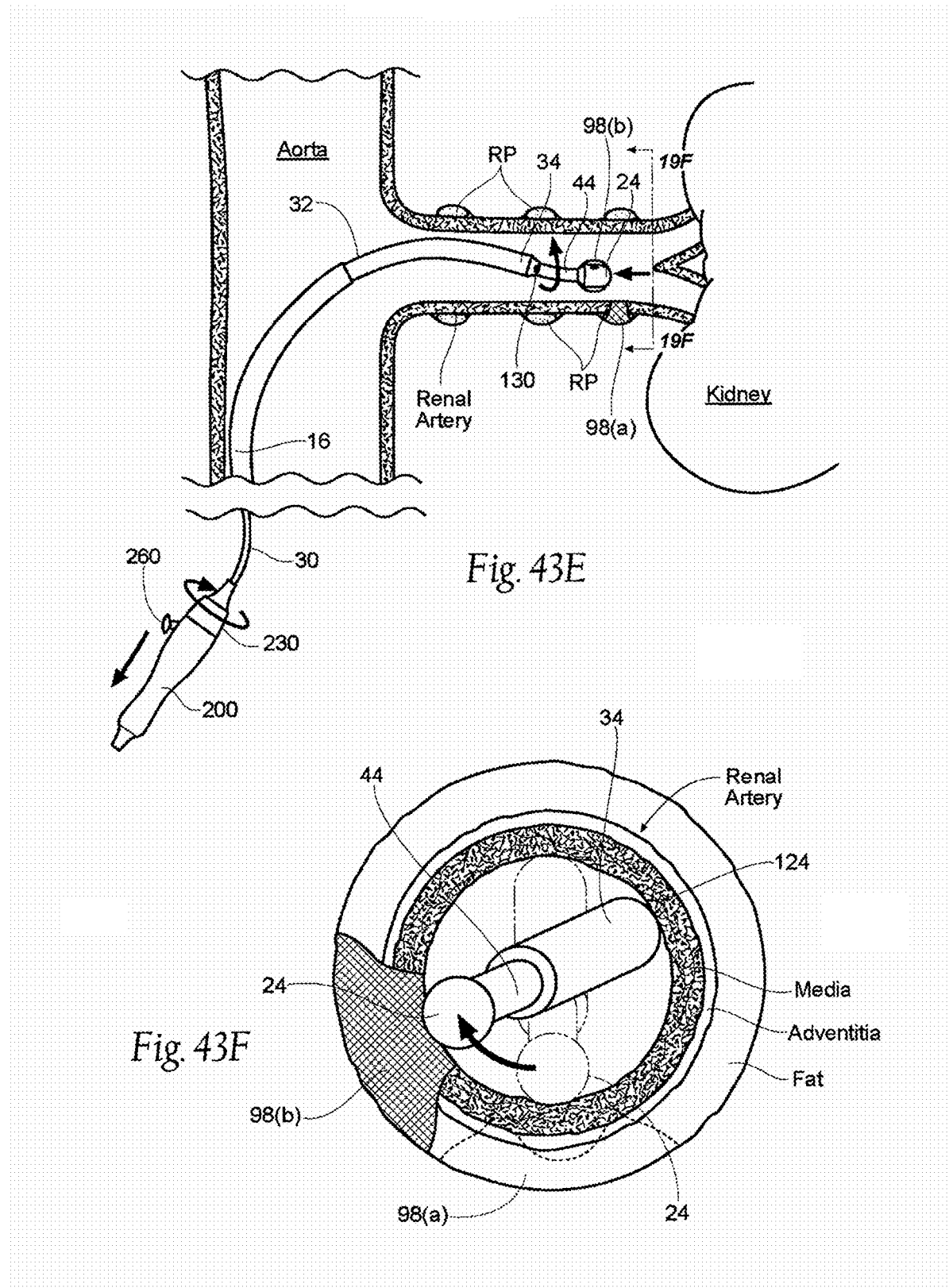

After formation of the first focal lesion at the first treatment zone 98a, the energy delivery element 24 optionally may be angularly repositioned relative to the renal artery (see FIGS. 43E and 43F). This angular repositioning may be achieved, for example, by angularly rotating the elongated shaft 16 of treatment device 12 via handle assembly 200 (see FIG. 16A). In addition to angular repositioning of the energy delivery element 24, the energy delivery element optionally may be repositioned along the lengthwise or longitudinal dimension of the renal artery (see FIG. 43E). This longitudinal repositioning may be achieved, for example, by translating the elongated shaft 16 of treatment device 12 via handle assembly 200, and may occur before, after or concurrent with angular repositioning of the energy delivery element 24.

Repositioning the energy delivery element 24 in both the longitudinal and angular dimensions places the energy delivery element in contact with the interior wall of the renal artery at a second treatment site for treating the renal plexus (see FIG. 43E). Energy then may be delivered via the energy delivery element to form a second focal lesion at this second treatment site, thereby creating a second treatment zone 98b and a second untreated zone (see FIG. 43F).

As with the first treatment zone created by the first focal lesion, the second treatment zone is not continuous about the complete circumference of the renal artery. However, the first and second treatment zones (as well as the first and second untreated zones) are angularly and longitudinally offset from one another about the angular and lengthwise dimensions of the renal artery, respectively (see FIG. 43G). Superimposing the first and second treatment zones, which are positioned along different cross-sections or radial planes of the renal artery, about a common cross-section provides a composite treatment zone that covers a greater portion of the circumference of the artery than either treatment zone individually. As this composite treatment zone is not continuous (i.e., it is formed from multiple, longitudinally and angularly spaced treatment zones), it is expected that a greater portion of the circumference of the arterial wall may be treated with reduced risk of vessel stenosis, as compared to formation of a single focal lesion covering an equivalent portion of the arterial circumference at a single treatment site (i.e., at a single lengthwise position or about a single cross-section of the renal artery).

One or more additional focal lesions optionally may be formed at one or more additional angularly and longitudinally spaced treatment sites to created additional angularly and longitudinally spaced treatment zones (see FIGS. 43G-43K). In one representative embodiment, superimposition of all or a portion of the treatment zones provides a composite treatment zone that is non-continuous (i.e., that is broken up along the lengthwise dimension or longitudinal axis of the renal artery), yet that is substantially circumferential (i.e., that substantially extends all the way around the circumference of the renal artery over a lengthwise segment of the artery). This superimposed treatment zone beneficially does not create a continuous circumferential lesion along any individual radial plane or cross-section normal to the artery, which may reduce a risk of acute or late stenosis formation, as compared to circumferential treatments that create such continuous circumferential lesions.

Non-continuous circumferential treatment by positioning energy delivery element(s) at different angular orientations along multiple lengthwise locations may preferentially affect anatomical structures that substantially propagate along the lengthwise dimension of the artery. Such anatomical structures can be neural fibers and/or structures that support the neural fibers (e.g., the renal plexus). Furthermore, such non-continuous circumferential treatment may mitigate or reduce potentially undesirable effects induced in structures that propagate about the angular dimension of the artery, such as smooth muscle cells. Were a continuous circumferential lesion alternatively to be formed, the angular or circumferential orientation of the smooth muscle cells relative to the artery may increase a risk of acute or late stenosis or acute vessel spasm.

In multiple energy delivery element configurations (e.g., multi-electrode configurations), such as in FIGS. 6C and 6D, multiple non-continuous circumferential treatment zones can be created during a single catheter placement within the renal artery. The multiple energy delivery elements can be spaced and located such that they are longitudinally and angularly spaced apart from one another and such that they create longitudinally offset and angularly opposed or offset treatment zones. Retraction and rotation of the treatment device 12 can reposition the energy delivery elements to create additional longitudinally and angularly separated treatment zones, thereby allowing the practitioner the ability to create multiple treatment zones per catheter placement and several treatment zones via only two catheter placements.

In some embodiments, as discussed later with respect to FIG. 26, the distal end region 20 of the treatment device 12 may comprise a helical deflected configuration with multiple thermal heating elements positioned along its length. When positioned in the helical deflected configuration within a renal artery, the multiple thermal heating elements 24 may be spaced circumferentially along the longitudinal length of the distal end region in contact with the wall of the artery. In some embodiments, a non-continuous circumferential treatment may be achieved via a single catheter placement without angular or longitudinal repositioning of the distal end region 20.

Figure 8A:
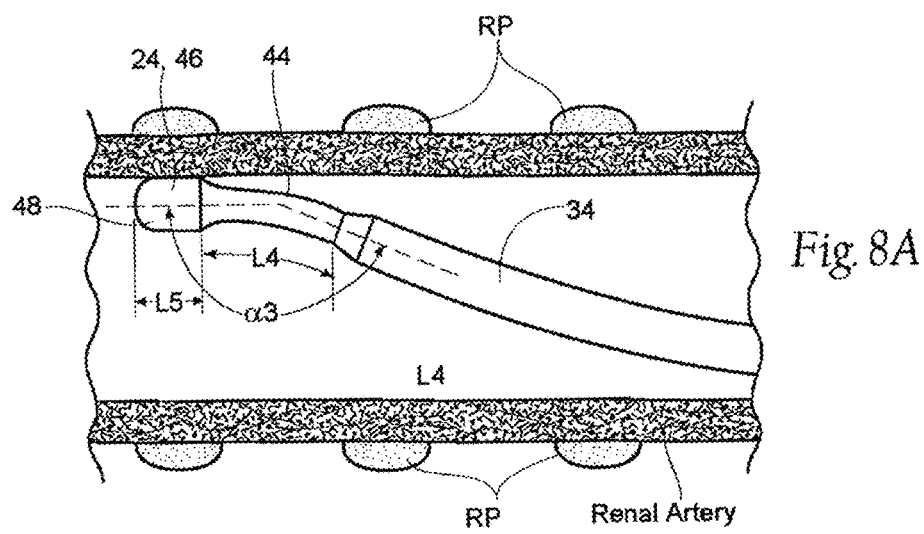
FIGS. 8A to 8C show the placement of a thermal heating element, which is carried at the distal end of the elongated shaft of the treatment device shown in FIG. 5, into contact with tissue along a renal artery.

As described (and as FIG. 8A shows), the energy delivery element 24 is sized and configured, in use, to contact an internal wall of the renal artery. In the illustrated embodiment (see FIG. 8A), the energy delivery element 24 takes the form of an electrode 46 sized and configured to apply an electrical field comprising radiofrequency (RF) energy from the generator 26 to a vessel wall. In the illustrated embodiment, the electrode 46 is operated in a monopolar or unipolar mode. In this arrangement, a return path for the applied RF electric field is established, e.g., by an external dispersive electrode (shown as 38 in FIG. 6A), also called an indifferent electrode or neutral electrode. The monopolar application of RF electric field energy serves to ohmically or resistively heat tissue in the vicinity of the electrode 46. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall, which is shown, e.g., in FIG. 9B. Alternatively, a RF electrical field can be delivered with an oscillating intensity that does not thermally injure the tissue whereby neuromodulation in the targeted nerves is accomplished by electrical modification of the nerve signals.

The active surface area of contact (ASA) between the energy delivery element 24 or electrode 46 and the vessel wall has great bearing on the efficiency and control of the transfer of a thermal energy field across the vessel wall to thermally affect targeted neural fibers in the renal plexus (RP). The active surface area of the energy delivery element 24 and electrode 46 is defined as the energy transmitting area of the element 24 or electrode 46 that can be placed in intimate contact against tissue. Too much contact between the energy delivery element and the vessel wall and/or too much power may create unduly high temperatures at or around the interface between the tissue and the energy delivery element, thereby creating excessive heat generation at this interface and/or spasm and contraction of the vessel wall. This excessive heat can also create a lesion that is circumferentially too large, increasing the risk of stenosis. This excessive heat can also lead to undesirable thermal damage at the vessel wall, which stiffens and desiccates the vessel tissue making it more susceptible to puncture and perforation. Additionally, the tissue desiccation (i.e., dehydration) reduces the electrical and thermal conductivity of the tissue. Reduced conductivity may potentially create a lesion that is too shallow to reach the neural fibers and may also result in the buildup of excessive heat, causing increased and undesirable damage to the vessel wall and increasing the likelihood of thrombus formation. Although the risks of excessive wall contact and heating are many, too little contact between the energy delivery element and the vessel wall may impair the efficacy of the treatment. For example, too little contact may result in superficial heating of the vessel wall, thereby creating a lesion that is too small (e.g., <10% of vessel circumference) and/or too shallow to reach the target renal neural fibers.

While the active surface area (ASA) of the energy delivery element 24 and electrode 46 is important to creating lesions of desirable size and depth, the ratio between the active surface area (ASA) and total surface area (TSA) of the energy delivery element 24 and electrode 46 is also important. The ASA to TSA ratio influences lesion formation in two ways: (1) the degree of resistive heating via the electric field, and (2) the effects of blood flow or other convective cooling elements such as injected or infused saline. As discussed above, the RF electric field causes lesion formation via resistive heating of tissue exposed to the electric field. The higher the ASA to TSA ratio (i.e., the greater the contact between the electrode and tissue), the greater the resistive heating. As discussed in greater detail below, the flow of blood over the exposed portion of the electrode (TSA−ASA) provides conductive and convective cooling of the electrode, thereby carrying excess thermal energy away from the interface between the vessel wall and electrode. If the ratio of ASA to TSA is too high (e.g., 50%), resistive heating of the tissue can be too aggressive and not enough excess thermal energy is being carried away, resulting in excessive heat generation and increased potential for stenotic injury, thrombus formation and undesirable lesion size. If the ratio of ASA to TSA is too low (e.g., 10%), then there is too little resistive heating of tissue, thereby resulting in superficial heating and smaller and shallower lesions.

Various size constraints for the energy delivery element 24 may be imposed for clinical reasons by the maximum desired dimensions of the guide catheter, as well as by the size and anatomy of the renal artery itself. Typically, the maximum outer diameter (or cross-sectional dimension for non-circular cross-section) of the electrode 46 comprises the largest diameter encountered along the length of the elongated shaft 16 distal to the handle assembly 200. Thus, the outer diameters of the force transmitting section 30, first, second and third flexure zones 32, 34, and 44 are equal to or (desirably) less than the maximum outer diameter of the electrode 46.

In a representative embodiment shown in FIG. 8A, the electrode 46 takes the form of a right circular cylinder, possessing a length L5 that is greater than its diameter. The electrode 46 further desirably includes a distal region that is rounded to form an atraumatic end surface 48. In the representative embodiment shown in FIG. 8B, the electrode 46 is spherical in shape, such that the length L5 is equal to the electrode's diameter. The spherical shape, too, presents an atraumatic surface to the tissue interface.

Figure 8B:
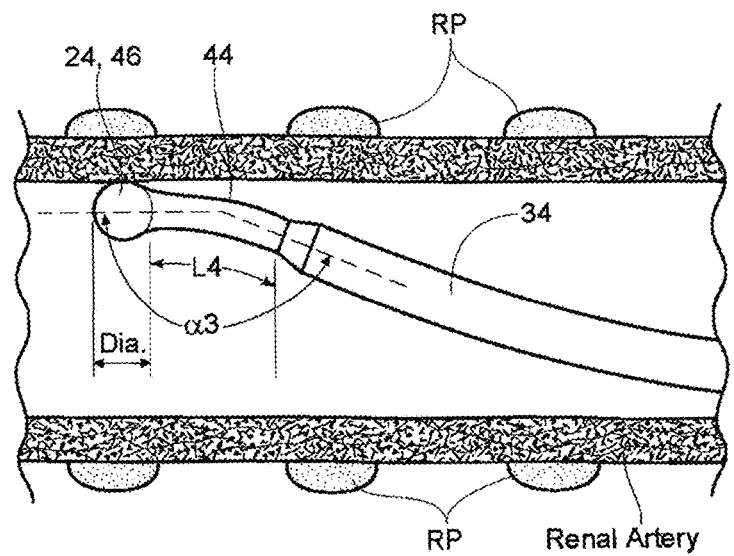
Figure 8C:
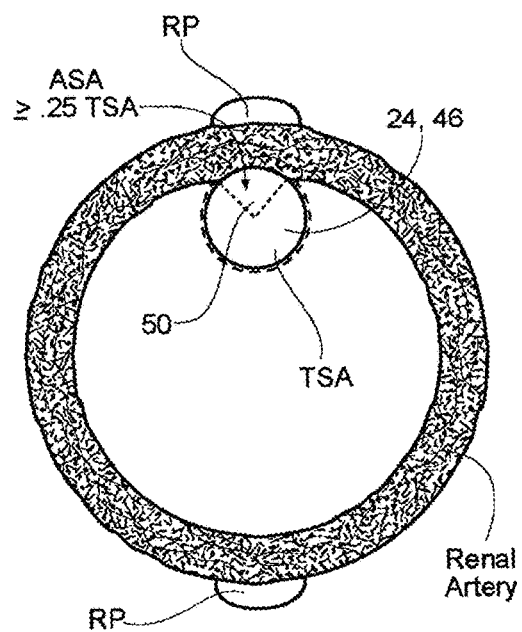

As shown in FIGS. 8A and 8B, the angle α3 and length L4 of the distal flexure zone 44 are specially sized and configured, given the TSA of the respective electrode, to optimize an active surface area of contact between tissue and the respective electrode 46 (ASA). The angle α3 and the length L4 of the distal flexure zone 44 make it possible to desirably lay at least a side quadrant 50 of the electrode 46 against tissue (see FIG. 8C), though it should be understood that the electrode 46 does not necessarily need to be positioned with its side quadrant 50 against tissue prior to power delivery. In a representative embodiment, the active surface area of the electrode 46 contacting tissue (ASA) can be expressed as ASA≥0.25 TSA and ASA≤0.50 TSA.

An ASA to TSA ratio of over 50% may be effective with a reduced power delivery profile. Alternatively, increasing the conductive or convective cooling of the electrode (e.g. vie active cooling) can compensate for a higher ASA to TSA ratio. As discussed further below, this could be achieved by injecting or infusing cooling fluids such as saline (e.g., room temperature saline or chilled saline) over the electrode and into the blood stream.

The stiffnesses of each of the second and third flexure zones 34 and 44 are also selected to apply via the electrode a stabilizing force that positions the electrode 46 in substantially secure contact with the vessel wall tissue. This stabilizing force also influences the amount of wall contact achieved by the energy delivery element (i.e., the ASA to TSA ratio). With greater stabilizing force, the energy delivery element has more wall contact and with less stabilizing force, less wall contact is achieved. Additional advantages of the stabilizing force include, (1) softening the contact force between the distal end 20 and vessel wall to minimize risk of mechanical injury to vessel wall, (2) consistent positioning of the electrode 46 flat against the vessel wall, and (3) stabilizing the electrode 46 against the vessel wall. As discussed above with respect to the combined effect of the first flexure zone and second/second flexure zone, this stabilizing force allows the catheter treatment device to maintain consistent contact with the vessel wall even during motion of the renal artery during respiration. The stabilizing force also allows the electrode to return to a neutral position after the electrode is removed from contact with the wall.

As previously discussed, for clinical reasons, the maximum outer diameter (or cross-sectional dimension) of the electrode 46 is constrained by the maximum inner diameter of the guide catheter through which the elongated shaft 16 is to be passed through the intravascular path 14. Assuming that an 8 French guide catheter 94 (which has an inner diameter of approximately 0.091 inches) is, from a clinical perspective, the largest desired catheter to be used to access the renal artery, and allowing for a reasonable clearance tolerance between the electrode 46 and the guide catheter, the maximum diameter of the electrode 46 is constrained to about 0.085 inches. In the event a 6 French guide catheter is used instead of an 8 French guide catheter, then the maximum diameter of the electrode 46 is constrained to about 0.070 inches. In the event a 5 French guide catheter is used, then maximum diameter of the electrode 46 is constrained to about 0.053 inches. Based upon these constraints and the aforementioned power delivery considerations, the electrode 46 desirably has a maximum outer diameter of from about 0.049 to about 0.051 inches. The electrode 46 also desirably has a minimum outer diameter of about 0.020 inches to provide sufficient cooling and lesion size. In some embodiments, the electrode 46 (i.e., the energy delivery element 24) may have a length of about 1 mm to about 3 mm. In some embodiments in which the energy delivery element is a resistive heating element, it can have a maximum outer diameter from about 0.049 to 0.051 inches and a length of about 10 mm to 30 mm.

D. Applying Energy to Tissue Via the Energy Delivery Element

Referring back to FIG. 5, in the illustrated embodiment, the generator 26 may supply to the electrode 46 a pulsed or continuous RF electric field. Although a continuous delivery of RF energy is desirable, the application of thermal energy in pulses may allow the application of relatively higher energy levels (e.g., higher power), longer or shorter total duration times, and/or better controlled intravascular renal neuromodulation therapy. Pulsed energy may also allow for the use of a smaller electrode.

The thermal therapy may be monitored and controlled, for example, via data collected with one or more sensors 52, such as temperature sensors (e.g., thermocouples, thermistors, etc.), impedance sensors, pressure sensors, optical sensors, flow sensors, chemical sensors, force sensors, strain sensors, etc. (see FIGS. 9A and 9B). Sensor(s) 52 may be incorporated into or on electrode 46 and/or in/on adjacent areas on the distal end region 20.

Advantageously, since the second flexure zone 34 deflects in a controlled manner, the surface of electrode 46 that contacts tissue during treatment may be known. As such, sensor(s) 52 may be incorporated into the electrode in a manner that specifies whether the sensor(s) are in contact with tissue at the treatment site and/or are facing blood flow. The ability to specify sensor placement relative to tissue and blood flow is highly significant, since a temperature gradient across the electrode from the side facing blood flow to the side in contact with the vessel wall may be up to about 15° C. Significant gradients across the electrode in other sensed data (e.g., flow, pressure, impedance, etc.) also are expected.

The sensor(s) 52 may, for example, be incorporated on the side of the electrode that contacts the vessel wall at the treatment site during power and energy delivery (see FIG. 9B), may be incorporated into the tip of the electrode, may be incorporated on the opposing side of the electrode that faces blood flow during energy delivery (see FIG. 9A), and/or may be incorporated within certain regions of the electrode (e.g., distal, proximal, quadrants, etc.). In some embodiments, multiple sensors may be provided at multiple positions along the electrode and/or relative to blood flow. For example, a plurality of circumferentially and/or longitudinally spaced sensors may be provided. In one embodiment, a first sensor may contact the vessel wall during treatment, and a second sensor may face blood flow.

Additionally or alternatively, various microsensors can be used to acquire data corresponding to the energy delivery element, the vessel wall and/or the blood flowing across the energy delivery element. For example, arrays of micro thermocouples and/or impedance sensors can be implemented to acquire data along the energy delivery element or other parts of the treatment device. Sensor data can be acquired or monitored prior to, simultaneously with, or after the delivery of energy or in between pulses of energy, when applicable. The monitored data may be used in a feedback loop to better control therapy, e.g., to determine whether to continue or stop treatment, and it may facilitate controlled delivery of an increased or reduced power or a longer or shorter duration therapy.

Figure 9A:
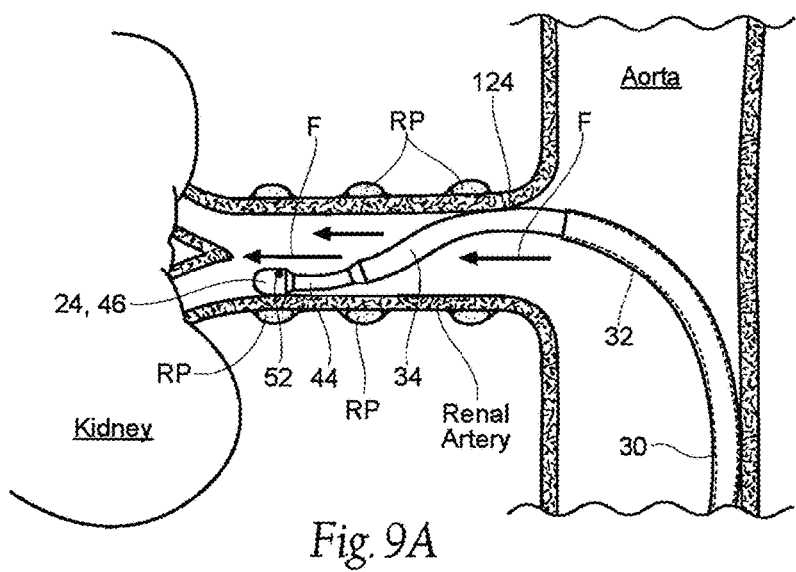
FIGS. 9A and 9B show placement of the thermal heating element shown in FIGS. 8A to 8C into contact with tissue along a renal artery and delivery of thermal treatment to the renal plexus.
Figure 9B:
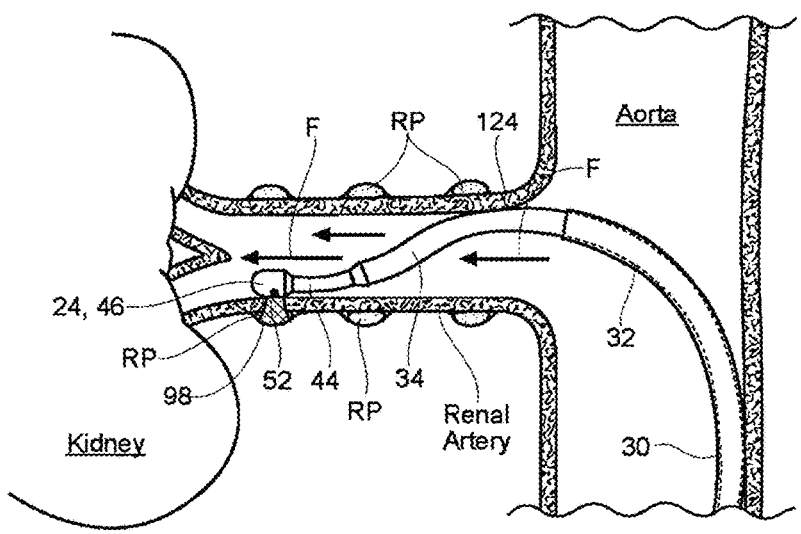

Non-target tissue may be protected by blood flow (F) within the respective renal artery that serves as a conductive and/or convective heat sink that carries away excess thermal energy. For example (as FIGS. 9A and 9B show), since blood flow (F) is not blocked by the elongated shaft 16 and the electrode 46 it carries, the native circulation of blood in the respective renal artery serves to remove excess thermal energy from the non-target tissue and the energy delivery element. The removal of excess thermal energy by blood flow also allows for treatments of higher power, where more power can be delivered to the target tissue as thermal energy is carried away from the electrode and non-target tissue. In this way, intravascularly-delivered thermal energy heats target neural fibers located proximate to the vessel wall to modulate the target neural fibers, while blood flow (F) within the respective renal artery protects non-target tissue of the vessel wall from excessive or undesirable thermal injury. When energy is delivered in pulses, the time interval between delivery of thermal energy pulses may facilitate additional convective or other cooling of the non-target tissue of the vessel wall compared to applying an equivalent magnitude or duration of continuous thermal energy.

It may also be desirable to provide enhanced cooling by inducing additional native blood flow across the energy delivery element. For example, techniques and/or technologies can be implemented by the caregiver to increase perfusion through the renal artery or to the energy delivery element itself. These techniques include positioning partial occlusion elements (e.g., balloons) within upstream vascular bodies such as the aorta or proximal portion of the renal artery to improve flow across the energy delivery element. Additionally or alternatively, autologous blood from another area of the vasculature may be siphoned off and re-directed into the renal artery to increase the volumetric flow rate and/or velocity of blood flowing through the artery.

In addition, or as an alternative, to passively utilizing blood flow (F) as a heat sink, active cooling may be provided to remove excess thermal energy and protect non-target tissues. For example, a thermal fluid infusate may be injected, infused, or otherwise delivered into the vessel in an open circuit system. Additionally or alternatively, the energy delivery element 24 (e.g., electrode 46) may be actively cooled in a closed circuit system (i.e., without delivering any agents into the bloodstream) to remove excess thermal energy, such as by circulating a thermal fluid infusate (e.g., a cryogenic or chilled fluid) within the distal end region 20 or by some other mechanism.

Thermal fluid infusates used for active cooling may, for example, comprise (room temperature or chilled) saline or some other biocompatible fluid. The thermal fluid infusate(s) may, for example, be introduced through the treatment device 12 via one or more infusion lumens and/or ports. When introduced into the bloodstream, the thermal fluid infusate(s) may, for example, be introduced through a guide catheter at a location upstream from the energy delivery element 24 or electrode 46, or at other locations relative to the tissue for which protection is sought. The delivery of a thermal fluid infusate in the vicinity of the treatment site (via an open circuit system and/or via a closed circuit system) may, for example, allow for the application of increased/higher power, may allow for the maintenance of lower temperature at the vessel wall during energy delivery, may facilitate the creation of deeper or larger lesions, may facilitate a reduction in treatment time, may allow for the use of a smaller electrode size, may compensate for acutely reduced blood flow, may compensate for anatomical characteristics resulting in relatively low blood flow at a treatment site, or a combination thereof.

Although many of the embodiments described herein pertain to electrical systems configured for the delivery of RF energy, it is contemplated that the desired treatment can be accomplished by other means, e.g., by coherent or incoherent light; direct thermal modification (e.g., with a heated or cooled fluid or resistive heating element); microwave; ultrasound (including high intensity focused ultrasound); diode laser; radiation; a tissue heating fluid; and/or a cryogenic fluid.

III. REPRESENTATIVE EMBODIMENTS

A. First Representative Embodiment (First, Second, and Third Flexure Zones with Distally Carried Energy Delivery Element)

FIGS. 10A to 15H show a representative embodiment of an elongated shaft 16 that includes a force transmitting section 30, as well as first, second and third flexure zones 32, 34, and 44, having the physical and mechanical features described above. In this embodiment, the thermal heating element 24 is carried distally of the third flexure zone 44 (see, e.g., FIG. 11A).

1. Force Transmitting Section

In the illustrated embodiment, as shown in FIGS. 10A and 10B, the force transmitting section 30 comprises a first elongated and desirably tubular structure, which can take the form of, e.g., a first tubular structure 54. The first tubular structure 54 is desirably a hypo tube that is made of a metal material, e.g. of stainless steel, or a shape memory alloy, e.g., nickel titanium (a.k.a., Nitinol or NiTi), to possess the requisite axial stiffness and torsional stiffness, as already described, for the force transmitting section 30. As already described, the force transmitting section 30 comprises the most stiff section along the elongated shaft 16, to facilitate axially movement of the elongated shaft 16, as well as rotational manipulation of the elongated shaft 16 within the intravascular path 14. Alternatively, the first tubular structure 54 may comprise a hollow coil, hollow cable, solid cable (w/embedded wires), a braided or braid reinforced shaft, a coil reinforced polymer shaft, a metal/polymer composite, etc.

The stiffness is a function of material selection as well as structural features such as interior diameter, outside diameter, wall thickness, geometry and other features that are made by micro-engineering, machining, cutting and/or skiving the hypo tube material to provide the desired axial and torsional stiffness characteristics. For example, the elongated shaft can be a hypo tube that is laser cut to various shapes and cross-sectional geometries to achieve the desired functional properties.

When the first tubular structure 54 is made from an electrically conductive metal material, the first tubular structure 54 may include a sheath 56 or covering made from an electrically insulating polymer material or materials, which is placed over the outer diameter of the underlying tubular structure. The polymer material can also be selected to possess a desired durometer (expressing a degree of stiffness or lack thereof) to contribute to the desired overall stiffness of the first tubular structure 54. Candidate materials for the polymer material include, but are not limited to, polyethylene terephthalate (PET); Pebax® material; nylon; polyurethane, Grilamid® material or combinations thereof. The polymer material can be laminated, dip-coated, spray-coated, or otherwise deposited/attached to the outer diameter of the tube.

2. First Flexure Zone

Figures 11A, 11B, 11C:
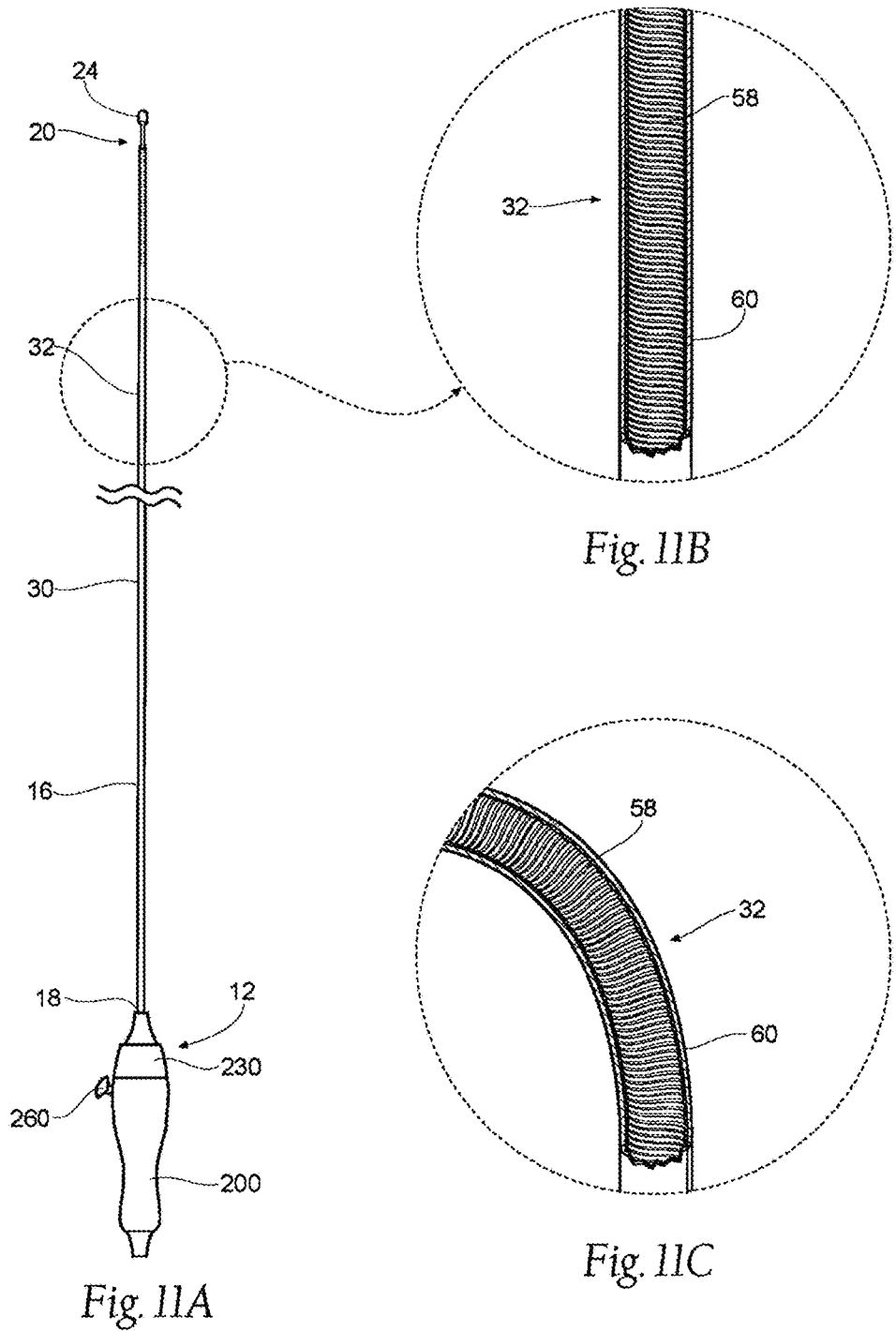
FIGS. 11A to 11C show a representative embodiment of the proximal flexure zone of the elongated shaft of the treatment device shown in FIG. 5.

As FIGS. 11A, 11B, and 11C show, the first flexure zone 32 comprises a second elongated and desirably tubular structure, which can take the form of, e.g., a second tubular structure 58. The second tubular structure 58 can be made from the same or different material as the first tubular structure 54. The axial stiffness and torsional stiffness of the second tubular structure 58 possesses the requisite axial stiffness and torsional stiffness, as already described, for the first flexure zone 32. As already described, the first flexure zone 32 may be less stiff and more flexible than the force transmitting section 30, to navigate the severe bend at and prior to the junction of the aorta and respective renal artery. The second tubular structure is desirably a hypo tube, but can alternatively comprise a hollow coil, hollow cable, braided shaft, etc.

It may be desirable for the first and second tubular structures 54 and 58 to share the same material. In this event, the form and physical features of the second tubular structure 58 may be altered, compared to the first tubular structure 54, to achieve the desired stiffness and flexibility differences. For example, the interior diameter, outside diameter, wall thickness, and other engineered features of the second tubular structure 58 can be tailored to provide the desired axial and torsional stiffness and flexibility characteristics. For example, the second tubular structure 58 can be laser cut along its length to provide a bendable, spring-like structure. Depending on the ease of manufacturability the first and second tubular structures may be produced from the same piece of material or from two separate pieces. In the event the first tubular structure and second tubular structure are not of the same material, the outside diameter of the second tubular structure 58 can be less than the outer diameter of first tubular structure 54 (or have a smaller wall thickness) to create the desired differentiation in stiffness between the first and second tubular structures 54 and 58.

When the second tubular structure 58 is made from an electrically conductive metal material, the second tubular structure 58, like the first tubular structure 54, includes a sheath 60 (see FIGS. 11B and 11C) or covering made from an electrically insulating polymer material or materials, as already described. The sheath 60 or covering can also be selected to possess a desired durometer to contribute to the desired differentiation in stiffness and flexibility between the first and second tubular structures 58.

The second tubular structure 58 can comprise a different material than the first tubular structure 54 to impart the desired differentiation in stiffness and flexibility between the first and second tubular structures 58. For example, the second tubular structure 58 can comprise a cobalt-chromium-nickel alloy, instead of stainless steel. Alternatively, the second tubular structure 58 can comprise a less rigid polymer, a braided or braid-reinforced shaft, a coil reinforced polymer shaft, a metal/polymer composite, nitinol or hollow cable-like structure. In addition to material selection, the desired differentiation in stiffness and overall flexibility can be achieved by selection of the interior diameter, outside diameter, wall thickness, and other engineered features of the second tubular structure 58, as already described. Further, a sheath 60 or covering made from an electrically insulating polymer material, as above described, can also be placed over the outer diameter of the second tubular structure 58 to impart the desired differentiation between the first and second tubular structures 54 and 58.

3. Second Flexure Zone

As FIGS. 12A, 12B, 12C, and 12D show, the second flexure zone 34 comprises a third elongated and desirably tubular structure, which can take the form of, e.g., a third tubular structure 62. The third tubular structure 62 can be made from the same or different material as the first and/or second tubular structures 54 and 58. The axial stiffness and torsional stiffness of the third tubular structure 62 possesses the requisite axial stiffness and torsional stiffness, as already described, for the second flexure zone 34. As already described, the second flexure zone 34 may be less stiff and more flexible than the first flexure zone 32, to facilitate controlled deflection of the second flexure zone 34 within the respective renal artery.

If the second and third tubular structures 58 and 62 share the same material, the form and physical features of the third tubular structure 62 are altered, compared to the second tubular structure 58, to achieve the desired stiffness and flexibility differences. For example, the interior diameter, outside diameter, wall thickness, and other engineered features of the third tubular structure 62 can be tailored to provide the desired axial and torsional stiffness and flexibility characteristics. For example, the third tubular structure 62 can be laser cut along its length to provide a more bendable, more spring-like structure than the second tubular structure 58.

When the third tubular structure 62 is made from an electrically conductive metal material, the third tubular structure 62 also may include a sheath 64 (see FIGS. 12B, 12C, and 12D) or covering made from an electrically insulating polymer material or materials, as already described. The sheath 64 or covering can also be selected to possess a desired durometer to contribute to the desired differentiation in stiffness and flexibility between the second and third tubular structure 62.

The third tubular structure 62 can comprise a different material than the second tubular structure to impart the desired differentiation in stiffness and flexibility between the second and third tubular structures 62. For example, the third tubular structure 62 can include a Nitinol material, to impart the desired differentiation in stiffness between the second and third tubular structures 58 and 62. In addition to material selection, the desired differentiation in stiffness and overall flexibility can be achieved by selection of the interior diameter, outside diameter, wall thickness, and other engineered features of the third tubular structure 62, as already described.

For example, in diameter, the outside diameter of the third tubular structure 62 is desirably less than the outer diameter of second tubular structure 58. Reduction of outside diameter or wall thickness influences the desired differentiation in stiffness between the second and third tubular structures 58 and 62.

As discussed in greater detail above, preferential deflection of the second flexure zone is desirable. This can be achieved by making the third tubular structure 62 compressible in the desired direction of deflection and resilient to compression opposite the direction of deflection. For example, as shown in FIGS. 12B and 12C, the third tubular structure 62 (unlike the second tubular structure 58) can include a laser-cut pattern that includes a spine 66 with connecting ribs 68. The pattern biases the deflection of the third tubular structure 62, in response to pulling on the control wire 40 coupled to the distal end of the third tubular structure 62, toward a desired direction. The control wire 40 is attached to a distal end of the deflectable section with solder 130. When the control wire is pulled the third tubular structure compresses on the compressible side biasing deflection in the direction of the compressible side. The benefits of preferential deflection within a renal artery have already been described.

As also shown in FIG. 12D, a flat ribbon material 70 (e.g., Nitinol, stainless steel, or spring stainless steel) can be attached to the third tubular structure 62. When the pulling force is removed from the control wire 40, the flat ribbon, which serves to reinforce the deflectable third tubular structure 62, will elastically straighten out the deflectable third tubular structure 62.

Further, a sheath 64 (see FIGS. 12B, 12C, and 12D) or covering made from an electrically insulating polymer material, as above described, and having a desired durometer can also be placed over the outer diameter of the second tubular structure 58 to impart the desired differentiation between the first and second tubular structures 54 and 58.

In the embodiment of FIGS. 12B-12D, the width of the spine 66 (i.e., the radial arc length of the spine 66 at regions along the longitudinal axis of the third tubular structure 62 that do not include ribs 68) affects the relative stiffness and elasticity of the third tubular structure 62. It should be understood that the width of the spine 66 may be specified to provide the third tubular structure 62 with a desired relative stiffness and/or elasticity. Furthermore, the width of the spine 66 may vary along the longitudinal axis of the third tubular structure 62, thereby providing the third tubular structure with a varying relative stiffness and/or elasticity along its length. Such variation in the width of the spine 66 may be gradual, continuous, abrupt, discontinuous, or combinations thereof.

The length L3 of the deflectable section 34 is between about 5 mm and 20 mm, for example less than or equal to about 12.5 mm. As the distal end region 20 is advanced from a guide catheter into a renal artery the energy delivery element 24 contacts the superior surface of the renal artery wall. The length L3 allows the energy delivery element 24 to be manipulated through deflection of the deflectable section 34 to contact dorsal, ventral and inferior surfaces of the renal artery wall within a short distance as long as a portion of the deflectable section 34 protrudes from the guide catheter. Thus the length L3 of the deflectable section 34 is chosen to be specially suited for use in a renal artery.

The width of the ribs 68 (i.e., the distance spanned by each rib along the longitudinal axis of the third tubular structure 62), as well as the spacing of the ribs 68 (i.e., the distance spanned by the spine 66 along the longitudinal axis of the third tubular member 62 between adjacent ribs 68), optionally may affect a maximal preferential deflection achievable by the second flexure zone 34 before adjacent ribs 68 contact one another, i.e. may limit the maximum amount of compression to the side of the third tubular structure that is compressible. Such contact between adjacent ribs 68 optionally may define the radius of curvature and/or the angle α2 (see FIG. 7C) of the deflectable section 34 under such maximal preferential deflection. The deflectable section is configured for a state of maximum flexure, wherein the state of maximum flexure is achieved when the deflectable body moves the energy delivery element away from the axis of the elongated tubular body by a predetermined distance. The maximum flexure avoids the risk of causing trauma to the renal artery wall which could happen if a deflectable section 34 of length L3 were deflected significantly more than the diameter of a renal artery. As will be discussed in more detail later, the force dampening section 44 is configured to dampen force exerted to the artery wall when the deflectable section 34 is deflected. Stable contact force between an energy delivery element 24 and an inner wall of a renal artery can be created by exerting a force that is greater than an instable force and less than a traumatic force. The force dampening section 44 dampens the contact force keeping it within a stable yet atraumatic range even when the deflectable section 34 moves the energy delivery element 24 away from the axis of the elongated tubular body by a distance greater than the diameter of a renal artery. For example, the force dampening section 44 may flex enough for the deflectable section 34 to be configured for a state of maximum flexure such that the predetermined distance is about 4 mm greater than a renal artery diameter. In one embodiment the distal assembly 53 has a length of about 3 mm to 6 mm (e.g. less than or equal to 5 mm), the deflectable section 34 has a length L3 of about 8 mm to 15 mm (e.g. less than or equal to 12.5 mm) and has a maximum flexure displacing the energy delivery element 24 a predetermined distance of about 10 to 14 mm. Alternatively or additionally, the predetermined distance can be adjusted by a deflection limiter in the handle 200 that limits the actuator 260 to displacing the control wire a maximum amount thus limiting the deflection to an adjusted state of maximum flexure.

It should be understood that the width and/or the spacing of the ribs 68 may be specified as desired to achieve a desired maximal preferential deflection. Furthermore, the width and/or the spacing of the ribs 68 may vary along the longitudinal axis of the third tubular structure 62, thereby providing the second flexure zone 34 with a varying radius of curvature under such maximal preferential deflection. Such variation in the width and/or spacing of the ribs 68 may be gradual, continuous, abrupt, discontinuous, or combinations thereof.

Figure 13A:
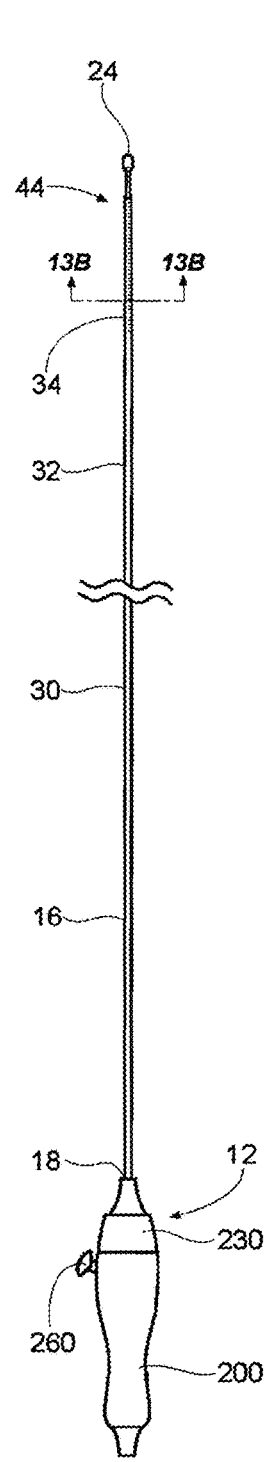
FIGS. 13A to 13C show alternative embodiments of an intermediate flexure zone having portions with different stiffnesses.
Figure 13B:
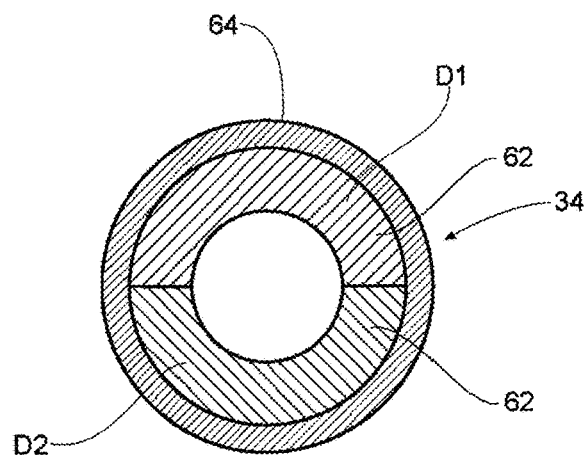
Figure 13C:
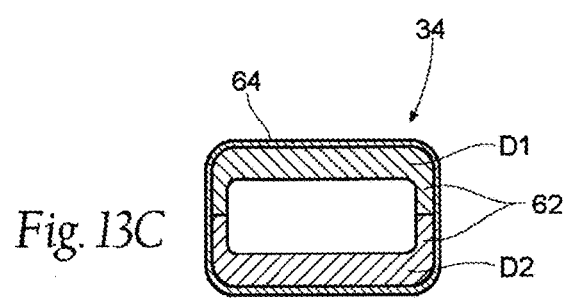
Figure 13D:
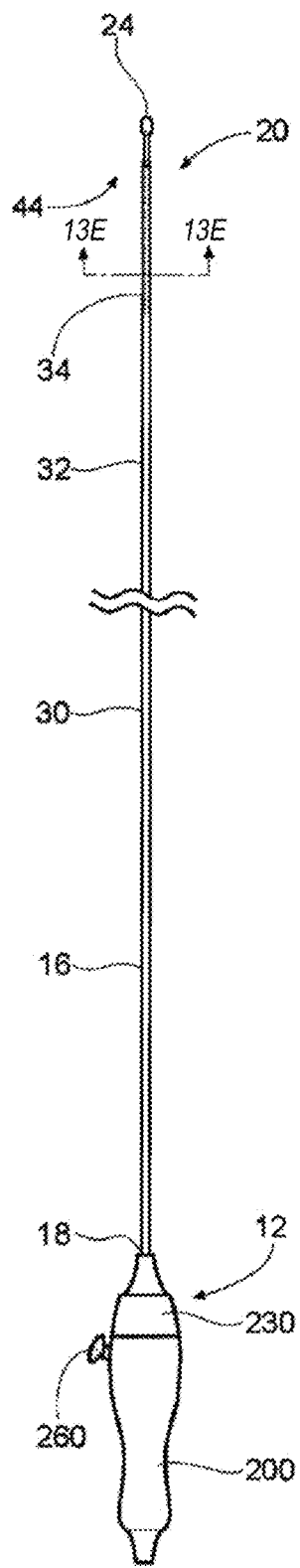
FIGS. 13D to 13F show alternative embodiments of an intermediate flexure zone comprising a braided or coiled tubular structure.

Preferential deflection from reduced stiffness in the direction of deflection, as described above, can be achieved in a number of additional ways. For example, as FIG. 13B shows, the third tubular structure 62 can comprise a tubular polymer or metal/polymer composite having segments with different stiffnesses D1 and D2, in which D1>D2 (that is, the segment with D1 is mechanically stiffer than the segment with D2). The third tubular structure 62 can also take the form of an oval, or rectangular, or flattened metal coil or polymer having segments with different stiffnesses D1 and D2, in which D1>D2 (as shown in FIG. 13C). In either arrangement, the segment having the lower stiffness D2 is oriented on the third tubular structure 62 on the same side as the actuator wire is attached.

Figure 13E:
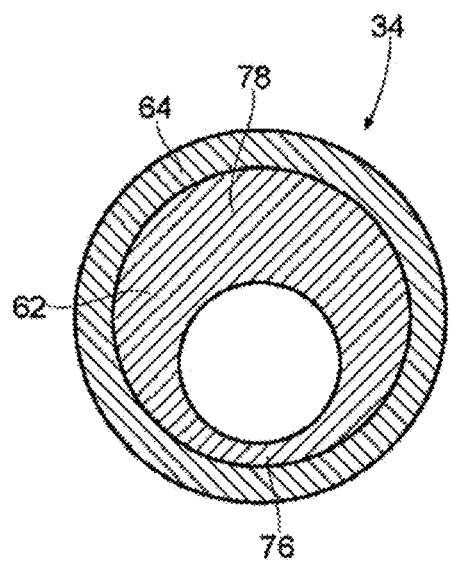
Figure 13F:
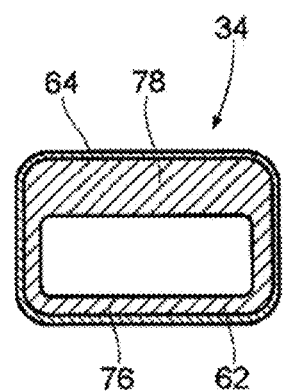

Alternatively, as FIGS. 13E and 13F show, the third tubular structure 62 can comprise an eccentric polymer or metal/polymer composite which can be braided or coiled. The third tubular structure 62 can also take the form of an eccentric oval, or rectangular, or flattened metal coil or polymer (as FIG. 13F shows). In either arrangement, the thinner (less stiff) wall segment 76 is oriented on the third tubular structure 62 on the same side as the actuator wire attached.

FIGS. 14A and 14B illustrate further treatment devices having flexure zones configured in accordance with embodiments of the technology. FIG. 14A illustrates a portion of a treatment device 1412 that includes a shaft 16 comprising a force transmitting section 30, a first flexure zone 32, and a second flexure zone 34 having properties and dimensions similar to those described above with reference to FIGS. 7A-13F. The force transmitting section 30 can have length L1 and a stiffness capable of advancing or withdrawing along an intravascular path while navigating curves within the path. In some embodiments, the force transmitting section 30 can be at least partially laminated with polyethylene terephthalate.

The first flexure zone 32 can have length L2 and can be sized and configured to accommodate significant flexure or bending to allow for flexible advancement through a tortuous vasculature. For example, at least a portion of the first flexure zone 32 can comprise a hypo tube, hollow coil, hollow cable, braided shaft, or other suitable structure that enables bending around curves. In the illustrated embodiment, the first flexure zone 32 comprises a tubular structure that has been cut (e.g., laser cut) along its length to provide a bendable, spring-like structure. In the illustrated embodiment, individual cuts 1418 are at least partially circumferential and have varying pitch with respect to the longitudinal axis of the shaft 16.

The second flexure zone 34 can have length L3 and is sized and configured to accommodate additional flexure or bending, independent of the first flexure zone 32. The second flexure zone 34 can include a laser-cut pattern that includes a spine 66 and ribs 68 projecting from the spine 66. The ribs 68, for example, can project radially from the spine 66 around only a portion of the circumference of the treatment device 1412. In some embodiments, at least a portion of the first flexure zone 32 and the second flexure zone 34 is laminated with a thermoplastic polyurethane (e.g., the trademarked product Carbothane). In a non-limiting representative embodiment, the length L2 of the first flexure zone 32 is about 89 mm and the length L3 of the second flexure zone 34 is about 12 mm. In a further embodiment, the entire length of the shaft 16 is from about 106 cm to about 110 cm.

FIG. 14B shows a portion of a treatment device 1413 in accordance with another embodiment of the technology that includes a shaft 16 comprising a force transmitting section 1430, a first flexure zone 1432, and a second flexure zone 1434 similar to those described above. The shaft 16 further comprises a transition section 1431 positioned longitudinally between the force transmitting section 1430 and the first flexure zone 1432.

The transition section 1431 includes a distal region 1414 near the first flexure zone 1432, a proximal region 1415 near the force transmitting section 1430, and flex features along at least a portion of the distal region 1414. The flex features can become increasingly spaced apart from each other toward the proximal region 1415 such that the distal region 1414 is more flexible than the proximal region 1415. For example, in the illustrated embodiment, the flex features can be laser cuts 1418 in which the laser cuts 1418 at the distal region 1414 are arranged in a pattern similar to the laser cut pattern of the first proximal zone 1432. However, the pitch of the flex features varies with longitudinal location along at least a portion of the transition section 1431. In one embodiment, the laser cuts 1418 can be spaced apart from each other by increasing distances in a proximal direction from the distal region 1414 to the proximal region 1415, and finally end at the proximal region 1415 of the transition section 1431. For example, in a representative embodiment, the laser cuts 1418 may be spaced apart from each other by an axial distance of about 0.38 mm at the distal region 1414, but spaced apart by an axial distance of about 5.71 mm closer to the proximal region 1415. In this manner, the density of the laser cuts 1418 is higher at the distal region 1414 than at the proximal region 1415. The laser cuts 1418 can comprise discrete cuts with a start or terminus in the transition section 1431, or the laser cut 1418 can be a continuous helical cut around the transition section 1431 and the first flexure zone 1432. In several embodiments, the laser-cut pattern is a variable pitch pattern in which the pitch with reference to the longitudinal axis of the shaft 16 is more gradual toward the proximal region 1415 (i.e., the pitch is steeper toward the distal region 1414). The pitch of the laser cuts 1418 can change continuously and linearly through the transition section 1431 such that the pitch increases progressively in a proximal direction, or the pitch can change in steps from one area to another through the transition section 1431.

The transition section 1431 provides a changeover length or conversion zone from the highly flexible first flexure zone 1432 to the comparatively stiff force transmitting section 1430. The transition section 1431 therefore reduces the abruptness of the stiffness changeover along the length of the shaft 16 in a manner that reduces kinking that can otherwise occur at such an abrupt stiffness change. This can ease vasculature navigation.

In some embodiments, the transition section 1431 has a length L6 from about 140 mm to about 200 mm. The transition section length L6, for example, can be established as a proportion of the overall length of the shaft 16 and/or as a function of the desired shaft flexibility. In several embodiments, the total length of the shaft 16 is the same as that of treatment devices not having a transition section 1431, so either the force transmitting section 1430, the first flexure zone 1432, or both are reduced in length to accommodate the length L6 of the transition section 1431. In a representative embodiment, the length L2 of the first flexure zone 1432 is about 89 mm, the length L3 of the second flexure zone 1434 is about 12 mm, and the length L6 of the transition section 1431 is about 169 mm. In various embodiments, the total length of the transition section 1431, the first flexure zone 1432, and the second flexure zone 1434 together (e.g., L2+L3+L6) is from about 10 cm to about 40 cm.

Several of the embodiments previously discussed are well-suited for entry to the renal artery via a path that includes a femoral artery, an iliac artery and the aorta. In further embodiments, the treatment devices can access a treatment site in the renal artery via the radial artery, through the subclavian artery, through the aortic arch, down the descending aorta, and into the renal arteries (e.g., a "transradial" approach). Transradial approaches can require more torquability of the treatment device 1413 in order to reach the treatment site compared to femoral approaches. In some embodiments, treatment devices suitable for transradial approaches can be generally shorter and have a shorter transition section 1431 than a treatment device used with a femoral approach. In one transradial embodiment, for example, the length L6 of the transition section 1431 is about 45.7 mm to about 55.9 mm (e.g., 50.8 mm), the length L2 of the first flexure zone 1432 is about 89 mm, and the length L3 of the second flexure zone 1434 is about 12 mm. In a particular embodiment suited for transradial delivery, the total cumulative length of the transition section 1431, the first flexure zone 1432, and the second flexure zone 1434 (e.g., L2+L3+L6) is from about 10 cm to about 20 cm. In some embodiments, the entire length of the shaft 16 is about 152 cm. In further embodiments, the shaft 16 or subsections of the shaft 16 can have alternate dimensions. Furthermore, a treatment device 1413 used with the transradial approach can be made of the same materials as those used in a femoral approach treatment device, or can comprise comparatively more flexible materials. In some embodiments, at least a portion of a transradial treatment device is comprised of a shape-memory material such as nitinol.

4. Third Flexure Zone

As shown in FIGS. 15A to 15H, the third flexure zone 44 comprises a flexible tubular structure 74. The flexible structure 74 can comprise a metal, a polymer, or a metal/polymer composite. The material and physical features of the flexible structure 74 are selected so that the third flexure zone 44 has (1) sufficient flexibility to elastically deform when an energy delivery element 24 applies a pressure to an inner wall of a renal artery that is less than a pressure that is at high risk of causing trauma; but (2) sufficient stiffness to create a contact force or pressure between the energy delivery element 24 and inner wall of the renal artery that allows for energy delivery and stable contact. The flexibility of the third flexure zone 44 dampens the force applied by the energy delivery element 24 to the artery wall so that the force remains in this suitable range as the second flexure zone 34 is deflected over a wide range. Furthermore, by elastically deforming, a third flexure zone 44 aligns an energy delivery element 24 so that its side is in contact with the artery wall as previously discussed.

The material and physical features of the flexible structure 74 could optionally be selected so that the axial stiffness and torsional stiffness of the flexible structure 74 is not greater than the axial stiffness and torsional stiffness of the third tubular structure 62. The overall flexibility of the flexible structure 74 could optionally be at least equal to or greater than the flexibility of third tubular structure 62 when the third tubular structure has not been deflected by the control wire 40.

The flexible structure 74, as a part of the third flexure zone 44, can be coupled to the second flexure zone as described above. Alternatively, in embodiments that do not provide a second flexure zone, the third flexure zone can be coupled to the first flexure zone. As shown in FIG. 15B, the energy delivery element 24 is carried at the distal end of the flexible structure 74 for placement in contact with tissue along a vessel wall of a respective renal artery.

The material selected for the flexible structure 74 can be radiopaque or non-radiopaque. For example, a radiopaque material, e.g., stainless steel, platinum, platinum iridium, or gold, can be used to enable visualization and image guidance. When using a non-radiopaque material, the material optionally may be doped with a radiopaque substance, such as barium sulfate, to facilitate visualization and image guidance.

The configuration of the flexible structure 74 can vary. For example, in the embodiment depicted in FIGS. 15B and 15C, the flexible structure 74 comprises a thread 104 encased in, or covered with, a polymer coating or wrapping 110. The thread 104 is routed through a proximal anchor 108, which is attached to the distal end of the second flexure zone 34, and a distal anchor 106, which is fixed within or integrated into the heating element 24/electrode 46. The distal anchor 106 may be fixed within the heating element 24/electrode 46 using, e.g., solder. Alternatively, the distal anchor 106 and heating element 24/electrode 46 may be fabricated as a single piece or unitary structure.

Although various types of materials can be used to construct the aforementioned structures, in order to have a flexible structure 74 that securely connects to the second flexure zone 34 and the energy delivery element 24, it is desirable for thread 104 to be comprised of Kevlar or similar polymer thread and for the proximal anchor 108 and distal anchor 106 to be comprised of stainless steel. While the coating 110 can be comprised of any electrically insulative material, and particularly those listed later with respect to sheath 80, it is desirable for the structures of the flexible structure 74 to be encased/coated/covered by a low-durometer polymer such as carbothane laminate 110. As shown in FIG. 15C, one or more supply wires 29 may run alongside or within the flexible structure 74. As previously mentioned these wires may provide the energy delivery element 24 with electrical current/energy from the generator 26 and also convey data signals acquired by sensor 52. As depicted in FIG. 15C, the control wire 40 extending from the handle actuator 260 can be formed into the proximal anchor 108 and attached to the elongated shaft using solder 130.

One advantage of the above-described configuration of the flexible structure 74 is that the flexible structure 74 creates a region of electrical isolation between the energy delivery element and the rest of the elongated shaft. Both the Kevlar thread 104 and laminate 110 are electrically insulative, thereby providing the supply wire(s) 29 as the sole means for electrical connectivity. Accordingly, the external surface of the flexible structure 74 and third flexure zone 44 is electrically inactive.

As shown in FIGS. 15D through 15F, the flexible structure 74 allows considerable passive deflection of the third flexure zone 44 when the energy delivery element 24 is put into contact with the vessel wall. As already described, this flexibility has several potential benefits. One such benefit may be the ability of the third flexure zone 44 to reduce force or stress applied between the energy delivery element 24 and the vessel wall when or as the second flexure zone 34 is deflected, relative to the force or stress that would be applied to the vessel wall during second flexure zone 34 deflection if the third flexure zone 44 were to be removed and the energy delivery element were to be coupled directly to the distal end of the second flexure zone 34. This may reduce a risk of trauma. Furthermore, the force or stress applied by the energy delivery element 24 to the vessel wall may be maintained in a consistent range during second flexure zone 34 deflection, particularly during movement caused by respiration and/or pulsatile flow, which may facilitate consistent and/or controlled lesion creation.

The size and configuration of the flexible structure 74 enables the energy delivery element to deflect in many directions because the third flexure zone may bend by angle Θ in any plane through the axis of the distal end region. For treatments within a peripheral blood vessel such as the renal artery, it is desirable that angle Θ≤90 degrees. Optionally, the flexible structure 74 is not very resilient, i.e., does not provide a significant restoring or straightening moment when deflected.

The energy delivery element 24 desirably may provide omni-directional delivery of energy in substantially any or all directions. As the third flexure zone 44 passively deflects at a treatment site about an angle Θ appropriate to a given patient's anatomical geometry, any portion of the energy delivery element 24 may be aligned with an interior wall of the renal artery for energy delivery to target renal nerves. Blood flow may remove heat during such energy delivery, thereby reducing or mitigating a need for shielding or other preferential directing of the energy delivered to the target renal nerves that could make the third flexure zone 44 undesirably stiffer or bulkier. Such omni-directional energy delivery without shielding/preferential directing may facilitate simpler or safer positioning of the energy delivery element 24 at a treatment site, as compared to shielded or directed energy delivery elements, e.g. energy delivery elements comprising a microwave or radioactive power source.

Figure 15G:
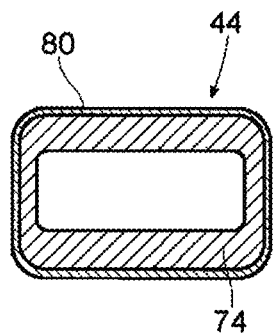
FIGS. 15G and 15H show alternative embodiments of the distal flexure zone corresponding to the elongated shaft of the treatment device shown in FIG. 5.
Figure 15H:
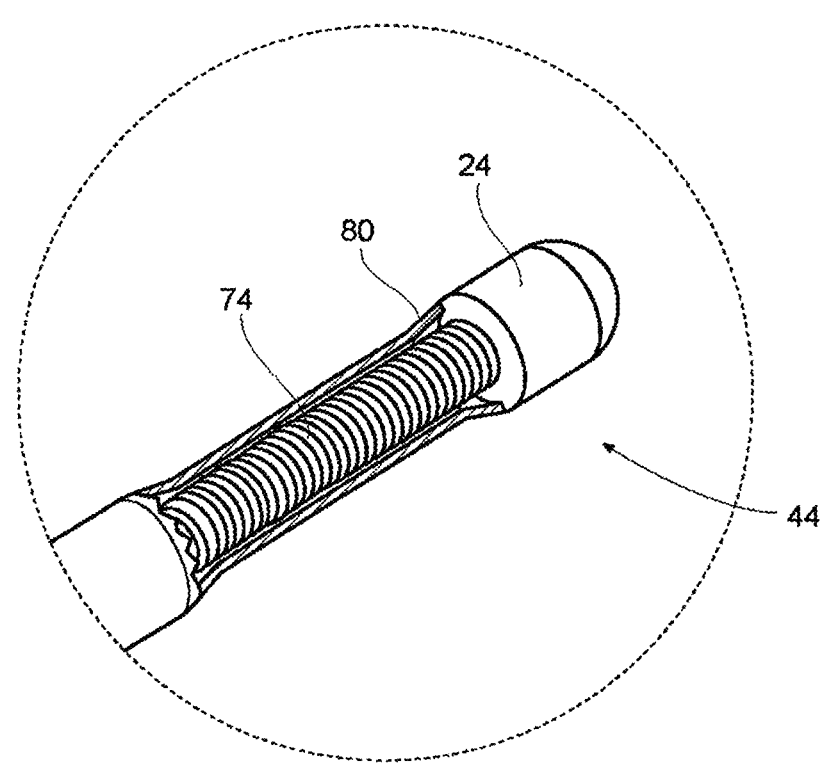

In alternative embodiments of the third flexure zone 44, the flexible structure 74 can take the form of a tubular metal coil, cable, braid, polymer or metal/polymer composite, as FIG. 15H shows. Alternatively, the flexible structure 74 can take the form of an oval, or rectangular, or flattened metal coil or polymer, as FIG. 15G shows. In alternate embodiments, the flexible structure 74 may comprise other mechanical structures or systems that allow the energy delivery element 24 to pivot in at least one plane of movement. For example, the flexible structure 74 may comprise a hinge or ball/socket combination.

If the flexible member comprises, in whole or in part, an electrically conductive material, the third flexure zone 44 desirably includes an outer sheath 80 (see FIGS. 15G and 15H) or covering over the flexible structure 74 made from an electrically insulating polymer material. The polymer material also possesses a desired durometer for flexibility of the flexible member (e.g., 25D to 55D).

Candidate materials for the polymer material include polyethylene terephthalate (PET); Pebax; polyurethane; urethane, carbothane, tecothane, low density polyethylene (LDPE); silicone; or combinations thereof. The polymer material can be laminated, dip-coated, spray-coated, or otherwise deposited/applied over the flexible structure 74. Alternatively, a thin film of the polymer material (e.g., PTFE) can be wrapped about the flexible structure 74. Alternatively, the flexible structure 74 can be inherently insulated, and not require a separate sheath 80 or covering. For example, the flexible structure can comprise a polymer-coated coiled wire.

Figure 16A:
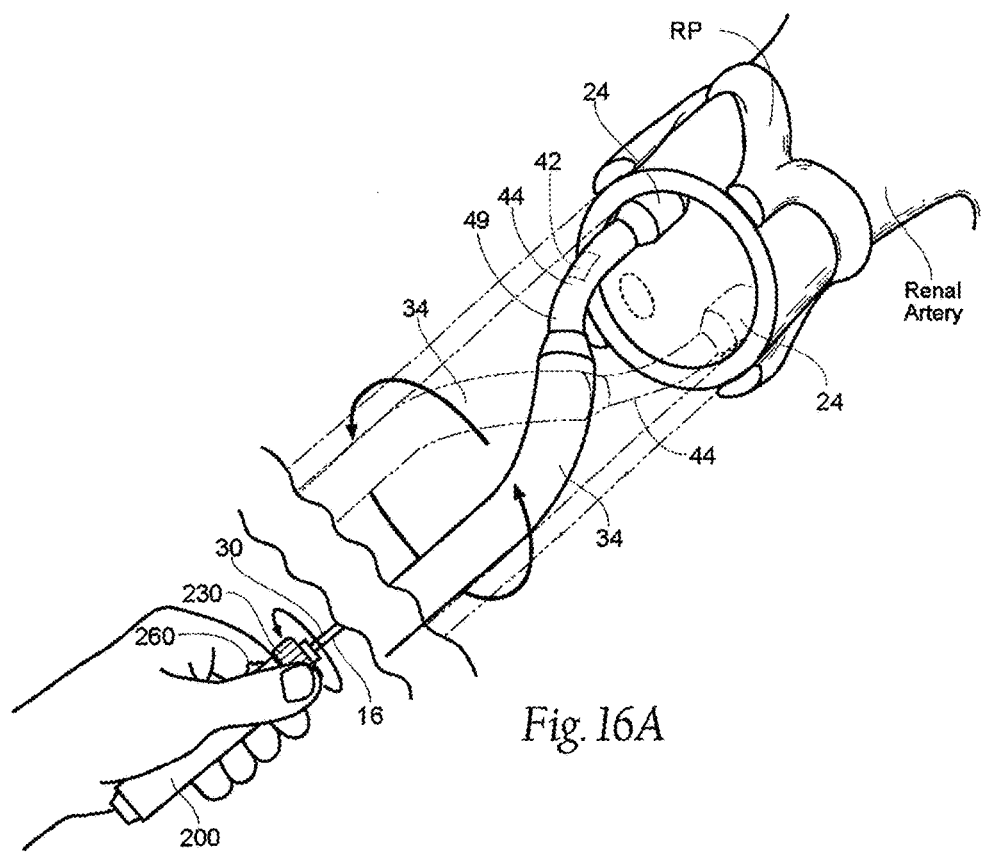
FIGS. 16A and 16B show a representative embodiment of a rotational control mechanism coupled to the handle assembly of the treatment device shown in FIG. 5.

Optionally, third flexure zone 44 can include a sensor 42 that indicates an amount of deflection of third flexure zone 44 as shown in FIG. 16A. The sensor 42 can be, for example, a piezo-resistive element that is a full or partial length of the third flexure zone 44 and can be mounted to a side of the third flexure zone. A pair of conductors (not shown) running through the elongated shaft 16 would connect the sensor 42 to an electrical supply and sensing circuit (not shown). When the third flexure zone 44 is deflected in response to a force applied to the energy delivery element 24 or a portion of the third flexure zone 44 by an inner wall of a renal artery, the sensor 42 will deliver a signal that quantifies the amount of deflection. When the sensor 42 is a piezo-resistive element its resistance will change proportional to its strain. The amount of deflection of third flexure zone 44 is an indication of contact force with the inner wall of the renal artery.

5. Rotation Controller

Figure 16B:
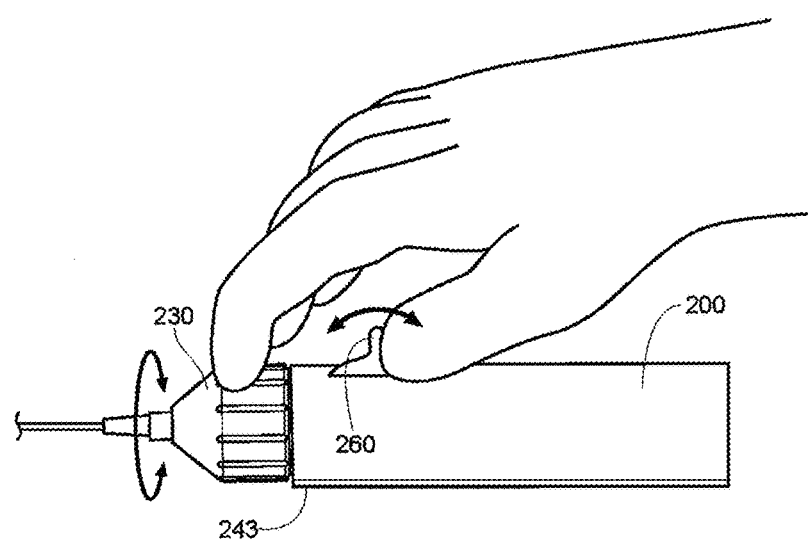

As will be discussed later in greater detail, it is desirable to rotate the device within the renal artery after the energy delivery element is in contact with the vessel wall. However, it may be cumbersome and awkward for a clinical practitioner to rotate the entire handle assembly at the proximal end of the device, particularly given the dimensions of the renal anatomy. In one representative embodiment, as shown in FIGS. 16A and 16B, the proximal end of the shaft 16 is coupled to the handle assembly 200 by a rotator 230.

The proximal end of the force transmitting section 30 is attached to a stationary coupling 88 on the rotator 230. Rotation of the rotator 230 (as FIG. 16A shows) thereby rotates the force transmitting section 30, and, with it, the entire elongated shaft 16, without rotation of the handle assembly 200. As FIG. 16A shows, a caregiver is thereby able to hold the proximal portion of the handle assembly 200 rotationally stationary in one hand and, with the same or different hand, apply a torsional force to the rotator 230 to rotate the elongated shaft 16. This allows the actuator to remain easily accessed for controlled deflection.

Since there are cables and wires running from the handle assembly through the shaft of the device (e.g., control 40, electrical transmission wire and/or sensor/thermocouple wire(s) 29, etc.), it is desirable to limit rotation of the shaft relative to these wires in order to avoid unnecessary entanglement and twisting of these wires. A rotational limiting element can be incorporated into the handle assembly and rotator to address this issue. The rotator 230 and handle assembly can be configured to allow for the optimal number of revolutions for the shaft, given such structural or dimensional constraints (e.g., wires). The components of the handle assembly may be configured, for example to allow for a finite number of revolutions of the shaft (e.g., two) independent of the handle assembly. Limiting rotation of the shaft to the optimal number of revolutions may be achieved by any number of commonly known mechanical features.

As has been described and will be described in greater detail later, by intravascular access, the caregiver can manipulate the handle assembly 200 to locate the distal end region 20 of the elongated shaft 16 within the respective renal artery. The caregiver can then operate the actuator 260 on the handle assembly 200 (see FIGS. 16A and 16B) to deflect the energy delivery element 24 about the second flexure zone 34. The caregiver can then operate the rotator 230 on the handle assembly 200 (see FIGS. 16A and 16B) to apply a rotational force along the elongated shaft 16. The rotation of the elongated shaft 16 when the second flexure zone 34 is deflected within the respective renal artery rotates the energy delivery element 24 within the respective renal artery, making it easier to achieve contact with the vessel wall and determine whether there is wall contact, particularly in planes where there is poor angiographic visualization.

In an additional aspect of the disclosed technology, the handle assembly 200 may be configured to minimize operator/caregiver handling of the device while it is within the patient. As shown, for example, in FIG. 16B, the handle assembly also comprises one or more surfaces 243 that substantially conform to the surface beneath (e.g., operating table). This surface 243, which is shown to be substantially flat in FIG. 16B, can alternatively be curved, shaped or angled depending on the configuration and/or geometry of the beneath surface. The conforming surface 243 enables the clinical operator to keep the handle assembly 200 stable when the treatment device 12 is within the patient. In order to rotate the device when it is inside the patient, the operator can simply dial the rotator 230 without any need to lift the handle assembly. When the operator desires to retract the device for subsequent treatments, the operator can simply slide the handle assembly along the beneath surface to the next position. Again, this mitigates the risk of injury due to operator error or over handling of the treatment device. Additionally or alternatively, the lower surface can engage the surface underneath using clips, texture, adhesive, etc.

Additional enhancements to the rotation mechanism disclosed herein include providing tactile and/or visual feedback on the rotational fitting so that the operator can exercise greater control and care in rotating the device. The rotator 230 can also be selectively locked to the handle assembly, thereby preventing further rotation, if the operator wishes to hold the treatment device in a particular angular position. Another optional enhancement includes providing distance markers along the shaft/handle assembly to enable the operator to gauge distance when retracting the treatment device.

B. Second Representative Embodiment (Third Flexure Zone Comprises a Flexible Thermal Heating Element)

Figure 17A:
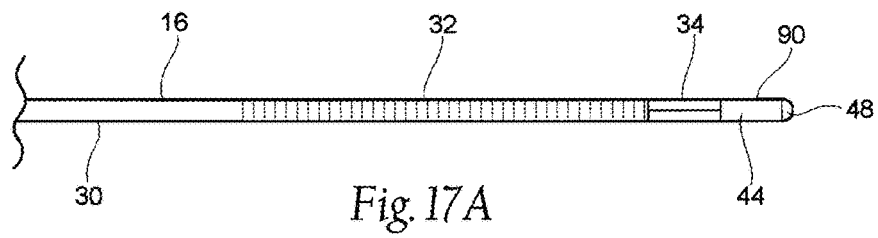
FIGS. 17A and 17B show an alternative representative embodiment of an elongated shaft for a treatment device like that shown in FIG. 5, showing examples of the different structural, mechanical and functional regions that the elongated shaft can incorporate.
Figure 17B:
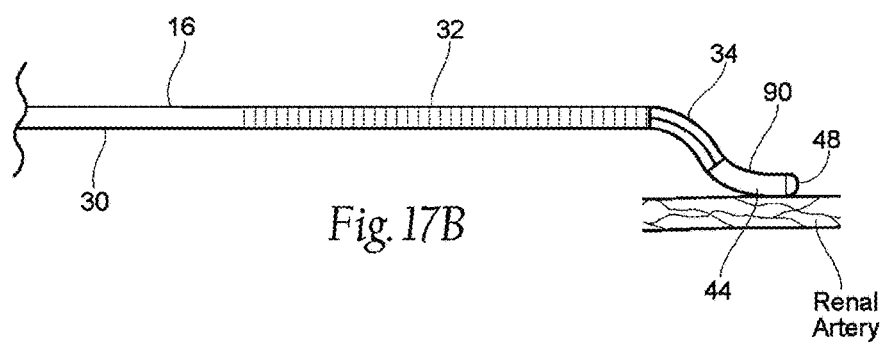

FIGS. 17A and 17B show a representative embodiment of an elongated shaft 16 that includes a force transmitting section 30, a first or proximal flexure zone 32, a second flexure zone 34, and a third flexure zone 44. In this embodiment, the materials, size, and configuration of the proximal force transmitting section 30, first flexure zone 32, and second flexure zone 34 are comparable to the respective counterparts described in the first representative embodiment.

In this embodiment, however, the third flexure zone 44 is sized and configured to itself serve as a flexible energy delivery 90. In diameter, the flexible energy delivery element 90 is sized and configured to be equal to or greater than the second flexure zone 34. The total surface area TSA of the flexible thermal heating element 90 is thereby increased, so that the possible active surface area of the electrode 46 is increased as well.

Also, in this arrangement, the entire length of the flexible thermal heating element 90 shares the flexibility properties of the third flexure zone 44, as previously described. The flexible thermal heating element can be an active flexible electrode. Materials are selected that, in addition to imparting the desired flexibility, are electrically conductive as well. The active flexible electrode can be made from a flexible conductive wire or tube, a laser cut conductive tube, a coiled conductor, or a multiple filament brush electrode. Alternatively, the flexible thermal heating element 90 can be a flexible resistive heating element made from an electrically insulated resistive metal that heats when electrical current is delivered through it. The flexible thermal heating element 90 is flexible enough along its entire length to conform closely against the vessel wall, thereby further increasing the possible active surface area of the thermal heating element. The flexible thermal heating element 90 may also more readily deflect away from the vessel wall when engaging the vessel wall head-on, to thereby minimize the forces exerted against the vessel wall as the flexible thermal heating element 90 is placed into side-on relationship with the vessel wall. The flexible thermal heating element 90 can thereby be considered more atraumatic.

In the illustrated embodiment, the active, flexible electrode 90 further desirably includes a distal region that is tapered to form a blunt, atraumatic end surface 48. The end surface 48 can be formed from metal materials by laser, resistive welding, or machining techniques. The end surface 48 can also be formed from polymer materials by bonding, lamination, or insert molding techniques.

C. Third Representative Embodiment (Third Flexure Zone Includes a Substantially Spherical Active Electrode)

Figure 18A:
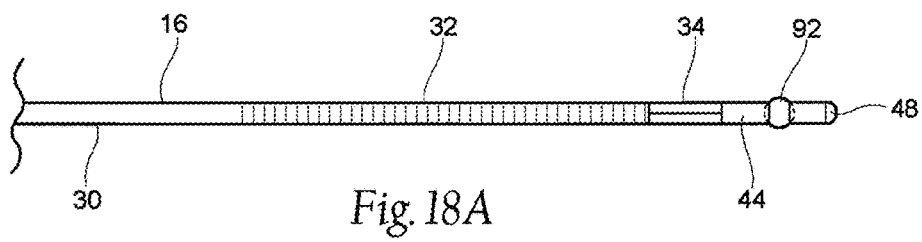
FIGS. 18A to 18C show additional alternative representative embodiments of an elongated shaft for a treatment device like that shown in FIG. 5, showing examples of the different structural, mechanical and functional regions that the elongated shaft can incorporate.
Figure 18B:
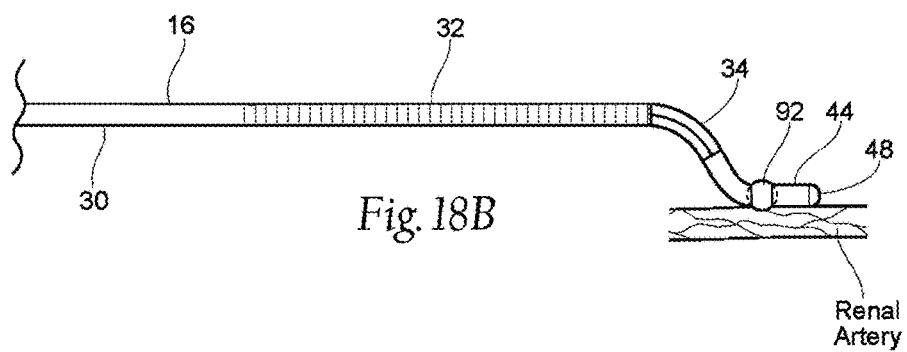
Figure 18C:
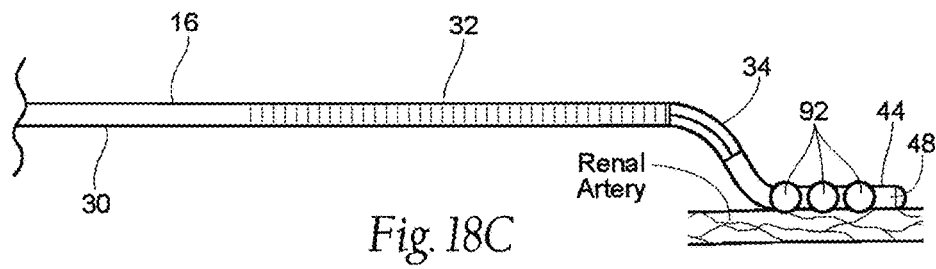

FIGS. 18A-18C show a representative embodiment of an elongated shaft 16 that includes a proximal force transmitting section 30, a first flexure zone 32, and a second flexure zone 34, and a third flexure zone 44. In this embodiment, the materials, size, and configuration of the proximal force transmitting section 30, first flexure zone 32, and second flexure zone 34 are comparable to the respective counterparts in the first and second embodiments.

In this embodiment, however, the third flexure zone 44 is sized and configured to carry at least one substantially spherical active electrode 92 at a location more proximally spaced from its distal end. While the at least one active electrode 92 alternatively may comprise a substantially cylindrical configuration, such that the active electrode is a band electrode, the preferred substantially spherical configuration of the at least one active electrode 92 advantageously is expected to reduce electrical edge effects that may be encountered at the more abrupt transition that exists at relatively sharp edges at the periphery of a cylindrically shaped electrode. For the purposes of the present invention, substantially spherical electrodes include electrodes that protrude outward from elongated shaft 16 and have rounded edges. Thus, substantially spherical electrodes may be spherical, oblong, ellipsoid, cylindrical with rounded edges, complex contoured, etc.

In this embodiment, the third flexure zone 44 shares the flexibility characteristics of the third flexure zone 44 described with respect to the previous embodiments. In diameter, the third flexure zone 44 of the third representative embodiment shown in FIG. 18 may be sized and configured to be smaller than or approximately equal to the diameter of the second flexure zone 34. In diameter, the at least one spherical active electrode 92 is sized to be larger than the diameter of the third flexure zone 44. Therefore, flexure of the third flexure zone 44 can place the spherical electrode 92 into contact with a greater tissue area, thereby increasing the active surface area (ASA) of the electrode.

In the illustrated embodiment, the third flexure zone 44 desirably includes a distal region that is tapered to form a blunt, atraumatic end surface 48. The end surface 48 can be formed from metal materials by laser, resistive welding, or machining techniques. The end surface 48 can also be formed from polymer materials by bonding, lamination, or insert molding techniques.

The at least one spherical electrode 92 can be attached to the distal flexure zone 44 e.g., by crimping, heat shrink, molding, spot welding, laser welding, or soldering techniques. The placement of the at least one spherical electrode 92 along the length of the third flexure zone 44 can vary. It can be placed, e.g., in the approximate mid-region of the third flexure zone 44, or closer to the distal end than the proximal end, or vice versa.

FIGS. 18A and 18B illustrate the third embodiment with a single spherical electrode 92. However, any number of additional spherical electrodes 92 may be provided along the third flexure zone 44, as desired. For example, FIG. 18C illustrates the third embodiment with three spherical electrodes 92 positioned along the length of the third flexure zone 44. In some embodiments, one or more spherical electrodes 92 can additionally or alternatively be placed along the second flexure zone 34, as described herein below.

D. Fourth Representative Embodiment (Third Flexure Zone Includes a Substantially Semi-Spherical Active Electrode)

Figure 19A:
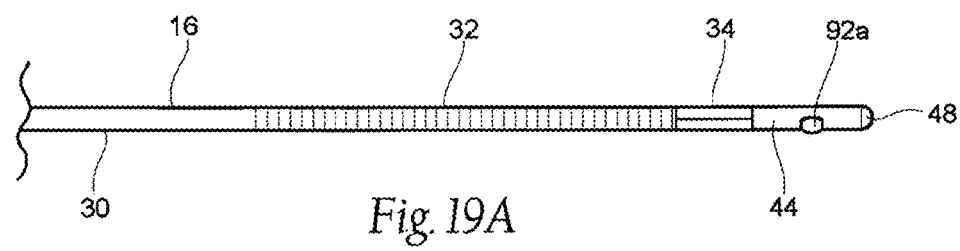
FIGS. 19A to 19C show additional alternative representative embodiments of an elongated shaft for a treatment device like that shown in FIG. 5, showing examples of the different structural, mechanical and functional regions that the elongated shaft can incorporate.
Figure 19B:
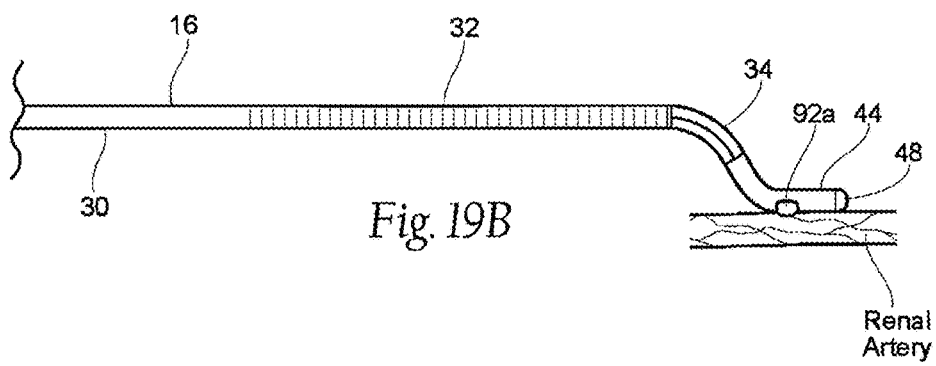
Figure 19C:
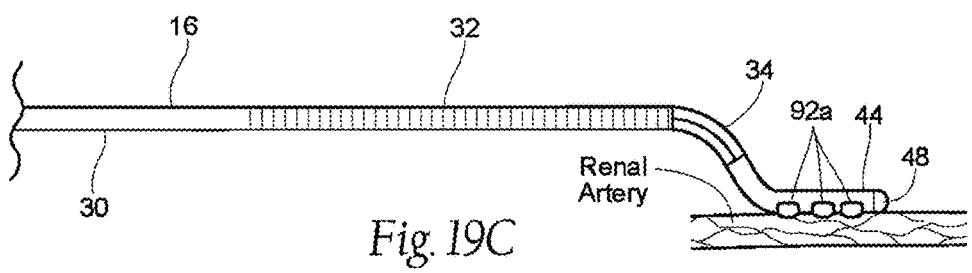

FIGS. 19A-19C show a representative embodiment of an elongated shaft 16 that includes a proximal force transmitting section 30, a first flexure zone 32, and a second flexure zone 34, and a third flexure zone 44. In this embodiment, the materials, size, and configuration of the proximal force transmitting section 30, first flexure zone 32, and second flexure zone 34 are comparable to the respective counterparts in the first, second and third embodiments.

In this embodiment, however, the third flexure zone 44 is sized and configured to carry at least one substantially semi-spherical active electrode 92a at a location more proximally spaced from its distal end. The semi-spherical active electrode is attached to the third flexure zone 44, such that it is directed toward target tissue in the deflected configuration of the third flexure zone. While the at least one active electrode 92a alternatively may comprise a substantially semi-cylindrical configuration, the preferred substantially semi-spherical configuration of the at least one active electrode 92a advantageously is expected to reduce electrical edge effects that may be encountered at relatively sharp edges at the periphery of a semi-cylindrically shaped electrode. For the purposes of the present invention, substantially semi-spherical electrodes include electrodes that protrude outward from one side of elongated shaft 16 and have rounded edges. Thus, substantially spherical electrodes may be semi-spherical, semi-oblong, semi-ellipsoid, semi-cylindrical with rounded edges, complex contoured along one side of shaft 16, etc.

In this embodiment, the third flexure zone 44 shares the flexibility characteristics of the third flexure zone 44 described with respect to the previous embodiments. In radius, the third flexure zone 44 of the third representative embodiment shown in FIG. 19 is sized and configured to be approximately equal to the radius of the second flexure zone 34. In radius (i.e., from the cross-sectional center of the third flexure zone 44), the at least one semi-spherical active electrode 92a is sized to be larger than the radius of the third flexure zone 44. Therefore, flexure of the third flexure zone 44 can place the semi-spherical electrode 92a into contact with a greater tissue area, thereby increasing the active surface area (ASA) of the electrode. Use of semi-spherical electrode 92a, rather than use of spherical electrode 92, is expected to increase the ASA to TSA ratio of the electrode.

In the illustrated embodiment, the third flexure zone 44 desirably includes a distal region that is tapered to form a blunt, atraumatic end surface 48. The end surface 48 can be formed from metal materials by laser, resistive welding, or machining techniques. The end surface 48 can also be formed from polymer materials by bonding, lamination, or insert molding techniques.

The at least one semi-spherical electrode 92 can be attached to the distal flexure zone 44 e.g., by spot welding, laser welding, or soldering techniques. The placement of the at least one spherical electrode 92 along the length of the third flexure zone 44 can vary. It can be placed, e.g., in the approximate mid-region of the third flexure zone 44, or closer to the distal end than the proximal end, or vice versa.

FIGS. 19A and 19B illustrate the fourth embodiment with a single semi-spherical electrode 92. However, any number of additional semi-spherical electrodes 92 may be provided along the third flexure zone 44, as desired. For example, FIG. 18C illustrates the fourth embodiment with three semi-spherical electrodes 92 positioned along the length of the third flexure zone 44. In some embodiments, one or more semi-spherical electrodes 92 can additionally or alternatively be placed along the second flexure zone 34, as described herein below

E. Fifth Representative Embodiment (Third Flexure Zone Includes a Multi-Filament Brush Active Electrode)

Figure 20A:
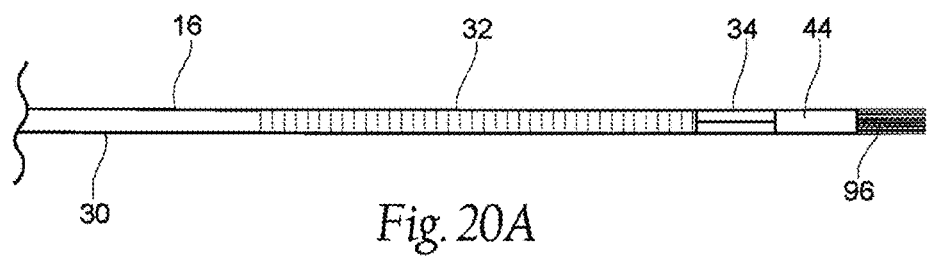
FIGS. 20A and 20B show additional alternative representative embodiments of an elongated shaft for a treatment device like that shown in FIG. 5, showing examples of the different structural, mechanical and functional regions that the elongated shaft can incorporate.
Figure 20B:
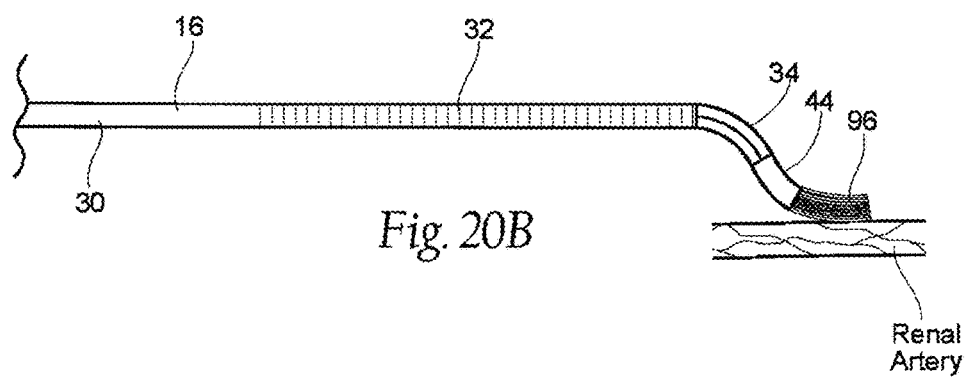

FIGS. 20A and 20B show a representative embodiment of an elongated shaft 16 that includes a proximal force transmitting section 30, a first flexure zone 32, and a second flexure zone 34, and a third flexure zone 44. In this embodiment, the materials, size, and configuration of the proximal force transmitting section 30, first flexure zone 32, and second flexure zone 34 are comparable to the respective counterparts in the previously described embodiments.

In this embodiment, however, the third flexure zone 44 is sized and configured to carry at its distal end a brush active electrode 96 having a plurality of filaments. In diameter, the brush electrode 96 is sized and configured to be equal to or greater than the second flexure zone 34. The diameter and multiple filaments of the brush electrode 96 increase the total surface area TSA of the brush electrode 96, so that the possible active surface area of the electrode 46 is increased as well.

Also, in this arrangement, the entire length of the brush electrode 96 shares the flexibility properties of, or is more flexible than, the third flexure zone 44, as previously described. Materials are selected that, in addition to imparting the desired flexibility, are electrically conductive as well. The brush electrode 96 is thereby flexible enough along its entire length to conform closely against the vessel wall with individual filaments of the electrode independently deflecting and conforming to the wall, thereby further increasing the possible active surface area of the electrode.

As compared to previously described embodiments of the electrode 46, filaments of the brush electrode 96 more readily may deflect away from the vessel wall when engaging the vessel wall head-on, thereby reducing the forces exerted against the vessel wall as the electrode 96 is placed into contact with the vessel wall. The multi-filament brush electrode 96 thereby may be considered atraumatic and may mitigate a need for the third flexure zone 44 (e.g., the brush electrode 96 may be coupled to a distal end of the second flexure zone 34 if the third flexure zone 44 is not provided). Furthermore, the increased TSA of the brush electrode 96 may enhance heat transfer due to active (e.g., via an injected thermal fluid) or passive (e.g., via blood flow) cooling of the electrode, which may facilitate delivery of higher power electrical fields through the electrode for thermally-induced modulation of target renal nerves with reduced injury to non-target tissue of the renal vasculature.

F. Sixth Representative Embodiment (Third Flexure Zone Includes Off-Axis Force Redistribution)

FIGS. 21A, 21B and 21C show a representative embodiment of an elongated shaft 16 that includes a force transmitting section 30, a first flexure zone 32, and a second flexure zone 34, and a third flexure zone 44. In this embodiment, the materials, size, and configuration of the proximal force transmitting section 30, first flexure zone 32, and second flexure zone 34 are comparable to the respective counterparts in the previously described embodiments.

In this embodiment, however, the third flexure zone 44 is sized and configured to promote buckling or bending in the first and/or second flexure zones with reduced vessel wall contact force, as compared to some previously described embodiments. This may be achieved by an off-axis bend 49 that positions the normal force vector applied between the third flexure zone and the vessel wall off-axis from the longitudinal axis of the elongated shaft 16. An off-axis bend 49 can reduce the risk of trauma by means of i) displacing an axial load on a catheter column to an eccentric load and/or a side load to facilitate buckling of the catheter shaft, ii) changing the direction of a force applied to a renal artery wall, iii) reducing pressure exerted to the renal artery wall by increasing surface area, and/or iv) facilitating navigation around a sharp bend. It should be understood that the term off-axis bend can be used interchangeably with force redirecting element, or pre-shaped geometry.

For example, as seen in FIG. 21, the flexible structure 74 of the third flexure zone 44, the polymer coating or wrapping 110, can comprise an off-axis bend 49 in an unconstrained configuration. The material and physical features of the flexible structure 74 are selected so that the axial stiffness and torsional stiffness of the flexible structure 74 is not greater than the axial stiffness and torsional stiffness of the third tubular structure 62, and the overall flexibility of the flexible structure 74 is at least equal to and desirably greater than the flexibility of third tubular structure 62 when the third tubular structure has not been deflected by the control wire 40. Alternatively the force redirecting element 49 can be a bend in a third flexure zone 44 made from a wire or tube with desired flexibility incorporated into the force dampening section 44 by means of material selection and dimension. For example, the force dampening section 44 can be made from Nitinol wire with a diameter of about 0.10 to 0.20 mm.

The curvature or off-axis bending of the flexible structure 74 in the unconstrained configuration (as shown in FIGS. 21A and 21B) positions the normal force vector exerted as the third flexure zone 44 engages the vessel wall out of alignment with the axis of the first flexure zone 32 and/or the second flexure zone 34 upon advancement of the catheter within a renal artery. It is expected that this positioning of the normal force vector may reduce the vessel contact force needed to cause buckling or bending of the first and/or second flexure zone, which also may reduce a risk of traumatic force application to the vessel wall. Additionally/alternatively, such a second flexure zone may facilitate the establishment of contact and treatment at angularly opposed luminal surfaces of the renal artery without necessitating rotation of elongated shaft 16.

For purposes of discussing the force interactions between the catheter and artery wall a simplified example with an effectively stiff and straight catheter 300 (as shown in FIG. 21D) follows. As discussed in more detail later, variables such as catheter flexibility, dimensions, and geometry as represented by the present invention modify the force interactions. Every force has both a magnitude and direction. The magnitude of the force applied by an effectively stiff and straight catheter on to the artery wall is essentially equal to the force applied by the caregiver advancing the catheter into the body. In this example the essentially straight and stiff catheter is advanced into a renal artery by pushing the proximal end of the catheter, thus the catheter's advancing trajectory is translation along the catheter's axis. Therefore, the direction of the force applied by the catheter on the artery wall is forward along the catheter's axis. In this simplified example, the artery wall is represented by an elastic wall that has a maximum distension and wall strength. The force exerted by the artery wall includes a normal force, the component perpendicular to the surface, which is characterized by the artery wall's ability to withstand distension and puncture (a function of elasticity and strength); and the component parallel to the artery wall surface, which is characterized by the friction between the artery wall and catheter surface.

Figure 21H:
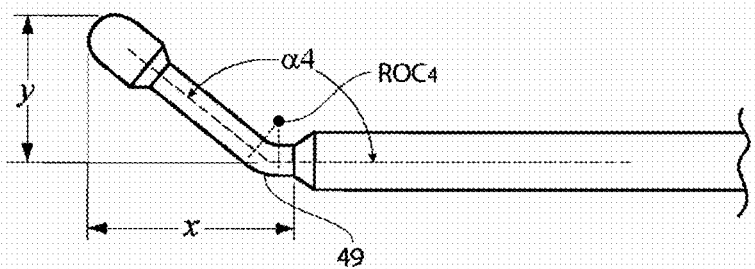
FIGS. 21H to 21L show examples of configurations of force redirecting elements.

A straight catheter shaft is similar to a column which can withstand a significant load along its axis before deforming. A load applied to the side of a column will cause it to bend at a lower force than an axial load. A load applied parallel to the column but at a distance from its axis, an eccentric load, will cause the column to buckle with a smaller load than an axial load. The more eccentric the load, the smaller the force required to buckle the column. A specially configured force redirecting element 49 distances the distal tip of the catheter from the axis such that as the distal tip is advanced into a renal artery wall the load applied to all parts of the distal end region 20 is eccentric. In particular, the load applied to the force dampening section 44 is at an angle to the axis, thereby promoting deformation or buckling of the force dampening section 44; the load applied to the deflectable section is eccentric causing it to buckle as shown in FIGS. 21F and 21G. Thus, the distal end region 20 is configured to deform under a load that is less than a load that could apply a pressure to an artery wall causing excessive trauma, thereby reducing the risk of trauma to the renal artery wall. Examples of distal end regions 20 comprising different embodiments of force redirecting element 49 are shown in FIGS. 21H to 21L.

Furthermore, the pressure applied by the catheter to the artery wall is the force divided by the area of contact. If only the tip of the catheter contacts the artery wall, the pressure is equal to the force divided by the contacting surface area of the tip. If the catheter contacts the artery wall over a large contacting surface area SA such as along the side of an energy delivery element 24 and force dampening section 44, as shown in FIG. 21F, then the pressure is greatly reduced as the force is divided by a much larger area. For example, the pressure exerted by a catheter with a 0.049" diameter tip is about 75% greater than pressure exerted dispersed over the length of a distal assembly with a force redirecting element 49.

Figure 21I:
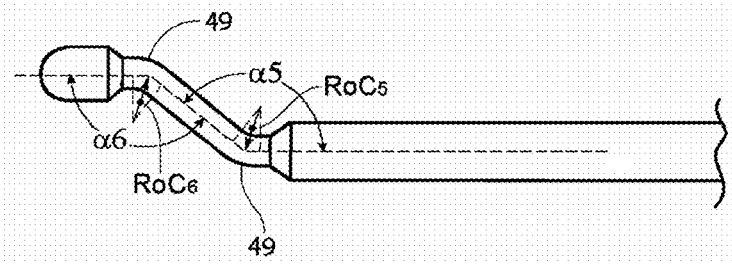
Figure 21J:
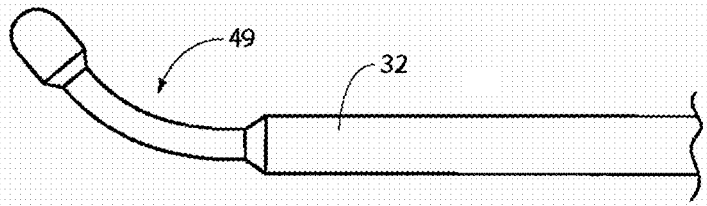
Figure 21K:
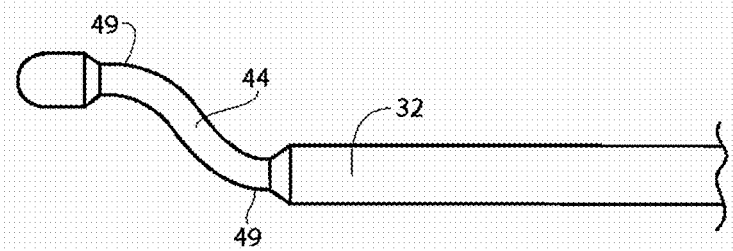
Figure 21L:
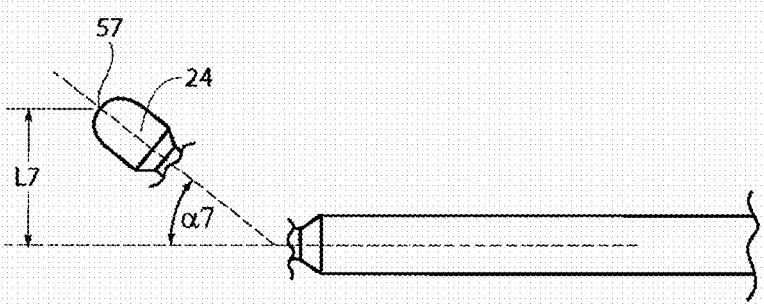
Figure 21M:
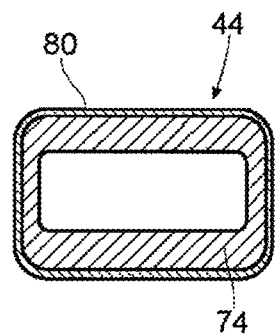
FIGS. 21M and 21N show alternative embodiments of the force dampening section corresponding to the elongated shaft of the treatment device shown in FIG. 21A.

In some embodiments force redirecting element 49 and force dampening section 44 comprise the same structure wherein the force redirecting element is a preformed bend or curve in the force dampening section 44 as shown in FIGS. 21H and 21J. Alternatively, force redirecting element can be two preformed bends or curves in the force dampening section 44 as shown in FIGS. 21I and 21K, or force redirecting element can be any number and combination of bends or curves that distance the distal tip 57 of an energy delivery element 24 from the axis of the elongated body 16 as shown in FIG. 21L.

Figure 21N:
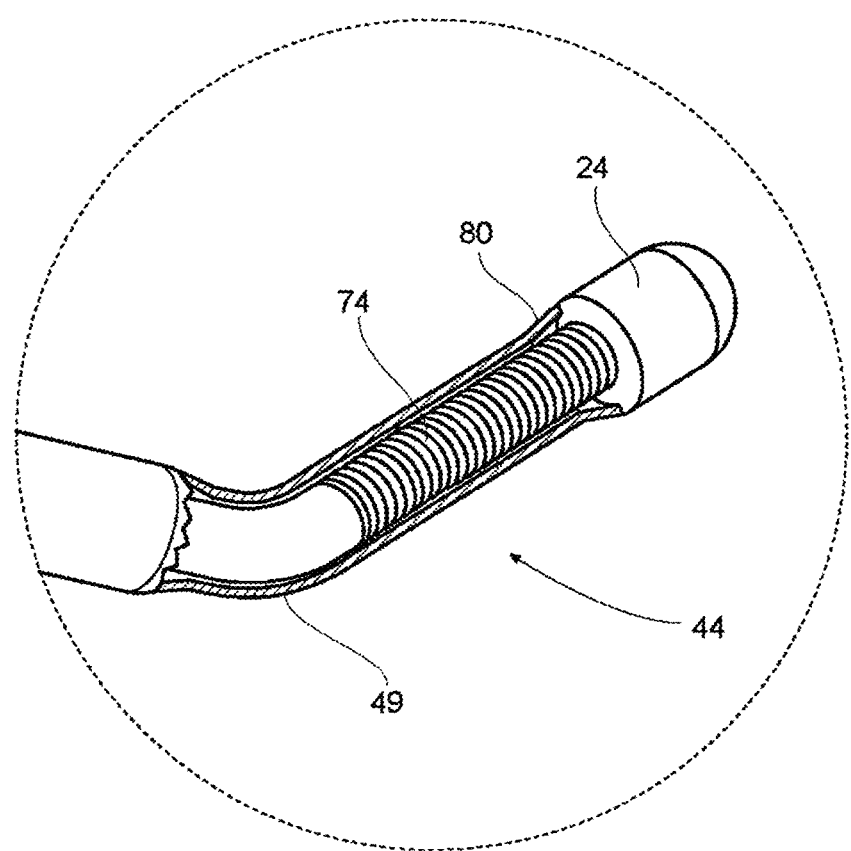

In other embodiments force redirecting element 49 and force dampening section 44 can comprise separate structures. For example, as shown in FIG. 21N force redirecting element 49 is a wire or tube with a preformed angular bend. The force redirecting element can be connected to a separate force dampening section 44, which in FIG. 21N is a spring coil.

Referring to FIG. 21H, a force redirecting element 49 can comprise an angular bend with an angle $\alpha 4$ between about 135° and 170°, for example less than or equal to about 160° and a radius of curvature RoC4 between about 0 mm and 1 mm, for example less than or equal to about 0.25 mm. The force redirecting element 49 can be positioned along the force dampening section 44 within about 0 mm to 2 mm from the proximal end of the force dampening section 44, for example less than or equal to about 0.25 mm. The length of the distal assembly 53 distal to the force redirecting element 49 can be between 3 mm and 10 mm, for example less than or equal to about 5 mm.

Referring to FIG. 21I a force redirecting element 49 can comprise a first angular bend with and angle α5 and radius of curvature RoC5 and a second angular bend with and angle α6 and radius of curvature RoC6; wherein the angles α5 and α6 is between 135° and 170°, for example less than or equal to about 145°, radius of curvature RoC5 and RoC6 is between 0 mm and 2 mm, for example less than or equal to about 0.25 mm.

As shown in FIGS. 21J and 21K the force redirecting element 49 of the first representative embodiment can comprise one or two curves. The force redirecting element 49 can be a curved force dampening section 44.

As shown in FIG. 21K a force redirecting element 49 can comprise any pre-formed geometry that places the distal end of a catheter relative to the axis of the deflectable section 34 by a preset angle α7 and distance L7, wherein the preset angle α7 is between about 15° to 45°, for example less than or equal to about 20°, and the distance L7 is between about 1 mm and 6 mm, for example less than or equal to about 2 mm.

The force redirecting elements described above can be oriented such that the energy delivery element 24 is displaced in a direction that is in about the opposite direction and same plane as the predetermined biased flexure of the deflectable section 34. Alternatively a force redirecting element can be oriented such that the energy delivery element 24 is displaced in a direction that is in about the same direction and plane as the predetermined biased flexure of the deflectable section 34.

G. Seventh Representative Embodiment (Second Flexure Zone Includes a Pre-Formed Shape)

FIGS. 22A-22K show representative embodiments of the seventh embodiment with an elongated shaft 16 that includes a force transmitting section 30, a first flexure zone 32, a second flexure zone 34, and an optional third flexure zone 44. In these embodiments, the materials, size, and configuration of the force transmitting section 30, first flexure zone 32, and optional third flexure zone 44 are comparable to their respective counterparts described in any of the previous embodiments.

In these embodiments, however, the second flexure zone 34 may comprise a third tubular structure 62 with a force redirecting element 49 comprising a pre-formed shape or geometry that, in an unrestrained configuration, is off-axis or deflected from the longitudinal axis of the elongated shaft 16 (see, e.g., FIGS. 22A and 22B), which may facilitate locating of the energy delivery element 24 into contact with a treatment site within a renal artery. The length and diameter of second flexure zone 34 may be comparable to those described in any of the previous embodiments of the second flexure zone 34. In one embodiment, the pre-formed shape of the third tubular structure 62 may be specified to provide the second flexure zone 34 with a desired radius of curvature RoC2 and angle α2 (see FIG. 7C), such as those described previously. In other embodiments, the pre-formed shape can take other geometrical and dimensional forms. The third tubular structure 62 may be fabricated, for example, from a shape memory material, such as a nickel-titanium alloy (i.e., Nitinol) or from spring steel, to provide the pre-formed shape.

When advanced within, and retrieved from, a renal artery via an intravascular path, the second flexure zone 34 may be positioned within a guide catheter, such as guide catheter 96, which may substantially straighten or constrain the third tubular structure 62 during such intravascular delivery and retrieval. After advancement of the second flexure zone 34 distal of the guide catheter, the third tubular structure 62 may re-assume its off-axis, pre-formed shape, e.g., to bring the energy delivery element 24 into contact with a wall of the renal artery. The second flexure zone 34 optionally may be actively deflected (e.g., as described previously via control wire 40 attached to handle actuator 260), in addition to the passive deflection provided by the pre-formed shape of the third tubular structure 62. Alternatively, deflection of the second flexure zone 34 may be entirely passive (i.e., may be entirely due to the pre-formed shape of the third tubular structure), mitigating a need for wire 40 and actuator 260.

1. Active Deflection in the Direction of the -Pre-Formed Shape

When the second flexure zone 34 is configured for both active and passive deflection, the third tubular structure 62 may be configured such that active deflection of the second flexure zone is biased in the direction of the third tubular structure's pre-formed shape. This can be achieved by making the third tubular structure 62 compressible in the direction of the structure's pre-formed shape and resilient to compression opposite the structure's pre-formed shape. In such a configuration, active deflection augments or magnifies the passive deflection provided by the third tubular structure's pre-formed shape.

Figure 22C:
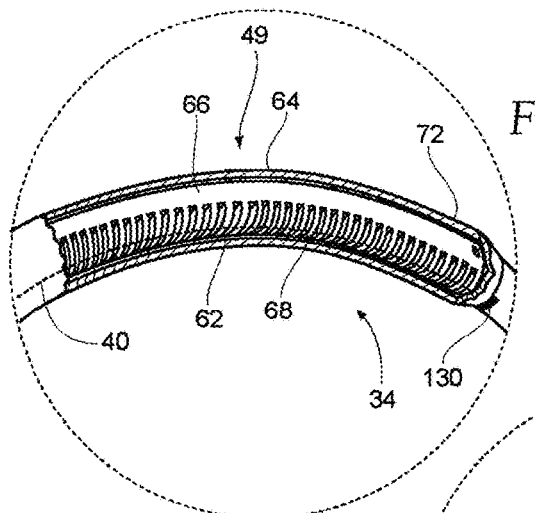

FIG. 22C provides a representative embodiment of a second flexure zone 34 that has a pre-formed shape and that is configured for active deflection in the direction of the pre-formed shape. In FIG. 22C, the third tubular structure 62 comprises a laser-cut pattern that includes spine 66 with connecting ribs 68. The spine 66 comprises a pre-formed shape that positions the second flexure zone 34 off-axis or deflected from the longitudinal axis of the elongated shaft 16 in an unrestrained configuration. The direction of the pre-formed shape is such that the laser-cut pattern biases active deflection of the third tubular structure 62, in response to pulling on the control wire 40 coupled to the distal end of the third tubular structure 62, toward the direction of the pre-formed shape. The control wire 40 is attached to a distal end of the second flexure zone with solder 130.

2. Active Deflection in the Opposite Direction of the Pre-Formed Shape for Bi-Directional Deflection via a Single Control Wire As an alternative to the embodiment of FIG. 22C, when the second flexure zone 34 is configured for both active and passive deflection, the third tubular structure 62 may be configured such that active deflection of the second flexure zone is biased in a substantially opposite direction of the third tubular structure's pre-formed shape. This can be achieved by making the third tubular structure 62 compressible in the opposite direction of the structure's pre-formed shape and resilient to compression in the direction of the structure's pre-formed shape. In such a configuration, active deflection reduces or reverses the passive deflection provided by the third tubular structure's pre-formed shape.

Figure 22D:
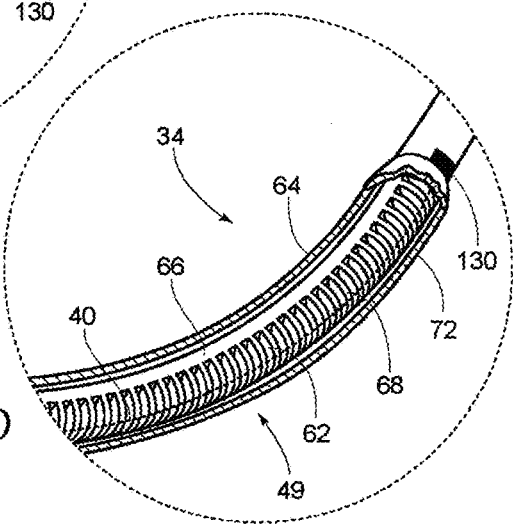

FIG. 22D provides a representative embodiment of a second flexure zone 34 that has a pre-formed shape and that is configured for active deflection in the opposite direction of the pre-formed shape. In FIG. 22D, the third tubular structure 62 again comprises a laser-cut pattern that includes spine 66 with connecting ribs 68. As in the embodiment of FIG. 22C, the spine 66 comprises a pre-formed shape that positions the second flexure zone 34 off-axis or deflected from the longitudinal axis of the elongated shaft 16 in an unrestrained configuration. However, in contrast to the embodiment of FIG. 22C, the direction of the pre-formed shape is such that the laser-cut pattern biases active deflection of the third tubular structure 62, in response to pulling on the control wire 40 coupled to the distal end of the third tubular structure 62, away from the direction of the pre-formed shape.

Figure 22E:
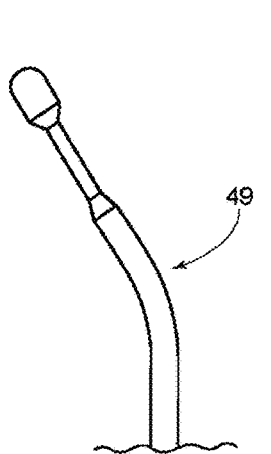
Figure 22F:
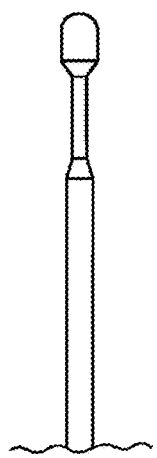
Figure 22G:
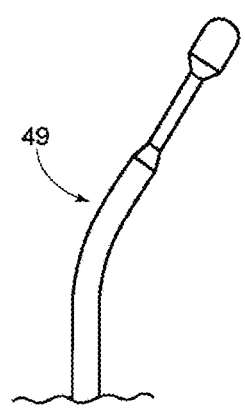

As seen in FIGS. 22E-22G, when the second flexure zone 34 has a pre-formed shape and is configured for active deflection in the opposite direction of the pre-formed shape, the second flexure zone desirably may achieve bi-directional bending via a single control wire 40. As seen in FIG. 22E, in the unrestrained configuration of the second flexure zone 34 without active deflection (e.g., when the control wire 40 is not being pulled in tension), the second flexure zone 34 assumes the pre-formed shape of its third tubular structure 62. As seen in FIG. 22F, tension applied to control wire 40 partially or completely straightens the bend in the second flexure zone 34. As seen in FIG. 22G, in some embodiments additional pulling (i.e. proximal retraction) of control wire 40 may deflect the second flexure zone in the opposite direction of its pre-formed shape, thereby providing bi-directional bending of the second flexure zone with a single control wire 40.

Optionally, the control wire 40 may be under tension, as in FIG. 22F, during delivery and/or retrieval of the energy delivery element 24 within a renal artery, in order to at least partially straighten the pre-formed shape of the second flexure zone 34 during such delivery/retrieval. When positioned within the renal artery, tension may be removed from the control wire 40 to deflect the second flexure zone in the direction of its pre-formed shape, as in FIG. 22E, in order to bring the energy delivery element 24 into contact with a wall of the renal artery. Additionally or alternatively, the control wire 40 may be pulled more proximally to deflect the second flexure zone in the opposite direction of its pre-formed shape, as in FIG. 22G, in order to bring the energy delivery element 24 into contact with an opposing wall of the renal artery without necessitating rotation of the elongated shaft 16. As discussed previously, the third flexure zone 44 desirably accommodates contact with any wall of the renal artery and passively deflects to bring the energy delivery element 24 into at least partial alignment with the contacted wall of the artery, thereby accommodating bi-directional deflection of the second flexure zone 34.

3. Active Deflection in any Desired Direction in Combination with the Pre-Formed Shape FIGS. 22C-22G illustrate representative embodiments of second flexure zone 34 that are configured for both active and passive deflection of the second flexure zone, wherein the active deflection is either in the direction of, or opposed to, the direction of passive deflection (i.e., the direction of the second flexure zone's pre-formed shape). However, it should be understood that in other contemplated embodiments active deflection of the second flexure zone may be in any plane(s), as desired, and is not limited to active deflection in the direction of pre-formed shape or in the opposite direction of pre-formed shape.

4. Active Deflection Longitudinally Offset from the Pre-Formed Shape

In FIGS. 22C-22G, active deflection and passive deflection of the second flexure zone occur along a common longitudinal segment. Active and passive deflection alternatively/additionally may be longitudinally spaced or offset from one another. For example, the second flexure zone 34 may comprise a more proximal section that is configured for active deflection and a more distal section that has a pre-formed shape, or vice versa. Active deflection may occur in the direction of the pre-formed shape, in the opposite direction of the pre-formed shape, or in any other direction, as desired.

FIG. 22H illustrates a representative embodiment of a second flexure zone 34 with a more proximal section configured for active deflection and a more distal section that has a pre-formed shape. The more proximal section of the second flexure zone 34 illustratively is configured for active deflection in the opposite direction of the more distal section's pre-formed shape. However, it should be understood that the pre-formed shape alternatively may be directed in the direction of active deflection or in any other direction.

As seen in FIG. 22H, the third tubular structure 62 comprises a laser-cut pattern that includes spine 66 with connecting ribs 68. In contrast to the embodiments of FIGS. 22A-22G, solder 130 connects control wire 40 to the third tubular structure 62 proximal of the second flexure zone's distal end, e.g., at the distal end of a more proximal section of the third tubular structure 62 and/or at the proximal end of a more distal section of the third tubular structure. Distal of the attachment of control wire 40 to the third tubular structure 62, spine 66 comprises a force redirecting element 49, which comprises a pre-formed, off-axis shape. The third tubular structure's laser-cut pattern biases active deflection of the third tubular structure 62, in response to pulling on the control wire 40 coupled to the third tubular structure 62 proximal of the spine's pre-formed shape, in the opposite direction of the pre-formed shape.

With reference now to FIGS. 22I-22K, when the second flexure zone 34 has a more proximal section configured for active deflection in an opposite direction of a more distal section's pre-formed shape, the second flexure zone desirably may promote buckling in the first or second flexure zones with reduced contact force applied to the vessel wall by the energy delivery element 24 which may provide a less traumatic treatment and/or may mitigate a need for the optional third flexure zone 44. Additionally/alternatively, such a second flexure zone may facilitate the establishment of contact and treatment at angularly opposed luminal surfaces of the renal artery without necessitating rotation of elongated shaft 16.

As seen in FIG. 22I, in the unrestrained configuration of the second flexure zone 34 without active deflection (e.g., when the control wire 40 is not being pulled in tension), the more distal section of the second flexure zone 34 assumes the pre-formed shape of its third tubular structure 62. As discussed previously, when positioned within a renal artery, the first flexure zone 32 may lie along or near a superior wall surface of the renal artery (see, for example, FIG. 7E). As seen in FIG. 22J, when not actively deflected, the pre-formed shape of the more distal section of the second flexure zone may urge energy delivery element 24 and optional third flexure zone 44 into contact with that superior wall surface. Previously described passive deflection of the optional third flexure zone may at least partially align the energy delivery element 24 with the superior wall surface, as shown.

As seen in FIG. 22K, tension applied to control wire 40 deflects the more proximal section of the second flexure zone 34 in the opposite direction of the more distal pre-formed shape, e.g., toward an inferior surface of the renal artery. The pre-formed shape may cause the energy delivery element 24 to contact the inferior surface at a lower contact angle (i.e., at an angle less than perpendicular to the surface) than it otherwise would without the pre-formed shape, thereby reducing buckling forces applied to the heating element (e.g. to the heating element and/or to the optional third flexure zone 44), as well as puncture forces applied to the vessel wall, which may provide a more atraumatic treatment and/or may mitigate a need for the optional third flexure zone 44. Previously described passive deflection of the optional third flexure zone may at least partially align the energy delivery element 24 with the inferior wall surface, as shown. FIGS. 22J and 22K illustrate establishment of contact and treatment at angularly opposed luminal surfaces of the renal artery without necessitating rotation of elongated shaft 16.

H. Eighth Representative Embodiment (the Force Redirecting Element is Configured to Facilitate Multi-Directional Access)

FIGS. 23A-23G show representative embodiments of the eighth embodiment having an elongated shaft 16 that includes a force transmitting section 30, a first flexure zone 32, and a force dampening section 44 comprising a force redirecting element. In these embodiments, the materials, size, and configuration of the force transmitting section 30, first flexure zone 32, force dampening section 44, force redirecting elements 49, and energy delivery element 24 are comparable to their respective counterparts described in any of the previous embodiments.

However, in the eighth representative embodiment the force dampening section 44 and force redirecting element 49 are configured to deflect the energy delivery element 24 in multiple directions so that the energy delivery element 24 can be placed in contact with an inner wall of a renal artery at various locations. In such embodiments, the force redirecting element 49 comprises multiple (i.e., more than one) bends. For example, as shown in FIG. 23D, bends 49' and 49" are spaced apart along the axis of the catheter. The eighth embodiment is configured to be advanced into a renal artery while retracted in a delivery sheath 95. When the distal assembly is retracted in the delivery sheath the force dampening section 44 and force redirecting element 49 flexibly conform to the delivery sheath (see FIG. 23B). When the distal assembly is advanced to a desired depth in a renal artery the delivery sheath is pulled back to expose a first bend 49' of the force redirecting element 49 which elastically deforms to deflect the force dampening section 44 a first angle $\alpha 8$, distancing and energy delivery element 24 from the axis of the elongated tubular body 16 in a first direction (see FIG. 23C). When the delivery sheath is pulled back further to expose a second bend 49" the second bend elastically deforms deflecting the force dampening section 44 a second angle $\alpha 9$, distancing the energy delivery element 24 from the axis of the elongated tubular body 16 in a second direction (see FIG. 23D).

Figure 23A:
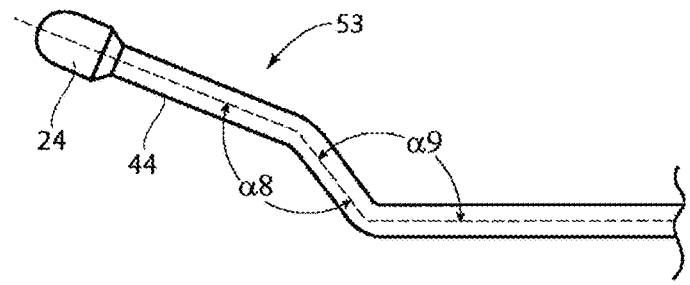
FIGS. 23A to 23G show additional alternative representative embodiments of an elongated shaft for a treatment device, showing examples of the different structural, mechanical and functional regions that the elongated shaft can incorporate.
Figure 23B:
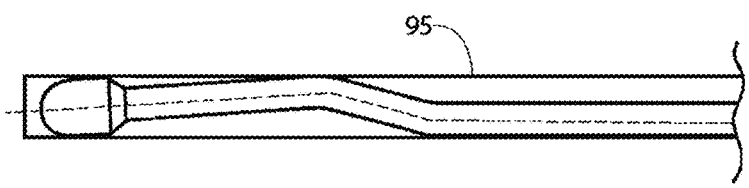
Figure 23C:
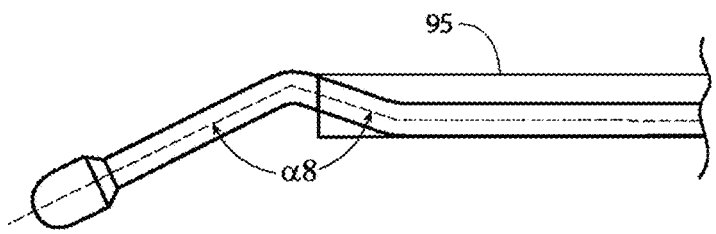
Figure 23D:
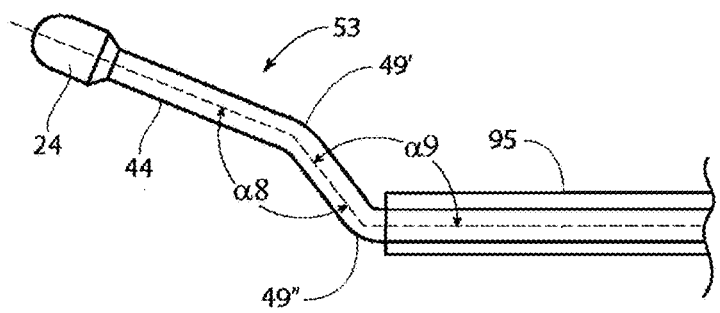
Figure 23E:
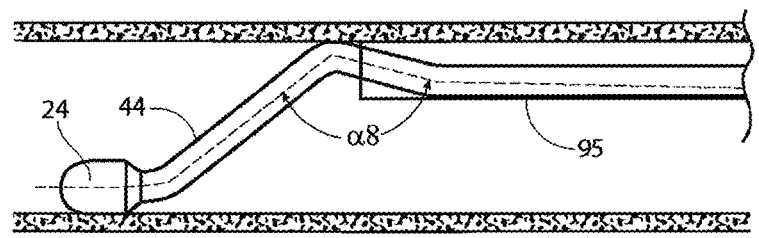
Figure 23F:
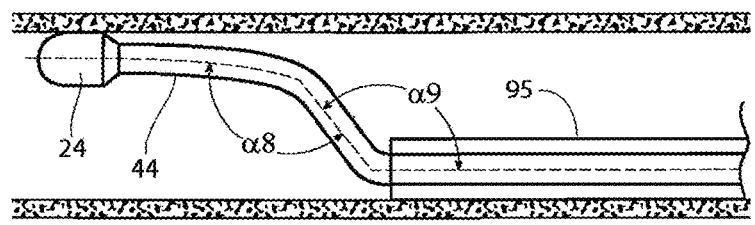

The force redirecting element 49 can be configured with multiple angles $\alpha 8$ and $\alpha 9$ as shown in FIG. 23A such that when deployed in a renal artery an energy delivery element 24 is placed in contact with an inner wall of a renal artery in multiple directions dependent on the portion of the force redirecting element 49 that protrudes from a delivery sheath as shown in FIGS. 23E and 23F. The angles $\alpha 8$ and $\alpha 9$ can be greater than 90° and less than 180° and such that a first angle $\alpha 8$ minus a second angle $\alpha 9$ is greater than 0° and less than 90°, for example first angle $\alpha 8$ can be between about 130° and 150°, for example less than or equal to 140°, and second angle $\alpha 9$ can be between about 90° and 130°, for example less than or equal to about 110°. The length of the force dampening section 44 and position of the force redirecting element 49 are configured so that the energy delivery element 24 is placed in contact with an inner wall of a renal artery with stable contact force. For example, the length from the distal end of an energy delivery element 24, including the force dampening section 44 to the first bend 49' can be about 8 mm to 11 mm (e.g. less than or equal to 9.5 mm); the first angle $\alpha 8$ can be about 130° to 150° (e.g. less than or equal to 140°); the length between the first and second angle can be about 1.25 mm to 3 mm (e.g. less than or equal to 1.5 mm); and the second angle $\alpha 9$ can be about 90° to 130° (e.g. less than or equal to 110°).

Figure 23G:
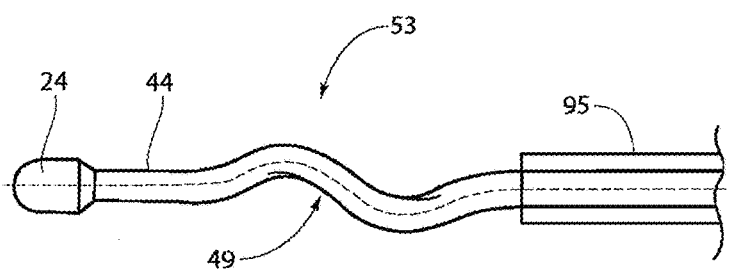

Alternatively, force redirecting element 49 can be configured with a gradual curve such as a helical shape as shown in FIG. 23G such the force dampening section 44 is deflected in multiple three dimensional directions, depending on the proportion of force redirecting element 49 that is protruded from a delivery sheath. The force redirecting element 49 in combination with the force dampening section 44 are configured such that as the force redirecting element 49 is advanced from a delivery sheath in its flexibly conformed retracted state it elastically deforms to place an energy delivery element 24, mounted on a distal end of the force dampening section 44, in contact with an inner wall of a renal artery. For example, the force redirecting element 49 can comprise a helical structure with a helical angle between about 20° and 50° (e.g. less than or equal to 30°); a diameter of about 2 mm to 4 mm (e.g. less than or equal to 3 mm); and about 0.5 to 3 turns (e.g. less than or equal to 1 turn); and the force redirecting element 49 can be positioned about 7 mm to 11 mm (e.g. less than or equal to 9.5 mm) from the distal end of the energy delivery element 24.

I. Ninth Representative Embodiment (the Length of the Force Dampening Section can be Telescopically Adjusted)

FIGS. 24A-24D show representative embodiments of the ninth embodiment having an elongated shaft 16 that includes a force transmitting section 30, a first flexure zone 32, a force redirecting element 49, and a force dampening section 44. In these embodiments, the materials, size, and configuration of the force transmitting section 30, first flexure zone 32, force redirecting element 49, force dampening section 44, and energy delivery element 24, are comparable to their respective counterparts described in any of the previous embodiments.

However, in the ninth representative embodiment the force redirecting element 49 is connected to a first flexure zone 32 and the force dampening section 44 comprises an elongated flexible wire or tube that is slidably contained in a lumen 17 passing through the force redirecting element 49 and elongated tubular body 16 such that the force dampening section 44 can be telescopically distanced from the distal opening of the lumen 17 by advancing the proximal end of the force dampening section 44 through the lumen 17. As with previous embodiments the force redirecting element 49 is configured to flexibly conform to the inner lumen of a guide catheter and elastically deflect to a predetermined angle when not constrained by the guide catheter. The force redirecting element 49 comprises an angle as discussed earlier that distances the energy delivery element 24 from the axis of the elongated tubular body 16 such that as the catheter is advanced along an axial trajectory and a force is applied to the energy delivery element 24 by a contacting inner artery wall, the force dampening section 44 and elongated tubular body are persuaded to buckle and the trajectory is modified to flow through an artery. The telescopically adjustable length of the force dampening section 44 can be shortened while the distal assembly 53 is being advanced through a renal artery. When the distal assembly is advanced to a desired distance in a renal artery the force dampening section 44 can be telescopically lengthened to facilitate contact between the energy delivery element 24 and an inner wall of the renal artery.

The force redirecting element 49 can deflect the force dampening section 44 at angle similar to an angle in previous embodiments (such as angle α4 shown in FIG. 7B). For example, the angle of the force redirecting element 49 can be between about 130° and 170° (e.g. less than or equal to 160°). The minimum length of the force dampening section 44 protruding distal from the bend of the force redirecting element 49 can also be similar to the length L4 of a force dampening section 44 in previous embodiments (as shown in FIG. 7A). For example, the minimum protruding length of the force dampening section 44 can be between about 2 mm and 5 mm. The length of the force dampening section 44 protruding from the distal opening of the lumen 17 can be telescopically increased to a maximum of between about 5 mm to 30 mm (e.g. less than or equal to 20 mm). Alternatively, a combination of the angle α4 and length of the telescopically protruding force dampening section 44 can distance an energy delivery element 24 from the axis of the elongated tubular body 16 by a distance of between about 1 mm and 15 mm.

Figure 24A:
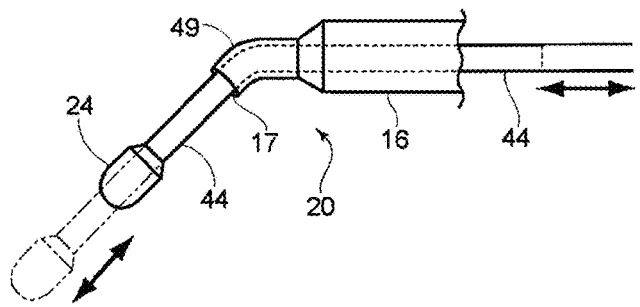
FIGS. 24A to 24D show additional alternative representative embodiments of an elongated shaft for a treatment device, showing examples of the different structural, mechanical and functional regions that the elongated shaft can incorporate.
Figure 24B:
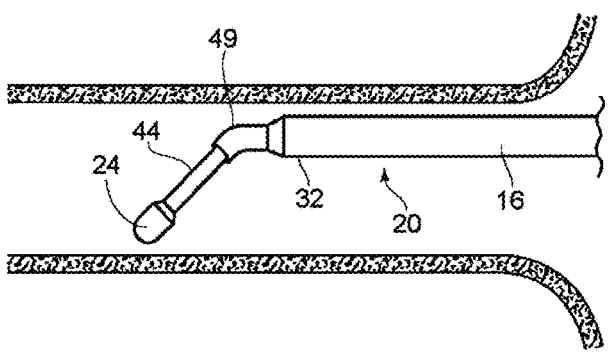
Figure 24C:
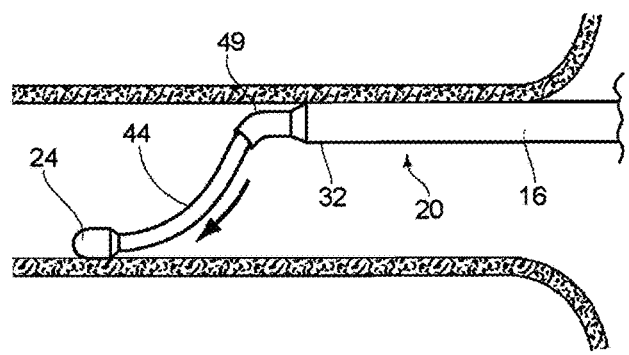
Figure 24D:
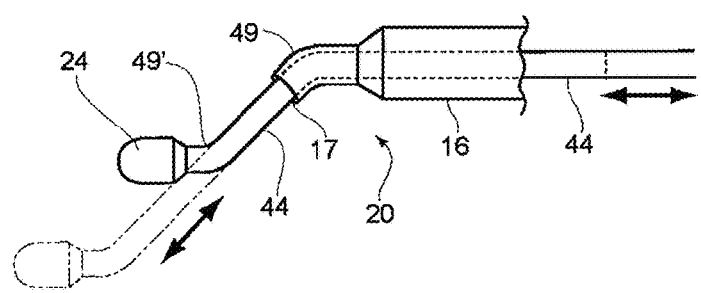

As shown in FIG. 24D force dampening section 44 can further comprise a second force redirecting element 49' that distances the distal tip of the energy delivery element 24 from the axis of the force dampening section 44 such that as the force dampening section 44 is telescopically advanced, a load created by contact with the artery is distanced from the axis of the force dampening section 44 promoting buckling of the force dampening section 44.

Force dampening section 44 can be comprised, for example, of an electrically insulated Nitinol wire and conducting wires that carry energy and sensor signals to and from the energy delivery element 24 and the generator 26 can be held in the space between the electrical insulation and the Nitinol wire. The proximal end of the force dampening section 44 can extend through a lumen to a proximal opening in the lumen of the elongated tubular body where it can be manipulated to telescopically lengthen the distal portion of the force dampening section 44 that protrudes from the distal opening of the lumen 17. Alternatively, the proximal end of the force dampening section 44 can be manipulated by an actuator 260 in a handle 200.

J. Tenth Representative Embodiment (Second Flexure Zone Facilitates Controlled, Multi-Directional Deflection)

Figures 25A, 25B, 25C:
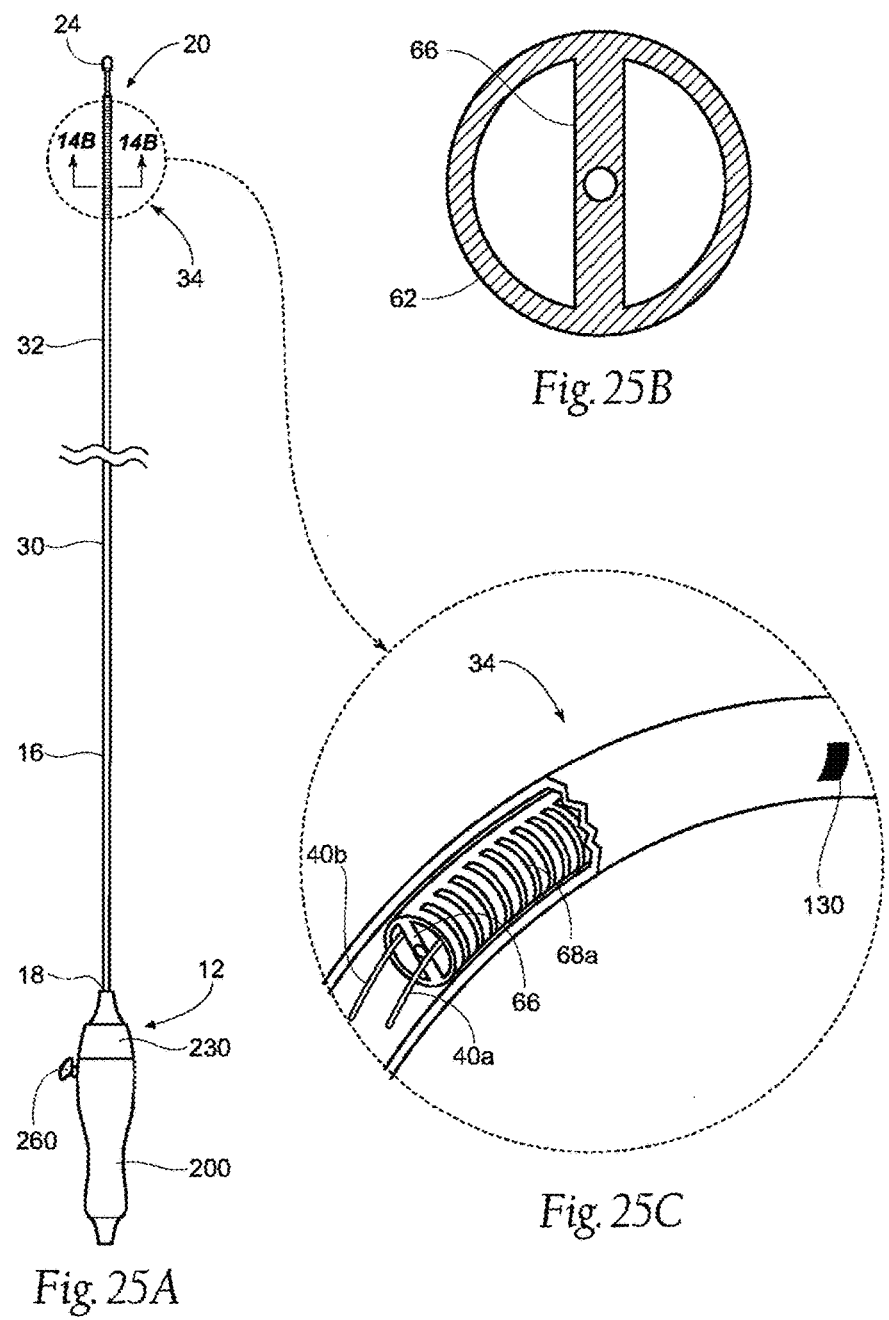
FIGS. 25A to 25C show an alternative representative embodiment of the second flexure zone of the elongated shaft of the treatment device shown in FIG. 5 configured for deflection in multiple directions.

FIGS. 25A-25W show representative embodiments having an elongated shaft 16 that includes a force transmitting section 30, a first flexure zone 32, a second flexure zone 34, an energy delivery element 24 and an optional third flexure zone 44 (see FIG. 25A). In these embodiments, the materials, size, and configuration of the force transmitting section 30, first flexure zone 32, and optional third flexure zone 44 are comparable to their respective counterparts described in any of the previous embodiments. Furthermore, the length and diameter of second flexure zone 34 in the embodiments of FIG. 25 may be comparable to those described in any of the previous embodiments of the second flexure zone 34. Also, controlled bending of the second flexure zone 34 may provide the second flexure zone with a desired radius of curvature RoC2 and angle α2 (see FIG. 7C), such as those described previously.

However, in this embodiment of the present invention, the second flexure zone 34 may facilitate controlled deflection in multiple different directions, e.g., may comprise multiple control wires 40 for controllably deflecting the second flexure zone in multiple different directions. Controlled, multi-directional bending of the second flexure zone may facilitate placement of energy delivery element 24 into stable contact with a treatment site or with multiple treatment sites within a renal artery. Such control over placement of the energy delivery element may be especially useful in patients with relatively tortuous vessels. For example, if placement of the energy delivery element 24 into contact with a renal arterial treatment site is sub-optimal under controlled bending of the second flexure zone in a first direction, the second flexure zone may be controllably deflected in a second direction to more optimally place the energy delivery element into contact with the treatment site, or with an alternative or additional treatment site. Furthermore, stable contact and energy delivery may be achievable at multiple treatment sites via controlled multi-directional deflection of the second flexure zone.

In some representative embodiments, the second flexure zone may comprise a centrally positioned spine coupled to ribs or surrounded by a coil; the centrally positioned spine may possess a geometry that facilitates controlled, multi-directional bending. The second flexure zone may comprise multiple circumferentially positioned spines connected by ribs, or a centrally positioned spine to facilitate controlled, multi-directional bending.

1. Centrally Positioned Spine

FIGS. 25B-25M provide representative embodiments with a second flexure zone 34 configured for controlled, multi-directional bending having a central spine and multiple control wires.

In the embodiment of FIGS. 25B and 25C, the second flexure zone is configured for controlled, bi-directional bending. As seen in the cross-section of FIG. 25B, the third tubular structure 62 of the second flexure zone 34 comprises a centrally positioned spine 66 having a substantially flat or ribbon shape (i.e., the spine's width is significantly greater than its depth) that substantially divides the third tubular structure in half. A central lumen of diameter less than the spine's depth may be formed through the center of the spine 66 for passage of electrical transmission wire(s) and/or sensor/thermocouple wire(s) 29. Alternatively, wire(s) 29 can pass through a lumen defined by centrally positioned spine 66 and ribs 68.

Third tubular structure 62 may be fabricated, for example, via Electrical Discharge Machining (EDM), micromachining and/or extrusion, to form a tube with a ribbon having a lumen, wherein the ribbon bisects the tube, as in FIG. 25B. As seen in FIG. 25C, a laser-cut pattern then may remove sections of the ribbed tube along its length to form connecting ribs 68a and 68b at spaced intervals along the tube's length that extend on opposing sides of spine 66 about the circumference of the third tubular structure 62. Control wires 40a and 40b are attached to a distal end of the second flexure zone with solder 130 on opposing sides of spine 66 and travel along the length of the third tubular structure radially positioned between the spine 66 and the ribs 68.

Alternatively, the deflectable section 34 may comprise a centrally positioned spine 66 that is resilient to compression and is surrounded by a third tubular structure 62. The third tubular structure is compressible and may comprise a laser-cut hypo tube, a hollow coil with a loose pitch, a hollow cable, a braided shaft, etc. The spine may be connected to the third tubular structure 62 along its length, may be connected to the structure at only one or a few locations (e.g., at its distal end), or may float or be friction fit within the coiling third tubular structure.

The geometry of spine 66, in combination with the geometry of ribs 68a and 68b and the distal attachment locations of control wires 40a and 40b, facilitate controlled, bi-directional bending of the second flexure zone 34, e.g., by substantially constraining buckling or bending of the spine 66 in response to pulling of a wire 40a or 40b to planes perpendicular to the width of the spine. The second flexure zone deflects in a first direction in response to pulling on the control wire 40a while the control wire 40b is not under significant tension (see FIG. 25C). The second flexure zone deflects in a second, opposing direction in response to pulling on the control wire 40b while the control wire 40a is not under significant tension.

Figure 25H:
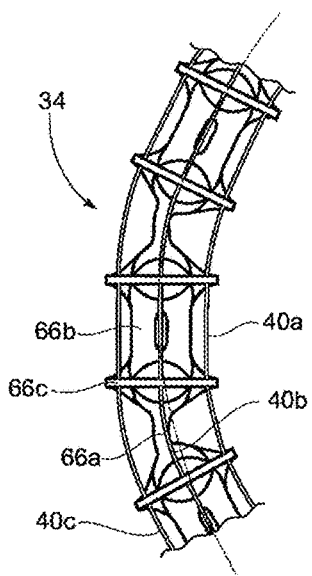
Figure 25I:
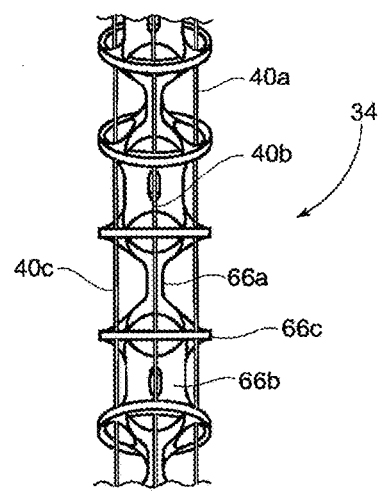

While FIGS. 25B and 25C illustrate a bi-directional bending embodiment of the second flexure zone 34, the third tubular structure 62 may be fabricated with a centrally positioned spine that facilitates bending in any number of directions, as desired. FIGS. 25D-25J illustrate an embodiment of the second flexure zone with a centrally positioned spine that is configured for controlled, quad-directional deflection. As seen in FIGS. 25G-25I, the third tubular structure 62 comprises centrally positioned spine 66 with longitudinally-spaced spinal ribbon sections 66a and 66b whose widths are angularly offset from one another by about 90° in an alternating pattern along the length of the third tubular structure. A centrally-positioned lumen extends through the ribbon sections along the length of the third tubular structure for passage of electrical transmission wire(s) and/or sensor/thermocouple wire(s) 29. Between each pair of the spinal ribbon sections 66a and 66b, the spine 66 flares radially outward to form a spinal ribbon connector section 66c that connects the pair of spinal ribbon sections.

In the embodiment of FIGS. 25G-25I, each connector section 66c has four sides or extensions that extend to the circumference of the third tubular structure 62. The four sides or extensions have radial-most points that are angularly offset by about 45° from the widths of ribbon sections 66a and 66b. Connecting ribs 68a, 68b, 68c and 68d connect each of the four sides or extensions of each connector section 66c at the radial-most points, forming a circumferential ring or hoop at the level of each connector section 66c.

Third tubular structure 62 thus comprises a series of repeating segments along the length of the structure. Each repeating segment has a first connector section 66c with ribs 68; followed lengthwise by a ribbon section 66a having a width that is 45° angularly offset from the radial-most points of the sides or extensions of the first connector section 66c; followed lengthwise by a second connector section 66c with ribs 68, the second connector section having sides or extensions with radial-most points that are 45° angularly offset from the width of the ribbon section 66a and that are angularly aligned with the radial-most points of the sides or extensions of the first connector section 66c; followed lengthwise by a ribbon section 66b having a width that is 45° angularly offset from the radial-most points of the sides or extensions of the second connector section 66c and that is 90° angularly offset from the width of ribbon section 66a; followed lengthwise by a repeating first connector section 66c; etc. The third tubular structure 62 of FIG. 25G may, for example, be fabricated from a combination of EDM, micro-machining and/or extrusion, as well laser cutting with ribs 68, the repeating first connector section having sides or extensions with radial-most points that are 45° angularly offset from the width of the ribbon section 66b and that are angularly aligned with the radial-most points of the sides or extensions of the second connector section 66c; etc.

The ribbon sections 66a and 66b preferably have widths that are less than the diameter of third tubular structure 62 at the level of each connector section 66c (e.g., less than the diameter of the rings formed by ribs 68), such that the geometry of the repeating segments of the third tubular structure 62 forms four lengthwise voids along the length of the third tubular structure. Two of the voids are substantially aligned with, but positioned radially outward of, the width of the spinal ribbon section 66a, while the remaining two voids are substantially aligned with, but positioned radially outward of, the width of the spinal ribbon section 66b. Thus, the four voids are about 45° angularly offset from the radial-most points of the sides or extensions of the connector sections 66c, i.e. the voids occupy the space between the sides or extensions where the sides or extensions extend to the circumference of the third tubular structure 62 and are connected by ribs 68.

A control wire 40a, 40b, 40c or 40d is positioned within each of the voids along the length of the third tubular structure and is attached to a distal end of the second flexure zone with solder 130. Pulling on any one of the control wires while the other three control wires are not under significant tension may provide controlled deflection of the second flexure zone 34 in the direction of the wire being pulled (alternatively, any three control wires may be pulled while the fourth control wire is not under significant tension in order to provide controlled deflection of the second flexure zone in the opposite direction of the control wire not being pulled). In this manner, the second flexure zone 34 may be configured for controlled, quad-directional bending in four directions that are about 90° angularly offset or out of phase from one another.

For example, as seen in FIG. 25H, pulling on wire 40a causes ribbon sections 66a, whose widths are in a plane perpendicular to the plane of wire 40a, to buckle or bend in the direction of the wire 40a, providing controlled bending of the third tubular structure 62 and second flexure zone 34 in the direction of the wire 40a. Likewise, as seen in FIG. 25I, pulling on wire 40b causes the ribbon sections 66b to buckle or bend in the direction of the wire 40b, providing controlled bending of the second flexure zone 34 in the direction of the wire 40b. Conversely, pulling on wire 40c would cause the ribbon sections 66a (and thereby the second flexure zone 34) to buckle or bend in the opposite direction of that achieved with wire 40a (not shown), while pulling on wire 40d would cause the ribbon sections 66b (and thereby the second flexure zone 34) to buckle or bend in the opposite direction of that achieved with wire 40b (not shown).

In some multi-directional deflection embodiments, such as those shown in FIGS. 25G to 25J, pulling on any two adjacent control wires while the remaining control wires are not under significant tension may provide controlled deflection of the second flexure zone 34 in additional directions offset or out of phase from the directions achieved by pulling on any single control wire 40. When two adjacent wires are pulled, substantially all of the alternating ribbon sections 66a and 66b would be expected to buckle or bend. Ribbon sections 66a would be expected to bend in their flexibly biased plane in the direction of applied tension by a first control wire, while alternate ribbon sections 66b would be expected to bend in their flexibly biased plane in the direction of applied tension by a second adjacent control wire. The alternating ribbon sections would bend in directions which are about 90° offset from one another. The amount of bending the alternating ribbon sections 66a and 66b would be proportionate to the amount of tension applied by each respective control wire. The cumulative effect, along the total length of the second flexure zone 34, of bending both alternating ribbon sections would be a bend in the direction between the two flexibly biased planes. In this manner, the second flexure zone 34 may be configured for controlled deflection in four directions by pulling one of the four control wires 40, and additional directions by pulling two adjacent control wires 40 with equal or disproportionate tensions.

As seen in FIG. 25D, the third tubular structure may be fabricated via EDM, micromachining and/or extrusion with the cross section of spinal connector sections 66c. As seen in FIG. 25F, laser cutting in a first side-sectional plane of the third tubular member 62 that is about 45° angularly offset from points at which the interior portion of the third tubular structure connects to the tubular outer portion, may form spinal ribbon sections 66a, as well as diametric narrowing at the level of spinal ribbon sections 66b. Likewise, as seen in FIG. 25E, laser cutting in a second side-sectional plane of the third tubular member 62 that is perpendicular to (i.e., that is 90° angularly offset from) the first side-sectional plane may form spinal ribbon sections 66b and spinal connector sections 66c, as well as diametric narrowing at the level of the spinal ribbon sections 66a. This provides the spinal connector sections 66c with four sides, as in FIG. 25G.

Figure 25J:
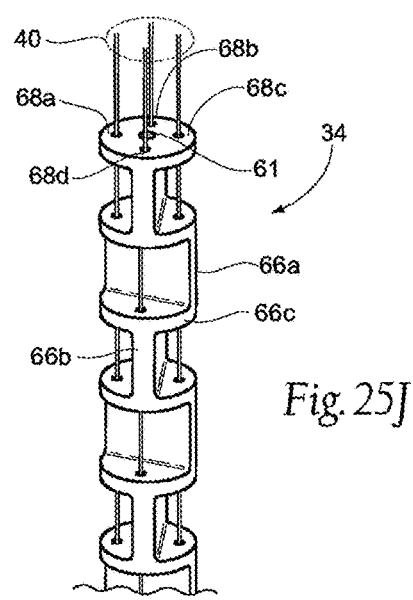

With reference now to FIG. 25J, an alternative configuration of the third tubular structure configured for quad-directional controlled deflection (and deflection in additional directions when two adjacent control wires are pulled, as previously described) is described. In FIG. 25J, each of the spinal ribbon sections 66a and 66b flares radially outward to connect to the spinal connector sections 66c along only two sides or extensions that extend to the circumference of the third tubular structure 62. The two sides or extensions have radial-most points that are substantially aligned with the widths of each of the ribbon sections 66a and 66b, respectively. Connecting ribs 68a and 68b, 68c and 68d connect each of the four sides or extensions found at each connector section 66c (two such sides or extensions emanating from each of the ribbon sections 66a and 66b, respectively, about 90° out of phase with the other two sides or extensions), forming a circumferential ring or hoop at the level of each connector section 66c.

Third tubular structure 62 thus comprises a series of repeating segments along the length of the structure. Each repeating segment has a first connector section 66c with ribs 68; followed lengthwise by a ribbon section 66a having a width that is angularly aligned with two of the radial-most points of the sides or extensions of the first connector section 66c and about 90° out of phase with the other two sides or extensions of the first connector section; followed lengthwise by a second connector section 66c with ribs 68, the second connector section having four sides or extensions with four radial-most points, two of which are again aligned with the width of the ribbon section 66a and two that are about 90° out of phase with the ribbon section 66a; followed lengthwise by a ribbon section 66b having a width that is 90° angularly offset from the two radial-most points of the sides or extensions of the second connector section 66c that are aligned with the width of ribbon section 66a, and having a width that is angularly aligned with the remaining two radial-most points of the second connector section 66c; followed lengthwise by a repeating first connector section 66c with ribs 68, the repeating first connector section having four sides or extensions with four radial-most points, two of which are again aligned with the width of the ribbon section 66b and two that are about 90° out of phase with the ribbon section 66b; etc.

In the embodiment of FIG. 25J, two lumens extend through each ribbon section 66a and 66b, respectively, near either end of the width of each ribbon section (i.e., four such lumens in all, in addition to the centrally-positioned lumen for passage of wire 29). Control wires 40 may be routed through these lumens for controlled quad-directional deflection (and deflection in additional directions when two adjacent control wires are pulled) of the second flexure zone 34, as described previously.

Figure 25K:
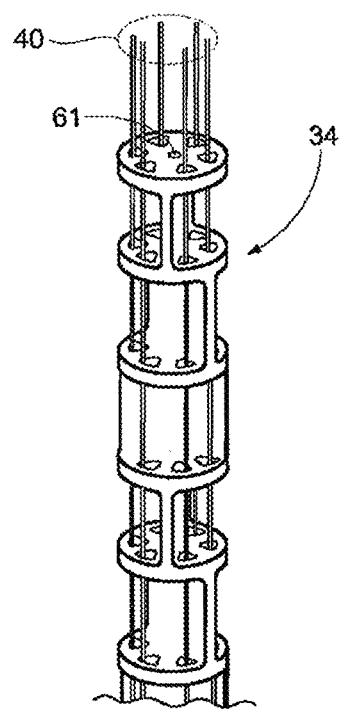

FIGS. 25B and 25C illustrate a second flexure zone 34 with a centrally positioned spine 66 configured for bi-directional controlled deflection, while FIGS. 25G to 25I illustrate second flexure zones 34 with a centrally positioned spine 66 configured for quad-directional controlled deflection (and deflection in additional directions when two adjacent control wires are pulled, as previously described). The second flexure zone alternatively may comprise a centrally positioned spine 66 configured for deflection in any number of additional directions, as desired. For example, additional ribbon sections may be provided at additional angular offsets and connected by spinal connector sections having additional sides (e.g., as seen in FIG. 25K, for six-directional bending, three alternating spinal ribbon sections may be provided at 60° angular offsets, connected by spinal connector sections having six sides or extensions whose radial-most points extend to the circumference of the third tubular structure 62 in angular alignment with the edges of the spinal ribbon sections, such that six voids are created that are offset by about 30° from the width of any spinal ribbon section). When combined with appropriate ribs 68 and control wires 40, controlled deflection in any number of directions may be achieved. However, it is expected that the second flexure zone 34 may become increasingly stiff as the number of alternating ribbon sections increases, which may place a practical limit on the attainable number of controlled deflection directions.

Figure 25L:
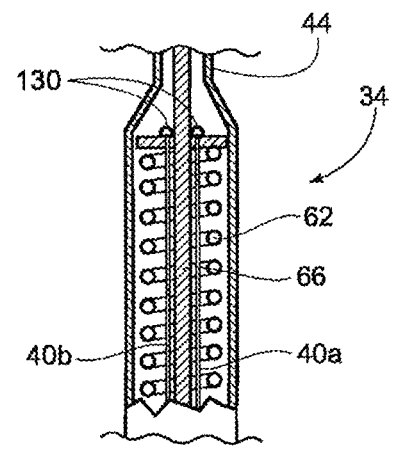
Figure 25M:
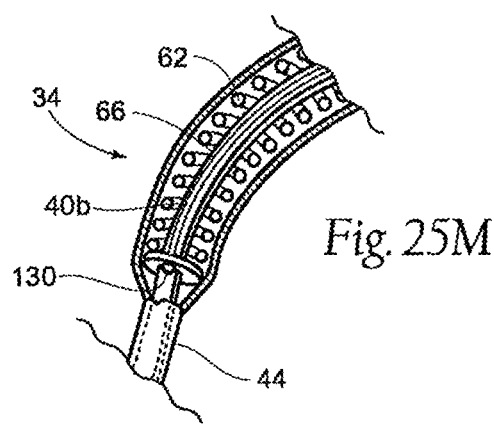

Referring now to FIGS. 25L and 25M, as an alternative to a second flexure zone 34 with a third tubular structure 62 comprising a centrally positioned spine in combination with a laser-cut pattern that forms connecting ribs, the second flexure zone 34 may comprise a centrally positioned spine 66 that is surrounded by a coiling third tubular structure 62. A coiling third tubular structure may increase flexibility of the second flexure zone 34. The coiling third tubular structure may comprise a laser-cut hypo tube, a hollow coil, a hollow cable, a braided shaft, etc. The spine may be connected to the coiling third tubular structure 62 along its length, may be connected to the structure at only one or a few locations (e.g., at its distal end), or may float or be friction fit within the coiling third tubular structure.

The spine 66 may comprise any of the spines seen in FIG. 25B to 25K (e.g., may be flat or ribbon-like, as in FIGS. 25B and 25C; or may comprise angularly offset, alternating ribbons, as in FIGS. 25G to 25K), or may comprise any additional number of alternating ribbons, as desired, to facilitate controlled deflection in any number of directions, as desired. The spine may be fabricated, for example, via EDM, micromachining and/or extrusion and may comprise a laser-cut pattern along its length that increases flexibility. The spine may alternate along its length, e.g., in a spiraling laser-cut pattern.

In FIGS. 25L and 25M, second flexure zone 34 illustratively is configured for controlled, bi-directional deflection. The spine 66 comprises a flat or ribbon-shaped spine, and the coiling third tubular structure 62 surrounds the spine. Control wires 40a and 40b are attached to a distal end of the second flexure zone with solder 130 on opposing sides of the spine 66. As in the embodiment of FIGS. 25B and 25C, pulling on the control wire 40a while the control wire 40b is not under significant tension (see FIG. 25M) deflects the second flexure zone 34 in a first direction. The second flexure zone deflects in a second, opposing direction in response to pulling on the control wire 40b while the control wire 40a is not under significant tension.

Embodiments comprising multiple-direction deflection may further comprise a third flexure zone 44 comprising a flexible structure 74 as previously described.

An alternative multi-directional actuator 260 may comprise a multidirectional joystick coupled to multiple control wires, as in FIG. 25W. Alternatively, one or more bi-directional actuators, each for actuation in two directions in a given plane, may be provided.

2. Circumferentially Positioned Spines

FIGS. 25N to 25S show representative embodiments of the second embodiment with an elongated shaft 16 that includes a proximal force transmitting section 30, a first or proximal flexure zone 32, a second or intermediate flexure zone 34, and an optional third or distal flexure zone 44. In these embodiments, the materials, size, and configuration of the proximal force transmitting section 30, first flexure zone 32, and optional third flexure zone 44 are comparable to their respective counterparts described in any of the previous embodiments.

In these embodiments, however, the second flexure zone 34 may comprise a third tubular structure 62 with two or more circumferentially positioned spines 66. As discussed in greater detail above, preferential deflection of the second flexure zone in multiple directions is desirable. This can be achieved by making the third tubular structure 62 compressible in the desired direction of deflection and resilient to compression along a plane perpendicular to the deflection. In this embodiment such variable compressibility is achieved with two or more circumferentially positioned spines that are resilient to compression yet are sufficiently flexible to bend in a direction of biased compressibility. Two circumferentially positioned spines that are resilient to compression form a plane that is resilient to compression and that passes through the two circumferentially positioned spines. FIGS. 25N to 25S illustrate representative embodiments of the second embodiment with a second flexure zone 34 having multiple circumferentially positioned spines and control wires 40 configured for controlled, multi-directional bending.

Figure 25N:
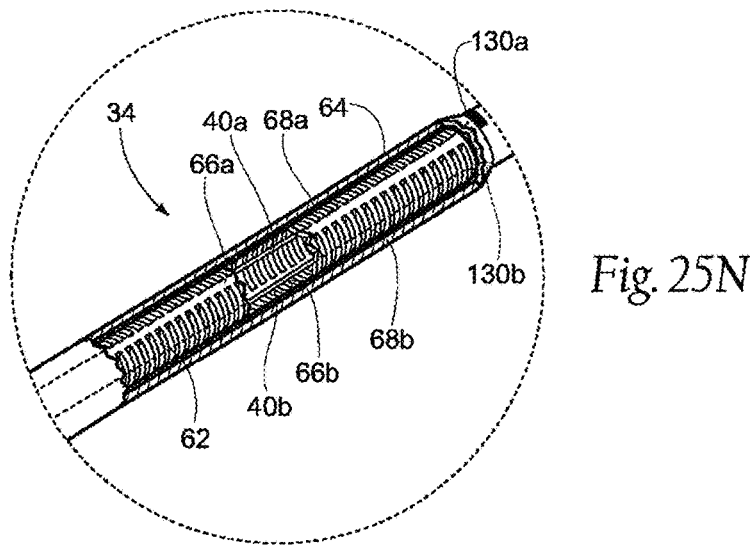
Figure 25O:
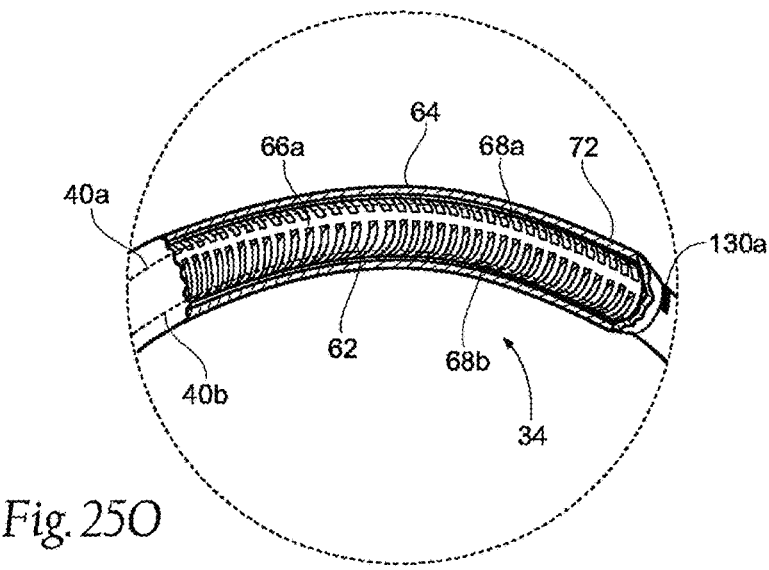

In the embodiment of FIGS. 25N and 25O, the second flexure zone 34 is configured for controlled, bi-directional bending. As seen in the cross-section of FIG. 25N, the third tubular structure 62 of the second flexure zone 34 comprises a laser-cut pattern that forms angularly opposed (i.e., about 180° angularly offset), circumferentially positioned spines 66a and 66b that divide the circumference of the third tubular structure into two halves that are connected by connecting ribs 68a and 68b, respectively, positioned on either side of the third tubular structure about its circumference. The connecting ribs 68a and 68b may each span an arcuate segment of about 180° about the circumference of the third tubular structure. Control wires 40a and 40b are attached to a distal end of the second flexure zone with solder 130a and 130b, respectively on opposing sides of third tubular structure 62, angularly offset from spines 66a and 66b.

The width of each spine 66a and 66b is not significantly greater than the depth of each spine, respectively (e.g., the width of each spine may be less than, or equal to, its depth), in order to facilitate bi-directional deflection of the third tubular structure 62 in the directions of the ribs 68a and 68b, while restricting deflection in the directions of the spines (i.e., restricting deflection in the plane including the two spines). Optionally, ribs 68a on a first side of the third tubular structure 62 may alternate with ribs 68b on the opposite side of the third tubular structure along the length of the structure, which may increase flexibility and/or facilitate controlled deflection of the second flexure zone 34.

The geometry of spines 66a and 66b, as well as of ribs 68a and 68b, in combination with the distal, angularly offset attachment locations of control wires 40a and 40b, facilitate controlled, bi-directional bending of the second flexure zone 34. The second flexure zone deflects in a first direction in response to pulling on the control wire 40a while the control wire 40b is not under significant tension (see FIG. 25O). The second flexure zone deflects in a second, opposing direction in response to pulling on the control wire 40b while the control wire 40a is not under significant tension.

Figure 25P:
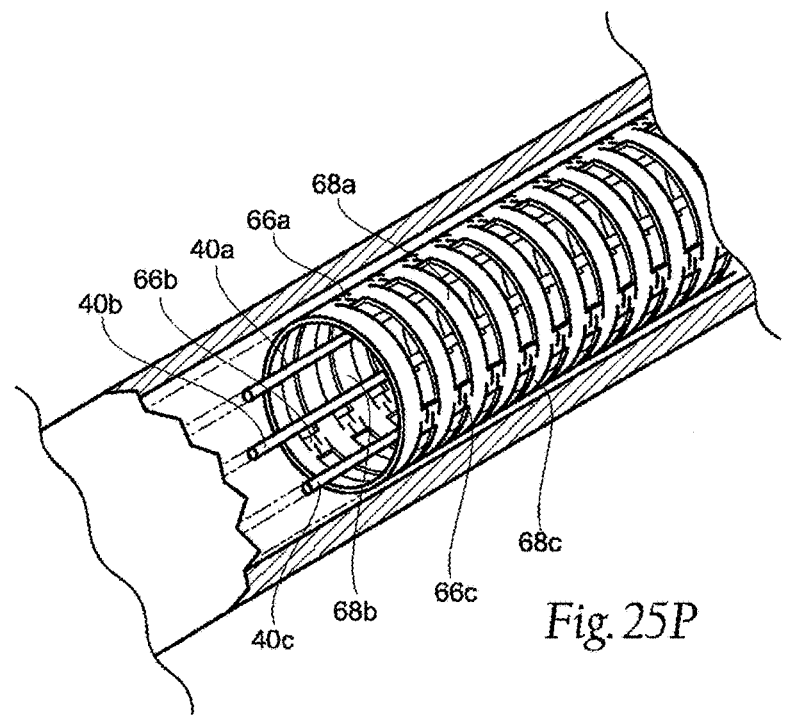
Figure 25Q:
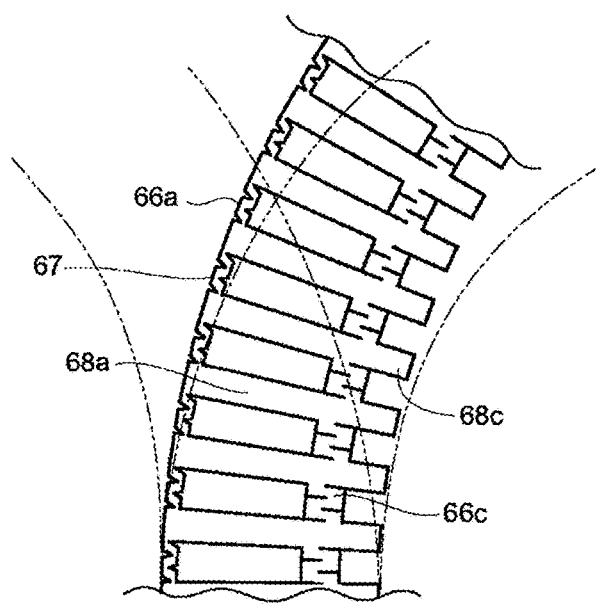

While FIGS. 25N and 25O illustrate a bi-directional bending embodiment of the second flexure zone 34, the third tubular structure 62 may be fabricated to facilitate bending in any number of directions, as desired, by adding additional circumferentially positioned spines connected by ribs, and by adding additional control wires. For example, FIGS. 25P and 25Q illustrate an embodiment of the second flexure zone configured for controlled, tri-directional deflection. In FIGS. 25P and 25Q, the third tubular structure 62 of the second flexure zone 34 comprises a laser-cut pattern that forms angularly offset, circumferentially positioned spines 66a, 66b and 66c that divide the circumference of the third tubular structure into thirds that are connected by connecting ribs 68a, 68b and 68c, respectively, positioned about the circumference of the third tubular structure. The spines may be angularly offset by about 120° from one another about the circumference of the third tubular structure.

The spines comprise longitudinally spaced expansion elements 67, such as undulating or S-shaped elements, which resist compression of the spines during compressive bending while facilitating moderate elongation of the spines during tensile bending. When a spine 66 is bent in a manner that elongates the spine (e.g., places the spine in tension), the expansion elements 67 at least partially straighten to accommodate such spinal elongation. Conversely, when a spine 66 is bent in a manner that shortens the spine (e.g., places the spine in compression), the expansion elements 67 have a geometry that resists such spinal compression. In this manner, the expansion elements 67 allow spines 66 to accommodate controlled deflection in desired directions, while resisting deflection in other directions. Optionally, expansion elements 67 (as well as the spines 66 or the third tubular structure 62) may be fabricated from a shape memory alloy, such as Nitinol, so that the expansion elements resume their undulating shape after removal of tension from a spine 66.

In each one third arc segment of the circumference of the third tubular structure 62 positioned between the spines, a control wire 40a, 40b or 40c is attached to a distal end of the second flexure zone with solder 130. The control wires 40a, 40b, and 40c can held in position relative to the spines 66a, 66b, and 66c by a spacing element (not shown) which could be, for example, a flexible extruded polymer tube comprising lumens for the control wires. Pulling on any one of the control wires while the other two control wires are not under significant tension may provide controlled deflection of the second flexure zone 34 in the direction of the wire being pulled. For example, when control wire 40c is pulled the two adjacent spines 66c and 66b resist compression and provide a bending moment. The third tubular structure 62 compresses on the side of the bending moment where the control wire 40c is being pulled, and expands on the opposing side of the bending moment. The expansion elements 67 of the spine 66a that is positioned substantially in angular opposition to the control wire 40c being pulled, at least partially expand (at least temporarily) to accommodate the bending of third tubular structure. In this manner, the second flexure zone 34 may be configured for controlled, tri-directional bending in three directions that are about 120° offset or out of phase from one another.

Figure 25R:
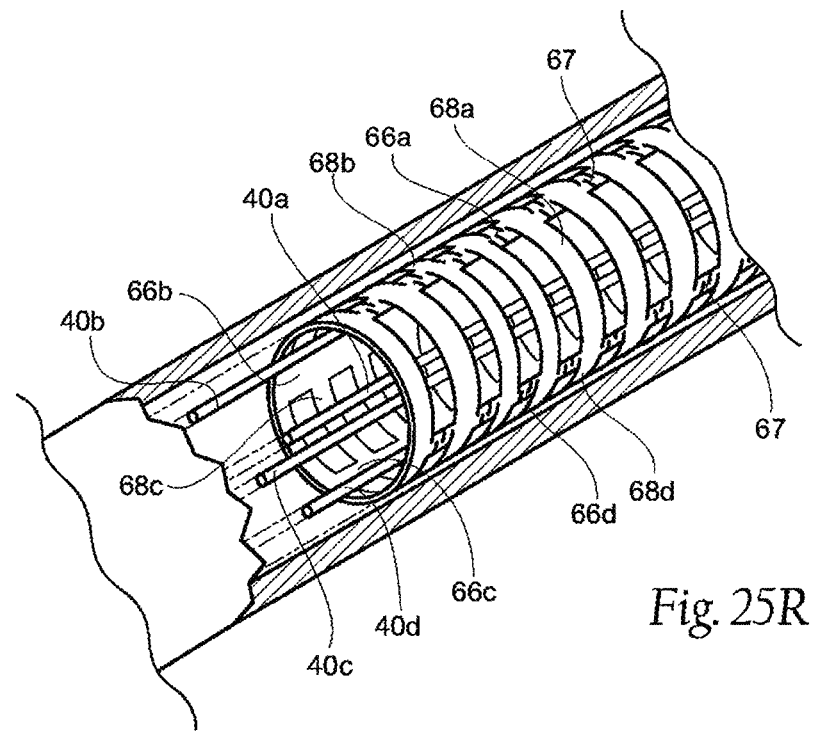
Figure 25S:
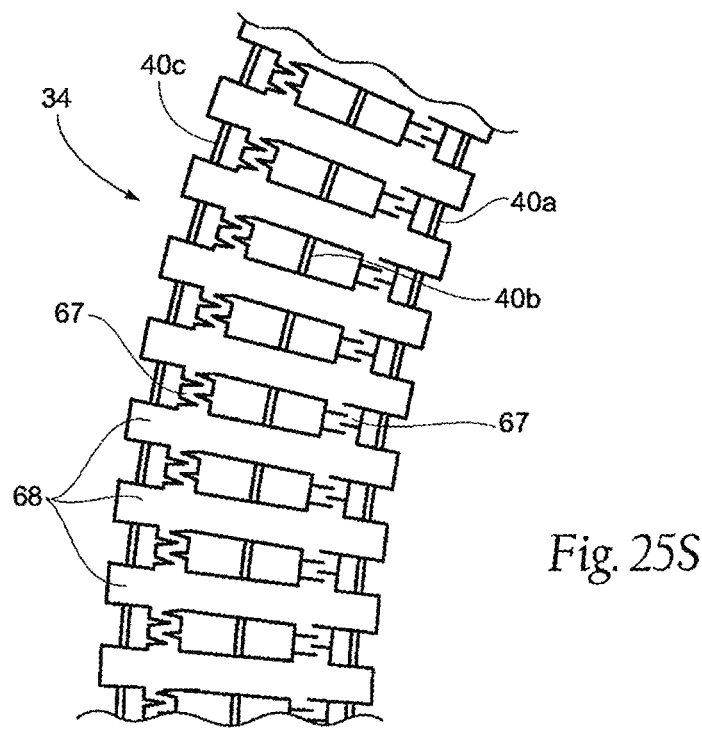

FIGS. 25R and 25S illustrate an embodiment of the second flexure zone configured for controlled, quad-directional deflection. In FIGS. 25R and 25S, the third tubular structure 62 of the second flexure zone 34 comprises a laser-cut pattern that forms angularly offset, circumferentially positioned spines 66a, 66b, 66c and 66d having expansions elements 67 and that divide the circumference of the third tubular structure into quartiles that are connected by connecting ribs 68a, 68b, 68c and 68d, respectively, positioned about the circumference of the third tubular structure. The spines may be angularly offset by about 90° about the circumference of the third tubular structure.

In each quartile arc segment of the circumference of the third tubular structure 62 positioned between the spines, a control wire 40a, 40b, 40c or 40d is attached to a distal end of the second flexure zone with solder 130. Pulling on any one of the control wires while the other three control wires are not under significant tension may provide controlled deflection of the second flexure zone 34 in the direction of the wire being pulled. In this manner, the second flexure zone 34 may be configured for controlled, quad-directional bending in four directions that are about 90° offset or out of phase from one another.

FIGS. 25N-25S illustrate a second flexure zone 34 with circumferentially positioned spines configured for bi-, tri-, or quad-directional controlled deflection. As will be apparent to those of skill in the art, the laser-cut pattern of third tubular structure 62 may comprise any number of circumferentially positioned spines 66 having expansion elements 67 and connected by connecting ribs 68 about the structure's circumference to divide the circumference into any number of arc segments (e.g., halves, thirds, quartiles, quintiles, sextiles, septiles, octiles, nontiles, deciles, etc.), as desired. When combined with appropriate control wires, controlled deflection in any number of directions may be achieved. However, it is expected that the second flexure zone 34 will become increasingly stiff as the number of arc segments about its circumference (i.e., as the number of circumferentially positioned spines) increases, which may place a practical limit on the attainable number of controlled deflection directions.

3. Centrally Positioned Spine in Combination with Circumferentially Positioned Spines FIGS. 25T-25U illustrate a representative embodiment of the eighth embodiment with a second flexure zone 34 configured for controlled, multi-directional deflection having a centrally positioned spine 66, in combination with multiple circumferentially positioned spines 66, and multiple control wires 40.

In the embodiment of FIGS. 25T and 25U, the second flexure zone 34 illustratively is configured for controlled, bi-directional deflection. The centrally positioned spine 66a is substantially flat or ribbon-shaped, while the third tubular structure 62 of the second flexure zone 34 comprises a laser-cut pattern that forms circumferentially positioned spines 66b and 66c, which are angularly aligned with the edges of the centrally positioned spine 66a (i.e., the spines 66b and 66c may be angularly offset by about 180° about the circumference of the third tubular structure), and that forms ribs 68a and 68b that connect the circumferentially positioned spines 66b and 66c about the circumference of the third tubular structure 62 (see FIG. 25T). The centrally positioned spine 66a and the circumferentially positioned spines 66b and 66c connected by connecting ribs 68a and 68b divide the circumference of the third tubular structure into two halves. Control wires 40a and 40b are attached to a distal end of the second flexure zone with solder 130 on opposing sides of the centrally positioned spine 66a, angularly offset from the circumferentially positioned spines 66b and 66c.

The width W of the centrally positioned spine 66a is substantially greater than the thickness T of the centrally positioned spine 66a. The geometries of the centrally positioned spine 66a and the circumferentially positioned spines 66b and 66c facilitate bi-directional deflection of the third tubular structure 62 in the directions of the ribs 68a and 68b (i.e., perpendicular to the width of the centrally positioned spine 66a), while restricting deflection in the directions of the circumferentially positioned spines 66b and 66c (i.e. parallel to the width of the centrally positioned spine 66a).

The edges of centrally positioned spine 66a may be attached to circumferentially positioned spines 66b and 66c along all or a portion of their lengths (e.g. at the distal end of the centrally positioned spine 66a), or the centrally positioned spine 66a may substantially float within the third tubular structure 62. Alternatively, the edges of centrally positioned spine 66a may be positioned in channels or detents (not shown) that are formed with, or in proximity to, circumferentially positioned spines 66b and 66c to maintain angular alignment between the edges of the centrally positioned spine and the circumferentially positioned spines 66b and 66c while facilitating variation in longitudinal alignment (this may enhance flexibility of the second flexure zone 34).

The geometry of centrally positioned spine 66a and circumferentially positioned spines 66b and 66c, as well as of connecting ribs 68a and 68b, in combination with the distal, angularly offset attachment locations of control wires 40a and 40b, facilitate controlled, bi-directional bending of the second flexure zone 34. The second flexure zone deflects in a first direction in response to pulling on the control wire 40a while the control wire 40b is not under significant tension (see FIG. 25U). The second flexure zone deflects in a second, opposing direction in response to pulling on the control wire 40b while the control wire 40a is not under significant tension.

While the second flexure zone 34 of FIGS. 25T and 25U illustratively is configured for controlled, bi-directional deflection, it should be understood that a second flexure zone with a centrally positioned spine and multiple circumferentially positioned spines alternatively may be configured for controlled deflection in any additional number of directions, as desired, by increasing the number of alternating, angularly offset spinal ribbon segments about the length of the centrally positioned spine; and by increasing the number of circumferentially positioned spines having expansion elements 67 and in alignment with the spinal ribbon segments of the centrally positioned spine. See, for example, the centrally positioned and circumferentially positioned spines described previously with respect to FIGS. 25G-25K and FIGS. 25P-25S. For example, the quad-directional centrally positioned spines of FIGS. 25G-25J may be utilized in combination with the four circumferentially positioned spines of FIGS. 25R and 25S to achieve controlled, quad-directional deflection of the second flexure zone 34. Additional directional controls may be provided, as desired.

4. Handle Actuator for Controlled, Multi-Directional Deflection

In one representative embodiment, as shown in FIG. 25V, the actuator 260 of handle assembly 200 comprises a ball-and socket joint for controlled multi-directional deflection of the second flexure zone 34 via controlled pulling on one or more control wires 40 that proximally terminate at the actuator and distally terminate in the second flexure zone. FIG. 25V illustratively shows four control wires 40 circumferentially spaced about the handle assembly 200 and that extend circumferentially to the second flexure zone. The actuator 260 can swivel in all directions relative to the handle assembly, allowing any wire (or wires) to be pulled in tension, as desired, to deflect the second flexure zone 34 in multiple directions in a controlled manner.

An alternative multi-directional actuator 260 may comprise a multidirectional joystick coupled to multiple control wires, as in FIG. 25W. Alternatively, one or more bi-directional actuators, each for actuation in two directions in a given plane, may be provided.

K. Eleventh Representative Embodiment (Second Flexure Zone Configured for Helical Deflection)

Figure 26H:
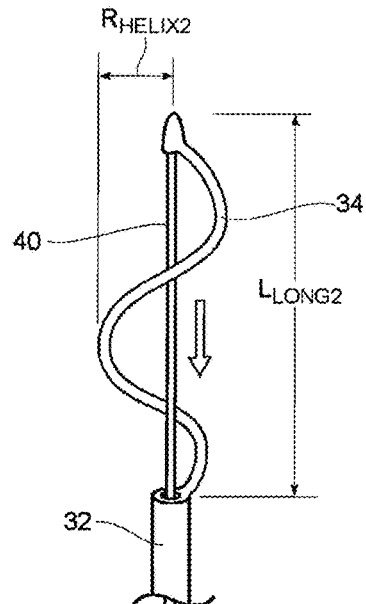

FIGS. 26A-26L show representative embodiments of the eleventh embodiment having an elongated shaft 16 that includes a proximal force transmitting section 30, a first flexure zone 32, a second or intermediate flexure zone 34, and an optional third or distal flexure zone 44 (see FIG. 26A). In these embodiments, the materials, size, and configuration of the proximal force transmitting section 30, first flexure zone 32, and optional third flexure zone 44 are comparable to their respective counterparts described in any of the previous embodiments. Furthermore, the length and diameter of second flexure zone 34 in the embodiments of FIG. 26 may be comparable to those described in any of the previous embodiments of the second flexure zone 34.

However, in the eleventh embodiment of the present invention, the second flexure zone 34 is configured for helical deflection. Helical deflection of the second flexure zone may facilitate establishment of complete or partial circumferential contact between the second flexure zone and an interior wall of a renal artery. This may reduce an angle of contact between the thermal element 24 and the interior wall of the artery, which may reduce forces applied by the thermal element to the vessel well, may provide a less traumatic treatment, may reduce a risk of acute dissection of the arterial wall, may provide better apposition between a side of the thermal element and the vessel wall and/or may stabilize the thermal element in place against the vessel wall for the duration of treatment and through the cardiac cycle. Furthermore, the helix may provide longitudinally spaced hoop strength along its contact path with the interior wall of the renal artery, which may reduce a risk of luminal narrowing and blood flow blockage due to vascular spasm during treatment.

In some representative embodiments of the eleventh embodiment, helical deflection of the second flexure zone 34 may mitigate a need for optional third flexure zone 44.

In some representative embodiments of the eleventh embodiment, one or more thermal elements 24 may be positioned along the length of the helically deflecting second flexure zone 34 and/or at its distal end. When multiple thermal elements are provided, the longitudinal and/or circumferential spacing of the thermal elements in the deployed configuration may be specified to facilitate creation of a treatment zone within a renal artery having desired longitudinal and/or circumferential spacing, while either avoiding entirely or reducing rotation and/or longitudinal repositioning of the thermal elements.

In some representative embodiments of the eleventh embodiment, one or more substantially spherical, cylindrical, semi-spherical or semi-cylindrical electrodes (as described previously) may be positioned along the length of the second flexure zone.

In some representative embodiments of the eleventh embodiment, a long and substantially continuous thermal element may be positioned along the length of the helically deflecting second flexure zone. The thermal element may be configured for direct thermal modification of tissue, such as via injection of a thermal fluid within the second flexure zone, and/or via resistive heating or via Peltier cooling of the helical second flexure zone. Direct heating of thermal element 24 may facilitate creation of a longer treatment zone than would be achievable with an electrode, for example, may facilitate creation of a helical treatment zone that provides a longitudinally spaced, circumferential treatment zone within a renal artery.

Direct heating also may facilitate renal neuromodulation via energy delivery for a relatively longer period of time at a relatively lower energy density than would be achievable with an electrode-based thermal element. This may allow blood flow to remove excess thermal energy from an interior wall of a renal artery, thereby reducing a risk of injury to non-target wall tissue, while facilitating an alteration in the temperature of target renal nerves (in response to the direct thermal modification applied via the thermal element 24) to a temperature sufficient to achieve desired renal neuromodulation.

It should be understood that any of the previously described thermal elements 24, and not just helical embodiments of the thermal element, may be long and continuous and/or may be configured for direct thermal modification of tissue. For example, the flexible electrode 90 of the second representative embodiment seen in FIG. 17 alternatively may comprise a thermal element configured for the direct thermal modification of tissue.

When the second flexure zone 34 is configured for helical deflection, the properties of its helix should be appropriate for placement in a target blood vessel, such as a renal artery, and for creation of a desired treatment zone. For example, the helix should be configured for delivery in a low profile configuration with a diameter and longitudinal length comparable to those described in any of the previous embodiments of the second flexure zone 34 and/or with a longitudinal length comparable to the previously described length of the renal artery (e.g., with a diameter configured for placement within a 5-8 French guide and a length L3 between about 5 mm and 30 mm, for example, a length L3 of about 10-30 mm). Furthermore, the helix should be configured for deployment to an expanded configuration with a diameter appropriate for establishment of partial or complete circumferential contact with the interior wall of the vessel along a desired longitudinal length. As discussed previously, the native inside diameter of a renal artery may vary between about 2 mm and about 10 mm, i.e. the native inside radius of the renal artery may vary between about 1 mm and 5 mm. It is most common for the diameter of the renal artery to vary between about 2 mm and about 8 mm, i.e. for the radius of the renal artery to vary between about 1 mm and about 4 mm.

The radius (i.e., ½ the diameter) of a helix, rHelix, is defined as:

$$r_{Helix} = \sqrt{\left(\frac{L_{Arc}}{t_{Helix}}\right)^2 - \left(\frac{P_{Helix}}{2\pi}\right)^2} \quad (16)$$

where $L_{Arc}$ is the arc length along the helix, $t_{Helix}$ is the arcuate angle circumscribed along the longitudinal length of the helix (i.e., the angle of rotation about the axis of elongated shaft 16 along the longitudinal length of the helix), and $P_{Helix}$ is the pitch of the helix. Helical pitch is defined as the longitudinal distance between two points on a helix that are separated by one full revolution of the helix.

The longitudinal length of the helix, $L_{Long}$, is thus defined as:

$$L_{Long} = \frac{P_{Helix} \times t_{Helix}}{2\pi} \quad (17)$$

By substituting Equation (17) into Equation (16), it can be shown that:

$$r_{Helix} = \frac{\sqrt{L_{Arc}^2 - L_{Long}^2}}{t_{Helix}} \quad (18)$$

The second flexure zone's initial helical radius, rHelix1, and initial longitudinal length, LLong1, in the delivery configuration are constrained by the previously described appropriate diameter (radius) and length of the second flexure zone 34 and/or by the length of the renal artery. Furthermore, the second flexure zone's deflected helical radius, rHelix2, in the deployed configuration is constrained by the interior diameter (radius) of the renal artery in which treatment is to be conducted. As specified in Equation (18), the second flexure zone's helical radius may be reversibly expanded from rHelix1 to rHelix2 by reversibly altering the helix's tHelix, LArc or LLong (or PHelix), or a combination thereof. Furthermore, from Equation (17), the helix's longitudinal length may change as the helix's PHelix and/or tHelix change.

When the helically deflecting second flexure zone comprises multiple thermal elements 24 positioned along its length, the thermal elements may be positioned along the deployed pitch PHelix2 of the second flexure zone's helix to provide desired longitudinal and/or circumferential spacing of the thermal elements in the deployed configuration of the second flexure zone (e.g., to provide minimal desired longitudinal and/or circumferential spacing of the thermal elements at maximal expected renal arterial radius). This may facilitate the creation of a treatment zone within a renal artery having desired circumferential and longitudinal spacing without necessitating rotation or longitudinal repositioning of the thermal elements after initial deployment.

In some representative embodiments of the eleventh embodiment, the second flexure zone's helix expands from rHelix1 to rHelix2 by reducing the longitudinal length of the helix from the initial longitudinal length, LLong1, to a deflected longitudinal length, LLong2, while tHelix and LArc remain constant (i.e., by reducing the pitch of the helix from PHelix1 to PHelix2). In some representative embodiments of the eleventh embodiment, the second flexure zone helically expands from rHelix1 to rHelix2 by reducing the helix's arcuate angle from an initial arcuate angle, tHelix1, to a deflected arcuate angle, tHelix2, while LLong and LArc remain constant (i.e., by increasing the pitch of the helix from PHelix1 to PHelix2). In some representative embodiments of the eleventh embodiment, the second flexure zone helically expands from rHelix1 to rHelix2 by enlarging the helix's arc length from an initial arc length, LArc1, to a deflected arc length, LArc2, while tHelix and LLong (and, thus, PHelix) remain constant. In some representative embodiments of the eleventh embodiment, the second flexure zone helically expands from rHelix1 to rHelix2 via a combination of reduction in the helix's longitudinal length, reduction in the helix's arcuate angle, and/or enlargement in the helix's arc length.

1. Helical Radius Expansion Via Reduction in Longitudinal Length

Delivery conditions of the second flexure zone's helix; rHelix1, LLong1, tHelix1 and LArc1; are specified or known. For example, rHelix1 and LLong1 are specified by the constraints that guide catheter delivery and the renal anatomy, respectively, place on the second flexure zone 34 in the delivery configuration, while tHelix1 and LArc1 may be chosen to provide the second flexure zone with desired deployed conditions. In this embodiment, the second flexure zone helically expands from rHelix1 to rHelix2 (e.g., to the interior radius of a renal artery) by reducing the longitudinal length of the helix from LLong1 to LLong2 (i.e., by reducing the pitch of the helix from PHelix1 to PHelix2), while tHelix and LArc remain constant (i.e., tHelix1=tHelix2=tHelix, and LArc1=LArc2=LArc).

By rearranging Equation (18), it can be shown that:

$$\frac{L_{Arc}}{t_{Helix}} = \sqrt{r_{Helix}^2 + \left(\frac{L_{Long}}{t_{Helix}}\right)^2} \quad (19)$$

Since LArc and tHelix (and, thus, the ratio LArc/tHelix) are held constant during radial expansion of the helix, the delivery and deployed conditions of the helix are related, as follows:

$$r_{Helix1}^2 + \left(\frac{L_{Long1}}{t_{Helix}}\right)^2 = r_{Helix2}^2 + \left(\frac{L_{Long2}}{t_{Helix}}\right)^2 \quad (20)$$

Thus, the longitudinal length in the expanded configuration, LLong2, is defined as:

$$L_{Long2} = \sqrt{L_{Long1}^2 - t_{Helix}^2(r_{Helix2}^2 - r_{Helix1}^2)} \quad (21)$$

For example, given an initial radius rHelix1 of 0.5 mm, a desired final radius rHelix2 of 4 mm (e.g., for use in an 8 mm diameter renal artery), an initial longitudinal length LLong1 of 27 mm, and a desired arcuate angle tHelix of $2\pi$ (e.g., 360° or one complete revolution of the helix for achieving circumferential contact within a renal artery), the second flexure zone's helix should be shortened to a deployed longitudinal length LLong2 of slightly more than 10 mm.

Conversely, Equation (21) may be rearranged and utilized to choose a tHelix (and, thereby, an LArc) that provides a desired rHelix2 and LLong2 in the deployed configuration:

$$t_{Helix} = \sqrt{\frac{L_{Long2}^2 - L_{Long1}^2}{r_{Helix1}^2 - r_{Helix2}^2}} \tag{22}$$

For example, given an initial radius rHelix1 of 0.5 mm, a desired final radius rHelix2 of 4 mm (e.g., for use in an 8 mm diameter renal artery), an initial longitudinal length LLong1 of 27 mm, and a desired final longitudinal length LLong2 of 10 mm (e.g. to achieve about a 5 mm spacing between multiple thermal elements 24 positioned at the proximal end, the midpoint and the distal end of the helix), the arcuate angle tHelix circumscribed by the helix along its longitudinal length should equal slightly more than 2π(i.e., slightly more than 360° or 1 complete revolution of the helix).

Advantageously, the deployed radius rHelix2 of the helix during expansion via longitudinal shortening of the second flexure zone 34 from LLong1 to LLong2 may be varied dynamically up to a maximum radius where the helix's deployed longitudinal length LLong2 equals zero:

$$r_{Max} = \frac{L_{Arc}}{t_{Helix}} \tag{23}$$

This may facilitate establishment of at least partial circumferential contact with the interior wall of renal arteries of various radii up to the maximum radius.

When the helically deflecting second flexure zone comprises multiple thermal elements 24 positioned along its length, Equations (16)-(23) may be utilized to provide desired longitudinal and/or circumferential spacing of the thermal elements in the deployed configuration of the second flexure zone. For example, the thermal elements may be positioned as desired along the deployed pitch PHelix2 of the second flexure zone's helix. This may facilitate the creation of a treatment zone within a renal artery having desired circumferential and longitudinal spacing without necessitating rotation or longitudinal repositioning of the thermal elements after initial deployment.

In the representative embodiments of FIGS. 26B-26G, third tubular structure 62 of second flexure zone 34 includes a laser-cut pattern that forms a helical spine 66 with connecting ribs 68. A control wire 40 is attached to a distal end of the second flexure zone 34 with solder 130. The helical spine biases deflection of the third tubular structure 62, in response to proximal retraction of the control wire 40, from a substantially straight configuration (see FIGS. 26B and 26C) with an initial helical radius rHelix1 (rHelix1 is approximately ½ the diameter of the third tubular structure 62) and initial longitudinal length LLong1, to a longitudinally shorter and radially wider helical configuration (see FIG. 26D) with a deflected helical radius rHelix2 and deflected longitudinal length LLong2.

The arc length LArc and arcuate angle tHelix of helical spine 66 are specified to achieve desired deployed conditions; they do not vary during radial expansion of the helix via longitudinal shortening. However, it is expected that as the arc length LArc and/or arcuate angle tHelix of the spine 66 are specified at relatively greater values, the tensile force applied to control wire 40 that would be necessary to helically deflect the second flexure zone into circumferential contact with an interior wall of a patient's renal artery (e.g., the force expected to provide a helical radius in the range of about 1-5 mm) would be increased relative to when the arc length LArc and/or arcuate angle tHelix of the spine are specified at relatively smaller values.

The helically deflecting second flexure zone 34 may be positioned proximal of the thermal heating element 24 carried by the third flexure zone 44. Alternatively, as seen in FIG. 26E, one or more thermal elements 24, such as previously described substantially spherical electrodes 92 or substantially semi-spherical electrodes 92a, may be positioned along the length of the second flexure zone 34. In FIG. 26E, third flexure zone 44 is provided as an atraumatic distal tip, but it should be understood that the elongated shaft 16 alternatively may be provided without the third flexure zone 44.

In FIG. 26F, a long and substantially continuous thermal element 24 is positioned along the length of the helically deflecting second flexure zone 34. Thermal element 24 of FIG. 26F may be configured for direct thermal modification of tissue, such as via injection of a thermal fluid within the second flexure zone, via resistive heating and/or via Peltier cooling of the helical second flexure zone. Although thermal element 24 in FIG. 26F is shown as long and substantially continuous, it should be understood that the thermal element alternatively may comprise multiple thermal elements spaced closely together. Furthermore, in FIG. 26F, the elongated shaft 16 illustratively is provided without the third flexure zone 44, though the third flexure zone alternatively may be provided.

In FIG. 26G, control wire 40 is positioned external to the third tubular structure 62 along the second flexure zone. For example, the control wire may exit the elongated shaft at or near a proximal end of the second flexure zone 34, e.g., through a side port or through a longitudinal space between connecting ribs 68. Positioning control wire 40 external to the second flexure zone along its length may reduce the tensile forces applied to the control wire 40 that are necessary to helically deflect the second flexure zone. As will be apparent, control wire(s) 40 optionally may be positioned external to the second flexure zone in any of the previously described second flexure zones, such as any of the previously described planar bending second flexure zones.

Referring to FIG. 26H another embodiment of the second flexure zone 34 is described wherein the second flexure zone 34 comprises an elastic or superelastic material or wire, such as Nitinol. In FIG. 26H, the second flexure zone 34 is distally coupled to control wire 40 and is proximally coupled to the first flexure zone 32, such that proximal retraction of the control wire longitudinally shortens the second flexure zone to the deployed configuration with a radially expanded helix. Removal of tension from the control wire causes the second flexure zone to resume a substantially straight delivery configuration.

Second flexure zone 34 of FIG. 26H alternatively may comprise a plastically deformable material, such as a polymer or metal wire or coil. In such an embodiment, proximal retraction of the control wire 40 may plastically deform the second flexure zone during longitudinal shortening and radial expansion of its helix. Control wire 40 may be sufficiently stiff that distally pushing the wire longitudinally lengthens the second flexure zone and radially collapses its helix for delivery and/or retrieval. Alternatively, advancing a sheath, such as the guide catheter, over the elongated shaft 16 and expanded second flexure zone 34 may straighten and lengthen the second flexure zone, thereby radially collapsing its helix for delivery and/or retrieval.

2. Helical Radius Expansion via Reduction in Arcuate Angle

As discussed previously, delivery conditions of the second flexure zone's helix; rHelix1, LLong1, tHelix1 and LArc1; are specified or known. For example, rHelix1 and LLong1 are specified by the constraints that guide catheter delivery and the renal anatomy, respectively, place on the second flexure zone 34 in the delivery configuration, while tHelix1 and LArc1 may be chosen to provide the second flexure zone with desired deployed conditions. In this embodiment, the second flexure zone helically expands from rHelix1 to rHelix2 (e.g., to the interior radius of a renal artery) by reducing the arcuate angle circumscribed by the helix from tHelix1 to tHelix2 (i.e., by increasing the pitch of the helix from PHelix1 to PHelix2), while LLong and LArc remain constant (i.e., LLong1=LLong2=LLong, and LArc1=LArc2=LArc).

By rearranging Equation (18), it can be shown that:

$$L_{Arc}^2 - L_{Long}^2 = r_{Helix}^2 \times t_{Helix}^2 \quad (24)$$

Since LArc and LLong (and, thus, LArc2−LLong2) are held constant during radial expansion of the helix, the delivery and deployed conditions of the helix are related, as follows:

$$r_{Helix1} \times t_{Helix1} = r_{Helix2} \times t_{Helix2} \quad (25)$$

Thus, the arcuate angle in the delivery configuration, tHelix1, is defined as:

$$t_{Helix1} = \frac{r_{Helix2} \times t_{Helix2}}{r_{Helix1}} \quad (26)$$

For example, given an initial radius rHelix1 of 0.5 mm, a desired deployed radius rHelix2 of 4 mm (e.g., for use in an 8 mm diameter renal artery), a fixed delivery and deployed longitudinal length (e.g., LLong=20 mm), and a desired deployed arcuate angle tHelix2 of $2\pi$ (i.e., 360° or one complete revolution of the helix for achieving circumferential contact within a renal artery), the second flexure zone's arcuate angle during delivery tHelix1 should be about $16\pi$ (i.e., about 2880° or 8 revolutions). When the desired deployed arcuate angle tHelix2 is reduced to $\pi$ (i.e., 180° or half a revolution), the second flexure zone's arcuate angle during delivery tHelix1 is reduced proportionally to about $8\pi$ (i.e., about 1440° or 4 revolutions).

Advantageously, the deployed radius rHelix2 of the helix during expansion via reduction in the arcuate angle may be varied dynamically to increase the radius by decreasing the deployed arcuate angle tHelix2. This may facilitate establishment of at least partial circumferential contact with the interior wall of renal arteries of various radii.

When the helically deflecting second flexure zone comprises multiple thermal elements 24 positioned along its length, Equations (16)-(18) and (24)-(26) may be utilized to provide desired longitudinal and/or circumferential spacing of the thermal elements in the deployed configuration of the second flexure zone. For example, the thermal elements may be positioned as desired along the deployed pitch PHelix2 of the second flexure zone's helix. This may facilitate the creation of a treatment zone within a renal artery having desired circumferential and longitudinal spacing without necessitating rotation or longitudinal repositioning of the thermal elements after initial deployment.

Figure 26I:
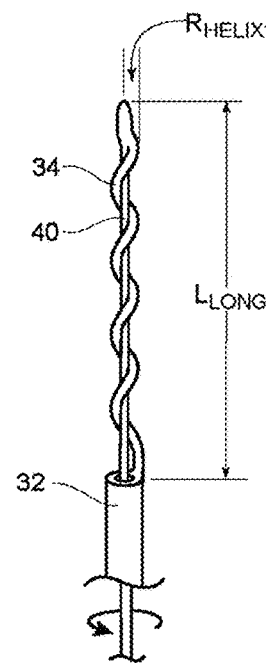
Figure 26J:
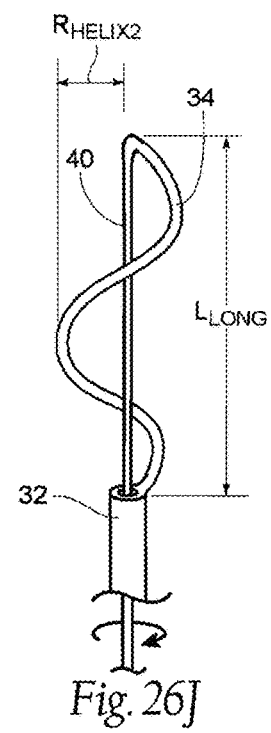

With reference now to FIGS. 26I and 26J, the second flexure zone 34 may be helically wrapped around control wire or shaft 40, which is positioned external to the second flexure zone. The control wire is connected to the distal end of the second flexure zone via solder 130 and may be relatively stiff at least in the vicinity of the second flexure zone 34, as compared to previously described control wires 40.

As seen in FIG. 26I, in the delivery configuration, the second flexure zone is wrapped relatively tightly around the control wire (e.g., rHelix1 is relatively similar to the diameter of the control wire) during delivery. As seen in FIG. 26J, the second flexure zone helically expands from the delivery radius rHelix1 to the deployed radius rHelix2 via rotation of the control wire 40 along its longitudinal axis, which untwists the helix. LArc and LLong remain constant during such expansion, while the arcuate angle of the helix is reduced from tHelix1 to tHelix2.

3. Helical Radius Expansion Via Enlargement in Arc Length

As discussed previously, delivery conditions of the second flexure zone's helix; rHelix1, LLong1, tHelix1 and LArc1; are specified or known. In this embodiment, the second flexure zone helically expands from rHelix1 to rHelix2 (e.g., to the interior radius of a renal artery) by increasing the arc length of the helix from LArc1 to LArc2, while LLong and tHelix (and, thus, PHelix) remain constant (i.e., LLong1=LLong2=LLong, and tHelix1=tHelix2= tHelix).

By rearranging Equation (18), it can be shown that:

$$L_{Long}^2 = L_{Arc}^2 - r_{Helix}^2 \times t_{Helix}^2 \quad (27)$$

Thus, the arc length of the helix is defined as:

$$L_{Arc} = \sqrt{L_{Long}^2 + r_{Helix}^2 \times t_{Helix}^2} \quad (28)$$

Furthermore, since LLong and tHelix are held constant during radial expansion of the helix, the delivery and deployed conditions of the helix are related, as follows:

$$L_{Arc1}^2 - r_{Helix1}^2 \times t_{Helix}^2 = L_{Arc2}^2 - r_{Helix2}^2 \times t_{Helix}^2 \quad (29)$$

Thus, the arc length in the delivery configuration, LArc1, is defined as:

$$L_{Arc1} = \sqrt{L_{Arc2}^2 + r_{Helix1}^2 \times t_{Helix}^2 - r_{Helix2}^2 \times t_{Helix}^2} \quad (30)$$

For example, given a desired deployed radius rHelix2 of 4 mm (e.g., for use in an 8 mm diameter renal artery), a fixed delivery and deployed longitudinal length LLong of 15 mm, and a desired delivery and deployed arcuate angle tHelix of $2\pi$ (i.e., 360° or one complete revolution of the helix for achieving circumferential contact within a renal artery in the deployed configuration), the desired deployed arc length LArc2 from Equation (28) using deployed conditions is slightly more than 29 mm. Thus, given a delivery radius rHelix1 of 0.5 mm the second flexure zone's arc length during delivery LArc 1 from Equation (28) or Equation (30) should be slightly more than 15 mm. When the desired deployed arcuate angle tHelix is increased to $4\pi$(720° or 2 revolutions), the second flexure zone's deployed arc length LArc2 is increased to about 52.5 mm, while the delivery arc length LArc1 is increased to slightly more than 16 mm.

Advantageously, the deployed radius rHelix2 of the helix during expansion via enlargement of the arc length may be varied dynamically to increase the radius as the helix's deployed arc length LArc2 is increased. This may facilitate establishment of at least partial circumferential contact with the interior wall of renal arteries of various radii.

When the helically deflecting second flexure zone comprises multiple thermal elements 24 positioned along its length, Equations (16)-(18) and (27)-(30) may be utilized to provide desired longitudinal and/or circumferential spacing of the thermal elements in the deployed configuration of the second flexure zone. For example, the thermal elements may be positioned as desired along the delivery and deployed pitch PHelix of the second flexure zone's helix. This may facilitate the creation of a treatment zone within a renal artery having desired circumferential and longitudinal spacing without necessitating rotation or longitudinal repositioning of the thermal elements after initial deployment.

Figure 26K:
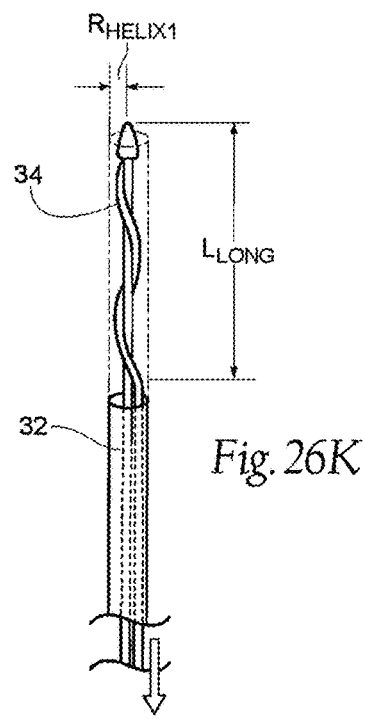
Figure 26L:
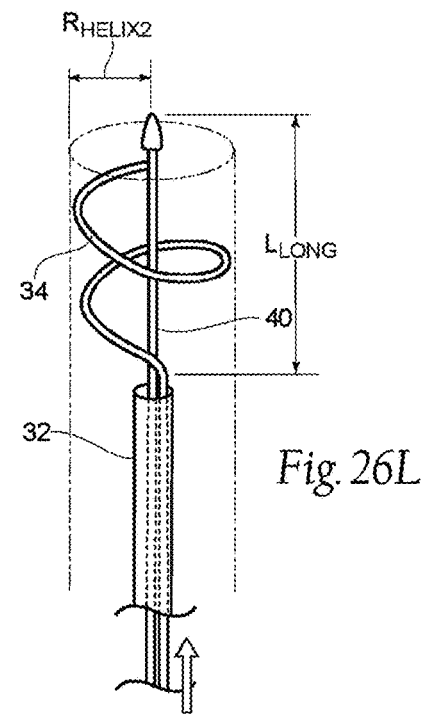

With reference now to FIGS. 26K and 26L, the second flexure zone 34 may be helically wrapped around control wire or shaft 40, which is positioned external to the second flexure zone. The control wire is connected to the distal end of the second flexure zone via solder 130 and may be relatively stiff at least in the vicinity of the second flexure zone 34, as compared to some of the previously described control wires 40.

The second flexure zone may be wrapped relatively tightly around the control wire (e.g., rHelix1 is relatively similar to the diameter of the control wire) during delivery. As seen in FIG. 26K, when positioned at a treatment site, the distal end of the second flexure zone may be positioned a desired longitudinal distance LLong from the guide catheter 94. As seen in FIG. 26L, while keeping LLong and tHelix (and, thus, PHelix) constant, the elongated shaft 16 may be advanced distally relative to the control wire 40 and the guide catheter 94. This increases the arc length LArc of the second flexure zone from the delivery arc length LArc1 to the deployed arc length LArc2, causing radial expansion of the helix from the delivery radius rHelix1 to the deployed radius rHelix2.

4. Helical Radius Expansion Via a Combination of Reduction of Longitudinal Length, Reduction of Arcuate Angle, Enlargement of Arc Length, and/or Alteration of Pitch As discussed previously, delivery conditions of the second flexure zone's helix; rHelix1, LLong1, tHelix1 and LArc1; are specified or known. Helical expansion from delivery radius rHelix1 to deployed radius rHelix2 (e.g., to the interior radius of a renal artery) may be achieved via a combination of reduction in the helix's longitudinal length LLong, reduction of the helix's arcuate angle tHelix, enlargement of the helix's arc length Larc, and/or alteration of the helix's pitch PHelix. Equations (16)-(30) may be utilized, as appropriate (given the specific mechanism of radial expansion), to achieve desired deployed conditions rHelix2, LLong2, tHelix2 and LArc2. Furthermore, when multiple thermal elements 24 are positioned along the length of the second flexure zone, the Equations may be used, as appropriate, to provide desired longitudinal and/or circumferential spacing of the thermal elements in the deployed configuration of the second flexure zone. For example, the thermal elements may be positioned as desired along the deployed pitch PHelix2 of the second flexure zone's helix. This may facilitate the creation of a treatment zone within a renal artery having desired circumferential and longitudinal spacing without necessitating rotation or longitudinal repositioning of the thermal elements after initial deployment.

Various combinations of reduction in the helix's longitudinal length LLong, reduction in the helix's arcuate angle tHelix, enlargement in the helix's arc length Larc and/or alteration of the helix's pitch PHelix may be utilized to achieve radial expansion of the helix. For example, in the embodiment of FIGS. 26I and 26J, the control wire 40 may both be rotated and proximally translated during deployment to both reduce the helix's longitudinal length and reduce the helix's arcuate angle to achieve desired radial expansion of the helix. As another example, in the embodiment of FIGS. 26K and 26L, the control wire 40 may be proximally retracted as the elongated shaft 16 is advanced distally and the guide catheter 94 is held in place to both reduce the helix's longitudinal length and increase the helix's arc length to achieve desired radial expansion of the helix. As yet another example, in the embodiment of FIGS. 26K and 26L, the control wire 40 may be rotated about its longitudinal axis as the elongated shaft 16 is advanced to both reduce the helix's arcuate angle and increase the helix's arc length to achieve desired radial expansion of the helix. Further still, in the embodiment of FIGS. 26K and 26L, the control wire 40 may be both rotated about its longitudinal axis and proximally translated as the elongated shaft 16 is advanced distally and the guide catheter 94 is held in place to reduce the helix's arcuate angle, reduce the helix's longitudinal length, and increase the helix's arc length to achieve desired radial expansion of the helix.

L. Twelfth Representative Embodiment (Second Flexure Zone Configured for Complex Deflection)

Figure 27D:
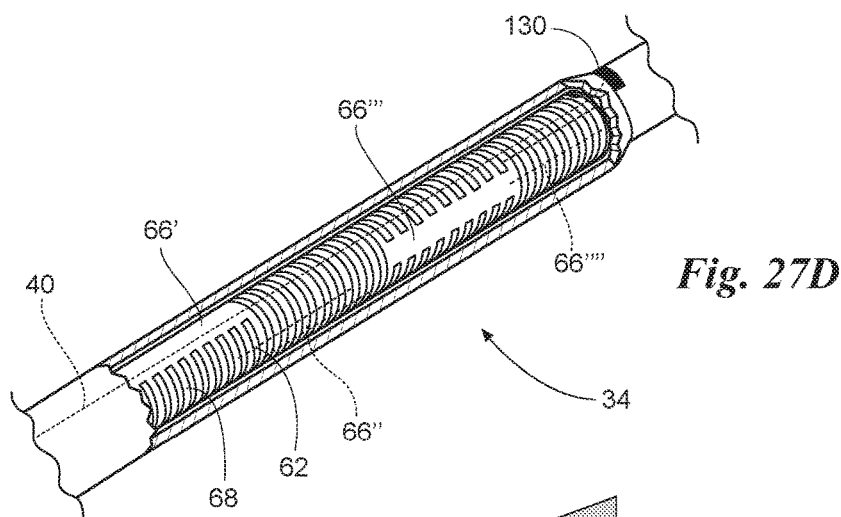
Figure 27E:
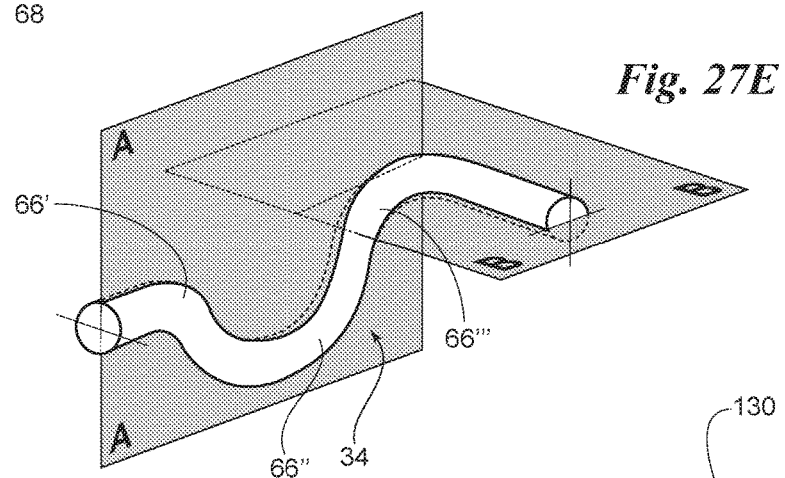
Figure 27F:
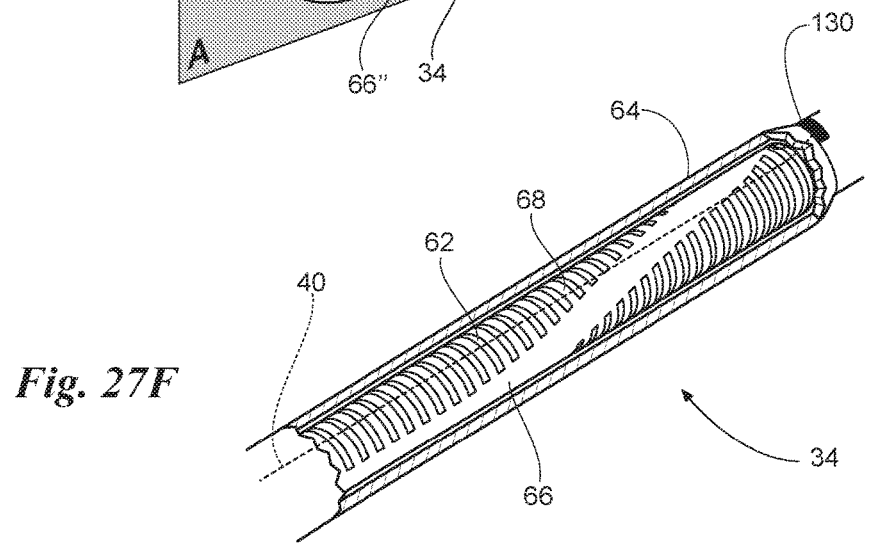

FIGS. 27A-27D show representative embodiments of the twelfth embodiment having an elongated shaft 16 that includes a proximal force transmitting section 30, a first or proximal flexure zone 32, a second or intermediate flexure zone 34, and an optional third or distal flexure zone 44 (see FIG. 27A). In these embodiments, the materials, size, and configuration of the proximal force transmitting section 30, first flexure zone 32, and optional third flexure zone 44 are comparable to their respective counterparts described in any of the previous embodiments. Furthermore, the length and diameter of second flexure zone 34 in the embodiments of FIG. 27 may be comparable to those described in any of the previous embodiments of the second flexure zone 34.

However, in the twelfth embodiment of the present invention, the second flexure zone 34 is configured for complex deflection. Complex deflection may comprise, for example, deflection in multiple directions in a single plane, deflection in multiple directions in multiple planes, planar deflection in combination with helical deflection, etc. Complex deflection of the second flexure zone 34 may facilitate placement of one or more thermal elements 24, which may be positioned along the length of the second flexure zone and/or coupled to optional third flexure zone 44, into contact with the interior wall of a renal artery at desired longitudinal and/or circumferential position(s).

In the representative embodiment of FIG. 27B, the third tubular structure 62 of the second flexure zone 34 comprises a laser-cut pattern that includes spine 66 with connecting ribs 68. Control wire 40 is attached to a distal end of the second flexure zone with solder 130. The spine 66 comprises first segment 66' and second segment 66" that are longitudinally spaced and angularly opposed (i.e., about 180° angularly offset from one another), as well as third segment 66''' that is longitudinally spaced and angularly opposed to the second segment 66", but that is angularly aligned with the first segment 66'. In response to pulling on the control wire 40, the positioning of the spine's first and second segments is such that the third tubular structure's laser-cut pattern biases deflection of the third tubular structure back and forth in a plane orthogonal to the first and second segments of the spine, such that the second flexure zone has an "S"-shape in the deflected configuration of FIG. 27C. As shown, thermal elements 24 optionally may be positioned along the length of the second flexure zone, as well as at the distal end of the third flexure zone 44, such that in the deflected configuration, the thermal elements are positioned at the apex of bends that may contact an interior wall of a renal artery at longitudinally spaced and circumferentially opposed positions.

In the representative embodiment of FIG. 27D, the spine 66 comprises first segment 66' and second segment 66" that are longitudinally spaced and angularly opposed, as well as third segment 66''' and fourth segment 66'''' that are longitudinally spaced and angular opposed from one another, as well as orthogonal (i.e., about 90° angularly offset) from the first segment 66' and second segment 66". In response to pulling on the control wire 40, the positioning of the spine's first and second segments is such that the third tubular structure's laser-cut pattern biases deflection of the third tubular structure back and forth in each of two orthogonal planes, such that the second flexure zone has a "U"-shape in each of the orthogonal planes in the deflected configuration of FIG. 27E. As shown, thermal elements 24 optionally may be positioned along the length of the second flexure zone 34, as well as at the distal end of the third flexure zone 44, such that in the deflected configuration, the thermal elements are positioned at the apex of bends that may contact an interior wall of a renal artery at longitudinally spaced circumferential positions that are about 90° angularly offset.

Complex deflection of the second flexure zone 34 optionally may be achieved using multiple control wires 40. For example, in the embodiment of FIG. 27B, a first control wire may be distally attached to the distal end of the first spinal segment 66', a second control wire may be distally attached to the distal end of the second spinal segment 66", and a third control wire may be distally attached to the distal end of the third spinal segment 66''' Pulling on the first control wire would deflect just the first spinal segment, while pulling on the second control wire would deflect both the first and the second spinal segments, and pulling on the third control wire would deflect all three spinal segments (as in FIG. 27B). Use of multiple pull wires thereby may facilitate deflection of portions, or all, of the second flexure zone 34, as desired.

M. Thirteenth Representative Embodiment (Second Flexure Zone Configured for Electrically-Initiated Deflection)

FIGS. 28A and 28B show representative embodiments of the thirteenth embodiment having an elongated shaft 16 that includes a proximal force transmitting section 30, a first or proximal flexure zone 32, a second or intermediate flexure zone 34, and an optional third or distal flexure zone 44 (see FIG. 28A). In these embodiments, the materials, size, and configuration of the proximal force transmitting section 30, first flexure zone 32, and optional third flexure zone 44 are comparable to their respective counterparts described in any of the previous embodiments. Furthermore, the length and diameter of second flexure zone 34 in the embodiments of FIG. 28 may be comparable to those described in any of the previous embodiments of the second flexure zone 34.

However, in the thirteenth embodiment of the present invention, the second flexure zone 34 is configured for electrically initiated deflection. In the representative embodiment of FIG. 28B, the third tubular structure 62 of the second flexure zone 34 comprises a laser-cut pattern that includes spine 66 with connecting ribs 68, though it should be understood that other patterns, biasing spines or other structural designs formed by laser cutting or mechanisms other than laser cutting alternatively may be utilized. Control wire 40 is attached to a distal end of the second flexure zone with solder 130. As with previous embodiments, in response to the control wire 40 pulling proximally on the distal end of the second flexure zone, the third tubular structure's laser-cut pattern biases deflection of the third tubular structure in a plane orthogonal to the spine. However, unlike in previously described embodiments, control wire 40 pulls on the distal end of the second flexure zone due to electrically initiated shortening of the control wire rather than mechanically initiated tension along its length.

As seen in FIG. 28B, control wire 40 also is attached to a proximal end of the second flexure zone via solder 130'. Unlike in previous embodiments, the control wire 40 does not extend proximal of the second flexure zone through the elongated shaft 16 to handle assembly 200. Rather, electrical supply wires 29 travel from handle 200 through the elongated shaft and are electrically connected to the control wire 40 at solder joints 130 and 130'. Actuator 260 of handle assembly 200 applies electrical current to supply wires 29, which transfer the electrical current to control wire 40. Control wire 40 is shortened in response to the electrical current, which causes deflection of the second flexure zone 34.

In contrast to this thirteenth embodiment, some of the previously described embodiments of the present invention have one or more control wires 40 extending all the way through elongated shaft 16 to handle assembly 200. Tension is applied to the control wire(s) 40 along their entire lengths via actuator 260 to pull on the second flexure zone 34 and cause its deflection. To facilitate such deflection, the elongated shaft 16 proximal of the second flexure zone is relatively resistant to buckling, as the shaft is placed in compression along its length when tension is applied to the control wire(s) 40. Thus, the elongated shaft 16 may be relatively stiff, and it may become stiffer during deflection of the second flexure zone. In the thirteenth embodiment, since the control wire 40 does not extend proximal of the second flexure zone, the more proximal sections of the elongated shaft 16 are not compressed and need not resist buckling as aggressively. Thus, the elongated shaft may be fabricated in a manner that provides greater flexibility, which may enhance deliverability and/or may reduce catheter whip during rotation. Electrically initiated control wire shape change or shortening may be utilized in conjunction with any of the previously described second flexure zones 34 and control wires 40.

In one representative embodiment of the thirteenth embodiment, control wire 40 comprises a shape memory material, such as Nitinol. Prior to its attachment to the second flexure zone, the control wire's temperature is raised above its transformation temperature (e.g., in the range of about 20° C. to 60° C., dependent on the relative proportions of nickel and titanium in the alloy) to place the Nitinol in an austenite phase. The control wire is straightened and allowed to cool below its transformation temperature, such that the wire is placed in a martensite phase. The control wire then is attached to the proximal and distal ends of the second flexure zone under significant elastic deformation (e.g., strain in the range of about 6-10%). Electricity applied to supply wires 29 resistively heats the control wire 40 above its transformation temperature, causing the control wire to transform back to the Austenite phase and resume its prior heat-set, substantially unstrained austenite configuration. This shortens the control wire, causing the second flexure zone to deflect. The control wire or the third tubular structure 62 (which optionally may be resistively heated via supply wires 29) alternatively may comprise a bent austenite shape that pulls the second flexure zone in the direction of the bend.

In one representative embodiment of the thirteenth embodiment, the control wire 40 comprises an electroactive polymer, commonly referred to as an artificial muscle. Electricity applied to the electroactive polymer control wire shortens the control wire, causing the second flexure zone to deflect. When the electricity is turned off, the control wire resumes its initial shape, allowing the second flexure zone to straighten (or to be straightened).

N. Fourteenth Representative Embodiment (Second Flexure Zone Configured for Deflection at a Joint)

Figure 29B:
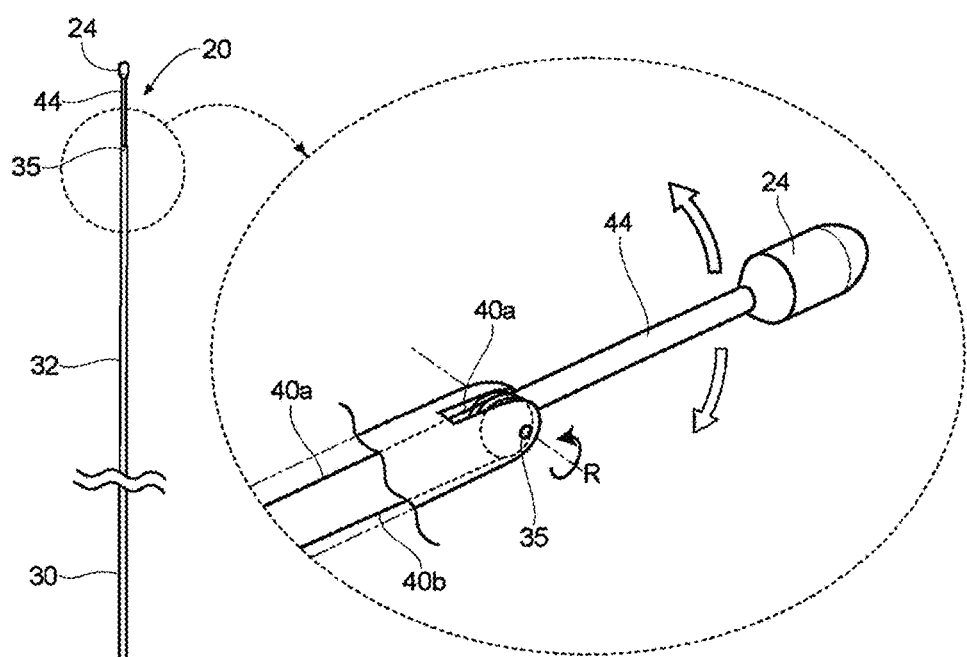
FIGS. 29A and 29E show additional alternative representative embodiments of an elongated shaft for a treatment device having hinge joint.
Figure 29A:
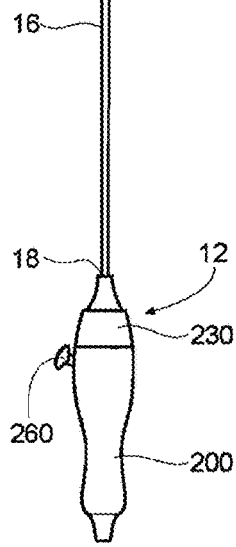

FIGS. 29A-29E show representative embodiments of the fourteenth embodiment having an elongated shaft 16 that includes a proximal force transmitting section 30, a first or proximal flexure zone 32, a joint 35, and an optional third or distal flexure zone 44 (see FIG. 29A). In these embodiments, the materials, size, and configuration of the proximal force transmitting section 30, first flexure zone 32, and optional third flexure zone 44 are comparable to their respective counterparts described in any of the previous embodiments.

Figure 29C:
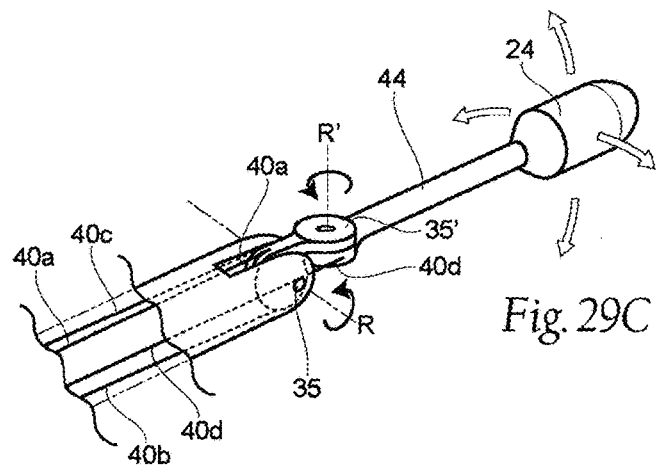

However, in the fourteenth embodiment of the present invention, the second flexure zone 34 is replaced by one or more joints 35 to facilitate deflection of the third flexure zone 44. Joints 35 may provide precise deflection control, as the joints may exhibit consistent deflection dynamics. Furthermore, joints may provide a sharper bend than would be achievable with some of the previously described embodiments of the second flexure zone since a joint represents a pivot point as opposed to a Radius of Curvature. Thus, the length of a jointed second flexure zone may be less than the length of a previously described biased spine second flexure zone. This may facilitate thermal neuromodulation in shorter renal arteries, and/or may facilitate use of a longer third flexure zone 44 as shown in FIG. 29E. A longer third flexure zone may dissipate vessel contact force over its longer length and resiliently apply pressure to the vessel wall to provide stable electrode contact during pulsatile blood flow and respiratory motion. Also, a longer third flexure zone may be easier to visualize with fluoroscopy. The third flexure zone 44 may be between about 6 mm and 16 mm long, for example about less than or equal to 9.5 mm, which could be suitable to provide sufficient flexure in renal arteries.

With reference to FIG. 29B, in one representative embodiment of the fourteenth embodiment, hinge joint 35 that connects the first flexure zone 32 to the third flexure zone 44. Control wires 40a and 40b are attached to either side of the joint 35 distal to the Axis of Rotation R for rotating the force dampening section 44 about the Axis of Rotation R of the hinge joint. Alternatively, one control wire is attached to a side of a joint 35 distal to the Axis of Rotation R for rotating the force dampening section 44 about the Axis of Rotation R of the hinge joint and a spring rotates the force dampening section 44 back to its undeflected state when tension in the control wire is relieved.

Alternatively, multiple third flexure zones can be connected to the first flexure zone via one or more joints. Each distal flexure zone can be attached to or comprise an electrode. Each distal flexure zone can be actuated to rotate about the joint independently or together with a single control wire. Alternatively, a spring can be positioned in the joint to push the distal flexure zones open and they can be closed by being retracted into a delivery sheath. When the distal flexure zones are open the electrodes are moved away from one another and placed in contact with a vessel wall.

Force dampening section 44 comprises, along its longitudinal length, a force redirecting element 49, which distances the energy delivery element 24 from the axis of the force dampening section 44 at a similar angle and distance as described in earlier embodiments. Since the slenderness ratio (length:diameter) is greater for a longer force dampening section 44, a longer force dampening section 44 is more susceptible to buckling especially when a load applied is distanced from its axis. As the distal assembly 53 is advanced into a renal artery and the energy delivery element 24 contacts a renal artery wall, the load applied to the energy delivery element 24 is distanced from the axis of the force dampening section 44 and could cause the force dampening section 44 to buckle at a load that is lower than a traumatic load. A force redirecting element 49 can be located on the force dampening section 44 longitudinally at about the midpoint. For example, on a 9.5 mm long force dampening section 44 the force redirecting element 49 can be about 4 to 5 mm proximal to the distal end. With reference to FIG. 29C, in one representative embodiment of the fourteenth embodiment, the second flexure zone 34 comprises first hinge joint 35 and second hinge joint 35'. Control wires 40a and 40b are attached to either side of the joint 35 for rotating the distal flexure zone about the Axis of Rotation R of the hinge joint 35, while control wires 40c and 40d are attached to either side of the second joint 35' for rotating the third flexure zone about the Axis of Rotation R' of the hinge joint 35'. The Axis of Rotation R' of hinge joint 35' preferably is orthogonal to the Axis of Rotation R of hinge joint 35 to provide deflection of the distal flexure zone 44 in two orthogonal planes.

Figure 29D:
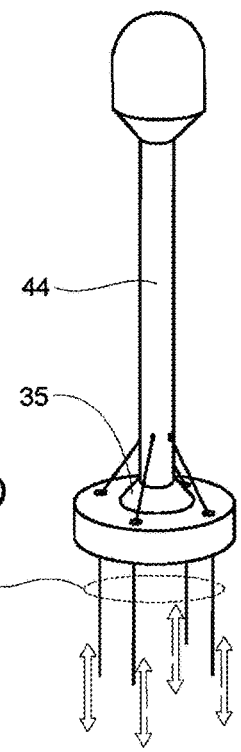
Figure 29E:
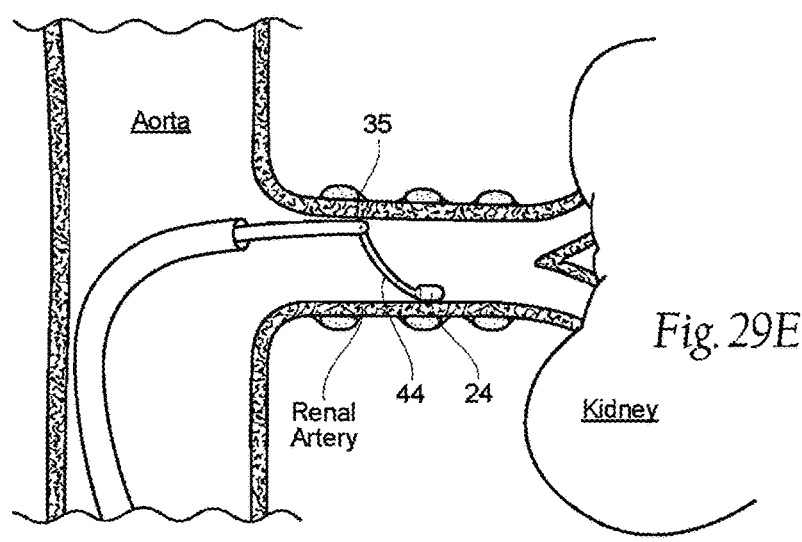

With reference to FIG. 29D, in one representative embodiment of the fourteenth embodiment, the second flexure zone 34 comprises ball-and-socket joint 35 that joins proximal and distal flexure zones and that facilitates rotation in any plane with a Radius of Curvature RoC of about zero. Any number of control wires 40 (illustratively four control wires) may be provided for deflecting the second flexure zone 34.

O. Fifteenth Representative Embodiment (Actively Cooled Energy Delivery Elements)

1. Energy Application to Intravascular Tissue in Combination with Active Cooling When utilized in a monopolar fashion, the previously described energy delivery element 24 may comprise an electrode that conducts RF current from the electrode through tissue to a return electrode, such as neutral electrode 38, positioned on the patient's skin. When utilized in a bipolar fashion, the thermal heating element 24 may comprise an electrode that conducts RF current from the active electrode 24 through tissue to a return electrode that is also positioned on the elongated shaft 16. RF current conducts through tissue from the active electrode to the return electrode along parallel tissue circuits.

RF current is most concentrated in the tissue near the surface of the active electrode. A simplified relationship of current density in a homogeneous tissue for a relatively spherical electrode describes current density to decay with distance from the active electrode surface at a rate of $r^4$. In an environment that has substantial differences in electrical and thermal properties (in particular, differences in impedance, heat capacity, convection), and as the electrode shape deviates from spherical, this relationship becomes more complicated.

Rapidly alternating current, such as RF, vibrates ions in tissue, generating heat. The heating effect is proportional to current density, as well as the rate of heat transfer due to conduction, convection and/or radiation in the tissue and blood. Generally speaking, the hottest tissue is at or near the surface of the electrode, and temperature decreases quickly with distance.

Figure 30A:
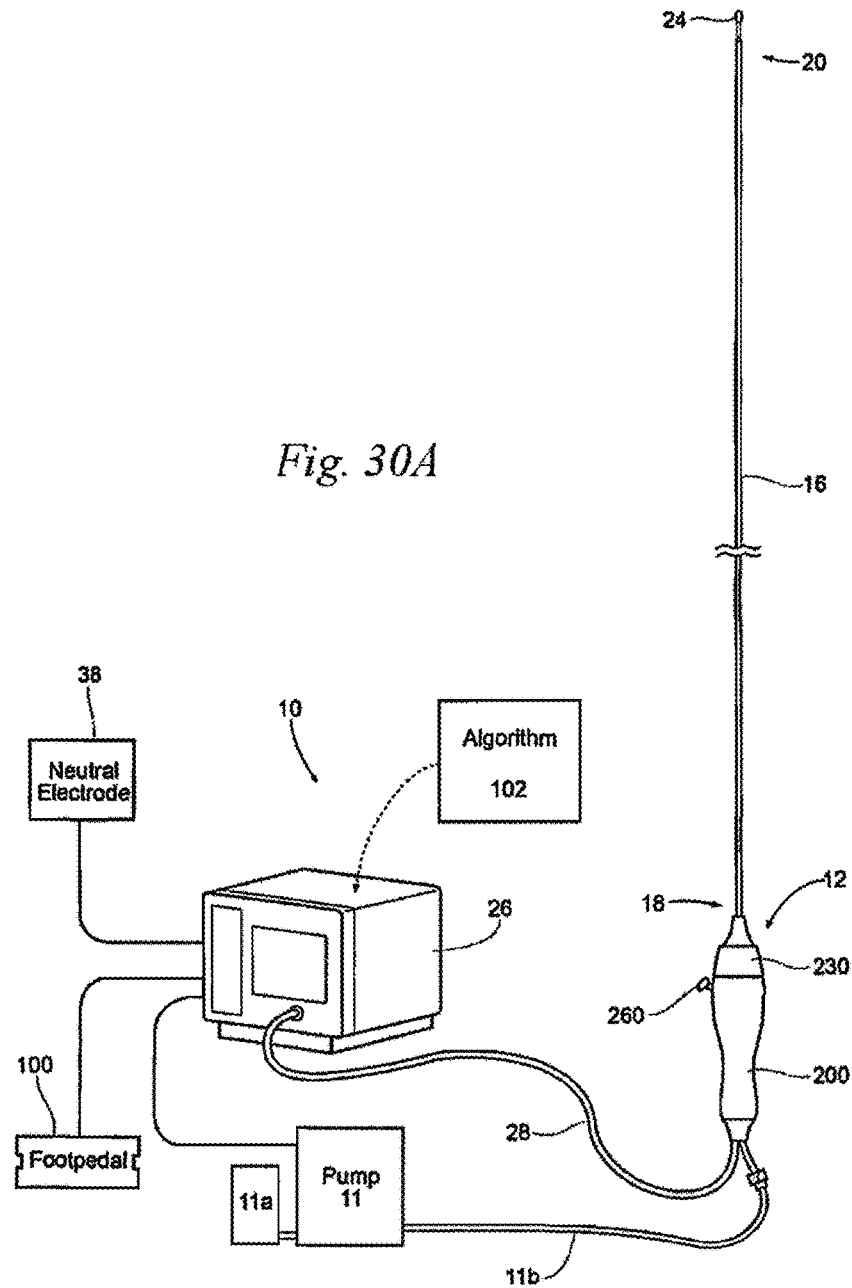
FIG. 30A is a perspective view of an additional embodiment of the system of FIG. 5 configured for active cooling of the treatment device.
Figure 30B:
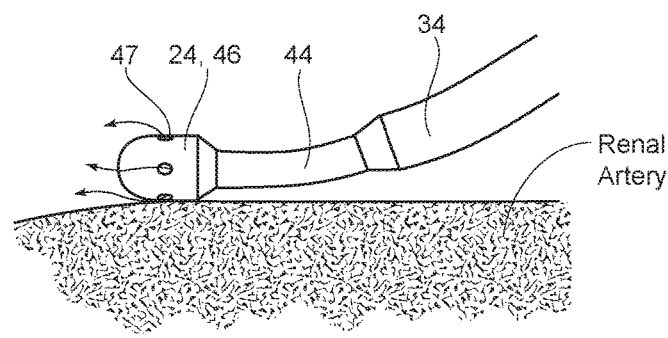
FIG. 30B shows an open circuit system for actively cooling the thermal heating element and/or the contacted tissue and its surroundings.
Figure 30C:
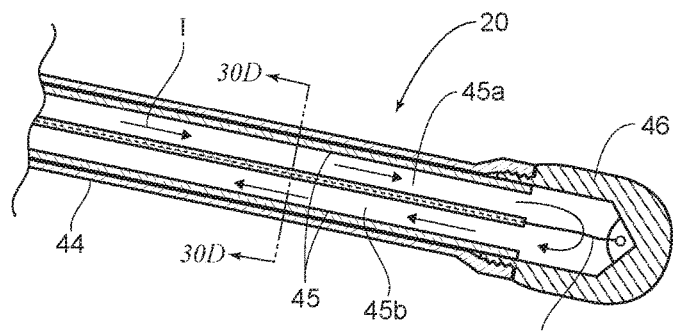
FIGS. 30C and 30D are side-sectional and cross-sectional views, respectively, of a closed circuit system for actively cooling the thermal heating element and/or the contacted tissue and its surroundings.
Figure 30D:
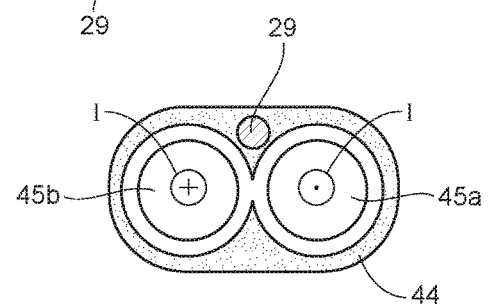

With respect to FIGS. 30B-30D, it may be beneficial to actively cool the thermal heating element and/or non-target tissue in the vicinity of the thermal heating element. Such cooling may facilitate formation of lesions with enhanced safety (e.g., lower intraluminal tissue surface temperature), enhanced efficacy, reduced electrode charring, shorter (or longer) duration, higher power, greater depth and/or larger size than would be achievable in the absence of cooling. As seen in FIG. 30A, when the intravascular treatment device 12 comprises open circuit active cooling, system 10 may comprise a fluid pump 11 for pumping a thermal fluid from a fluid source 11a through a fluid delivery tube 11b, and through a lumen of the treatment device 12 to its distal end region 20 in the vicinity of the thermal heating element 24. When the intravascular treatment device 12 comprises closed circuit active cooling, for example as shown in FIGS. 30C and 30D, system 10 may additionally comprise a return lumen 45b of the treatment device in fluid communication with a fluid return tube (not shown) which returns thermal fluid to a fluid source for recirculation or disposes of the thermal fluid external to the patient.

The velocity, volumetric flow rate and total volume of thermal fluid pumping via fluid pump 11 may be controlled manually by the caregiver or, as in FIG. 30A, may be controlled by algorithm 102. The treatment device 12 is provided with sufficient strength against bursting to facilitate safe infusion or delivery of thermal fluids via pump 11. Furthermore, the treatment device and its distal end region 20 comprise material and mechanical properties for maintaining the position of the thermal heating element 24 while the infusate is infused or delivered.

For example, infusate, such as a thermal fluid infusate (e.g., room temperature or chilled saline), may be injected (open circuit system) into the patient's blood stream in the vicinity of the treatment site during power or energy delivery to act as a conductive and/or convective heat sink that removes thermal energy (see FIG. 30B). Infusate injection (e.g., continuous infusate injection) may provide more—or more rapid—heat transfer, as well as more uniform and/or predictable heat transfer dynamics, as compared to the passive cooling provided by pulsatile blood flow. Infusate injection also may remove blood proteins from the thermal heating element, thereby reducing a risk of coagulum formation. In addition or as an alternative to infusate injection, active cooling may comprise a closed circuit system with a circulating or stationary coolant (e.g., a cryogenic fluid, chilled saline, etc.) that removes heat from the thermal heating element, and indirectly from non-target tissue, during power or energy delivery (see FIGS. 30C and 30D).

Figure 31A:
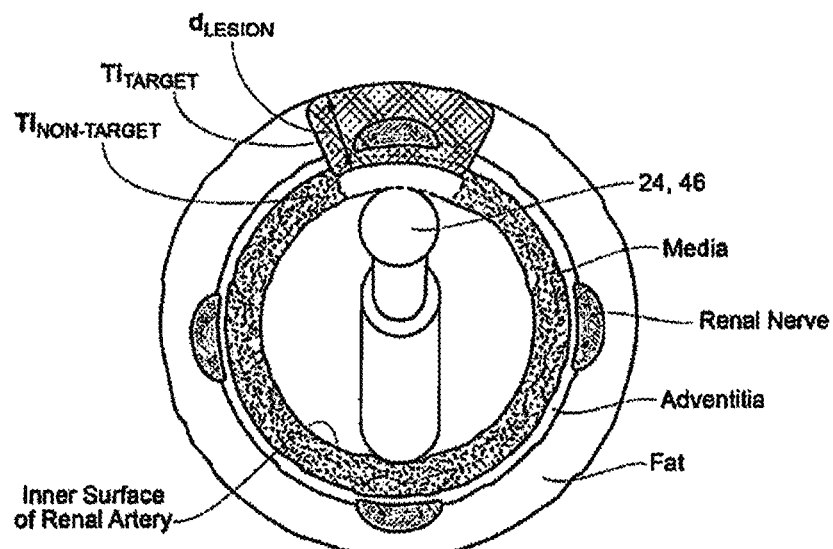
FIG. 31A is a cross-sectional view of the renal artery at the treatment site, demonstrating an impact of active cooling.
Figure 31B:
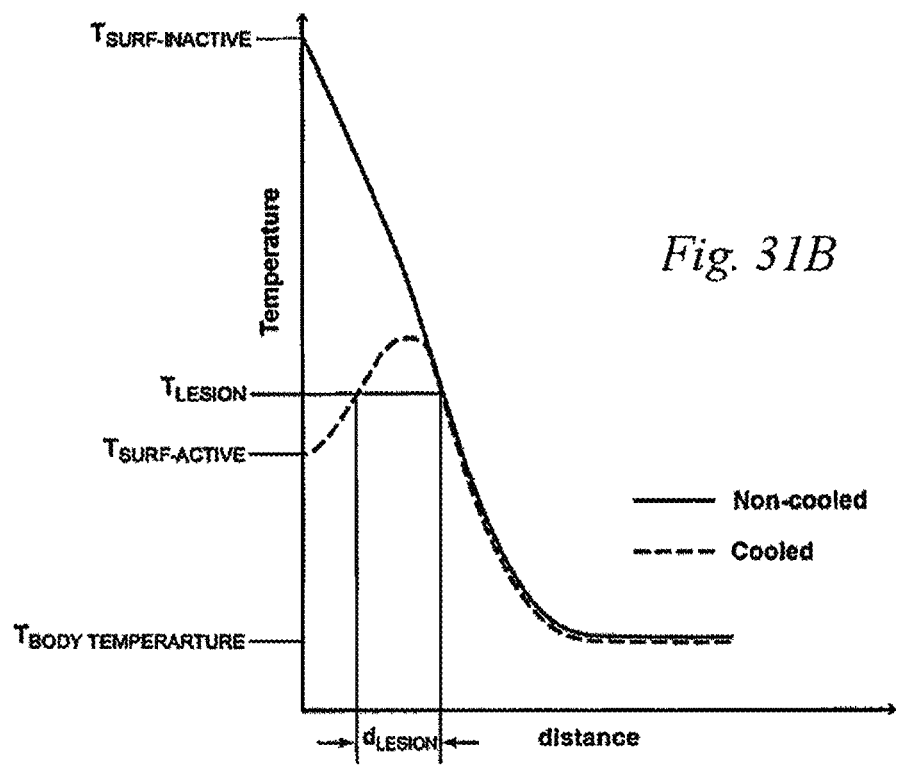
FIG. 31B is a graph plotting temperature against tissue depth in the presence and in the absence of active cooling with other parameters kept constant.

Energy is defined as Power×Time. When closed or open circuit active cooling is provided, if the power and time over which energy is delivered are not altered as compared to when active cooling is not provided, then the energy delivered also is not altered. Thus, as seen in FIGS. 31A and 31B, the active cooling may further protect non-target tissue $Ti_{NON-TARGET}$ at or near the vessel wall from thermal injury, e.g., may lower the surface temperature $T_{SURF-ACTIVE}$ of the vessel wall during power delivery as compared to treatment without active cooling $T_{SURF-INACTIVE}$, while maintaining a desired tissue temperature $T_{LESION}$ at a desired treatment depth $d_{LESION}$ within target tissue $Ti_{TARGET}$ from the luminal surface of the vessel wall.

Figure 32A:
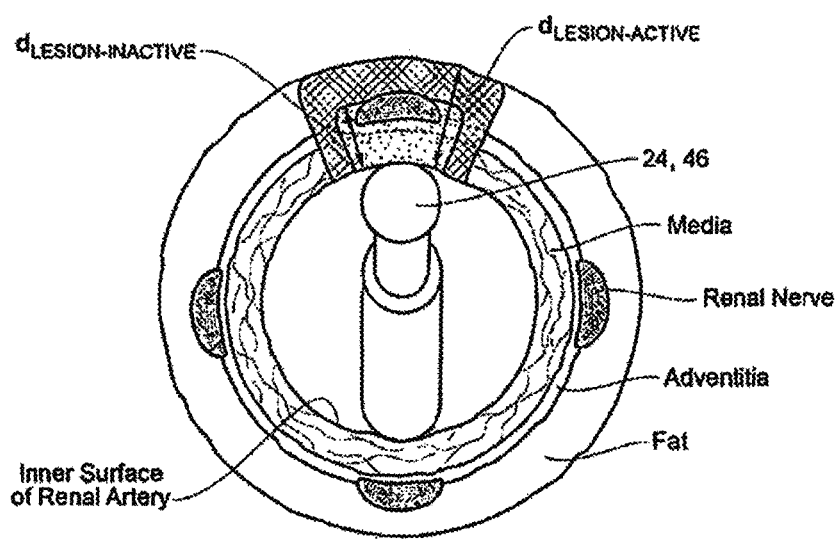
FIG. 32A is a cross-sectional view of the renal artery at the treatment site, demonstrating an alternative impact of active cooling.
Figure 32B:
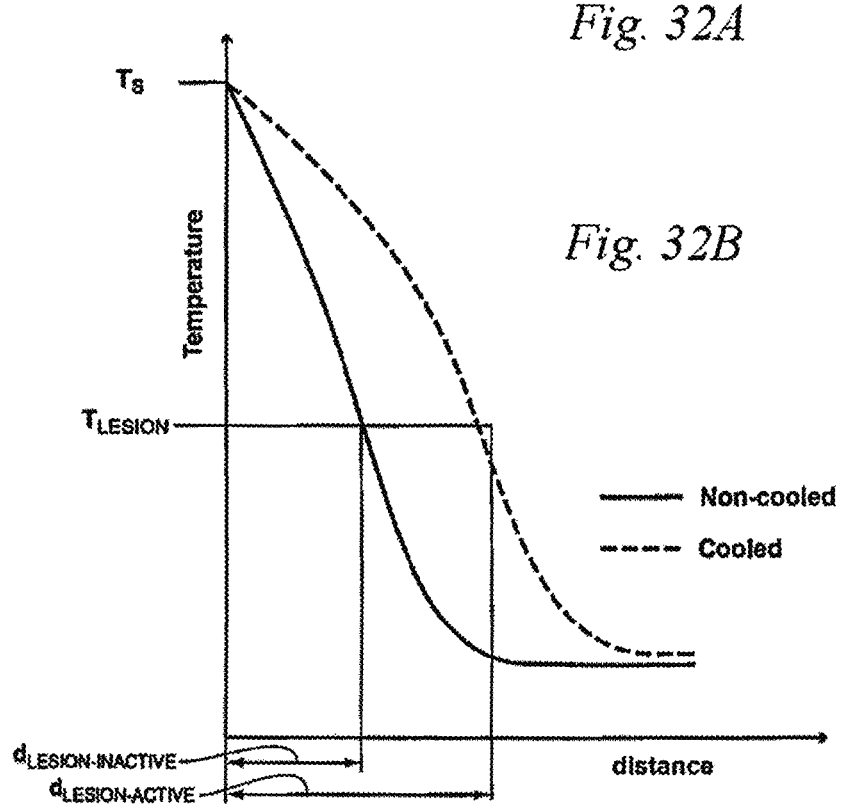
FIG. 32B is a graph of temperature against tissue depth in the presence and in the absence of active cooling in combination with increased energy delivery during active cooling.

If, however, active cooling is provided in combination with increased power but consistent duration of power delivery, the energy delivered is increased, which may facilitate the safe creation of a deeper or larger lesion than would be feasible without active cooling that protects both the electrode from resistive heat and the non-target tissue at the vessel wall. Likewise, providing active cooling in combination with increased duration of power delivery but consistent magnitude of power level would increase the energy delivered, again potentially facilitating the safe creation of a deeper or larger lesion than would be feasible absent active cooling. For example, as seen in FIGS. 32A and 32B, increased energy delivery in the presence of active cooling may maintain a consistent surface temperature $T_s$ (or may decrease the surface temperature) with that achieved with lower energy in the absence of active cooling, while increasing the depth of treatment $d_{LESION-ACTIVE}$ at which the target temperature $T_{LESION}$ is reached as compared to the depth of treatment at which the target temperature is reached when utilizing lower energy in the absence of active cooling $d_{LESION-INACTIVE}$.

Figure 33A:
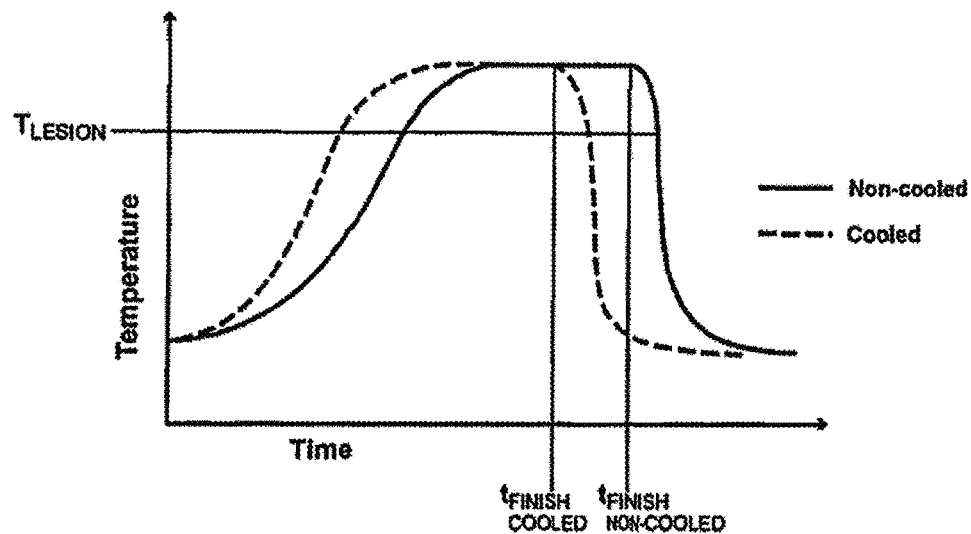
FIGS. 33A and 33B are, respectively, graphs of temperature vs. time at a target tissue depth in the presence and in the absence of active cooling showing i) a faster rate of increase of temperature, and ii) a greater magnitude of temperature, resulting in decreased treatment duration during active cooling.
Figure 33B:
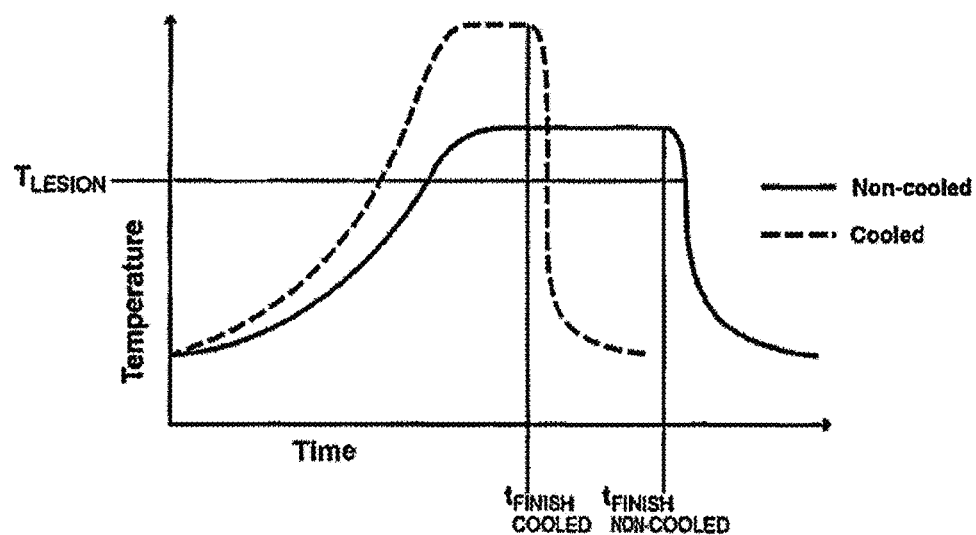

Active cooling also may facilitate delivery of energy via an increased power level in combination with decreased power delivery duration. As seen in FIGS. 33A and 33B, this may facilitate more rapid lesion creation, which could shorten the duration of power delivery, which is the time until the power delivery is turned off, $t_{FINISH}$, while maintaining the desired lesion depth $d_{LESION}$ at which the target temperature $T_{LESION}$ is achieved, as well as the surface tissue temperature Ts at or below a desired level. Depending on the relative degrees of power magnitude increase and power duration decrease, such alteration also may facilitate the delivery of more energy in less time, which may facilitate the safe creation of a deeper or larger lesion in less time. For example FIG. 33A shows temperature vs. time at a distance from a thermal heating element 24 within target tissue $T_{TARGET}$. By cooling the surface of the treatment site power can be increased at a faster rate which can raise temperature of target tissue above a target temperature $T_{LESION}$ sooner, the temperature of the target tissue can be held above the target temperature for an equal duration, and power can be turned off sooner, resulting in an earlier finish time $t_{FINISH-COOLED}$ compared to the finish time without cooling $t_{FINISH-NON-COOLED}$. Thus the treatment duration could be reduced. In a different algorithm, as shown in FIG. 33B which shows temperature vs. time at a distance from a thermal heating element within target tissue, treatment duration can be reduced by providing an equivalent thermal dose that is at a higher temperature for a shorter duration.

The three effects of cooling previously described (lower surface temperature, larger/deeper lesions, and faster lesions) were simplified for purposes of discussion by keeping a variable constant. Variations or combinations of these effects can be achieved by changing variables including: power, rate of power increase, duration of power delivery, and cooling rate. An algorithm, such as algorithm 102, optionally may be utilized to control these variables.

2. Volume and Rate of Infusate Infusion During Open Circuit Active Cooling

When active cooling is achieved via an open circuit system utilizing intravascular infusate (e.g., saline) infusion (see, e.g., FIG. 30B), the volume and rate of infusate infusion are of note. Intravascular infusate infusion may, for example, be provided in the vicinity of a treatment site from between about 0-10 seconds (e.g., about 5 seconds) prior to power delivery, then during power delivery, and for about 0-10 seconds (e.g., about 5 seconds) after power delivery. In some patients, intravascular infusion of a significant saline volume may induce pulmonary edema or heart failure, and some patient groups may be at higher risk of such complications. These higher risk patient groups may include patient groups that are therapeutically indicated for renal neuromodulation, including, for example, those with a history of heart failure or heart disease, renal insufficiency and/or diabetes mellitus.

Advantageously, the magnitude of maximum power delivered during renal neuromodulation treatment in accordance with embodiments described in the present application may be relatively low (e.g., less than about 15 Watts, for example, less than about 10 Watts or less than about 8 Watts) as compared, for example, to the power levels utilized in electrophysiology treatments to achieve cardiac tissue ablation (e.g., power levels greater than about 15 Watts, for example, greater than about 30 Watts). Furthermore, the relative volume of an electrode or thermal heating element 24 described in embodiments within the present application configured for use in the renal vasculature for renal neuromodulation is expected to be significantly lower than the volume of an electrode utilized to achieve cardiac tissue ablation (e.g., ~10% relative volume).

Since relatively low power levels may be utilized in combination with relative small electrodes to achieve renal neuromodulation, the flow rate and/or total volume of intravascular infusate injection needed to maintain the thermal heating element and/or non-target tissue at or below a desired temperature during power delivery (e.g., at or below about 50° C., for example, at or below about 45° C.) also may be relatively lower than would be required at the higher power levels used, for example, in electrophysiology treatments (e.g., power levels above about 15 Watts). This relative reduction in flow rate and/or total volume of intravascular infusate infusion advantageously may facilitate the use of intravascular infusate in higher risk patient groups that would be contraindicated were higher power levels and, thus, correspondingly higher infusate rates/volumes utilized (e.g., patients with heart disease, heart failure, renal insufficiency and/or diabetes mellitus).

When the intravascular infusate comprises saline, one liter of the saline may comprise about 9 grams of sodium chloride, which includes about 3.6 grams of sodium. 3.6 grams of sodium is about 150% of the recommended daily allowance for patients with heart failure or hypertension. Each liter of saline also may contain about 1,000 Units of the anti-coagulant heparin. Furthermore, saline injection increases venous pressure, and thereby capillary pressure, which increases the amount of fluid leaving the vasculature. If lymphatic drainage and renal excretion (urine output) are not able to maintain homeostasis, fluid accumulates and may cause pulmonary edema or heart failure.

Based on the foregoing, it may be desirable to limit saline (e.g., room temperature saline) infusion to less than about 1 Liter, for example, less than about 500 mL, less than about 250 mL or less than about 100 mL. Such limitation of saline infusion volume may facilitate infusion in higher risk patient groups, for example, those with heart disease, heart failure, diabetes mellitus and/or renal insufficiency. When the maximum power level does not exceed about 15 Watts, e.g., does not exceed about 10 Watts, it is expected that an infusion rate less than or equal to about 15 mL/minute, e.g., less than or equal to about 10 mL/minute, would be sufficient to maintain the thermal heating element at or below a desired temperature, e.g., at or below about 50° C., for example, at or below about 45° C. For treatment times of two minutes or less, these infusion rates facilitate treatment at multiple sites while maintaining a total infusion volume below about 1 Liter, 500 mL, 250 mL and/or 100 mL. A control algorithm, such as algorithm 102 or a manual controller, may be provided to control the infusion rate and/or total infusion volume, while a fluid pump may be provided to propel the infusate through the elongated shaft 16 at the desired (e.g., controlled) rate.

As an example, were saline to be injected for 5 seconds pre- and post-treatment, as well as during 2 minutes of treatment (i.e., were saline to be injected for about 130 seconds per treatment site), each treatment at an infusion rate of 15 mL/minute would result in a total infusion volume of about 32.5 mL. Thus, treatment may be performed at about 3 treatment sites while maintaining a total infusion volume below about 100 mL, at over 7 treatment sites while maintaining a total infusion volume below about 250 mL, at about 15 treatment sites while maintaining a total infusion volume below about 500 mL, and at over 30 treatment sites while maintaining a total infusion volume below about 1 Liter. Treatments of less than 2 minutes may facilitate total infusion volumes that are even lower for a given number of treatment sites and/or may facilitate treatment at more sites while maintaining total infusion volume below a desired threshold.

Likewise, were saline to be injected for 5 seconds pre- and post-treatment, as well as during 2 minutes of treatment (i.e., were saline to be injected for about 130 seconds per treatment site), each treatment at an infusion rate of 10 mL/minute would result in a total infusion volume of about 21.7 mL. Thus, treatment may be performed at over 4 treatment sites while maintaining a total infusion volume below about 100 mL, at over 11 treatment sites while maintaining a total infusion volume below about 250 mL, at about 23 treatment sites while maintaining a total infusion volume below about 500 mL, and at about 46 treatment sites while maintaining a total infusion volume below about 1 Liter. Treatments of less than 2 minutes may facilitate total infusion volumes that are even lower for a given number of treatment sites (and/or may facilitate treatment at more sites while maintaining total infusion volume below a desired threshold).

In addition or as an alternative to limiting the volume of infusate intrasvascularly infused during renal neuromodulation, urinary catheterization may be provided to offload excess fluids. Also, a hybrid open and closed cooling system may be provided to reduce or limit the volume of infusate by removing at least a portion of any excess thermal energy via the closed component of the cooling system (e.g., via a circulated coolant, as in FIGS. 30C and 30D).

As yet another alternative, rather than infusing saline, the infusate may comprise blood, either autologous or from an external donor. When autologous, the blood may be arterial or venous and may be withdrawn from some other point in the vasculature, such as at or near the femoral artery access point, for injection within the renal arteries. In this manner, the total fluid volume in the patient is not altered, while the flow rate and volume through the renal arteries (and thereby the rate of thermal heat transfer from the thermal heating element and/or non-target wall tissue) is increased.

3. Impact of Open Circuit Cooling on Thermal Heating Element Contact Stability, and Mitigation Thereof Active cooling via infusate injection from an irrigated electrode, such as in FIG. 30B, might destabilize stable contact at the interface between tissue at the treatment site and the electrode 46. As fluid flows out of the electrode through ports 47, e.g., radially and/or perpendicular from the electrode, the fluid may urge the electrode away from the treatment site tissue.

As seen in FIGS. 34A-34L, various embodiments of the irrigated electrode 46 and/or of ports 47 may be provided that may enhance or facilitate maintenance of stable contact between the treatment site tissue and the electrode. In these embodiments, ports 47 are configured to direct the thermal fluid infusate away from the tissue/electrode interface and/or to direct the infusate with a lower force vector directed perpendicular to the interface. Since the infusate is not directed at the tissue/electrode interface (or is not directed at the interface with as great a force), there may be less cooling at the interface than would be achieved if the infusate were directed perpendicular to the interface along a common cross-section. However, the fluid flow through the electrode would still pull heat from the tissue through the electrode and into the blood.

Figure 34A:
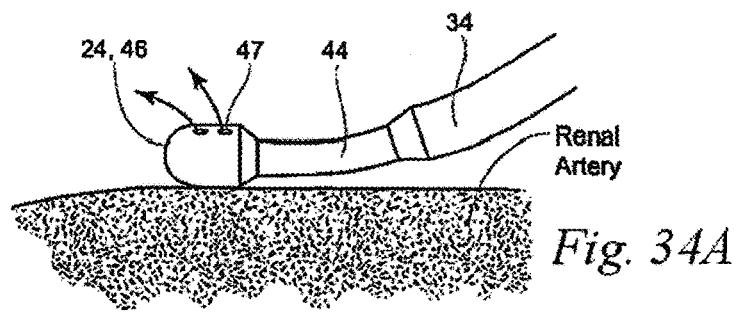
FIGS. 34A-34L show additional representative embodiments of an open circuit system for actively cooling the thermal heating element and/or the contacted tissue and its surroundings.
Figure 34B:
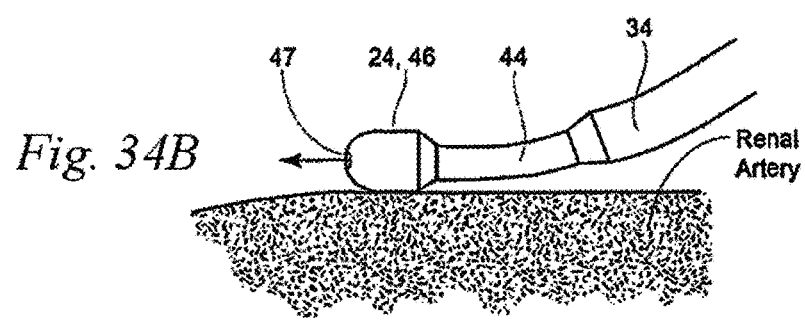
Figure 34C:
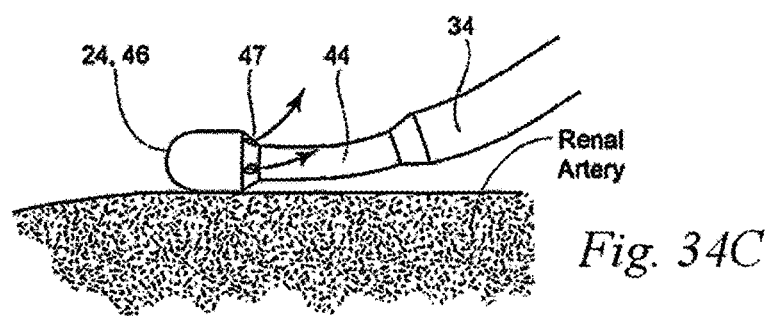
Figure 34D:
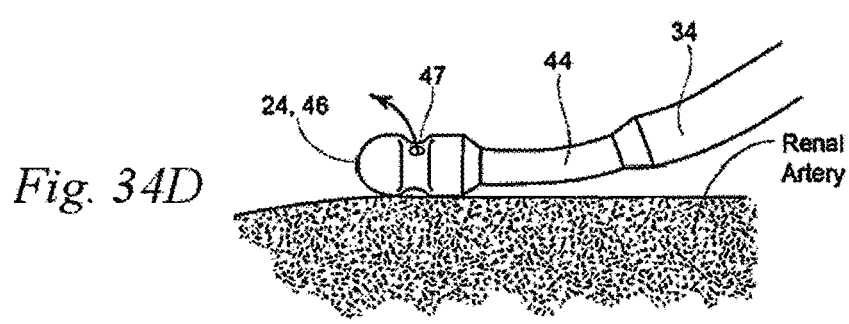

With reference to FIG. 34A, irrigation ports 47 of electrode 46 may be positioned on the side of the electrode that does not contact tissue in order to direct the thermal fluid infusate away from the tissue/electrode interface. Additionally or alternatively, one or more irrigation ports 47 may be provided at the tip of the electrode 46 (e.g., irrigated electrode tip), as in FIG. 34B. In an additional embodiment seen in FIG. 34C, electrode 46 is wider in diameter than more proximal portions of the distal end region 20 of elongated shaft 12, and proximal-facing port(s) 47 are positioned along a proximal surface of the electrode between the elongated shaft and the outer diameter of the electrode. In FIG. 34D, electrode 46 comprises a contoured shape with at least one reduced diameter waist or groove positioned along the length of the cylindrical electrode; port(s) 47 are positioned within the groove, recessed from the tissue/electrode interface.

Figure 34E:
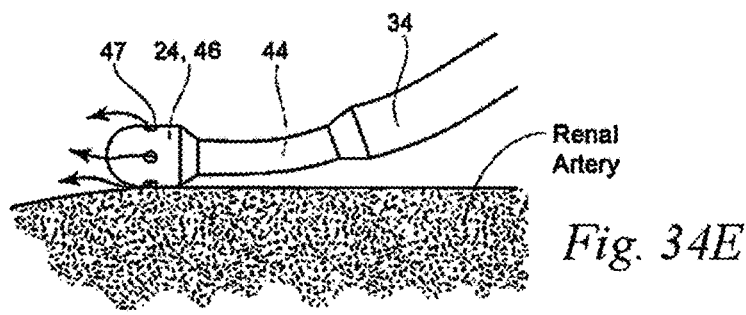
Figure 34F:
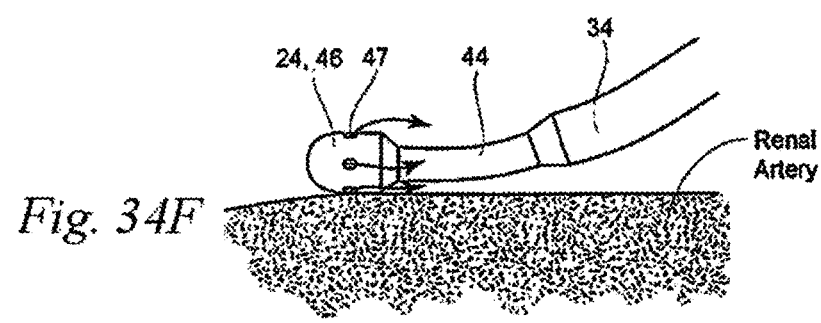
Figure 34G:
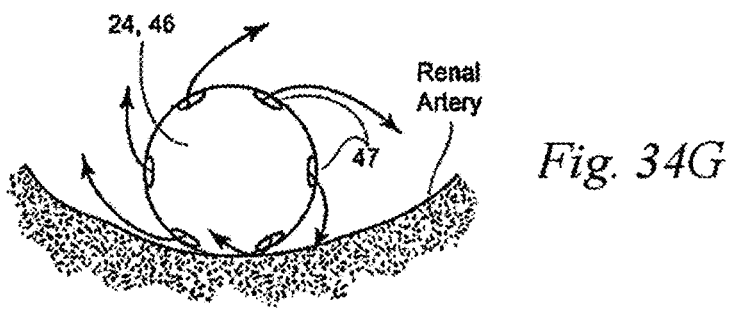
Figure 34H:
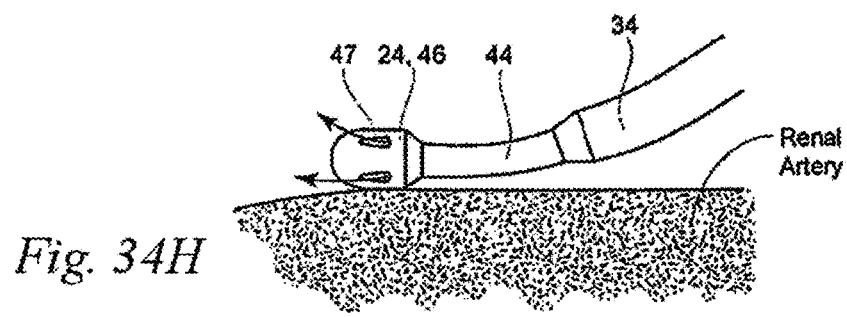

In FIG. 34E-34H, irrigation port(s) 47 direct flow at a smaller angle to the electrode surface, such that the perpendicular force vector at the tissue/electrode interface is less. In FIG. 34E, the port(s) 47 are angled to deliver distally-directed fluid (i.e., antegrade or in the direction of blood flow) at an acute angle to the vessel wall. In FIG. 34F, the port(s) 47 are angled to deliver proximally-directed fluid (i.e., retrograde or in the opposite direction of blood flow) at an acute angle to the vessel wall. In FIG. 34G, the port(s) 47 are angled to deliver fluid an acute angle to the vessel wall in a circumferential direction (i.e., neither antegrade nor retrograde). In FIG. 34H, the port(s) 47 are angled and recessed relative to the outermost diameter of the electrode 46 for delivering fluid an acute angle to the vessel wall. As will be apparent, any combination of distally-directed, proximally-directed and/or circumferentially-directed fluid infusion at an acute angle to the vessel wall may be provided.

Optionally, port(s) 47 may be utilized to draw blood into the thermal heating element 24 to increase heat transfer from the thermal heating element to the blood. The blood may, for example, be drawn through one or more ports 47, such as one or more tip ports as in FIG. 34B, and through the elongated shaft 12 to a syringe or blood reservoir positioned external to the body. The blood optionally may be deposited back into the patient's bloodstream at the same or a different location, during or after the procedure. Additionally or alternatively, blood drawn through port(s) 47 may be re-routed from the renal artery to a location of lower blood pressure, such as the femoral artery or a vein.

As seen in FIGS. 34I-34L, irrigation port(s) 47 optionally may be located proximal of the electrode 46 rather than in or on the electrode itself, such that the fluid infusate flows in the direction of renal blood flow over the electrode, rather than flowing out of the electrode. Blood flow through the renal artery may be substantially laminar, and there is much less flow over the electrode positioned at the wall than though the center of the vessel. Thus, infusate delivered through irrigation ports 47 positioned proximal of the electrode 46 (e.g., positioned along the third flexure zone 44 or the second flexure zone 34) may reduce the temperature of the fluid flowing over the electrode and/or may increase flow at the wall.

Figure 34I:
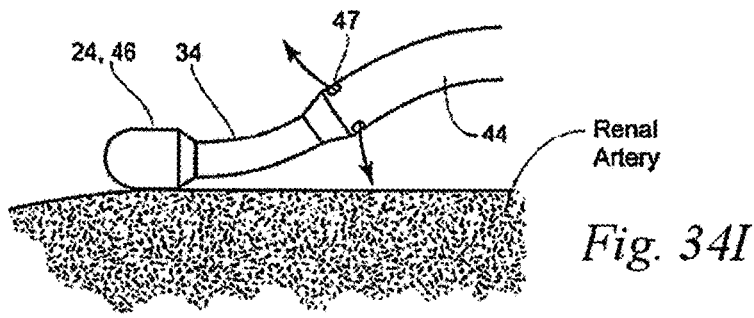
Figure 34J:
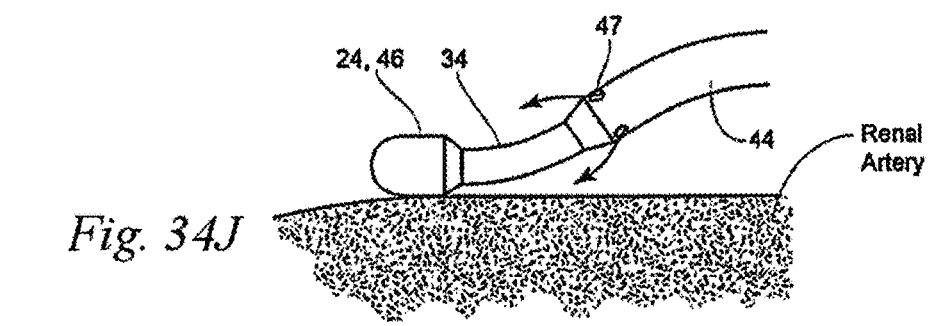
Figure 34K:
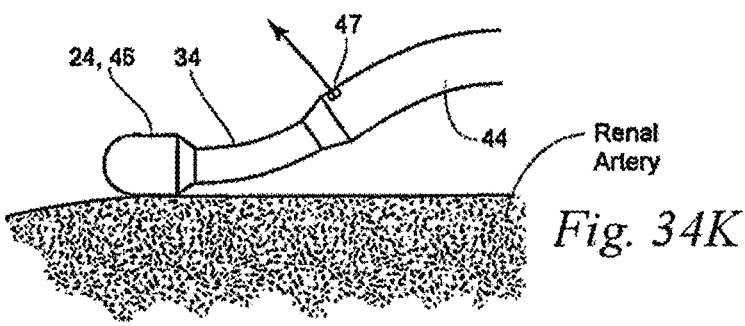
Figure 34L:
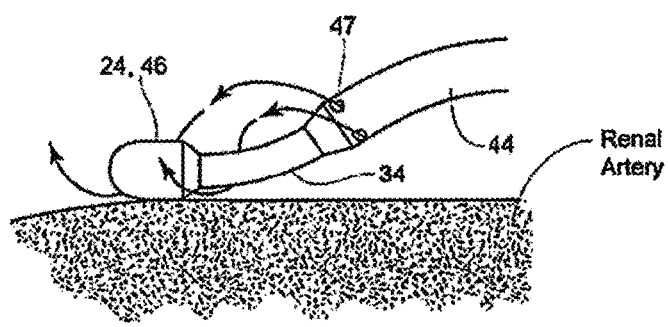
Figure 34S:
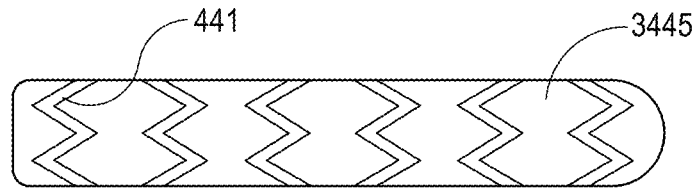

In FIG. 34I, port(s) 47 positioned proximal of the electrode 46 are directed in radial directions for delivering infusate substantially perpendicular to the elongated shaft 12. In FIG. 34J, the port(s) are directed in radial directions at (distally- and/or proximally-directed) acute angles to the elongated shaft 12 for delivering infusate at an acute angle to the shaft. In FIG. 34K, port(s) 47 are directed toward the center of the vessel, generally away from the tissue/electrode interface. In FIG. 34L, the port(s) are directed circumferentially relative to the vessel, which may establish vortices in the vicinity of the electrode 46 and/or redirect blood flow towards treatment site.

FIGS. 34M-34W illustrate electrodes configured to provide active cooling in accordance with further embodiments of the technology. FIG. 34M illustrates an electrode 3405 that comprises an interior portion 3408 configured to accommodate a fluid supply and/or return lumen and an exterior portion 3409 configured to contact a wall of a renal artery. The electrode 3405 has a plurality of ports 47 from the interior portion 3408 to the exterior portion 3409. In some embodiments, the electrode 3405 has six ports 47 arranged around a circumferential perimeter of the electrode 3405. In further embodiments, there can be more or fewer ports 47 and the ports 47 can be located in an alternate arrangement on the electrode 47. For example, in further embodiments the ports 47 can be located on only a portion of the circumferential perimeter of the electrode 3405, on a distal end 3406 of the electrode 3405, or a combination of these locations.

The distal end 3406 of the electrode 3405 can be smooth and substantially flat. The flat shape can provide consistent contact between the electrode 3405 and an artery wall to provide for more consistent energy delivery. In one embodiment the electrode 3405 comprises a platinum-iridium alloy (e.g., 90% platinum, 10% iridium). In further embodiments, other materials having similar properties can be used. FIG. 34N illustrates an irrigation electrode 3415 in accordance with another embodiment of the technology having features generally similar to those described with reference to FIG. 34M, but alternately includes a rounded, or domed, distal end 3416.

FIGS. 34O-34Q illustrate an electrode 3425 in accordance with another embodiment of the technology having several features similar to those described above. Referring to FIGS. 34O-34Q together, the electrode 3425 has an electrode length $E_L$ that, in some embodiments, ranges from about 0.04 inch (1.02 mm) to about 0.08 inch (2.32 mm). In a particular embodiment, $E_L$ is 0.065 inch (1.65 mm). The electrode 3425 can have a distal length $D_L$ from the midpoint of the ports 47 to a distal end 3426 of the electrode 3425 from about 0.01 inch (0.254 mm) to about 0.05 inch (1.27 mm), and, in a particular embodiment, of about 0.02 inch (0.508 mm). In particular embodiments, the ports 47 have a diameter from about 0.008 inch (0.203 mm) to about 0.012 inch (0.305 mm). Although the illustrated embodiment includes circular ports 47, in further embodiments the ports 47 can take on alternate shapes. In general, an increased size of the ports 47 and/or an increased number of ports 47 provides for an increased degree of irrigation/cooling.

In some embodiments, an inner portion 3418 of the electrode 3425 includes a base portion 3417 having a base length $B_L$ ranging from about 0.03 inch (0.76 mm) to about 0.07 inch (1.78 mm). In a particular embodiment, the base length $B_L$ is 0.052 inch (1.32 mm). The distal end of the base portion 3417 can slope inward to form an inner tip 3428. The inner tip 3428 can be separated from the distal end 3426 by a tip length $T_L$. In some embodiments, the tip length $T_L$ can range from about 0.001 inch (0.025 mm) to about 0.01 inch (0.25 mm). In a particular embodiment, the tip length $T_L$ is 0.004 inch (0.11 mm). In some embodiments, the inner portion 3418 is formed by a drill. In further embodiments, other methods are used to form the inner portion 3418.

The electrode 3425 can have an inner diameter $D_I$ (e.g., a diameter of the inner portion 3418) and an outer diameter $D_O$. In some embodiments, the inner diameter can range from about 0.03 inch (0.762 mm) to about 0.07 inch (1.78 mm). In particular embodiments, the inner diameter $D_I$ is 0.039 inch (0.99 mm), 0.043 inch (1.09 mm), or 0.054 inch (1.37 mm). The outer diameter $D_O$ can range from about 0.04 inch (1.02 mm) to about 0.08 inch (2.03 mm), and, in particular embodiments, 0.049 inch (1.24 mm) or 0.060 inch (1.52 mm). The various combinations of inner and outer diameters $D_I$, $D_O$ can provide for various electrode wall thicknesses.

FIG. 34R illustrates an electrode 3435 in accordance with yet another embodiment of the technology having several features similar to the electrode 3425 described above. The electrode 3435 illustrated in FIG. 34R further includes several protrusions 3421 extending radially inward from an interior surface 3419 of the electrode 3435.

FIGS. 34S-34W illustrate further embodiments of electrodes configured to provide active cooling. The embodiments of electrodes shown in FIGS. 34S-34W include apertures, ports, or other fluid passageways that are part of the electrode structure itself. These apertures, ports, or other fluid passageways provide for active cooling along the length of the electrode. For example, electrode 3445 illustrated in FIG. 34S includes a plurality of laser-cut apertures 441 through which coolant can flow. The apertures 441 are illustrated in a zig-zag shape, but can have various shapes and spacing in other embodiments of the technology.

Figure 34T:
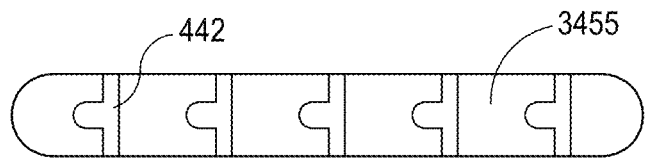
Figure 34U:
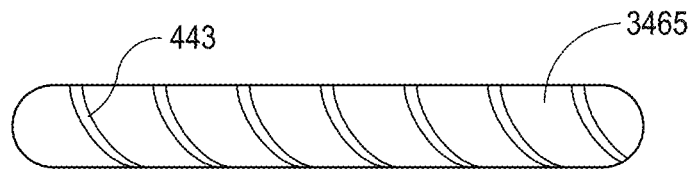

FIGS. 34T and 34U illustrate further embodiments of electrodes 3455 and 3465 respectively. The electrodes 3455, 3465 include laser-cut patterns of apertures 442, 443 in alternate shapes and spacing configurations (e.g., discrete apertures 442 on the electrode 3455 and a continuous helical aperture 443 on the electrode 3465).

Figure 34V:

FIG. 34V illustrates a wound electrode 3475. The electrode 3475 can be wound around a fluid lumen in a helical shape, allowing coolant to disperse through the space between helical turns.

Figure 34W:
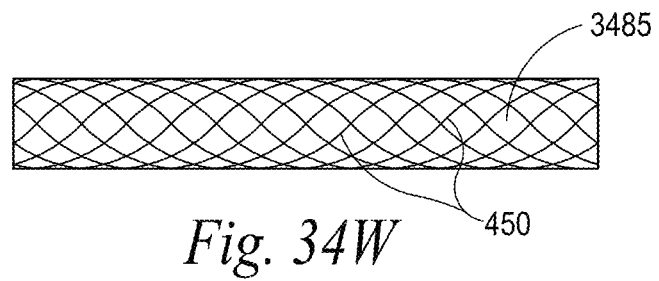

FIG. 34W illustrates a braided electrode 3485 comprising a plurality of braided filaments 450. In some embodiments, coolant can be dispersed between the filaments 450 (e.g., through interstitial openings in the braid).

Additional techniques for directing the thermal fluid infusate away from the tissue/electrode interface and/or for directing the infusate with a lower force vector directed perpendicular to the interface may comprise varying the velocity or pressure infusion through the port(s) 47. For example, a relatively greater number of ports may be provided in all directions, such that each port has less volumetric flow through it for a given volumetric flow rate; this may reduce the velocity or pressure of flow through each port. Additionally or alternatively, port(s) positioned on the interface side of the electrode 46 and/or elongated shaft 12 may be relatively smaller than ports positioned on the bloodflow-facing side of the electrode. Furthermore, the volumetric flow rate may be controlled, as discussed previously, to provide as little flow as is needed to achieve a desired cooling effect. Cooling the electrode 46 with a hybrid open-circuit and closed-circuit cooling system also may reduce the volumetric flow rate of infusion needed to achieve the desired cooling effect.

Maintenance of stable contact between treatment site tissue and the electrode during delivery of infusate through ports 47 also may be achieved by providing the distal end region 20 and its complex bend configuration with sufficient mechanical stabilization. Mechanical stabilization can be designed into the device to make up for any destabilization induced by irrigation. For example, a large force applied over a large surface area will apply less pressure while providing stabilization. This can be achieved by making contact between the catheter and artery wall over a large surface area as in lengthwise contact, helical contact, multiple point contact with bends, deployable contact, etc. Furthermore, contact or stabilization feedback may be provided (e.g., via one or more sensor(s) 52) to tell the caregiver whether or not tissue/electrode interface stability is insufficient for effective ablation. Such feedback may, for example, comprise feedback of impedance or pressure measurements at or in the vicinity of the interface. Further still, fluid flowing through lumen 45 during open circuit cooling may stiffen the distal end region 20 of the elongated shaft 12, which may offset any destabilization induced by infusion of such fluid.

Irrigation-induced orthogonal forces that push the electrode 46 away from the vessel wall optionally may be utilized to aid delivery of the electrode into stable contact with the vessel wall. For example, such forces may reduce potentially traumatic forces as the electrode and/or the distal end region 20 is advanced into the artery wall. Additionally, the forces and the infusate may establish a lubricious layer that aids placement of the electrode and/or reduces friction or scraping during placement, repositioning and/or withdrawal of the electrode. When irrigation or infusion is directed retrograde at an acute angle to the vessel wall (see FIG. 34F), the infusate may both push the electrode away from the vessel wall and propel the electrode forward into the vessel, which may aid delivery and placement of the electrode.

4. Impact of Active Cooling on Temperature Measurement, and Mitigation Thereof

Figure 35:
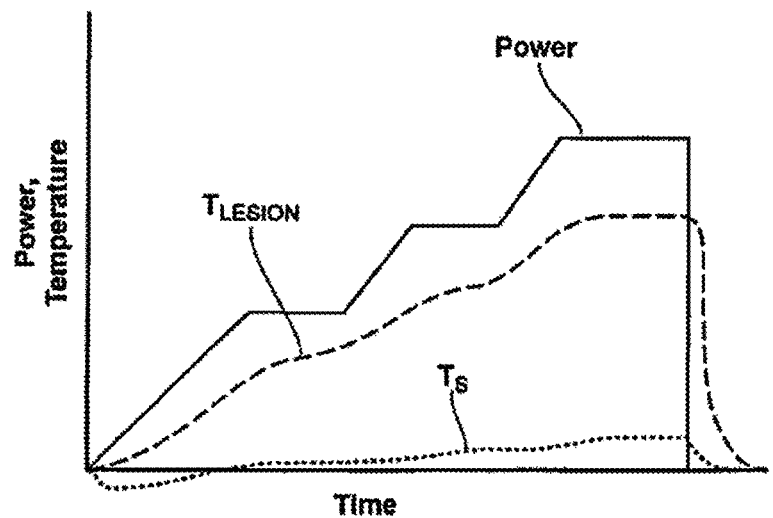
FIG. 35 is a graph plotting power and temperature against time at the tissue surface and at lesion depth in the presence of active cooling.

When utilizing active cooling, temperature measurement may be less accurate or less useful than when cooling is not provided. As seen in FIG. 35, because the electrode and the tissue surface are cooled (directly in an open circuit system, indirectly in a closed circuit system), when a temperature sensor 52 (e.g., a thermocouple) is provided in or on the electrode, a significant rise in tissue temperature at lesion depth from the luminal surface $T_{lesion}$ may correspond to only a small rise in electrode and/or surface temperature $T_S$ (and, thus, monitored temperature sensor temperature). A correlation can be made between the cooled electrode temperature and this deeper lesion tissue temperature, but such a correlation is expected to be significantly less accurate in the presence of active cooling.

In order to account for the decreased accuracy or usefulness of temperature measurements at the treatment site, a complex algorithm, such as an embodiment of algorithm 102, may be provided to enhance the accuracy of the correlation between the electrode temperature and the deep tissue temperature. The algorithm may model the complex fluid dynamic and thermodynamic environment in the vicinity of the temperature sensor and/or the treatment site. Variables utilized in such an algorithm may include, for example, flow rate, infusate or coolant temperature, blood flow rate, blood temperature, tissue temperature, tissue electrical and thermal characteristics, coolant and blood temperature downstream of the treatment site, etc. Additional and alternative variables may be used. Additional sensors may be provided to measure one or more of these variables.

Additionally or alternatively, an indicator of treatment efficacy and safety other than temperature may be utilized. For example, the relative change in impedance measured at the electrode over time as a lesion is being created may be used an indicator of the lesion formation. Typically, as tissue heats, its impedance decreases up to a certain temperature threshold; as tissue properties change with increasing temperature, impedance then increases. A suitable lesion size may, for example, be correlated to a relative decrease in impedance, a relative change in slope in the impedance curve, and/or a relative increase in impedance following a decrease, as measured at an impedance sensor 52.

The placement of temperature sensor(s) 52 relative to electrode 46 and/or irrigation port(s) 47 may be specified to reduce or mitigate the impact of active cooling on surface temperature Ts measurement accuracy and/or usefulness in assessing lesion temperature $T_{lesion}$ at a desired depth. Temperature sensor(s) 52 may, for example, be placed externally or remotely relatively to the electrode 46 and/or port(s) 47, such that the temperature sensor(s) are not cooled, or cooled less, by delivery of infusate or coolant. For example, a protruding temperature sensor that protrudes from the electrode and distends or inserts into the tissue may be provided. Additionally or alternatively, a needle temperature sensor may be deployed from the device to a target depth. When irrigation is directed away from the tissue/electrode interface (see, e.g., FIG. 34A), temperature sensor(s) 52 may be located on the side of the electrode that contacts tissue.

Figure 36:
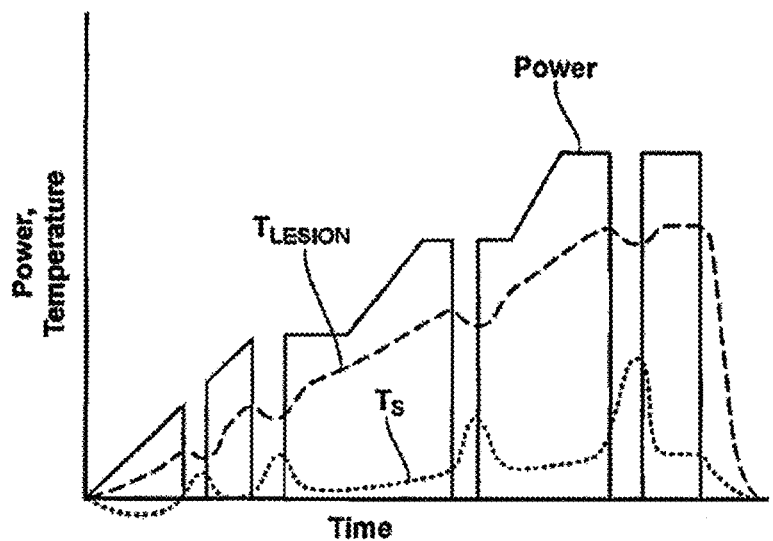
FIG. 36 is a graph plotting power and temperature against time at the tissue surface and at lesion depth in the presence of active cooling when utilizing an algorithm incorporating intermittent power delivery and cooling.

Furthermore, as described in more detail below with regard to FIG. 36, energy can be delivered with an algorithm incorporating intermittent power delivery and cooling, which may facilitate more accurate and/or useful temperature measurement.

5. Control Systems for Energy Delivery During Active Cooling

As discussed previously, it may be desirable to reduce, control or minimize the volume of infusate delivered during open circuit cooling. The control algorithm, such as previously described algorithm 102, may comprise one or more control loops that control or alter the volumetric flow rate of infusate infusion in response to one or more monitored parameters of power delivery (e.g., power magnitude, duration of power delivery, the impact of power delivery on sensor measurements, such as temperature, flow, pressure, and/or impedance measurements, etc.). For example, during idle state (i.e., while energy is not being delivered), a relatively low volumetric flow rate of infusate infusion may be provided (e.g., a rate that is sufficient to prevent blood from clotting within port(s) 47 and/or lumen(s) 45) in order to reduce/control saline infusion into patient. Optionally, a low power, pre-treatment energy pulse may be provided in the presence of low flow infusion to measure impedance and/or relative impedance to verify stable contact at the electrode/tissue interface. When activating energy delivery, power may be ramped while maintaining the relatively low infusate flow rate until a greater infusate flow rate is required. For example, if measured temperature increases above a pre-determined level at or below a predetermined power level, e.g. a 5° C. or more increase over baseline at less than or equal to 5 W, then the infusate flow rate may be increased. This initial phase of energy delivery with low infusate flow rate can provide a more accurate temperature measurement compared to a higher infusate flow rate. This temperature measurement can be compared to the energy delivered to indicate if blood flow is sufficient, too low, or if there is poor contact with tissue. For example, a high temperature rise can indicate low blood flow and cooling can be increased; an ideal temperature rise can indicate sufficient blood flow; a low temperature rise can indicate poor contact with tissue. Indication of blood flow can be incorporated into the energy delivery algorithm in a subsequent phase of energy delivery. For example, low blood flow can be compensated with increased infusate flow rate or decreased power; ideal blood flow can result in maintaining a low infusate flow rate; poor tissue contact can result in an message to recheck electrode contact and position.

As previously described the dimensions of an electrode can be configured such that when placed in contact with an inner wall of a renal artery an active surface area to total surface area ratio (ASA:TSA) can produce a suitable sized lesion when used in an environment with an appropriate range of volumetric blood flow rate. If volumetric blood flow rate is lower than the appropriate range, convection of heat from the electrode and tissue surface may not be sufficient resulting in a higher surface temperature that could cause blood coagulation, and/or excessive tissue injury at the surface of the vessel wall, and/or impede the ability to effectively raise the temperature of target tissue. An electrode can be configured to have an appropriate ASA:TSA with a given power delivery profile to create an effective lesion with minimal or low active cooling in a majority of patients having a renal artery volumetric blood flow within range. Active cooling can be initiated or increased as needed if the volumetric blood flow rate in a respective renal artery is below the range. For example, volumetric blood flow rate in a renal artery being treated can be below range when the artery is stenotic, when more than one main renal artery feeds the same kidney, when the main renal artery is very short and the blood flow is divided among branches. In situations such as these, when volumetric blood flow is lower than a range for which an electrode is configured, active cooling can be increased by manual control or automatically. Automatic increase of active cooling can be initiated by a control algorithm that responds to monitored parameters as previously described.

Irrigation or infusion also may be used in conjunction with algorithm control loops that adjust the flow rate to compensate for abrupt changes in electrode contact and/or renal blood flow. For example, an abrupt change in renal blood flow can be caused by an acute constriction of a renal artery, a change in heart rate, a change in renal vasculature resistance. Active cooling can be initiated or increased manually or automatically in response to an abrupt change of renal blood flow.

After power delivery reaches steady-state, flow rate and/ or power optionally may be temporarily adjusted within a preset range to allow temperature to rise to some measurable amount over normal blood temperature in order to increase the utility of temperature measurements, but not so high as to cause potential heating issues such as blood coagulation or excessive tissue injury. Allowing temperature to rise may provide additional feedback that an effective lesion has been created. After a rise in temperature is detected, then the flow rate and/or power may return to levels where the measured temperature does not rise or decreases back to baseline.

Algorithm 102 optionally may incorporate intermittent power delivery and (open circuit or closed circuit) active cooling. As seen in FIG. 36, when the cooling, or power and cooling are intermittently stopped or reduced for brief periods, heat conducts from tissue at lesion depth to the tissue surface and the temperature sensor. The surface temperature Ts may better approximate or may more reliably correlate with the lesion temperature $T_{lesion}$ during such intermittent idle periods. Thus, the information gathered during the idle periods may be used to calculate a more accurate representation of lesion temperature $T_{lesion}$.

6. Additional Representative Embodiments i. Open Circuit Embodiment

When multiple irrigation ports 47 and multiple temperature sensors 52 (e.g., multiple thermocouples) are incorporated into electrode 46, the flow rate to each port (or to each group of ports coupled to a common infusion lumen 45) may be adjusted based on local temperature measurements. For example, a temperature sensor that measures cooler temperatures may indicate that that portion of the electrode is relatively distant from the tissue/electrode interface. Thus, the irrigation flow rate to port(s) 47 in the vicinity of that temperature sensor may be reduced to reduce the amount of saline infused in the patient and/or to improve sensitivity to changes in temperature.

Likewise, a temperature sensor that measures warmer temperatures may indicate that that portion of the electrode is relatively near the tissue/electrode interface, and the irrigation flow rate to port(s) in the vicinity of the warmer temperature sensor may be increased to increase heat transfer in the vicinity of the tissue/electrode interface. Reducing irrigation or infusion on the side of the electrode facing blood flow may facilitate delivery of more irrigation on the tissue/electrode interface side of the electrode, while maintaining the total infusate volume below a desired threshold.

ii. Closed Circuit Embodiment

Figure 37:
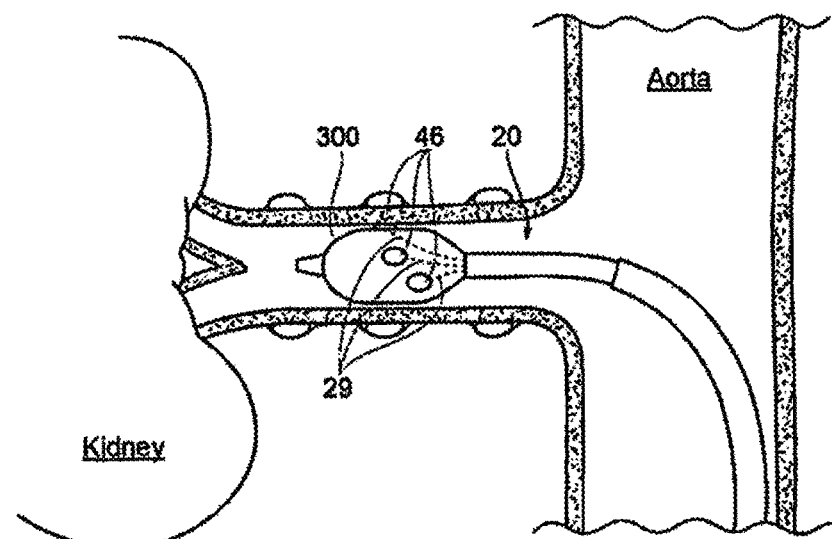
FIG. 37 shows an additional representative embodiment of a closed circuit system for actively cooling the thermal heating element and/or the contacted tissue and its surroundings.

FIG. 37 illustrates an additional embodiment of the present invention. In FIG. 37, the distal end region 20 of elongated shaft 12 comprises balloon catheter 300 with one or more electrodes 46 bonded, coupled or laminated to the interior or exterior of the expandable balloon. Electrical connections to each electrode 46 may be provided by wires 29 or by electrical traces on the surface of the balloon catheter 300. The wires/electrical traces are electrically coupled to generator 26.

Balloon catheter 300 is pliable and may conform to a range of expected anatomies upon inflation within a renal artery. The fluid used to inflate the balloon may provide a heat sink for closed circuit cooling of the electrode(s) 46 and/or of contacted tissue. Optionally, the fluid may be circulated to enhance convective cooling and/or to maintain the temperature of the fluid at a desired level.

Since balloon 300 blocks blood flow, accurate modeling of the complex thermodynamic and fluid dynamic environment during treatment may be more tractable, which may facilitate better control of treatment, lower risk treatment and/or more efficacious treatment.

When multiple electrodes 46 are provided, as in FIG. 37, the longitudinal and/or circumferential spacing of the electrodes may be specified, as desired, to facilitate treatment at multiple longitudinal/circumferential positions without necessitating re-positioning of the distal end region 20.

iii. Open Circuit Embodiment with an Occluding Balloon

Figure 38:
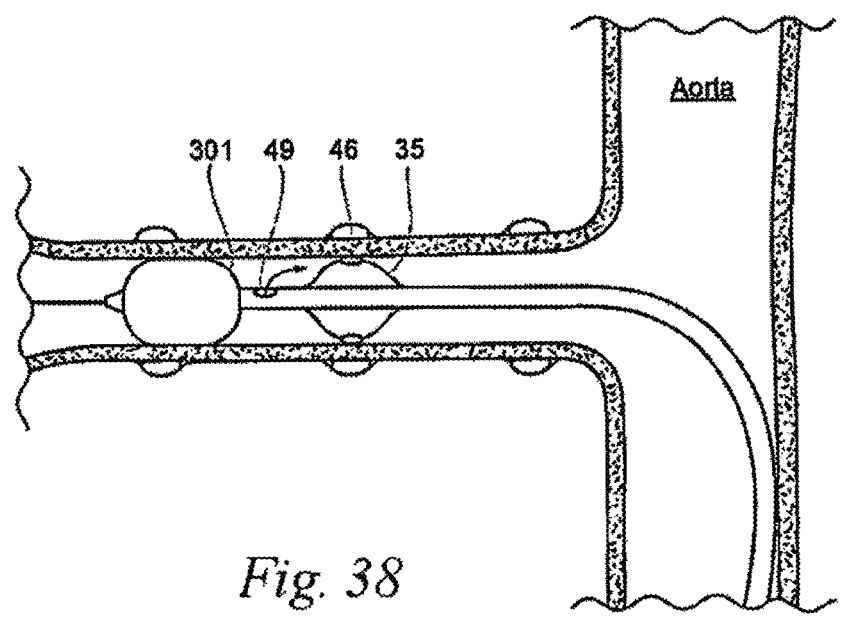
FIGS. 38 to 41 show additional representative embodiments of an open circuit system for actively cooling the thermal heating element and/or the contacted tissue and its surroundings.

FIG. 38 shows an additional embodiment of the present invention. In FIG. 38 the distal end region 20 of elongated shaft 12 comprises a distal occluding balloon 301 mounted to the catheter. Proximal to the distal occluding balloon 301 is an infusion port 49 coupled to a lumen in fluid communication with a source of infusate and a pumping mechanism with a flow rate monitor. Proximal to the infusion port 49 is one or more electrodes 46 placed on a mechanically or self-expanding member 35. Electrode 46 may comprise a temperature sensor. A temperature sensor may be included to measure the temperature of infusate. For example, a thermocouple or thermistor can be placed in an infusate supply lumen (not shown) in the elongate shaft, at the opening of the infusate port 49, in the infusate supply source, and/or in the pumping mechanism. The flow rate of infusate can be monitored with a flow meter or a flow sensor or be controlled by the speed of the pumping mechanism.

Blood flow though a renal artery flows from the aorta to the kidney, in other words, towards the distal end of the elongate shaft 12. In this embodiment the distal occluding balloon slows or stops flow temporarily and infusion of infusate through infusion port 49 flows in reverse direction across electrode 46 in to the aorta.

Since the flow rate and temperature of infusate is known, accurate modeling of the complex thermodynamic and fluid dynamic environment during treatment may be more tractable, which may facilitate better control of treatment, lower risk treatment and/or more efficacious treatment.

Figure 39:
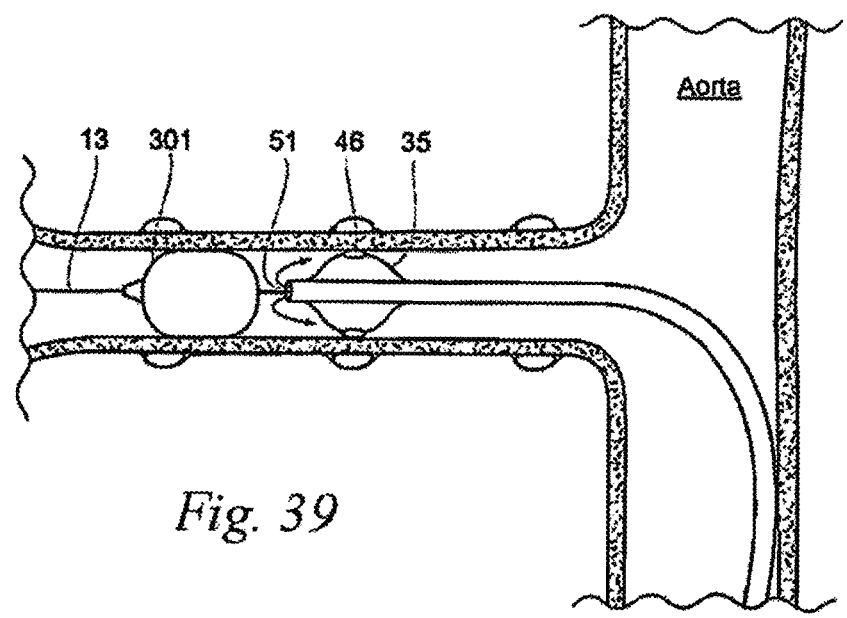

FIG. 39 illustrates an embodiment of the present invention with an occluding balloon 301 mounted on a balloon catheter 13 that is introduced through a lumen 51 in the ablation catheter. The ablation catheter comprises one or more electrodes 46 placed on a mechanically or self-expanding member 35.

Similar to the embodiment of FIG. 38 infusate is pumped in to the renal artery and flows in a reverse direction over the electrode 46 in to the aorta. In the embodiment of FIG. 39 the infusion port 51 can be the same port through which a balloon catheter 13 is delivered or it can be a separate lumen and port.

Figure 40:
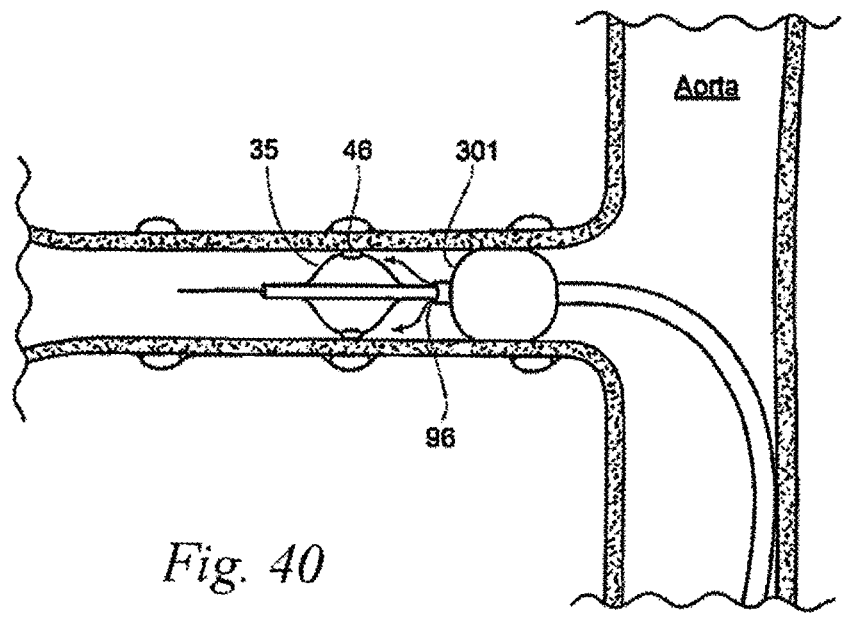

FIG. 40 illustrates an embodiment of the present invention with an occluding balloon 301 mounted on the distal end of a guide catheter 95. An ablation catheter can be an embodiment shown in FIGS. 5 through 34L, with or without a port 47. The guide catheter 95 of FIG. 40 comprises an inflation lumen in communication with the inner volume of the balloon 301 and with an inflation port (not shown) on the proximal end of the guide catheter 95. The guide catheter 95 also comprises a lumen 96 through which an ablation catheter is introduced into a renal artery.

Similar to the embodiment of FIG. 38 infusate is pumped in to the renal artery. However, in the embodiment of FIG. 40 infusate is delivered through lumen 96 and flows over electrode 46 in forward direction in to a kidney. Occluding balloon 301 restricts or stops blood flow from entering the artery.

Figure 41:
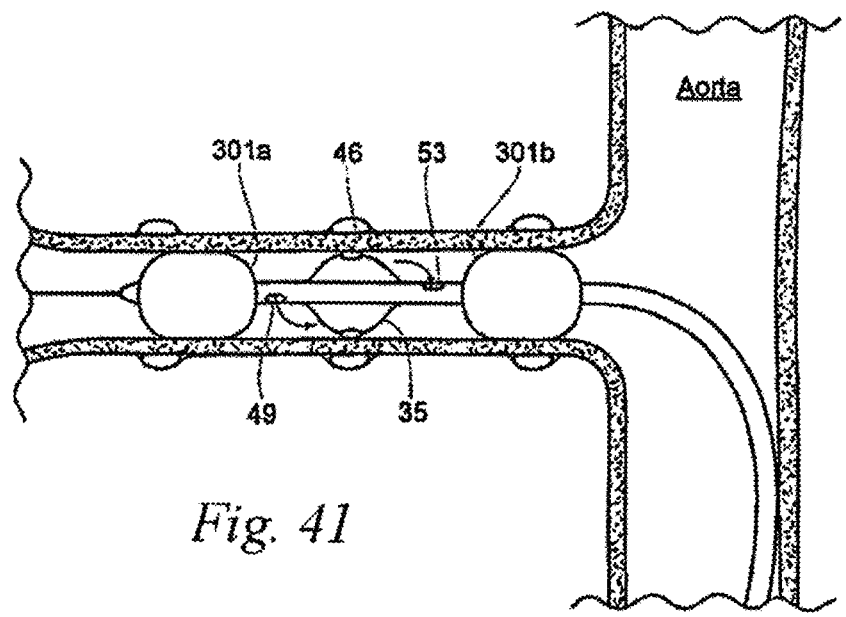

FIG. 41 illustrates an embodiment comprising a distal occluding balloon 301a and a proximal occluding balloon 301b mounted to elongate shaft 12 distal and proximal to one or more electrode 46, respectively. Elongate shaft 12 further comprises infusion port 49 and aspiration port 53 placed distal and proximal to electrode 46, respectively. The infusion port 49 is in fluid communication with a supply lumen (not shown) running the length of the elongate shaft to an infusate supply connector on the proximal end of the catheter. The aspiration port 53 is in fluid communication with an aspiration lumen (not shown) running the length of the elongate shaft to an aspiration connector on the proximal end of the catheter. One or more electrodes 46 are placed on a mechanically or self-expanding member 35.

A supply of infusate is mechanically pumped into the supply connector and aspirated infusate is disposed of or collected in a collection container. The Infusate flows over the electrode 46 and is removed from the artery through the aspiration port 53.

iv. Open Circuit Embodiment with a Weeping Balloon/Mesh

Figure 42:
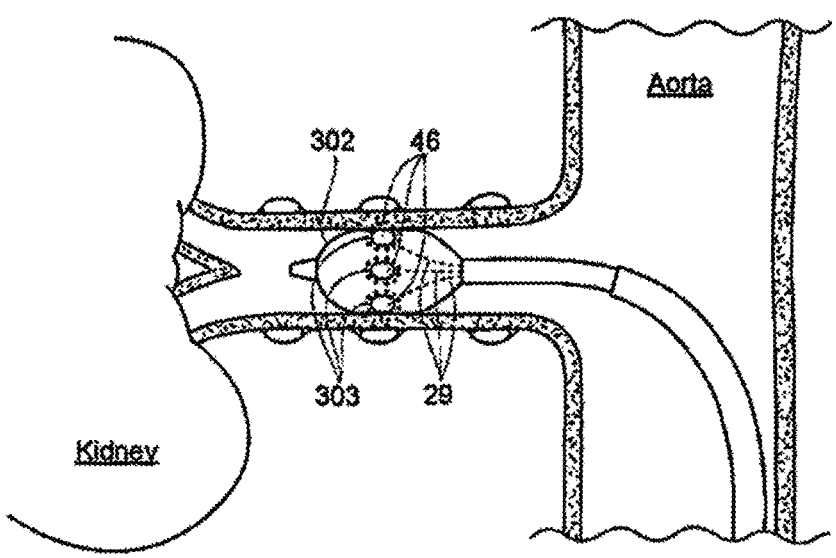
FIG. 42 shows an additional representative embodiment of an open circuit system for actively cooling the thermal heating element and/or the contacted tissue and its surroundings

FIG. 42 shows an additional embodiment of the present invention. In FIG. 42, the distal end region 20 of elongated shaft 12 comprises a weeping balloon 302 with one or more electrodes 46 bonded or laminated to the interior or exterior of the expandable weeping balloon. Electrical connections to each electrode 46 may be provided by wires 29 or by electrical traces on the surface of the weeping balloon 302. The wires/electrical traces are electrically coupled to generator 26.

Weeping balloon 302 is pliable and may conform to a range of expected anatomies upon inflation within a renal artery. Weeping balloon 302 comprises pores 303 that allow for fluid inside the balloon to pass through. Pores 303 are positioned near or proximal to electrode(s) 46. The fluid, such as saline, used to inflate the weeping balloon and pass through the pores 303 may provide a heat sink and/or convective cooling of the electrode(s) 46 and/or of contacted tissue. Additionally, the fluid could be chilled.

Since weeping balloon 302 blocks blood flow, accurate modeling of the complex thermodynamic and fluid dynamic environment during treatment may be more tractable, which may facilitate better control of treatment, lower risk treatment and/or more efficacious treatment.

When multiple electrodes 46 are provided, as in FIG. 42, the longitudinal and/or circumferential spacing of the electrodes may be specified, as desired, to facilitate treatment at multiple longitudinal/circumferential positions without necessitating re-positioning of the distal end region 20.

Alternatively, an expandable braid, mesh or fabric can be used instead of a weeping balloon. The expandable braid, mesh or fabric could be expanded by injecting fluid into it. Alternatively, it could be expanded by mechanical means such as a pull wire that reduces the length of the braid or the expandable braid could be self-expanding.

IV. USE OF THE SYSTEM

A. Intravascular Delivery, Deflection and Placement of the Treatment Device

Any one of the embodiments of the treatment devices 12 described herein can be delivered over a guide wire using conventional over-the-wire techniques. When delivered in this manner (not shown), the elongated shaft 16 includes a passage or lumen accommodating passage of a guide wire.

In one exemplary approach, a guide wire (not shown) is inserted through the access site and passed using image guidance through the femoral artery, into the iliac artery and aorta, and into either the left or right renal artery. A guide catheter can be passed over the guide wire into the accessed renal artery. The guide wire is then removed.

In a second exemplary approach, a first guide catheter is placed at the entrance of the renal artery (with or without a guide wire). A second guide catheter is passed via the first guide catheter (with or without the assistance of a guide wire) into the renal artery. The treatment device is then routed via the second guide catheter into the renal artery. Once the treatment device is properly positioned within the renal artery the second guide catheter is retracted, leaving the first guide catheter at the entrance to the renal artery. In this approach the first and second guide catheters should be sized and configured to accommodate passage of the second guide catheter within the first guide catheter (i.e., the inner diameter of the first guide catheter should be greater than the outer diameter of the second guide catheter). For example, the first guide catheter could be 8 French in size and the second guide catheter could be 5 French in size.

In a third exemplary approach, and as shown in FIG. 43A, a renal guide catheter 94 (e.g. a 6 French renal guide catheter) is positioned within the abdominal aorta, just proximal to the entrance of the renal artery. As now shown in FIG. 43B, the treatment device 12 as described herein is passed through the guide catheter 94 and into the accessed renal artery. The elongated shaft makes atraumatic passage through the guide catheter 94, in response to forces applied to the force transmitting section 30 through the handle assembly 200. The first or proximal flexure zone 32 accommodates significant flexure at the junction of the left/right renal arteries and aorta to gain entry into the respective left or right renal artery through the guide catheter 94 (as FIG. 43B shows).

As FIG. 43C shows, the second flexure zone 34 on the distal end portion of the elongated shaft 16 can now be axially translated into the respective renal artery, remotely deflected (illustratively, planar deflection or bending, but alternatively any other previously described deflection, such as helical deflection, may be provided) and/or rotated in a controlled fashion within the respective renal artery to attain proximity to and a desired alignment with an interior wall of the respective renal artery. As FIG. 43C further shows, the optional third flexure zone 44 bends to place the thermal energy heating element 24 into contact with tissue on the interior wall (alternatively or additionally, one or more energy delivery elements 24 may positioned along the length of the second flexure zone 34 and brought into contact with tissue on the interior wall during remote deflection of the second flexure zone).

B. Creation of Thermally Affected Tissue Regions

As previously described (and as FIG. 43B shows), the energy delivery element 24 can be positioned by bending along the first flexure zone 32 at a first desired axial location within the respective renal artery. As FIG. 43C shows, the energy delivery element 24 can be radially positioned by deflection of second flexure zone 34 toward the vessel wall. As FIG. 43C also shows, the energy delivery element 24 can be placed into a condition of optimal surface area contact with the vessel wall by further deflection of the third flexure zone 44.

Once the energy delivery element 24 is positioned in the desired location by a combination of deflection of the second flexure zone 34, deflection of the third flexure zone 44 and/or rotation of the catheter, treatment can be administered. Optionally, infusate, such as saline, may be delivered (e.g., may be infused through the energy delivery element, as in FIG. 30B) in the vicinity of the treatment site before, during and/or after treatment to provide conductive and/or convective cooling in excess of that provided by blood flow. By applying energy through the energy delivery element 24, a first thermally affected tissue region 98(*a*) can be formed, as FIG. 43D shows. In the illustrated embodiment, the thermally affected region 98(*a*) takes the form of a lesion on the vessel wall of the respective renal artery.

After forming the first thermally affected tissue region 98(a), the catheter optionally may be repositioned for another thermal treatment. As described above in greater detail, it is desirable to create multiple focal lesions that are circumferentially spaced along the longitudinal axis of the renal artery. To achieve this result, the catheter optionally may be retracted and, optionally, rotated to position the energy delivery element proximally along the longitudinal axis of the blood vessel. Rotation of the elongated shaft 16 from outside the access site (see FIG. 43E) may circumferentially reposition the energy delivery element 24 about the renal artery. Once the energy delivery element 24 is positioned at a second axial and circumferential location within the renal artery spaced from the first-described axial position, as shown in FIG. 43E (e.g., 98(b)), another focal treatment can be administered treatment (with or without saline infusion). By repeating the manipulative steps just described (as shown in FIGS. 43F through 43K), the caregiver can create several thermally affected tissue regions 98(a), 98(b), 98(c) and 98(d) on the vessel wall that are axially and circumferentially spaced apart, with the first thermally affected tissue region 98(a) being the most distal and the subsequent thermally affected tissue regions being more proximal. FIG. 43I provides a cross-sectional view of the lesions formed in several layers of the treated renal artery. This figure shows that several circumferentially and axially spaced-apart treatments (e.g., 98(a)-98(d)) can provide substantial circumferential coverage and, accordingly, cause a neuromodulatory effect to the renal plexus. Clinical investigation indicates that each lesion will cover approximately 20 to 30 percent of the circumferential area surrounding the renal artery. In other embodiments, the circumferential coverage of each lesion can be as much as 50 percent.

In an alternative treatment approach, the treatment device can be administered to create a complex pattern/array of thermally affected tissue regions along the vessel wall of the renal artery. As FIG. 43L shows, this alternative treatment approach provides for multiple circumferential treatments at each axial site (e.g., 98, 99 and 101) along the renal artery. Increasing the density of thermally affected tissue regions along the vessel wall of the renal artery using this approach might increase the probability of thermally-blocking the neural fibers within the renal plexus.

Figure 43G:
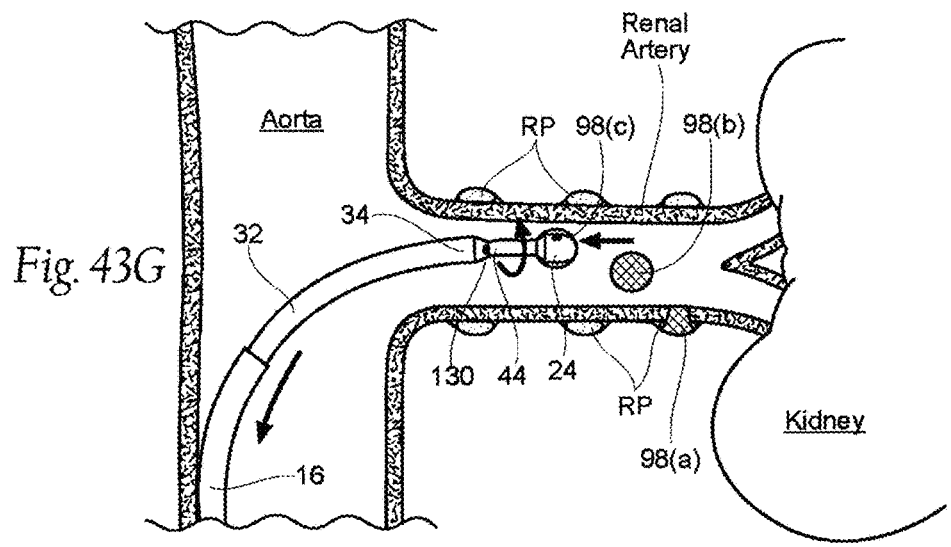
Figure 43H:
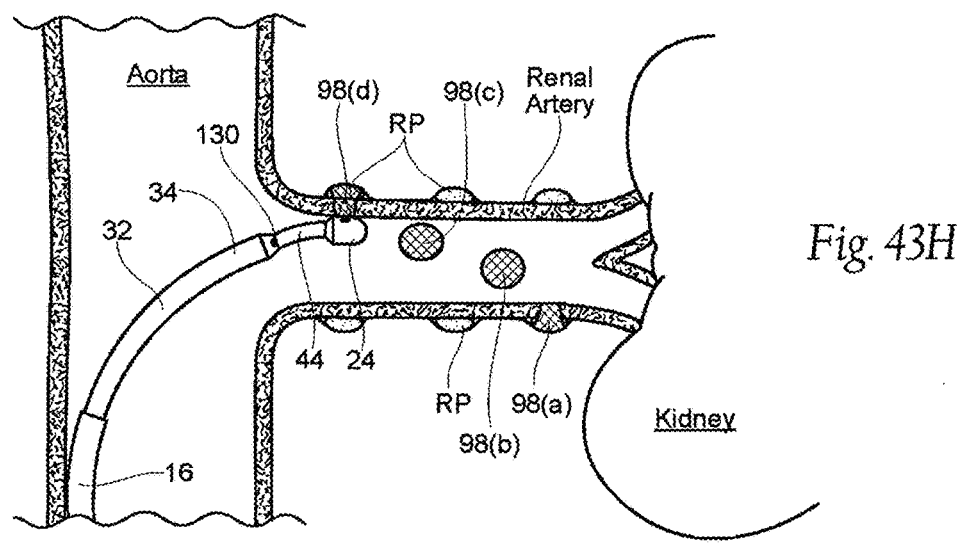
Figure 43K:
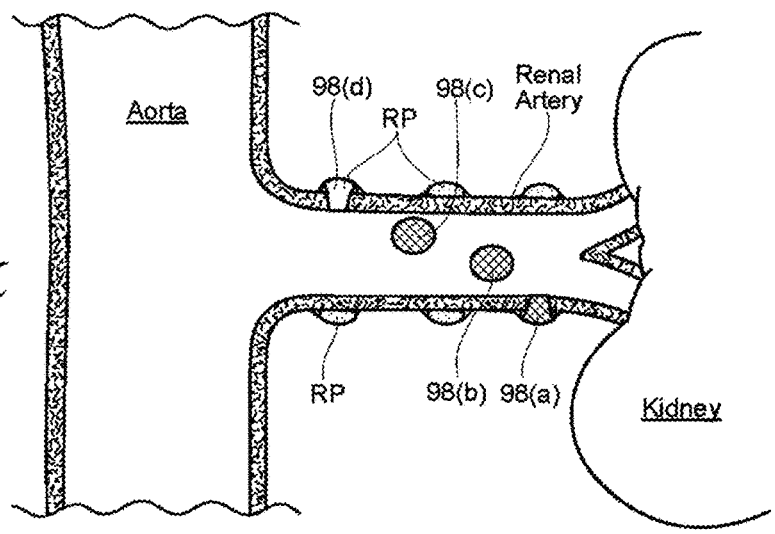
Figure 43L:
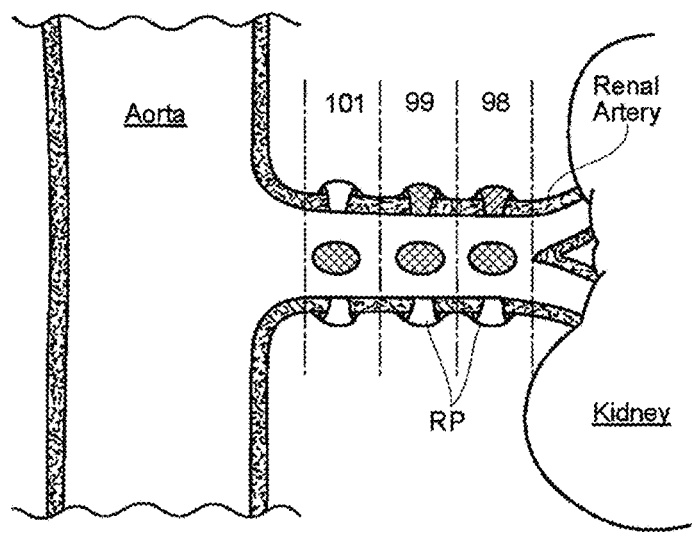
FIG. 43L shows an alternative intravascular treatment approach using a treatment device, like that shown in FIG. 5.

The rotation of the energy delivery element 24 within the renal artery as shown in FIG. 43G may improve the reliability and consistency of the treatment. Since angiographic guidance such as fluoroscopy only provides visualization in two dimensions, it is generally only possible in the anterior/posterior view to obtain visual confirmation of wall contact at the superior (vertex) and inferior (bottom) of the renal artery. For anterior and posterior treatments, it may be desirable to first obtain confirmation of contact at a superior or inferior location and then rotate the catheter such that the energy delivery element travels circumferentially along the vessel wall until the desired treatment location is reached. Physiologic data such as impedance can be concurrently monitored to ensure that wall contact is maintained or optimized during catheter rotation. Alternatively, the C-arm of the fluoroscope can be rotated to achieve a better angle for determining wall contact.

FIG. 43 illustrate multiple longitudinally and circumferentially spaced focal lesions that are created by repositioning an energy delivery element 24 through a combination of second flexure zone deflection, and elongated shaft rotation and/or translation. In some of the previously described embodiments of the treatment device, such multiple focal lesions may be created with multiple energy delivery elements 24 positioned along the length of the distal end region 20. Additionally or alternatively, in some of the previously described embodiments of the treatment device, such multiple focal lesions may be created by repositioning energy delivery element(s) 24 solely through second flexure zone deflection in multiple planes, solely through elongated shaft translation, solely through elongated shaft rotation, or solely through any subset of second flexure zone deflection, elongated shaft translation and elongated shaft rotation.

Figure 46A:
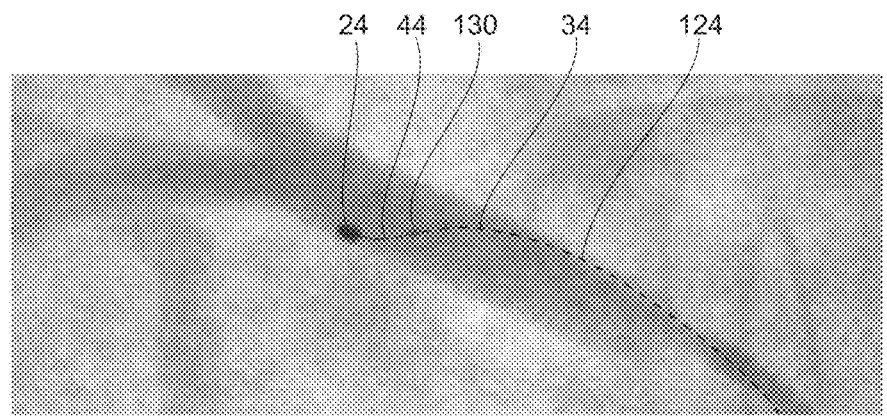
FIGS. 46A to 46C show fluoroscopic images of a treatment device, like that shown in FIG. 5, in multiple treatment positions within a renal artery of an animal.
Figure 46B:
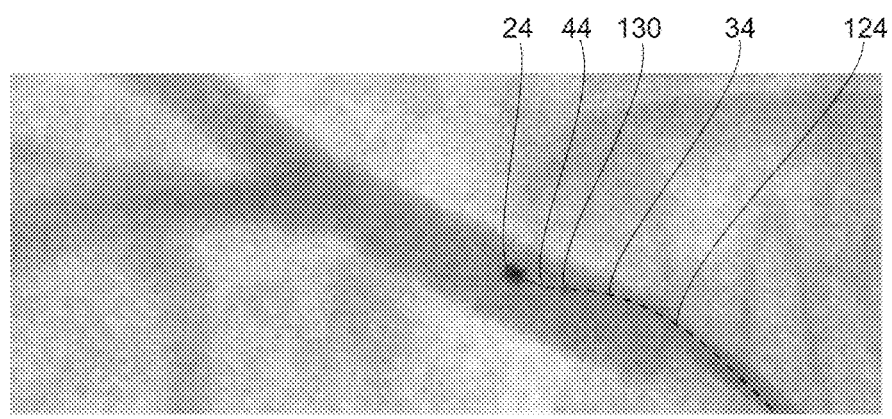
Figure 46C:
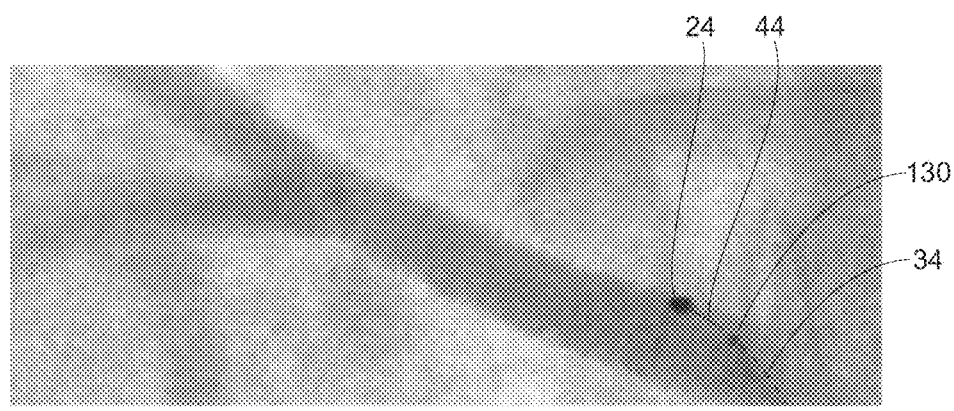
Figure 46D:
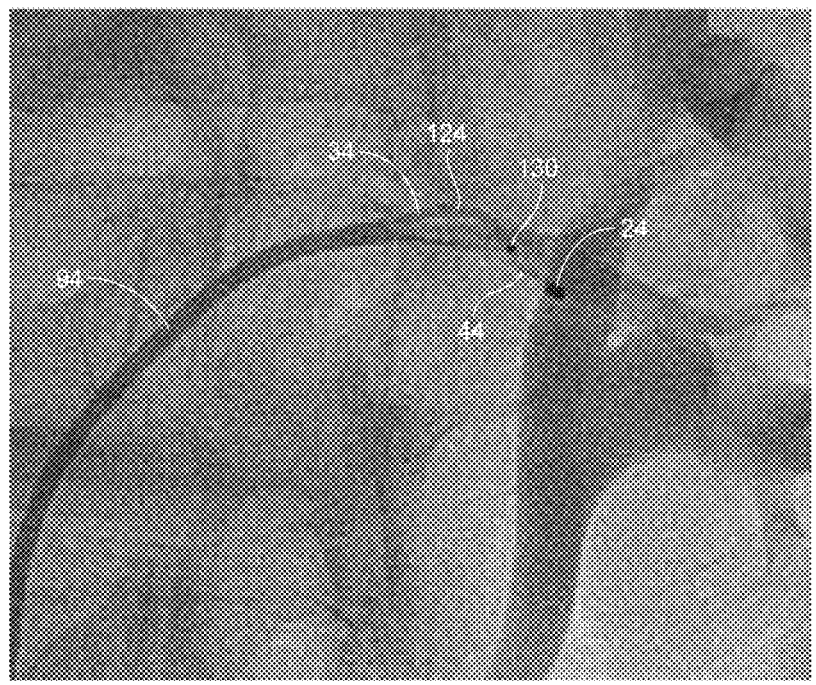
FIGS. 46D and 46E show fluoroscopic images of a treatment device, like that shown in FIG. 5, in multiple treatment positions within a renal artery during a human study.
Figure 46E:
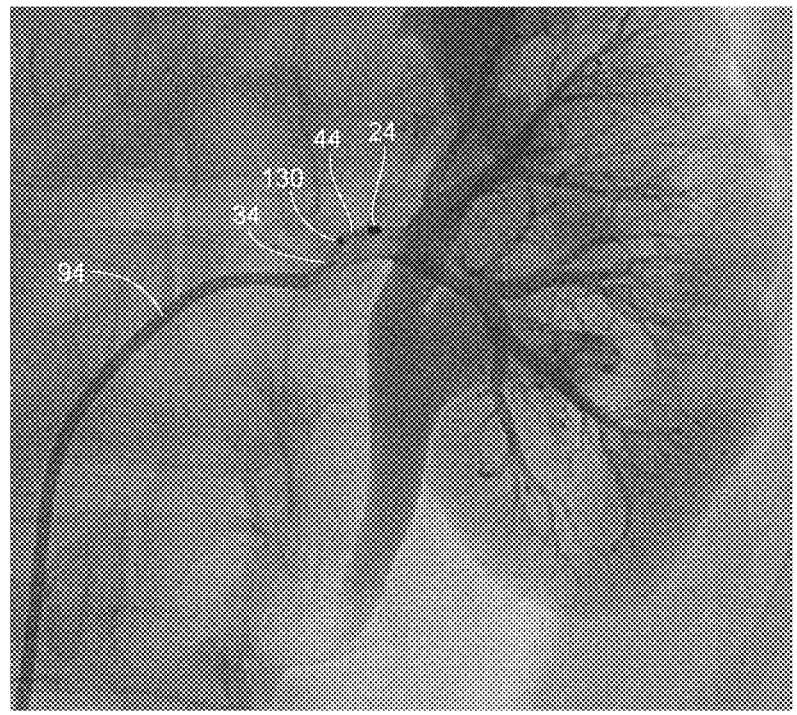

FIGS. 46A to 46C provide fluoroscopic images of a treatment device within a renal artery during an animal study. FIG. 46A shows positioning of the treatment device and energy delivery element 24 at a distal treatment location. The second flexure zone 34 has been deflected to position the energy delivery element 24 in contact with the vessel wall and to cause flexure in the third flexure zone 44. FIG. 46A also shows contact region 124 where the apex of the bend of the second flexure zone 34 is in contact with the vessel wall in radial or angular opposition to contact between the energy delivery element and vessel wall. FIG. 46B shows the placement of the treatment device at a more proximal treatment location following circumferential rotation and axial retraction. FIG. 46C shows the placement of the treatment device at a proximal treatment location just distal to the junction of the aorta and renal artery. FIGS. 46D and 46E provide analogous fluoroscopic images depicting the treatment device positioned for treatment within a human renal artery. FIG. 46D shows the treatment device advanced to a distal treatment location similar to that described above with respect to FIG. 46A. FIG. 46E shows the treatment device in a proximal treatment position similar to that described above with respect to FIG. 46C.

Since both the energy delivery element 24 and solder 130 at the distal end of the second flexure zone 34 can be radiopaque, as shown in FIGS. 46A to 46C, the operator using angiographic visualization can use the image corresponding to the first treatment location to relatively position the treatment device for the second treatment. For example, in renal arteries of average length, it is desirable for the clinical operator to treat at about every 5 mm along the length of the main artery. In embodiments where the length of the third flexure zone 44 is 5 mm, the operator can simply retract the device such that the current position of the energy delivery element 24 is longitudinally aligned with the position of the solder 130 in the previous treatment.

In another embodiment, a different type of radiopaque marker can replace solder 130. For example, a band of platinum can be attached to the distal end of the second flexure zone to serve as a radiopaque marker.

Since angiographic visualization of the vasculature generally requires contrast agent to be infused into the renal artery, it may be desirable to incorporate within or alongside the treatment device a lumen and/or port for infusing contrast agent into the blood stream. Alternatively, the contrast agent can be delivered into the blood alongside the treatment device within the annular space between the treatment device and the guide catheter through which the device is delivered.

Exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected.

C. Control of Applied Energy

Figure 44:
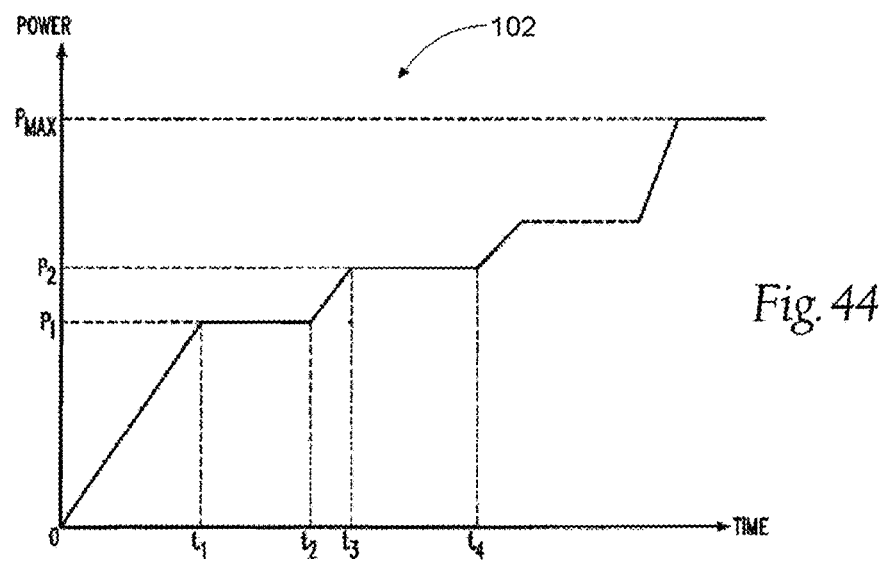
FIG. 44 shows an energy delivery algorithm corresponding to the energy generator of a system, like that shown in FIG. 5.

With the treatments disclosed herein for delivering therapy to target tissue, it may be beneficial for energy to be delivered to the target neural structures in a controlled manner. The controlled delivery of energy will allow the zone of thermal treatment to extend into the renal fascia while reducing undesirable energy delivery or thermal effects to the vessel wall. A controlled delivery of energy may also result in a more consistent, predictable and efficient overall treatment. Accordingly, the generator 26 desirably includes programmed instructions comprising an algorithm 102 (see FIG. 5) for controlling the delivery of power and energy to the thermal heating device. The algorithm 102, a representative embodiment of which is shown in FIG. 44, can be implemented as a conventional computer program for execution by a processor coupled to the generator 26. A caregiver using step-by-step instructions can also implement the algorithm 102 manually.

The operating parameters monitored in accordance with the algorithm may include, for example, temperature, time, impedance, power, flow velocity, volumetric flow rate, blood pressure, heart rate, etc. Discrete values in temperature may be used to trigger changes in power or energy delivery. For example, high values in temperature (e.g. 85 degrees C.) could indicate tissue desiccation in which case the algorithm may decrease or stop the power and energy delivery to prevent undesirable thermal effects to target or non-target tissue. Time additionally or alternatively may be used to prevent undesirable thermal alteration to non-target tissue. For each treatment, a set time (e.g., 2 minutes) is checked to prevent indefinite delivery of power.

Impedance may be used to measure tissue changes. Impedance indicates the electrical property of the treatment site. If a thermal inductive, electric field is applied to the treatment site the impedance will decrease as the tissue cells become less resistive to current flow. If too much energy is applied, tissue desiccation or coagulation may occur near the electrode, which would increase the impedance as the cells lose water retention and/or the electrode surface area decreases (e.g., via the accumulation of coagulum). Thus, an increase in tissue impedance may be indicative or predictive of undesirable thermal alteration to target or non-target tissue.

Additionally or alternatively, power is an effective parameter to monitor in controlling the delivery of therapy. Power is a function of voltage and current. The algorithm may tailor the voltage and/or current to achieve a desired power.

Derivatives of the aforementioned parameters (e.g., rates of change) also may be used to trigger changes in power or energy delivery. For example, the rate of change in temperature could be monitored such that power output is reduced in the event that a sudden rise in temperature is detected. Likewise, the rate of change of impedance could be monitored such that power output is reduced in the event that a sudden rise in impedance is detected.

As seen in FIG. 44, when a caregiver initiates treatment (e.g., via the foot pedal), the algorithm 102 commands the generator 26 to gradually adjust its power output to a first power level $P_1$ (e.g., 5 watts) over a first time period $t_1$ (e.g., 15 seconds). The power increase during the first time period is generally linear. As a result, the generator 26 increases its power output at a generally constant rate of $P_1/t_1$. Alternatively, the power increase can be non-linear (e.g., exponential or parabolic) with a variable rate of increase. Once $P_1$ and $t_1$ are achieved, the algorithm can hold at $P_1$ until a new time $t_2$ for a predetermined period of time $t_2-t_1$ (e.g., 3 seconds). At $t_2$ power is increased by a predetermined increment (e.g., 1 watt) to $P_2$ over a predetermined period of time, $t_3-t_2$ (e.g., 1 second). This power ramp in predetermined increments of about 1 watt over predetermined periods of time can continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In FIG. 44, algorithm 102 illustratively comprises a power-control algorithm. However, it should be understood that algorithm 102 alternatively may comprise a temperature-control algorithm. For example, power may be gradually increased until a desired temperature (or temperatures) is obtained for a desired duration (durations). In another embodiment, a combination power-control and temperature-control algorithm may be provided.

As discussed, the algorithm 102 includes monitoring certain operating parameters (e.g., temperature, time, impedance, power, flow velocity, volumetric flow rate, blood pressure, heart rate, etc.). The operating parameters can be monitored continuously or periodically. The algorithm 102 checks the monitored parameters against predetermined parameter profiles to determine whether the parameters individually or in combination fall within the ranges set by the predetermined parameter profiles. If the monitored parameters fall within the ranges set by the predetermined parameter profiles, then treatment can continue at the commanded power output. If monitored parameters fall outside the ranges set by the predetermined parameter profiles, the algorithm 102 adjusts the commanded power output accordingly. For example, if a target temperature (e.g., 65 degrees C.) is achieved, then power delivery is kept constant until the total treatment time (e.g., 120 seconds) has expired. If a first temperature threshold (e.g., 70 degrees C.) is achieved or exceeded, then power is reduced in predetermined increments (e.g., 0.5 watts, 1.0 watts, etc.) until a target temperature is achieved. If a second power threshold (e.g., 85 degrees C.) is achieved or exceeded, thereby indicating an undesirable condition, then power delivery can be terminated. The system can be equipped with various audible and visual alarms to alert the operator of certain conditions.

The following is a non-exhaustive list of events under which algorithm 102 may adjust and/or terminate/discontinue the commanded power output:

(1) The measured temperature exceeds a maximum temperature threshold (e.g., about 70 degrees to about 85 degrees C.).

(2) The average temperature derived from the measured temperature exceeds an average temperature threshold (e.g., about 65 degrees C.).

(3) The rate of change of the measured temperature exceeds a rate of change threshold.

(4) The temperature rise over a period of time is below a minimum temperature change threshold while the generator 26 has non-zero output. Poor contact between the energy delivery element 24 and the arterial wall can cause such a condition.

(5) A measured impedance exceeds an impedance threshold (e.g., <20 Ohms, or >500 Ohms).

(6) A measured impedance exceeds a relative threshold (e.g., impedance decreases from a starting or baseline value and then rises above this baseline value)

(7) A measured power exceeds a power threshold (e.g., >8 Watts or >10 Watts).

(8) A measured duration of power delivery exceeds a time threshold (e.g., >120 seconds).

V. PREPACKAGED KIT FOR DISTRIBUTION, TRANSPORT AND SALE OF THE DISCLOSED APPARATUSES AND SYSTEMS

Figure 45:
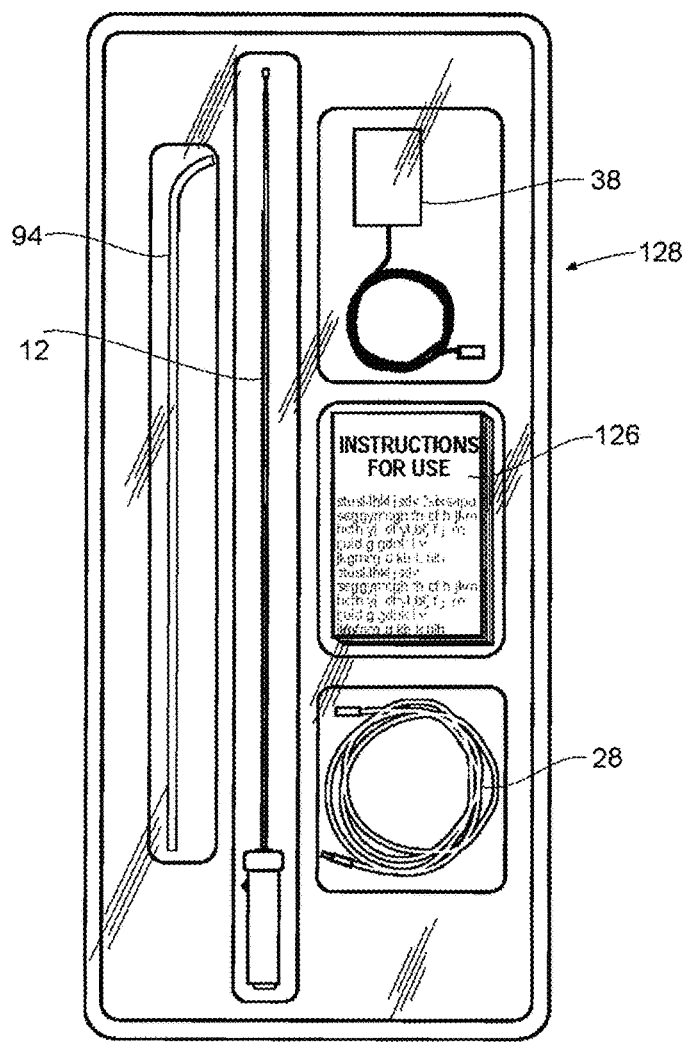
FIG. 45 shows several components of a system and treatment device packaged within a single kit.

As shown in FIG. 45, one or more components of the system 10 shown in FIG. 5 can be packaged together for convenient delivery to and use by the customer/clinical operator. Components suitable for packaging include, the treatment device 12, the cable 28 for connecting the treatment device 12 to the generator 26, the neutral or dispersive electrode 38, and one or more guide catheters 94 (e.g., a renal guide catheter). Cable 28 can also be integrated into the treatment device 12 such that both components are packaged together. Each component may have its own sterile packaging (for components requiring sterilization) or the components may have dedicated sterilized compartments within the kit packaging. This kit may also include step-by-step instructions for use 126 that provide the operator with technical product features and operating instructions for using the system 10 and treatment device 12, including all methods of insertion, delivery, placement and use of the treatment device disclosed herein.

VI. ADDITIONAL CLINICAL USES OF THE DISCLOSED APPARATUSES, METHODS AND SYSTEMS

Although much of the disclosure in this Specification relates to at least partially denervating a kidney of a patient to block afferent and/or efferent neural communication from within a renal blood vessel (e.g., renal artery), the apparatuses, methods and systems described herein may also be used for other intravascular treatments. For example, the aforementioned catheter system, or select aspects of such system, can be placed in other peripheral blood vessels to deliver energy and/or electric fields to achieve a neuromodulatory affect by altering nerves proximate to these other peripheral blood vessels. There are a number of arterial vessels arising from the aorta which travel alongside a rich collection of nerves to target organs. Utilizing the arteries to access and modulate these nerves may have clear therapeutic potential in a number of disease states. Some examples include the nerves encircling the celiac trunk, superior mesenteric artery, and inferior mesenteric artery.

Sympathetic nerves proximate to or encircling the arterial blood vessel known as the celiac trunk may pass through the celiac ganglion and follow branches of the celiac trunk to innervate the stomach, small intestine, abdominal blood vessels, liver, bile ducts, gallbladder, pancreas, adrenal glands, and kidneys. Modulating these nerves either in whole (or in part via selective modulation) may enable treatment of conditions including (but not limited to) diabetes, pancreatitis, obesity, hypertension, obesity related hypertension, hepatitis, hepatorenal syndrome, gastric ulcers, gastric motility disorders, irritable bowel syndrome, and autoimmune disorders such as Crohn's disease.

Sympathetic nerves proximate to or encircling the arterial blood vessel known as the inferior mesenteric artery may pass through the inferior mesenteric ganglion and follow branches of the inferior mesenteric artery to innervate the colon, rectum, bladder, sex organs, and external genitalia. Modulating these nerves either in whole (or in part via selective modulation) may enable treatment of conditions including (but not limited to) GI motility disorders, colitis, urinary retention, hyperactive bladder, incontinence, infertility, polycystic ovarian syndrome, premature ejaculation, erectile dysfunction, dyspareunia, and vaginismus.

While arterial access and treatments have received attention in this Specification, the disclosed apparatuses, methods and systems can also be used to deliver treatment from within a peripheral vein or lymphatic vessel.

VII. CONCLUSION

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the invention. Where the context permits, singular or plural terms may also include the plural or singular term, respectively. For example, much of the disclosure herein describes an energy delivery element 24 or electrode 46 in the singular. It should be understood that this application does not exclude two or more energy delivery elements or electrodes.

It should also be understood that energy delivery element 24 can be an electrode, radiofrequency electrode, cooled radiofrequency electrode, thermal element, thermal heating element, electrically resistive heating element, cryoablative applicator, microwave antenna, ultrasound transducer, high intensity focused ultrasound transducer, or laser emitter.

Additionally, other terms used herein may be expressed in different and interchangeable ways. For example, a force transmitting section can also be an proximal force transmitting section, elongated tubular shaft; a first flexure zone can also be a flexible tubular structure; a deflectable section can also be an intermediate flexure zone or a second flexure zone or a deflectable tubular body; a control wire can be a flexure control element; a force dampening section can be a third flexure zone or distal flexure zone or passively flexible structure; a force redirecting element can be a pre-shaped geometry.

Moreover, unless the word "or" is expressly limited to mean only a single item exclusive from the other items in reference to a list of two or more items, then the use of "or"

in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the invention. Accordingly, the invention is not limited except as by the appended claims.

We claim:

1. A method of treating a human patient diagnosed with hypertension, the method comprising:
   intravascularly positioning a catheter within a renal artery of the patient and adjacent to target neural fibers innervating a kidney of the patient, the catheter comprising a distal region including a first flexure zone and a second flexure zone extending distally from the first flexure zone, wherein the second flexure zone includes a plurality of electrodes, and wherein the second flexure zone is configured for spiral deflection;
   delivering a thermal fluid infusate through one or more of the individual electrodes and into the renal artery; and
   at least partially ablating the target neural fibers via radio frequency (RF) energy delivered via the electrodes.

2. The method of claim 1 wherein each of the electrodes includes a plurality of infusion outlets through which the thermal fluid infusate is delivered.

3. The method of claim 1 wherein delivering the thermal fluid infusate through one or more of the individual electrodes and into the renal artery comprises delivering the thermal infusate at an infusion rate of less than or equal to 15 mL/minute.

4. The method of claim 1 wherein delivering the thermal fluid infusate through one or more of the individual electrodes and into the renal artery comprises delivering the thermal infusate at an infusion rate of less than or equal to 10 mL/minute.

5. The method of claim 1 wherein the thermal fluid infusate comprises a cooling fluid.

6. The method of claim 1 wherein the thermal fluid infusate comprises saline.

7. The method of claim 6 wherein the saline comprises room temperature saline.

8. The method of claim 6 wherein the saline comprises chilled saline.

9. The method of claim 1 wherein each of the electrodes comprises a plurality of ports configured to direct the thermal fluid infusate into the renal artery and away from the target neural fibers during ablation.

10. The method of claim 1 wherein each of the electrodes comprises a plurality of ports arranged around a circumference of the respective electrode.

11. The method of claim 1 wherein the second flexure zone comprises four electrodes.

12. The method of claim 1 wherein intravascularly positioning the catheter within a renal artery of the patient comprises advancing the catheter through a radial artery, through a subclavian artery of the patient, through an aortic arch of the patient, down a descending aorta of the patient, and into the renal artery.

13. The method of claim 1 wherein intravascularly positioning the catheter within a renal artery of the patient comprises advancing the catheter through a radial artery, through a subclavian artery and a brachiocephalic artery of the patient, through an aortic arch of the patient, down a descending aorta of the patient, and into the renal artery.

14. The method of claim 1 wherein at least a portion of the catheter comprises nitinol.

15. The method of claim 1 wherein the catheter further comprises one or more irrigation ports positioned proximal of the electrodes.

16. The method of claim 1 wherein the plurality of electrodes provide a non-continuous circumferential ablation treatment of the target neural fibers when the second flexure zone is positioned in its spiral deflected configuration.

17. The method of claim 1 wherein the second flexure zone further comprises a hypo tube having a spiral spine with connecting ribs.

18. The method of claim 1, further comprising monitoring a parameter of target tissue and/or non-target tissue within the patient before and during delivery of the RF energy.

19. The method of claim 18 wherein monitoring the parameter comprises monitoring a temperature of target tissue, and wherein the method further comprises maintaining the target tissue at a desired temperature during delivery of the RF energy.

20. The method of claim 18, further comprising altering delivery of the RF energy in response to the monitored parameter.

21. The method of claim 18, further comprising altering delivery of the thermal fluid infusate into the renal artery in response to the monitored parameter.

22. The method of claim 1 wherein at least partially ablating the target neural fibers results in a therapeutically beneficial reduction in blood pressure of the patient.

* * * * *